(12) United States Patent
Liu et al.

(10) Patent No.: US 11,524,012 B1
(45) Date of Patent: Dec. 13, 2022

(54) QUINOLONE ANALOGS AND THEIR SALTS, COMPOSITIONS, AND METHOD FOR THEIR USE

(71) Applicant: Senhwa Biosciences, Inc., New Taipei (TW)

(72) Inventors: Hshiou-ting Liu, Milpitas, CA (US); John Soong, Chino, CA (US)

(73) Assignee: SENHWA BIOSCIENCES, INC., New Taipei (TW)

( * ) Notice: Subject to any disclaimer, the term of this patent is extended or adjusted under 35 U.S.C. 154(b) by 0 days.

(21) Appl. No.: 17/394,541

(22) Filed: Aug. 5, 2021

Related U.S. Application Data

(63) Continuation of application No. 16/277,089, filed on Feb. 15, 2019.

(60) Provisional application No. 62/631,174, filed on Feb. 15, 2018, provisional application No. 62/631,171, filed on Feb. 15, 2018.

(51) Int. Cl.
| | | |
|---|---|---|
| *A61K 31/551* | (2006.01) | |
| *A61P 35/00* | (2006.01) | |
| *A61K 9/19* | (2006.01) | |
| *A61K 47/26* | (2006.01) | |

(52) U.S. Cl.
CPC .............. *A61K 31/551* (2013.01); *A61K 9/19* (2013.01); *A61K 47/26* (2013.01); *A61P 35/00* (2018.01)

(58) Field of Classification Search
CPC combination set(s) only.
See application file for complete search history.

(56) References Cited

U.S. PATENT DOCUMENTS

| | | |
|---|---|---|
| 4,559,157 A | 12/1985 | Smith et al. |
| 4,608,392 A | 8/1986 | Jacquet et al. |
| 4,820,508 A | 4/1989 | Wortzman |
| 4,938,949 A | 7/1990 | Borch et al. |
| 4,992,478 A | 2/1991 | Geria |
| 5,703,055 A | 12/1997 | Feigner et al. |
| 7,179,805 B2 | 2/2007 | Grant, III et al. |
| 7,928,100 B2 | 4/2011 | Nagasawa et al. |
| 8,853,234 B2 | 10/2014 | Nagasawa et al. |
| 9,688,697 B2 | 6/2017 | Achiron et al. |
| 9,957,282 B2 | 5/2018 | Ryckman et al. |
| 10,857,156 B2 | 12/2020 | Soong |
| 2005/0227919 A1 | 10/2005 | Ashworth et al. |
| 2007/0099951 A1 | 5/2007 | Dube et al. |
| 2009/0093455 A1 | 4/2009 | Nagasawa et al. |
| 2009/0291437 A1 | 11/2009 | O'Brien et al. |
| 2010/0305136 A1 | 12/2010 | Nagasawa |
| 2011/0218184 A1 | 9/2011 | Nagasawa et al. |
| 2013/0274198 A1 | 10/2013 | Kufe et al. |
| 2014/0086839 A1 | 3/2014 | Achiron et al. |
| 2014/0113951 A1 | 4/2014 | Vincent et al. |
| 2014/0364434 A1 | 12/2014 | Daeman et al. |
| 2015/0125463 A1 | 5/2015 | Cogswell et al. |
| 2015/0284410 A1 | 10/2015 | Achiron et al. |
| 2017/0166590 A1 | 6/2017 | Ryckman et al. |
| 2018/0369143 A1 | 12/2018 | Bally et al. |
| 2019/0224209 A1 | 7/2019 | Soong |
| 2019/0374550 A1 | 12/2019 | Liu |
| 2021/0046071 A1 | 2/2021 | Soong |
| 2021/0046082 A1 | 2/2021 | Liu |
| 2021/0113584 A1 | 4/2021 | Soong |
| 2022/0062294 A1 | 3/2022 | Liu et al. |
| 2022/0088029 A1 | 3/2022 | Soong |

FOREIGN PATENT DOCUMENTS

| | | |
|---|---|---|
| JP | 2006-519827 A | 8/2006 |
| JP | 2007-537291 A | 12/2007 |
| JP | 2010-540663 A | 12/2010 |
| RU | 2330678 C2 | 8/2008 |
| RU | 2404183 C2 | 11/2010 |
| WO | WO 2000/059882 | 10/2000 |
| WO | WO 2003/050107 | 6/2003 |
| WO | WO 2004/014893 | 2/2004 |
| WO | WO 2004/080976 | 9/2004 |
| WO | WO 2005/012305 | 2/2005 |
| WO | WO 2005/025410 A2 | 3/2005 |
| WO | WO 2005/113556 A1 | 12/2005 |
| WO | WO 2006/034113 | 3/2006 |
| WO | WO 2007/019295 | 2/2007 |
| WO | WO 2007/022474 | 2/2007 |
| WO | WO 2007/056113 | 5/2007 |
| WO | WO 2007/146813 | 12/2007 |
| WO | WO 2007/146831 | 12/2007 |
| WO | WO 2008/060693 | 5/2008 |
| WO | WO 2008/092681 | 8/2008 |
| WO | WO 2008/131134 | 10/2008 |
| WO | WO 2009/046383 | 4/2009 |

(Continued)

OTHER PUBLICATIONS

International Search Report and Written Opinion for International Application No. PCT/US2008/078859, dated Dec. 24, 2008, 8 pages.

International Search Report and Written Opinion for International Application No. PCT/US2015/065443, dated Oct. 4, 2016, 12 pages.

International Search Report and Written Opinion for International Application No. PCT/US2016/061176, dated Jan. 19, 2017, 10 pages.

Extended European Search Report for EP. Application No. 16866873.9, dated May 21, 2019, 9 pages.

Abdelwahed W., et al. "Freeze-drying of nanoparticles: formulation, process and storage considerations", Adv Drug Deliv Rev.;58(15):1688-713. (Dec. 30, 2006). Epub Oct. 6, 2006.

(Continued)

*Primary Examiner* — Kathrien A Cruz
(74) *Attorney, Agent, or Firm* — Cooley LLP

(57) ABSTRACT

The present invention includes a solid lyophilized form of 2-(4-Methyl-[1,4]diazepan-1-yl)-5-oxo-5H-7-thia-1,11b-diaza-benzo[c]fluorene-6-carboxylic acid (5-methyl-pyrazin-2-ylmethyl)-amide (Compound I) and the process of producing the solid lyophilized form. Furthermore, the present invention provides compositions comprising Compound I, or a pharmaceutically acceptable salt and/or solvate thereof and therapeutic use of the composition.

26 Claims, 30 Drawing Sheets

(56) References Cited

FOREIGN PATENT DOCUMENTS

| WO | WO 2009/127414 | 10/2009 |
|---|---|---|
| WO | WO 2012/123938 | 9/2012 |
| WO | WO 2014/209804 | 12/2014 |
| WO | WO 2015/079411 | 6/2015 |
| WO | WO2015125159 A1 | 8/2015 |
| WO | WO 2017/087235 | 5/2017 |
| WO | WO 2017/205832 A1 | 11/2017 |
| WO | WO 2019/168688 | 9/2019 |
| WO | WO 2021/030671 | 2/2021 |
| WO | WO 2021/030686 | 2/2021 |
| WO | WO 2022/051491 A1 | 3/2022 |

OTHER PUBLICATIONS

Ansell, R.J. et al., "Molecularly imprinted polymers for bioanalysis: chromatography, binding assays and biomimetic sensors", Curr Opin Biotechnol; 7:89-94.(1996).

Bastin, et al. "Salt Selection and Optimisation Procedures for Pharmaceutical New Chemical Entities", Org. Proc. Res. Dev.; 4 (5), pp. 427-435. (2000).

Berge, S.M. et al., "Pharmaceutical Salts", Journal of Pharmaceutical Sciences; 66(1):1-19. (Jan. 1977).

Braga et al., "Crystal Polymorphism and Multiple Crystal Forms", Struct. Bond;132:25-50. (2009).

Caira, M. R. "Crystalline Polymorphism of Organic Compounds", In: Weber E. et al. (eds) Design of Organic Solids. Topics in Current Chemistry;198:163-208; Springer, Berlin, Heidelberg. (1998). Epub Feb. 26, 1999.

Devlin, J. R., et al. "Combination Therapy Targeting Ribosome Biogenesis and mRNA Translation Synergistically Extends Survival in MYC-Driven Lymphoma", Cancer Discov.; 6(1):59-70. (Jan. 2016). Epub Oct. 21, 2015.

Drygin, D. et al., "Targeting the nucleolus for cancer-specific activation of p53", Drug Discovery Today; 19(3):259-65. (Mar. 2014) Epub Aug. 28, 2013.

Gibson, U.E.M. et al., "A Novel Method for Real Time Quantitative RT-PCR," Genome Res; 6:995-1001.(1996).

Haddach, M. et al. "Discovery of CX-5461, the First Direct and Selective Inhibitor of RNA Polymerase I, for Cancer Therapeutics", ACS Med Chem Lett.; 3(7): 602-606. (Jul. 12, 2012).

Heid, C.A. et al., "Real Time Quantitative PCR," Genome Res; 6:986-994. (1996).

Jin, C.H. et al., "Human Vitamin D Receptor-Dependent Transactivation in *Saccharomyces cerevisiae* Requires Retinoid X Receptor," Mol Endocrinol; 10:196-205. (1996).

Kriz, D. et al., "Introducing Biomimetic Sensors Based on Molecularly Imprinted Polymers as Recognition Elements," Analytical Chemistry; 67:2142-2144. (1995).

Li, L. et al. "CX-5461 induces autophagy and inhibits tumor growth via mammalian target of rapamycin-related signaling pathways in osteosarcoma", Onco Targets Ther.; 9: 5985-5997. (2016). [Retrieved from the Internet May 7, 2019]. Published online Sep. 29, 2016.

Mei, H. et al., "Rapid In Vivo Oral Screening in Rats: Reliability, Acceptance Criteria, and Filtering Efficiency," The AAPS Journal; 8(3) Article 58:E493-E500. (2006).

Morissette, S. L., et al. "High-throughput crystallization: polymorphs, salts, co-crystals and solvates of pharmaceutical solids", Adv Drug Deliv Rev.; 56(3): 275-300. (Feb. 23, 2004).

Quin, J. E. et al., "Targeting the nucleolus for cancer intervention," Biochimica et Biophysica Acta, 1842(6):802-16. (Jun. 2014).

Rodriguez-Spong, B. et al. "General principles of pharmaceutical solid polymorphism: a supramolecular perspective", Adv Drug Deliv Rev.; 56(3):241-74. (Feb. 23, 2004).

Negi, S. S. et al. "rRNA synthesis inhibitor, CX-5461, activates ATM/ATR pathway in acute lymphoblastic leukemia, arrests cells in G2 phase and induces apoptosis", Oncotarget.; 6(20): 18094-18104. (Jul. 20, 2015). Published online Jun. 5, 2015.

Negi, S. S. et al. "Transient rRNA synthesis inhibition with CX-5461 is sufficient to elicit growth arrest and cell death in acute lymphoblastic leukemia cells", Oncotarget.; 6(33): 34846-34858. (Oct. 27, 2015). Published online Oct. 12, 2015.

Schwaebe, M. K. et al. "Facile and efficient generation of quinolone amides from esters using aluminum chloride", Tetrahedron Letters; 52(1):1096-1100. (Mar. 9, 2011).

Shea, K.J., "Molecular Imprinting of synthetic Network Polymers: The De Novo Synthesis of Macromolecular Binding and Catalytic Sites," Trends in Polymer Sci; 2(5):166-173. (1994).

Vaickus, L. et al., "Immune markers in hematologic malignancies," Crit Revin Oncol/Hematol; 11:267-297. (1991).

Vlatakis, G. et al., "Drug assay using antibody mimics made by molecular imprinting," Nature; 361:645-647. (1993).

International Search Report and Written Opinion for International Application No. PCT/US2019/018225, dated Aug. 19, 2019, 13 pages.

National Center for Biotechnology Information. "PubChem Database. CID=68237161"; [retrieved on Aug. 30, 2019]. Retrieved from the Internet. <https://pubchem.ncbi.nlm.nih.gov/compound/68237161>, 5 pages.

Yang, D. L. "Polymorphic Drugs", People's Health Publishing House. (2009).

Search Report dated Jun. 24, 2020 for Chinese Application No. 201580085777.5, 6 pages.

Azar et al., "The effect of shot peening on fatigue and corrosion behavior of 316A stainless steel in Ringer's solution", Surface & Coatings Technology, 2010, 204, pp. 3546-3551.

Brittain H.G. Ed. Polymorphism in Pharmaceutical Solids, vol. 192, Jan. 1, 1999; Part I, section 1 (pp. 1-23); Part III, section 8 (pp. 288-317); Part IV, sections 9-12 (pp. 318-480).

Drygin, Denis, et al. "Targeting RNA polymerase I with an oral small molecule CX-5461 inhibits ribosomal RNA synthesis and solid tumor growth," Cancer research 71.4 (2011): 1418-1430.

International Search Report and Written Opinion for International Application No. PCT/US2021/048861, dated Dec. 14, 2021, 8 pages.

Lheureux, Stephanie, et al. "Safety evaluation of olaparib for treating ovarian cancer," Expert opinion on drug safety 14.8 (2015): 1305-1316 (Published Jan. 8, 2015).

Rohani, S., "Applications of the crystallization process in the pharmaceutical industry", Frontiers of Chemical Engineering in China, 2010, 4(1), pp. 2-9.

Extended European Search Report for Application No. EP19761078.5, dated Jan. 28, 2022, 11 pages.

International Preliminary Report on Patentability for International Application No. PCT/US2020/046368, dated Feb. 8, 2022, 5 pages.

International Preliminary Report on Patentability for International Application No. PCT/US2020/046329, dated Feb. 8, 2022, 5 pages.

Office Action for RU Application No. 2018124599, dated Dec. 24, 2021, 31 pages (Translation included).

Byrski et al. "Pathologic Complete Response Rates in Young Women With BRCA1-Positive Breast Cancers After Neoadjuvant Chemotherapy," Journal of Clinical Oncology, Jan. 2010, vol. 28, No. 3, pp. 375-379.

Carey, Lisa A., "Targeted Chemotherapy? Platinum in BRCA1-Dysfunctinal Breast Cancer," Journal of Clinical Oncology, 2010, 28, 361-365.

Byrn et al., "Pharmaceutical Solids: S Strategic Approach to Regulatory Considerations," Pharma. Res. 12(7), pp. 945-954, Jul. 1995.

Cains, Peter W., "Handbook of Phamaceutical Salts; Properties, Selection, and Use Part II 4. Classical Methods of Preparation of Polymorphs and Alternative Solid Forms," Verlag Helvetica Chimica Acta. Zürich, Switzerland, and Wiley-VCH, Weinheim, Germany, pp. 76-138 ISBN 3-906390-26-8, 2002.

Hilfiker et al., "Polymorphism in the Pharmaceutical Industry," Wiley-VCH, Jan. 2006, 18 pages.

Kumar et al., "An overview of automated systems relevant in pharmaceutical salt screening," Drug Discovery Today, 12(23-24), pp. 1046-1053, Dec. 2007.

Serajuddin, "Salt formation to improve drug solubility," Advanced Drug Delivery Reviews, 59, pp. 603-616, May 2007.

QUINOLONE ANALOGS AND THEIR SALTS, COMPOSITIONS, AND METHOD FOR THEIR USE

CROSS-REFERENCE TO RELATED APPLICATIONS

This application is a continuation of U.S. patent application Ser. No. 16/277,089, filed Feb. 15, 2019, which claims the priority benefit of U.S. Provisional Application No. 62/631,171, filed Feb. 15, 2018 and U.S. Provisional Application No. 62/631,174, filed Feb. 15, 2018, the disclosures of which are incorporated by reference herein in their entireties.

FIELD OF THE DISCLOSURE

The present invention generally relates to fused naphthyridinone or quinolone analogs, pharmaceutical composition containing them, and methods of using them and a solid lyophilized composition of tetracyclic quinolone compounds or the salts and/or solvates of the tetracyclic quinolone compounds, pharmaceutical composition containing them, and methods of using them.

BACKGROUND OF THE DISCLOSURE

A variety of tetracyclic quinolone compounds or napththyridinone fused tetracyclic compounds have been suggested to function by interacting with quadruplex-forming regions of nucleic acids and modulating ribosomal RNA transcription. See, for example, U.S. Pat. Nos. 7,928,100 and 8,853,234. Specifically, the tetracyclic quinolone compounds can stabilize the DNA G-quadruplexes (G4s) in cancer cells and thereby induce synthetic lethality in cancer cells. Since treatment of cells with G4-stabilizing agents can lead to the formation of DNA double strand breaks (DSBs), DSB formation induced by G4-stabilizing ligand/agent (such as the tetracyclic quinolones) treatment would be more pronounced in cells genetically deficient in, or chemically inhibited in, repair pathways including both non-homologous end joining (NHEJ) and homologous recombination (HR) repair. Furthermore, the tetracyclic quinolone compounds selectively inhibit rRNA synthesis by RNA polymerase I (Pol I) in the nucleolus, but do not inhibit mRNA synthesis by RNA polymerase II (Pol II) and do not inhibit DNA replication or protein synthesis. It is suggested that targeting RNA polymerase I (Pol I) to activate p53 through the nucleolar stress pathway may results in selective activation of p53 in tumor cells. The p53 protein normally functions as a tumor suppressor by causing cancer cells to self-destruct. Activating p53 to kill cancer cells is a well validated anticancer strategy and many approaches are being employed to exploit this pathway. Selective activation of p53 in tumor cells would be an attractive method of treating, controlling, ameliorating tumor cells while not affecting normal healthy cells. The aforementioned tetracyclic quinolones are disclosed in U.S. Pat. Nos. 7,928,100 and 8,853,234, and the contents of this publication are herein incorporated by reference in their entirety for all intended purposes.

Those skilled in the pharmaceutical arts understand that a solid form an active pharmaceutical ingredient offers the best method for controlling important physiochemical qualities, such as stability, solubility, bioavailability, particle size, bulk density, flow properties, polymorphic content, and other properties. Thus, there is a need for processes to produce such solid forms that has excellent shelf life and is advantageous in obtaining optimal formulation of the tetracyclic quinolone compounds. These solid forms should be suitable for pharmaceutical use.

SUMMARY OF THE DISCLOSURE

In one embodiment of the present invention provides a pharmaceutical composition comprising Compound I:

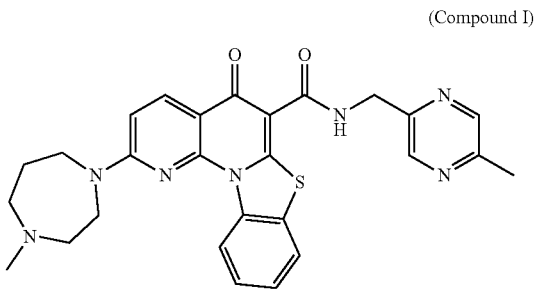

(Compound I)

or a pharmaceutically acceptable salt and/or solvate thereof; wherein the composition comprises less than about 1% impurities.

In one embodiment, the pharmaceutical composition is a solid composition comprising a lyophilized Compound I or a pharmaceutically acceptable salt and/or solvate thereof.

In one embodiment, the pharmaceutical composition comprises less than about 1% impurities after the composition is stored at a temperature in the range of about 2° C. to about 30° C. for at least 28 days. In another embodiment, the pharmaceutical composition comprises less than about 1% impurities after the composition is stored at a temperature in the range of about 2° C. to about 30° C. for 28 days. In one embodiment, the pharmaceutical composition comprises less than about 1% impurities after the composition is stored at room temperature for 28 days.

In one embodiment, the pharmaceutical composition comprises less than 0.5% impurities after the composition is stored at room temperature for 42 days. In one embodiment, the pharmaceutical composition comprises less than about 0.4% impurities resulting from oxidation of Compound I after the composition is stored at room temperature for 28 days. In one embodiment, the pharmaceutical composition comprises less than 0.1% impurities resulting from oxidation of Compound I after the composition is stored at room temperature for 28 days; wherein the oxidation of Compound I is at one or more hydrocarbons.

In one embodiment, the pharmaceutical composition comprises less than 0.1% of Compound 10 after the composition is stored at room temperature for 28 days.

In one embodiment, the pharmaceutical composition comprises less than 0.2% impurities resulting from oxidation of Compound I after the composition is stored at room temperature for 14 days; wherein the oxidation of Compound I is an N-oxide of Compound I. In one embodiment, the pharmaceutical composition comprises less than 0.2% of Compound 9 after the composition is stored at room temperature for 14 days.

In one embodiment, the pharmaceutical composition comprises less than 0.1% impurities resulting from oxidation of Compound I after the composition is stored at a temperature in the range of about 2° C. to about 30° C. for at least 28 days; wherein the oxidation of Compound I is at one or more hydrocarbons. In one embodiment, the pharmaceutical composition comprises less than 0.1% of Compound 10 after the composition is stored at a temperature in the range of about 2° C. to about 30° C. for at least 28 days.

In one embodiment, the pharmaceutical composition comprises less than 0.2% impurities resulting from oxidation of Compound I after the composition is stored at a temperature in the range of about 2° C. to about 30° C. for 14 days; wherein the oxidation of Compound I is an N-oxide of Compound I. In one embodiment, the pharmaceutical composition comprises less than 0.2% of Compound 9 after the composition is stored at a temperature in the range of about 2° C. to about 30° C. for 14 days.

In another embodiment, the pharmaceutical composition comprises less than about 1% impurities after the composition is stored at a temperature in the range of about 2° C. to about 30° C. for at least 1 month. In another embodiment, the pharmaceutical composition comprises less than about 1% impurities after the composition is stored at a temperature in the range of about 2° C. to about 30° C. for 1 month. In one embodiment, the pharmaceutical composition comprises less than about 1% impurities after the composition is stored at room temperature for 1 month.

In one embodiment, the pharmaceutical composition comprises less than 0.5% impurities after the composition is stored at room temperature for 1 month. In one embodiment, the pharmaceutical composition comprises less than about 0.4% impurities resulting from oxidation of Compound I after the composition is stored at room temperature for 1 month. In one embodiment, the pharmaceutical composition comprises less than 0.1% impurities resulting from oxidation of Compound I after the composition is stored at room temperature for 1 month; wherein the oxidation of Compound I is at one or more hydrocarbons.

In one embodiment, the pharmaceutical composition comprises less than 0.1% of Compound 10 after the composition is stored at room temperature for 1 month.

In one embodiment, the pharmaceutical composition comprises less than 0.2% impurities resulting from oxidation of Compound I after the composition is stored at room temperature for 1 month; wherein the oxidation of Compound I is an N-oxide of Compound I. In one embodiment, the pharmaceutical composition comprises less than 0.2% of Compound 9 after the composition is stored at room temperature for 1 month.

In one embodiment, the pharmaceutical composition comprises less than 0.1% impurities resulting from oxidation of Compound I after the composition is stored at a temperature in the range of about 2° C. to about 30° C. for 1 month; wherein the oxidation of Compound I is at one or more hydrocarbons. In one embodiment, the pharmaceutical composition comprises less than 0.1% of Compound 10 after the composition is stored at a temperature in the range of about 2° C. to about 30° C. for 1 month.

In one embodiment, the pharmaceutical composition comprises less than 0.2% impurities resulting from oxidation of Compound I after the composition is stored at a temperature in the range of about 2° C. to about 30° C. for 1 month; wherein the oxidation of Compound I is an N-oxide of Compound I. In one embodiment, the pharmaceutical composition comprises less than 0.2% of Compound 9 after the composition is stored at a temperature in the range of about 2° C. to about 30° C. for 1 month.

In one embodiment, the pharmaceutical composition comprises less than about 1.0% impurities after the composition is stored at a temperature in the range of about 2° C. to about 8° C. for about 36 months. In one embodiment, the pharmaceutical composition comprises less than 0.3% of Compound 10 after the composition is stored at a temperature in the range of about 2° C. to about 8° C. for about 36 months. In one embodiment, the pharmaceutical composition comprises less than 0.2% of Compound 9 after the composition is stored at a temperature in the range of about 2° C. to about 8° C. for about 36 months.

In one embodiment, the pharmaceutical composition comprises less than about 1.2% impurities after the composition is stored at room temperature for about 36 months. In one embodiment, the pharmaceutical composition comprises less than 0.6% of Compound 10 after the composition is stored at room temperature for about 36 months. In one embodiment, the pharmaceutical composition comprises less than 0.3% of Compound 9 after the composition is stored at room temperature for about 36 months.

In one embodiment, the pharmaceutical composition comprises less than about 1% impurities after the composition is stored at a temperature in the range of about 2° C. to about 30° C. for about 24 months. In one embodiment, the pharmaceutical composition comprises less than about 1% impurities after the composition is stored at a temperature in the range of about 2° C. to about 30° C. for about 12 months. In one embodiment, the pharmaceutical composition comprises less than about 1% impurities after the composition is stored at a temperature in the range of about 2° C. to about 30° C. for about 6 months. In one embodiment, the pharmaceutical composition comprises less than about 1% impurities after the composition is stored at a temperature in the range of about 2° C. to about 30° C. for about 3 months.

In one embodiment, the pharmaceutical composition is substantially free of an N-oxide impurity of Compound I.

In one embodiment of the pharmaceutical composition which is a solid composition comprising a lyophilized Compound I or a pharmaceutically acceptable salt and/or solvate thereof, the solution for lyophilizing composition comprises Compound I at a concentration greater than 15 mg/ml. In one embodiment, the solution for lyophilizing composition comprises Compound I at a concentration greater than 25 mg/ml.

In one embodiment, the pharmaceutical composition is substantially free of an antioxidant. In one embodiment, the pharmaceutical composition is substantially free of ascorbic acid.

In one embodiment of the pharmaceutical composition, the composition upon reconstitution with a pharmaceutically acceptable diluent, provides a pH ranging from about 4 to about 6. In one embodiment of the pharmaceutical composition, the composition upon reconstitution with a pharmaceutically acceptable diluent, provides a pH ranging from about 4 to about 5.5.

In one embodiment, the pharmaceutical composition exhibits a differential scanning calorimetry (DSC) thermogram having exotherm peaks at about −18.23±2.0° C. and about −27.26±2.0° C.

In one embodiment, the pharmaceutical composition has a water content of less than 1%.

In one embodiment, the pharmaceutical composition comprises about 150 mg of Compound I, or a pharmaceutically acceptable salt and/or solvate thereof.

In one embodiment, the pharmaceutical composition comprises less than 0.5% impurities. In one embodiment, the pharmaceutical composition comprises less than 0.3% impurities.

In one embodiment, the pharmaceutical composition less than 0.7% impurities after the composition is stored at room temperature for 6 months. In one embodiment, the pharmaceutical composition less than about 0.5% impurities resulting from oxidation of Compound I after the composition is stored at room temperature for 6 months. In one embodiment, the pharmaceutical composition comprises less than 0.5% impurities after the composition is stored at room temperature for 3 months.

In one embodiment, the pharmaceutical composition comprises less than 0.1% of Compound 10.

In one embodiment, the pharmaceutical composition comprises less than 0.2% impurities resulting from oxidation of Compound I, wherein the oxidation of Compound I is a N-oxide of Compound I. In one embodiment, the pharmaceutical composition comprises less than 0.2% of Compound 9.

In one embodiment, the pharmaceutical composition comprises less than 1.2% impurities after the composition is stored at a temperature in the range of about 2° C. to about 30° C. for 36 months. In one embodiment, the pharmaceutical composition comprises less than 1.0% impurities after the composition is stored at a temperature in the range of about 2° C. to about 30° C. for 24 months. In one embodiment, the pharmaceutical composition comprises less than 1.0% impurities after the composition is stored at a temperature in the range of about 2° C. to about 30° C. for 6 months. In one embodiment, the pharmaceutical composition comprises less than 0.7% impurities after the composition is stored at a temperature in the range of about 2° C. to about 30° C. for 3 months. In one embodiment, the pharmaceutical composition comprises less than about 0.5% impurities resulting from oxidation of Compound I after the composition is stored at a temperature in the range of about 2° C. to about 30° C. for 2 months.

In one embodiment, the pharmaceutical composition comprises less than 0.1% of Compound 10.

In one embodiment, the pharmaceutical composition comprises less than 0.2% impurities resulting from oxidation of Compound I, wherein the oxidation of Compound I is a N-oxide of Compound I. In one embodiment, the pharmaceutical composition comprises less than 0.2% of Compound 9.

In one embodiment of the pharmaceutical composition as disclosed herein, the testing of said impurities is performed using parameters as in Example 5 at room temperature or at 50° C., 14 days after lyophilization, 28 days after lyophilization, 42 days after lyophilization, 96 days after lyophilization, 6 months after lyophilization, 12 months after lyophilization, 24 months after lyophilization, and/or 36 months after lyophilization. In one embodiment of the pharmaceutical composition as disclosed herein, the testing of said impurities is performed using parameters as in Example 5 or Example 10 at about −20° C., at a range of about 2° C. to about 8° C., at about 5° C., room temperature, at about 25° C., at about 30° C., at about 40° C., or at about 50° C., 14 days after lyophilization, 28 days after lyophilization, 1 month after lyophilization, 42 days after lyophilization, 96 days after lyophilization, 6 months after lyophilization, 12 months after lyophilization, 24 months after lyophilization, and/or 36 months after lyophilization. In one embodiment, the pharmaceutical composition comprises less than about 0.5% of Compound 7 after the composition is stored at room temperature for 3 months or less. In another embodiment, the pharmaceutical composition comprises less than about 0.35% of Compound 7 after the composition is stored at room temperature for 3 months or less.

In one embodiment, the pharmaceutical composition comprises a bulking agent. In one embodiment, the bulking agent selected from one or more of the group consisting of sucrose, mannitol, and trehalose. In some embodiments, the bulking agent is sucrose. In other embodiments, the bulking agent is mannitol.

In one embodiment, the pharmaceutical composition is a liquid composition comprising Compound I or a pharmaceutically acceptable salt and/or solvate thereof. In one embodiment, the pharmaceutical composition is an aqueous composition comprising Compound I or a pharmaceutically acceptable salt and/or solvate thereof.

In one embodiment, the liquid or the aqueous pharmaceutical composition comprises less than or equal to 1 ppm of dissolved oxygen. In one embodiment, the liquid or the aqueous pharmaceutical composition comprises less than 1 ppm of dissolved oxygen.

In one embodiment, the liquid or the aqueous pharmaceutical composition comprises a bulking agent. In one embodiment, the bulking agent selected from one or more of the group consisting of sucrose, mannitol, and trehalose. In some embodiments, the bulking agent is sucrose. In other embodiments, the bulking agent is mannitol.

In one embodiment, the liquid or the aqueous pharmaceutical composition has a pH of 4.5±1. In one embodiment, the liquid or the aqueous pharmaceutical composition has a pH of 4.5±0.5. In one embodiment, the liquid or the aqueous pharmaceutical composition has a pH of 4.5±0.1. In one embodiment, the liquid or the aqueous pharmaceutical composition has a pH of 4.0±0.5.

In one embodiment, the liquid or the aqueous pharmaceutical composition comprises less than about 1% impurities after the composition is stored at a temperature in the range of about 2° C. to about 30° C. for at least 28 days. In one embodiment, the liquid or the aqueous pharmaceutical composition comprises less than about 0.7% impurities after the composition is stored at a temperature in the range of about 2° C. to about 30° C. for 28 days. In one embodiment, the liquid or the aqueous pharmaceutical composition comprises less than about 1% impurities after the composition is stored at a temperature in the range of about 2° C. to about 30° C. for at least 2 months. In one embodiment, the liquid or the aqueous pharmaceutical composition comprises less than about 1% impurities after the composition is stored at a temperature in the range of about 2° C. to about 30° C. for 3 months.

In one embodiment, the liquid or the aqueous pharmaceutical composition comprises less than about 0.1% of Compound 10 after the composition is stored at temperature in the range of about 25° C./60% RH for 28 days. In one embodiment, the liquid or the aqueous pharmaceutical composition comprises less than about 0.2% of Compound 10 after the composition is stored at temperature in the range of about 25° C./60% RH for 2 months.

In one embodiment, the liquid or the aqueous pharmaceutical composition at the time of preparation comprises less than 1 ppm of dissolved oxygen.

In one embodiment, the liquid or the aqueous pharmaceutical composition comprises less than about 0.5% of Compound 7 after the composition is stored for 3 months or less. In one embodiment, the liquid or the aqueous pharmaceutical composition comprises less than about 0.5% of Compound 7 after the composition is stored for 3 months or less at a storage temperature of about 5° C., 25° C., 30° C. or 40° C.

In one embodiment, the liquid or the aqueous pharmaceutical composition comprises less than about 0.4% of Compound 7 after the composition is stored for 3 months or less. In one embodiment, the liquid or the aqueous pharmaceutical composition comprises less than about 0.4% of Compound 7 after the composition is stored for 3 months or less at a storage temperature is about 5° C., 25° C., 30° C. or 40° C.

In one embodiment, the liquid or the aqueous pharmaceutical composition comprises less than about 0.5% of Compound 10 after the composition is stored for 3 months or less. In one embodiment, the liquid or the aqueous pharmaceutical composition comprises less than about 0.2% of Compound 10 after the composition is stored for 3 months or less at room temperature. In one embodiment, the liquid or the aqueous pharmaceutical composition comprises less than about 0.25% of Compound 10 after the composition is stored for 3 months or less at about 30° C. In one embodiment, the liquid or the aqueous pharmaceutical composition comprises less than about 0.25% of Compound 10 after the composition is stored for 1 month or less at about 40° C. In one embodiment, the liquid or the aqueous pharmaceutical composition comprises less than about 0.35% of Compound 10 after the composition is stored for 2 months or less at about 40° C.

In one embodiment, the liquid or the aqueous pharmaceutical composition is in a vial.

In one embodiment, the liquid or the aqueous pharmaceutical composition is further diluted in an I.V. solution/fluid bag or I.V. solution line.

In one embodiment, the pharmaceutical composition is a liquid composition which is a reconstituted solution from a solid lyophilized Compound I or a pharmaceutically acceptable salt and/or solvate thereof.

In one embodiment, the liquid reconstituted pharmaceutical composition comprises less than about 1% impurities. In one embodiment, the liquid reconstituted pharmaceutical composition comprises less than about 0.5% impurities. In one embodiment, the liquid reconstituted pharmaceutical composition comprises less than 0.5% impurities after the solid lyophilized composition is stored at room temperature for 42 days. In one embodiment, the liquid reconstituted pharmaceutical composition comprises less than about 0.4% impurities resulting from oxidation of Compound I after the solid lyophilized composition is stored at room temperature for 28 days.

In one embodiment, the liquid reconstituted pharmaceutical composition comprises less than 0.1% impurities resulting from oxidation of Compound I after the solid lyophilized composition is stored at room temperature for 28 days; wherein the oxidation of Compound I is at one or more hydrocarbons. In one embodiment, the liquid reconstituted pharmaceutical composition comprises less than 0.1% of Compound 10 after the solid lyophilized composition is stored at room temperature for 28 days.

In one embodiment, the liquid reconstituted pharmaceutical composition comprises less than 0.2% impurities resulting from oxidation of Compound I after the composition is stored at room temperature for 14 days; wherein the oxidation of Compound I is a N-oxide of Compound I.

In one embodiment, the liquid reconstituted pharmaceutical composition comprises less than 0.2% of the Compound 9 after the solid lyophilized composition is stored at room temperature for 14 days.

In one embodiment, the liquid reconstituted pharmaceutical composition comprises less than about 0.4% impurities resulting from oxidation of Compound I after the solid lyophilized composition is stored at a temperature in the range of about 2° C. to about 30° C. for at least 28 days. In one embodiment, the liquid reconstituted pharmaceutical composition comprises less than about 0.4% impurities resulting from oxidation of Compound I after the solid lyophilized composition is stored at a temperature in the range of about 2° C. to about 30° C. for 28 days.

In one embodiment, the liquid reconstituted pharmaceutical composition comprises less than 0.5% impurities after the solid lyophilized composition is stored at a temperature in the range of about 2° C. to about 30° C. for 42 days.

In one embodiment, the liquid reconstituted pharmaceutical composition comprises less than 0.1% impurities resulting from oxidation of Compound I after the solid lyophilized composition is stored at a temperature in the range of about 2° C. to about 30° C. for 28 days; wherein the oxidation of Compound I is at one or more hydrocarbons. In one embodiment, the liquid reconstituted pharmaceutical composition comprises less than 0.1% of Compound 10 after the solid lyophilized composition is stored at a temperature in the range of about 2° C. to about 30° C. for 28 days.

In one embodiment, the liquid reconstituted pharmaceutical composition comprises less than 0.2% impurities resulting from oxidation of Compound I after the composition is stored at a temperature in the range of about 2° C. to about 30° C. for 14 days; wherein the oxidation of Compound I is a N-oxide of Compound I. In one embodiment, the liquid reconstituted pharmaceutical composition comprises less than 0.2% of the Compound 9 after the solid lyophilized composition is stored at a temperature in the range of about 2° C. to about 30° C. for 14 days.

In one embodiment, the liquid reconstituted pharmaceutical composition comprises less than 0.3% impurities.

In one embodiment, the liquid reconstituted pharmaceutical composition comprises less than 0.1% of Compound 10.

In one embodiment, the liquid reconstituted pharmaceutical composition comprises less than 0.2% impurities resulting from oxidation of Compound I, wherein the oxidation of Compound I is a N-oxide of Compound I. In one embodiment, the liquid reconstituted pharmaceutical composition comprises less than 0.2% of Compound 9.

In one embodiment, the liquid reconstituted pharmaceutical composition comprises Compound I at a concentration of about ≥15 mg/ml. In one embodiment, the liquid reconstituted pharmaceutical composition comprises Compound I at a concentration of about ≥25 mg/ml.

In one embodiment, the liquid reconstituted pharmaceutical composition comprises a bulking agent. In one embodiment, the bulking agent selected from one or more of the group consisting of sucrose, mannitol, and trehalose. In some embodiments, the bulking agent is sucrose. In other embodiments, the bulking agent is mannitol.

In one embodiment, the liquid reconstituted pharmaceutical composition is substantially free of an N-oxide degradant of Compound I. In one embodiment, the liquid reconstituted pharmaceutical composition is substantially free of an antioxidant.

In one embodiment, the liquid reconstituted pharmaceutical composition provides a pH ranging from about 4 to about 6. In one embodiment, the liquid reconstituted pharmaceutical composition provides a pH ranging from about 4 to about 5.5.

In one embodiment, the liquid reconstituted pharmaceutical composition comprises about 150 mg of Compound I, or a pharmaceutically acceptable salt and/or solvate thereof.

In one embodiment, the liquid reconstituted pharmaceutical composition is in a vial.

In one embodiment, the liquid reconstituted pharmaceutical composition is further diluted in an I.V. solution/fluid bag or I.V. solution line.

In another embodiment, the liquid reconstituted pharmaceutical composition has any of the above-described characteristics after the solid lyophilized composition is stored for 1 month at about 2° C. to about 30° C.

In one embodiment, the pharmaceutical composition is a liquid composition comprising Compound I or a pharmaceutically acceptable salt and/or solvate thereof.

In one embodiment, the pharmaceutical composition comprises less than about 1% impurities. In one embodiment, the pharmaceutical composition comprises less than about 0.5% impurities. In one embodiment, the pharmaceutical composition comprises less than 0.5% impurities after the solid lyophilized composition is stored at room temperature for 1 month. In one embodiment, the pharmaceutical composition comprises less than about 0.4% impurities resulting from oxidation of Compound I after the solid lyophilized composition is stored at room temperature for 1 month.

In one embodiment, the pharmaceutical composition comprises less than 0.1% impurities resulting from oxidation of Compound I after the solid lyophilized composition is stored at room temperature for 1 month; wherein the oxidation of Compound I is at one or more hydrocarbons. In one embodiment, the pharmaceutical composition comprises less than 0.1% of Compound 10 after the solid lyophilized composition is stored at room temperature for 1 month.

In one embodiment, the pharmaceutical composition comprises less than 0.2% impurities resulting from oxidation of Compound I after the composition is stored at room temperature for 1 month; wherein the oxidation of Compound I is a N-oxide of Compound I.

In one embodiment, the pharmaceutical composition comprises less than 0.2% of the Compound 9 after the solid lyophilized composition is stored at room temperature for 1 month.

In one embodiment, the pharmaceutical composition comprises less than about 0.4% impurities resulting from oxidation of Compound I after the solid lyophilized composition is stored at a temperature in the range of about 2° C. to about 30° C. for 1 month. In one embodiment, the pharmaceutical composition comprises less than about 0.4% impurities resulting from oxidation of Compound I after the solid lyophilized composition is stored at a temperature in the range of about 2° C. to about 30° C. for 1 month.

In one embodiment, the pharmaceutical composition comprises less than 0.5% impurities after the solid lyophilized composition is stored at a temperature in the range of about 2° C. to about 30° C. for 1 month.

In one embodiment, the pharmaceutical composition comprises less than 0.1% impurities resulting from oxidation of Compound I after the solid lyophilized composition is stored at a temperature in the range of about 2° C. to about 30° C. for 1 month; wherein the oxidation of Compound I is at one or more hydrocarbons. In one embodiment, the pharmaceutical composition comprises less than 0.1% of Compound 10 after the solid lyophilized composition is stored at a temperature in the range of about 2° C. to about 30° C. for 1 month.

In one embodiment, the pharmaceutical composition comprises less than 0.2% impurities resulting from oxidation of Compound I after the composition is stored at a temperature in the range of about 2° C. to about 30° C. for 1 month; wherein the oxidation of Compound I is a N-oxide of Compound I. In one embodiment, the pharmaceutical composition comprises less than 0.2% of the Compound 9 after the solid lyophilized composition is stored at a temperature in the range of about 2° C. to about 30° C. for 1 month.

In one embodiment, the pharmaceutical composition comprises less than 0.3% impurities.

In one embodiment, the pharmaceutical composition comprises less than 0.1% of Compound 10.

In one embodiment, the pharmaceutical composition comprises less than 0.2% impurities resulting from oxidation of Compound I, wherein the oxidation of Compound I is a N-oxide of Compound I. In one embodiment, the pharmaceutical composition comprises less than 0.2% of Compound 9.

In one embodiment, the pharmaceutical composition comprises Compound I at a concentration of about ≥15 mg/ml. In one embodiment, the pharmaceutical composition comprises Compound I at a concentration of about ≥25 mg/ml.

In one embodiment, pharmaceutical composition comprises a bulking agent. In one embodiment, the bulking agent selected from one or more of the group consisting of sucrose, mannitol, and trehalose. In some embodiments, the bulking agent is sucrose. In other embodiments, the bulking agent is mannitol.

In one embodiment, the pharmaceutical composition is substantially free of an N-oxide degradant of Compound I. In one embodiment, the pharmaceutical composition is substantially free of an antioxidant.

In one embodiment, the pharmaceutical composition provides a pH ranging from about 4 to about 6. In one embodiment, the pharmaceutical composition provides a pH ranging from about 4 to about 5.5.

In one embodiment, the pharmaceutical composition comprises about 150 mg of Compound I, or a pharmaceutically acceptable salt and/or solvate thereof.

In one embodiment, the pharmaceutical composition is in a vial.

In one embodiment, the pharmaceutical composition is further diluted in an I.V. solution/fluid bag or I.V. solution line.

In one embodiment, the present disclosure provides a pharmaceutical composition comprising Compound I or a pharmaceutically acceptable salt and/or solvate thereof; wherein the composition further comprises one or more compound selected from the group consisting of Compound 1, Compound 7, Compound 8, Compound 9 and Compound 10.

In one embodiment, the present disclosure provides a pharmaceutical composition comprising Compound I or a pharmaceutically acceptable salt and/or solvate thereof; wherein the composition further comprises Compound 1.

In one embodiment, the present disclosure provides a pharmaceutical composition comprising Compound I or a pharmaceutically acceptable salt and/or solvate thereof; wherein the composition further comprises Compound 7.

In one embodiment, the present disclosure provides a pharmaceutical composition comprising Compound I or a pharmaceutically acceptable salt and/or solvate thereof; wherein the composition further comprises Compound 8.

In one embodiment, the present disclosure provides a pharmaceutical composition comprising Compound I or a pharmaceutically acceptable salt and/or solvate thereof; wherein the composition further comprises Compound 9.

In one embodiment, the present disclosure provides a pharmaceutical composition comprising Compound I or a pharmaceutically acceptable salt and/or solvate thereof; wherein the composition further comprises Compound 10.

In one embodiment, the pharmaceutical composition comprises Compound I or a pharmaceutically acceptable salt and/or solvate thereof, and Compound 9 and Compound 10. In one embodiment, the pharmaceutical composition comprises Compound I or a pharmaceutically acceptable salt and/or solvate thereof, Compound 1, Compound 7, Compound 8, Compound 9 and Compound 10. In one embodiment, the pharmaceutical composition further comprises one or more compounds selected from the group consisting of Compound 2, Compound 3, Compound 4, Compound 5, Compound 6, Compound 11, and Compound 12. In one embodiment, the pharmaceutical composition comprises Compound I or a pharmaceutically acceptable salt and/or solvate thereof, and Compound 1-12.

In one embodiment, the present disclosure relates to Compounds 1-6 and 8-12, or a pharmaceutically acceptable salt thereof. In one embodiment, Compounds 1-6 and 8-12, or a pharmaceutically acceptable salt thereof are isolated. In another embodiment, Compounds 1-6 and 8-12, or a pharmaceutically acceptable salt thereof are purified. In some embodiment, the compound is In other embodiment, the present disclosure relates to at least one of Compounds 1-6 and 8-12, or a pharmaceutically acceptable salt thereof which is substantially pure. In some embodiments, the at least one of Compounds 1-6 and 8-12, or a pharmaceutically acceptable salt thereof is at least about 95% pure. In another embodiment, Compound 7 or a pharmaceutically acceptable salt thereof is at least 95% pure.

In one embodiment, the present disclosure relates to a pharmaceutical composition comprising a pharmaceutically acceptable excipient and at least one of Compounds 1-6 and 8-12, or a pharmaceutically acceptable salt thereof. In another embodiment, the present disclosure relates to a pharmaceutical composition comprising a pharmaceutically acceptable excipient and at least one of Compounds 1 and 8-10, or a pharmaceutically acceptable salt thereof.

In one embodiment, the Compounds 1-6 and 8-12, or a pharmaceutically acceptable salt thereof in any one of the pharmaceutical composition as disclosed herein is substantially pure. In some embodiments, the Compounds 1-6 and 8-12, or a pharmaceutically acceptable salt thereof in any one of the pharmaceutical composition as disclosed herein is at least about 95% pure. In other embodiments, the Compounds 1-6 and 8-12, or a pharmaceutically acceptable salt thereof in any one of the pharmaceutical composition as disclosed herein is at least about 97% pure. In some embodiments, the Compounds 1-6 and 8-12, or a pharmaceutically acceptable salt thereof in any one of the pharmaceutical composition as disclosed herein is at least 95% pure. In other embodiments, the Compounds 1-6 and 8-12, or a pharmaceutically acceptable salt thereof in any one of the pharmaceutical composition as disclosed herein is at least 97% pure.

In one embodiment, the present disclosure relates to a pharmaceutical composition comprising a pharmaceutically acceptable excipient and substantially pure Compound 7, or a pharmaceutically acceptable salt thereof. In another embodiment, Compound 7, or a pharmaceutically acceptable salt thereof in any one of the pharmaceutical composition as disclosed herein is about 95% pure. In one embodiment, Compound 7, or a pharmaceutically acceptable salt thereof in any one of the pharmaceutical composition as disclosed herein is 95% pure.

In one embodiment of the present disclosure, the Compounds 1-12, or a pharmaceutically acceptable salt thereof, in any one of the pharmaceutical composition as disclosed herein, demonstrates sensitivity to a BRCA2 null cell line relative to the parental cell line wherein BRCA2 is wild type. In one embodiment, the sensitivity is at least two fold higher. In other embodiments, the sensitivity is at least twenty fold higher. In some embodiments, the sensitivity is at least 200 fold higher.

In one embodiment, the pharmaceutical composition as disclosed herein further comprises at least one pharmaceutically active agent. In one embodiment, the at least one pharmaceutically active agent is a PARP inhibitor or a CDK inhibitor.

In one embodiment, the pharmaceutical composition as disclosed herein further comprises at least one PARP inhibitor selected from 4-(3-(1-(cyclopropanecarbonyl)piperazine-4-carbonyl)-4-fluorobenzyl)phthalazin-1(2H)-one (olaparib, AZD2281, Ku-0059436), 2-[(2R)-2-methylpyrrolidin-2-yl]-1H-benzimidazole-4-carboxamide (veliparib, ABT-888), (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one (talazoparib, BMN 673), 4-iodo-3-nitrobenzamide (iniparib, BSI-201), 8-fluoro-5-(4-((methylamino)methyl)phenyl)-3,4-dihydro-2H-azepino[5,4,3-cd]indol-1(6H)-one phosphoric acid (rucaparib, AG-014699, PF-01367338), 2-[4-[(dimethylamino)methyl]phenyl]-5,6-dihydroimidazo[4,5,1-jk][1,4]benzodiazepin-7(4H)-one (AG14361), 3-aminobenzamide (INO-1001), 2-(2-fluoro-4-((S)-pyrrolidin-2-yl)phenyl)-3H-benzo[d]imidazole-4-carboxamide (A-966492), N-(5,6-dihydro-6-oxo-2-phenanthridinyl)-2-acetamide hydrochloride (PJ34, PJ34 HCl), MK-4827, 3,4-dihydro-4-oxo-3,4-dihydro-4-oxo-N-[(1S)-1-phenylethyl]-2-quinazolinepropanamide (ME0328), 5-(2-oxo-2-phenylethoxy)-1(2H)-isoquinolinone (UPF-1069), or 4-[[4-fluoro-3-[(4-methoxy-1-piperidinyl)carbonyl]phenyl]methyl]-1(2H)-phthalazinone (AZD 2461).

In one embodiment, the pharmaceutical composition as disclosed herein further comprises at least one CDK inhibitor selected from AZD-5438, BMI-1040, BMS-032, BMS-387, CVT-2584, flavopyridol, GPC-286199, MCS-5A, PD0332991, PHA-690509, seliciclib (CYC202, R-roscovitine), ZK-304709 AT7519M, P276-00, SCH 727965, AG-024322, LEE011, LY2835219, P1446A-05, BAY 1000394, SNS-032, or 5-((3-chlorophenyl)amino)benzo[c][2,6]naphthyridine-8-carboxylic acid.

In one embodiment, the present invention provides a method for treating or ameliorating cell proliferation disorder in a subject, wherein the method comprises administering to a subject in need thereof a therapeutically effective amount of any one of the pharmaceutical composition comprising a Compound I, or a pharmaceutically acceptable salt and/or solvate thereof as described herein. In one embodiment of the method as described herein, the pharmaceutical composition is injected directly into the subject. In other embodiments, the pharmaceutical composition is diluted in an I.V. solution/fluid bag or I.V. line that is then administration to the subject.

In one embodiment, the cell proliferation disorder is cancer in methods as described herein. In another embodiment, cancer is selected from the group consisting of heme cancer, colorectum cancer, breast cancer, lung cancer, liver cancer, ovarian cancer, cervical cancer, Ewing's sarcoma, pancreatic cancer, cancer of the lymph nodes, colon cancer, prostate cancer, brain cancer, cancer of the head and neck, skin cancer, kidney cancer, osteosarcoma, cancer of the heart, uterine cancer, gastrointestinal malignancies, and carcinomas of the larynx and oral cavity. In some embodiments, the cancer is selected from the group consisting of breast cancer, ovarian cancer, pancreatic cancer, prostate cancer, lung cancer, Ewing's sarcoma, head and neck cancer, and cervical cancer. In one embodiment, the heme cancer is selected from the group consisting of: leukemia, lymphoma, myeloma, and multiple myeloma.

In one embodiment, cancer treated or ameliorated by the method as described herein, is homologous recombination (HR) dependent double strand break (DSB) repair deficient cancer or non-homologous end joining (NHEJ) DSB repair deficient cancer. In one embodiment, the present disclosure relates to a method for treating or ameliorating cancer in a subject, comprising administering to a subject in need thereof a therapeutically effective amount of the pharmaceutical composition comprising a Compound I, or a pharmaceutically acceptable salt and/or solvate thereof as described herein, wherein the cancer is a BRCA mutant or BRCA-like mutant cancer. In some embodiments, the BRCA mutant cancer is a BRCA2-mutated cancer. In other embodiments, the BRCA mutant or BRCA-like mutant cancer is breast cancer, ovarian cancer, pancreatic cancer, or prostate cancer. In one embodiment, the BRCA mutant or BRCA-like mutant cancer is breast cancer or prostate cancer.

In one embodiment, the present disclosure relates to a method for treating or ameliorating cancer in a subject, comprising administering to a subject in need thereof a therapeutically effective amount of the pharmaceutical composition comprising a Compound I, or a pharmaceutically acceptable salt and/or solvate thereof as described herein, wherein the cancer is BRCA2 deficient or BRCA1 deficient cancer. In some embodiments, the cancer is BRCA2 deficient cancer.

In one embodiment, the present disclosure relates to a method for treating or ameliorating cell proliferation disorder in a human subject, comprising administering to a subject in need thereof a therapeutically effective amount of the pharmaceutical composition comprising a Compound I, or a pharmaceutically acceptable salt and/or solvate thereof as described herein. In some embodiments, the human subject carries a BRCA mutation. In other embodiments, the human subject carries t a BRCA2 mutation.

In one embodiment, the methods provided herein further comprise administering one or more additional therapeutic agents. In some embodiments, the one or more additional therapeutic agent is an anticancer agent or immunotherapeutic agent. In one embodiment, the one or more therapeutically active agent is an immunotherapeutic agent. In some embodiments, one or more immunotherapeutic agents includes, but is not limited to, a monoclonal antibody, an immune effector cell, adoptive cell transfer, an immunotoxin, a vaccine, or a cytokine.

In another embodiment, the methods provided herein further comprise administering radiotherapy to the patient before, during, or after the administration of a pharmaceutical composition comprising a Compound I, or a pharmaceutically acceptable salt and/or solvate thereof as described herein.

In one embodiment of any one of the methods disclosed herein, the therapeutically effective amount of any one of the pharmaceutical composition comprising Compound I, or a pharmaceutically acceptable salt and/or solvate thereof as described herein, is administered intravenously. In one embodiment, the pharmaceutical composition comprises about 25 mg to about 850 mg of the Compound I or a pharmaceutically acceptable salt and/or solvate thereof, per body surface area of the subject ($m^2$). In one embodiment, the pharmaceutical composition comprises about 150 mg to about 750 mg of the Compound I or a pharmaceutically acceptable salt and/or solvate thereof, per body surface area of the subject ($m^2$). In one embodiment, the pharmaceutical composition comprises about 375 mg to about 750 mg of the Compound I or a pharmaceutically acceptable salt and/or solvate thereof, per body surface area of the subject ($m^2$). In one embodiment, the pharmaceutical composition comprises about 550 mg to about 750 mg of the Compound I or a pharmaceutically acceptable salt and/or solvate thereof, per body surface area of the subject ($m^2$). In one embodiment, the pharmaceutical composition comprises about 25 mg to about 250 mg of the Compound I or a pharmaceutically acceptable salt and/or solvate thereof, per body surface area of the subject ($m^2$). In another embodiment, the pharmaceutical composition comprises about 50 mg to about 170 mg of the Compound I or a pharmaceutically acceptable salt and/or solvate thereof, per body surface area of the subject ($m^2$). In another embodiment, the pharmaceutical composition comprises about 150 mg of the Compound I or a pharmaceutically acceptable salt and/or solvate thereof.

In one embodiment of the method of treating cancer as disclosed herein, the method further comprises co-administering one or more additional therapeutic agents and/or radio therapy. In one embodiment, the one or more additional therapeutic agent is an anticancer agent or immunotherapeutic agent.

In one embodiment, the present invention provides a method of inhibiting Pol I transcription in a subject, wherein the method comprises administering to the subject a therapeutically effective amount of any one of the pharmaceutical composition comprising a Compound I, or a pharmaceutically acceptable salt and/or solvate thereof as described herein. In one embodiment, the inhibiting Pol I transcription is in peripheral blood mononuclear cells. In other embodiments, an average level of about 15% or greater inhibition is observable 1 hour after administering therapeutically effective amount of the pharmaceutical composition. In one embodiment, the therapeutically effective amount of the pharmaceutical composition comprising a Compound I, or a pharmaceutically acceptable salt and/or solvate thereof as described herein, is administered intravenously. In one embodiment of the method as described herein, the pharmaceutical composition is injected directly into the subject. In other embodiments, the pharmaceutical composition is diluted in an I.V. solution/fluid bag or I.V. line that is then administration to the subject.

In one embodiment, the present disclosure relates to a method for treating or ameliorating cell proliferation disorder in a subject, comprising administering to a subject in need thereof a therapeutically effective amount of any one of the pharmaceutical composition disclosed herein comprising at least one of Compounds 1-12, or a pharmaceutically acceptable salt thereof. In one embodiment, the cell proliferation disorder is cancer.

In one embodiment, the present disclosure relates to a method for treating or ameliorating cancer in a subject, comprising administering to a subject in need thereof a therapeutically effective amount of any one of the pharmaceutical composition disclosed herein comprising at least one of Compounds 1-12, or a pharmaceutically acceptable salt thereof, wherein the cancer is selected from the group consisting of heme cancer, colorectal cancer, ovarian cancer, breast cancer, cervical cancer, lung cancer, liver cancer, pancreatic cancer, cancer of the lymph nodes, colon cancer, prostate cancer, brain cancer, cancer of the head and neck, bone cancer, Ewing's sarcoma, skin cancer, kidney cancer, osteosarcoma, and cancer of the heart. In some embodiments, the cancer is selected from the group consisting of wherein the cancer is selected from the group consisting of breast cancer, ovarian cancer, pancreatic cancer, prostate cancer, lung cancer, Ewing's sarcoma, head and neck cancer, and cervical cancer. In one embodiment, the heme cancer is selected from the group consisting of leukemia, lymphoma, myeloma, and multiple myeloma.

In one embodiment, the present disclosure relates to a method for treating or ameliorating cancer in a subject, comprising administering to a subject in need thereof a therapeutically effective amount of any one of the pharmaceutical composition disclosed herein comprising at least one of Compounds 1-12, or a pharmaceutically acceptable salt thereof, wherein the cancer is a BRCA mutant cancer. In some embodiment, the BRCA mutant cancer is a BRCA2-mutated cancer. In other embodiments, the BRCA mutant cancer is breast cancer, ovarian cancer, pancreatic cancer, or prostate cancer. In one embodiment, the BRCA mutant cancer is breast cancer or prostate cancer.

In one embodiment, the present disclosure relates to a method for treating or ameliorating cancer in a subject, comprising administering to a subject in need thereof a therapeutically effective amount of any one of the pharmaceutical composition disclosed herein comprising at least one of Compounds 1-12, or a pharmaceutically acceptable salt thereof, wherein the cancer is BRCA2 deficient or BRCA1 deficient cancer. In some embodiments, the cancer is BRCA2 deficient cancer.

In one embodiment, the present disclosure relates to a method for treating or ameliorating cell proliferation disorder in a human subject, comprising administering to a subject in need thereof a therapeutically effective amount of any one of the pharmaceutical composition disclosed herein comprising at least one of Compounds 1-12, or a pharmaceutically acceptable salt thereof. In some embodiment, the human subject carries a BRCA mutation. In other embodiments, the human subject carries t a BRCA2 mutation.

DETAILED DESCRIPTIONS OF THE DISCLOSURE

Figure 1:
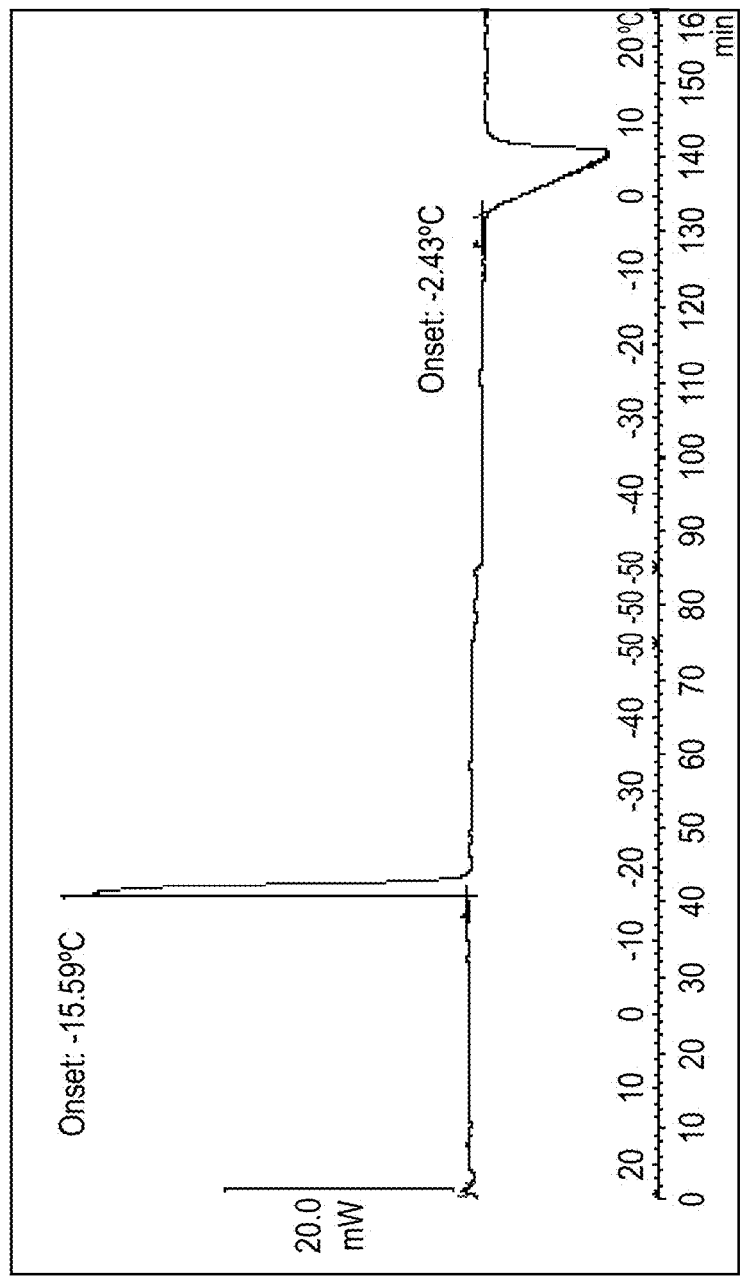
FIG. 1 is a differential scanning calorimetry (DSC) thermogram of Run 1 as described in Example 4.

The present invention relates to a solid lyophilized form of tetracyclic quinolone compounds, which stabilize G-quadruplexes (G4s) and/or inhibit Pol I, as well as a solid lyophilized form of the salts and/or solvates of the tetracyclic quinolone compounds. These solid materials can be formulated into pharmaceutical compositions and used for treating disorders characterized by proliferation of cells.

Definitions

It is to be understood that the terminology used herein is for the purpose of describing particular embodiments only and is not intended to be limiting.

Unless defined otherwise, all technical and scientific terms used herein have the same meaning as commonly understood to one of ordinary skill in the art to which the present application belongs. Although any methods and materials similar or equivalent to those described herein can be used in the practice or testing of the present application, representative methods and materials are herein described.

Following long-standing patent law convention, the terms "a", "an", and "the" refer to "one or more" when used in this application, including the claims. Thus, for example, reference to "a carrier" includes mixtures of one or more carriers, two or more carriers, and the like.

The term "compound(s) of the present invention" or "present compound(s)" refers "refers to 2-(4-Methyl-[1,4] diazepan-1-yl)-5-oxo-5H-7-thia-1,11b-diaza-benzo[c]fluorene-6-carboxylic acid (5-methyl-pyrazin-2-ylmethyl)-amide (Compound I) or isomers, salts, N-oxides, sulfoxides, sulfones, or solvates thereof, or Compounds 1-12, or a pharmaceutically acceptable salt or ester thereof.

The solid lyophilized forms of Compound I described throughout the application includes a solid lyophilized form of any single isomer of Compound I, or a mixture of any number of isomers of Compound I.

Compound I

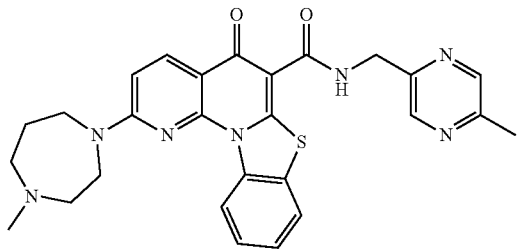

Compounds 1-12, or a pharmaceutically acceptable salt or ester thereof are related to Compound I as described herein.

The term "degradant" of a compound as used herein, means a chemical change of the compound over time. Common degradants of a compound are often the product of, but are not limited to, hydrolysis, oxidation, decarboxylation and isomerization of the compound.

The term "oxidation product" or "oxidation byproduct," as used herein, refers to oxygenated derivatives (addition of an oxygen to the structure) of said product, including but are not limited to alcohol, aldehyde, ketone, N-oxide, sulfoxide, and sulfone derivatives. In one embodiment, oxidation can take place on a hydrocarbon to form a new alcohol, aldehyde, or ketone moiety. In another embodiment, oxidation can take place a nitrogen to form an N-oxide moiety. In some embodiments, oxidation can take place on a sulfur to form a sulfoxide or a sulfone moiety. In one embodiment, oxidation products may be identified by mass spectrometry where addition of 16 atomic mass units (e.g., N-oxide and hydroxyl like oxidation) or addition of 14 atomic mass units (e.g., oxidation of a methylene to a keto group) are observed.

The term "impurity" of a compound, as used herein, means chemicals other than the compound, including, derivatives of the compound, or degradants of the compound that remain with the compound due to incomplete purification, or that develop over time, such as during stability testing, formulation development of the compound or storage of the compound.

The term "co-administration" or "coadministration" refers to administration of a formulation or a composition reconstituted from (a) a solid lyophilized form of Compound I, or a solid lyophilized form of pharmaceutically acceptable salt, solvate and/or prodrug of Compound I; and (b) one or more additional therapeutic agent and/or radio therapy, in combination, i.e., together in a coordinated fashion.

The term "isomer" refers to compounds having the same chemical formula but may have different stereochemical formula, structural formula, or special arrangements of atoms. Examples of isomers include stereoisomers, diastereomers, enantiomers, conformational isomers, rotamers, geometric isomers, and atropisomers.

"N-oxide", also known as amine oxide or amine-N-oxide, means a compound that derives from a compound of the present invention via oxidation of an amine group of the compound of the present invention. An N-oxide typically contains the functional group $R_3N^+$—$O^-$ (sometimes written as $R_3N{=}O$ or $R_3N{\rightarrow}O$).

The term "ester" refers to any ester of a compound of the present invention in which any of the —COOH functions of the molecule is replaced by a —COOR function, in which the R moiety of the ester is any carbon-containing group which forms a stable ester moiety, including but not limited to alkyl, alkenyl, alkynyl, cycloalkyl, cycloalkylalkyl, aryl, arylalkyl, heterocyclyl, heterocyclylalkyl and substituted derivatives thereof. The term "ester" includes but is not limited to pharmaceutically acceptable esters thereof. Pharmaceutically acceptable esters include, but are not limited to, alkyl, alkenyl, alkynyl, aryl, heteroaryl, aralkyl, heteroaralkyl, cycloalkyl and heterocyclyl esters of acidic groups, including, but not limited to, carboxylic acids, phosphoric acids, phosphinic acids, sulfonic acids, sulfinic acids and boronic acids.

"Sulfoxide" refers to a compound that derived from a compound of the present invention via oxidation of a sulfur (S) atom. Sulfoxides are commonly written as —S(=O)—, —S(O)—, or —(S→O)—. "Sulfone" refers to a compound that derived from a compound of the present invention via further oxidation of a sulfur atom. Sulfones are commonly written as —S(=O)$_2$—, —S(O)$_2$—, or —(S(→O)$_2$)—.

"Ketone impurity" refers to a byproduct of a compound where a methylene group (—CH$_2$—) is oxidized to a keto group (—C(=O)—).

The term "room temperature" as used herein, means from 21 degrees Celsius to 27 degrees Celsius.

The term "composition" denotes one or more substance in a physical form, such as solid, liquid, gas, or a mixture thereof. One example of composition is a pharmaceutical composition, i.e., a composition related to, prepared for, or used in medical treatment. The term "formulation" is also used to indicate one or more substance in a physical form, such as solid, liquid, gas, or a mixture thereof.

The term "carboxylic acid" refers to an organic acid characterized by one or more carboxyl groups, such as acetic acid and oxalic acid. "Sulfonic acid" refers to an organic acid with the general formula of R—(S(O)$_2$—OH)$_n$, wherein R is an organic moiety and n is an integer above zero, such as 1, 2, and 3. The term "polyhydroxy acid" refers to a carboxylic acid containing two or more hydroxyl groups. Examples of polyhydroxy acid include, but are not limited to, lactobionic acid, gluconic acid, and galactose.

As used herein, "pharmaceutically acceptable" means suitable for use in contact with the tissues of humans and animals without undue toxicity, irritation, allergic response, and the like, commensurate with a reasonable benefit/risk ratio, and effective for their intended use within the scope of sound medical judgment.

"Salts" include derivatives of an active agent, wherein the active agent is modified by making acid or base addition salts thereof. Preferably, the salts are pharmaceutically acceptable salts. Such salts include, but are not limited to, pharmaceutically acceptable acid addition salts, pharmaceutically acceptable base addition salts, pharmaceutically acceptable metal salts, ammonium and alkylated ammonium salts. Acid addition salts include salts of inorganic acids as well as organic acids. Representative examples of suitable inorganic acids include hydrochloric, hydrobromic, hydroiodic, phosphoric, sulfuric, nitric acids and the like. Representative examples of suitable organic acids include formic, acetic, trichloroacetic, trifluoroacetic, propionic, benzoic, cinnamic, citric, fumaric, glycolic, lactic, maleic, malic, malonic, mandelic, oxalic, picric, pyruvic, salicylic, succinic, methanesulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, sulphates, nitrates, phosphates, perchlorates, borates, acetates, benzoates, hydroxynaphthoates, glycerophosphates, ketoglutarates and the like. Base addition salts include but are not limited to, ethylenediamine, N-methylglucamine, lysine, arginine, ornithine, choline, N,N'-dibenzylethylenediamine, chloroprocaine, diethanolamine, procaine, N-benzylphenethylamine, diethylamine, piperazine, tris-(hydroxymethyl)-aminomethane, tetramethylammonium hydroxide, triethylamine, dibenzylamine, ephenamine, dehydroabietylamine, N-ethylpiperidine, benzylamine, tetramethylammonium, tetraethylammonium, methylamine, dimethylamine, trimethylamine, ethylamine, basic amino acids, e. g., lysine and arginine dicyclohexylamine and the like. Examples of metal salts include lithium, sodium, potassium, magnesium salts and the like. Examples of ammonium and alkylated ammonium salts include ammonium, methylammonium, dimethylammonium, trimethylammonium, ethylammonium, hydroxyethylammonium, diethylammonium, butylammonium, tetramethylammonium salts and the like. Examples of organic bases include lysine, arginine, guanidine, diethanolamine, choline and the like. Standard methods for the preparation of pharmaceutically acceptable salts and their formulations are well known in the art, and are disclosed in various references, including for example, "Remington: The Science and Practice of Pharmacy", A. Gennaro, ed., 20th edition, Lippincott, Williams & Wilkins, Philadelphia, Pa.

As used herein, "solvate" means a complex formed by solvation (the combination of solvent molecules with molecules or ions of the compounds of the present invention), or an aggregate that consists of a solute ion or molecule (the compounds of the present invention) with one or more solvent molecules. In the present invention, the preferred solvate is hydrate. Examples of hydrate include, but are not limited to, hemihydrate, monohydrate, dihydrate, trihydrate, hexahydrate, etc. It should be understood by one of ordinary skill in the art that the pharmaceutically acceptable salt of the present compound may also exist in a solvate form. The solvate is typically formed via hydration which is either part of the preparation of the present compound or through natural absorption of moisture by the anhydrous compound of the present invention. Solvates including hydrates may be consisting in stoichiometric ratios, for example, with two, three, four salt molecules per solvate or per hydrate molecule. Another possibility, for example, that two salt molecules are stoichiometric related to three, five, seven solvent or hydrate molecules. Solvents used for crystallization, such as alcohols, especially methanol and ethanol; aldehydes; ketones, especially acetone; esters, e.g. ethyl acetate; may be embedded in the crystal grating. Preferred are pharmaceutically acceptable solvents.

The term "substantially similar" as used herein with regards to bioavailability of pharmacokinetics means that the two or more therapeutically active agents or drugs provide the same therapeutic effects in a subject.

The term "substantially free of" as used herein, means free from therapeutically effective amounts of compounds when administered in suggested doses, but may include trace amounts of compounds in non-therapeutically effective amounts.

The terms "excipient", "carrier", and "vehicle" are used interchangeably throughout this application and denote a substance with which a compound of the present invention is administered.

"Therapeutically effective amount" means the amount of a solid lyophilized form that is further formulated or reconstituted in a composition, when administered to a patient for treating a disease or other undesirable medical condition, is sufficient to have a beneficial effect with respect to that disease or condition. The therapeutically effective amount will vary depending on the solid lyophilized form, the disease or condition and its severity, and the age, weight, etc. of the patient to be treated. Determining the therapeutically effective amount of a given solid lyophilized form is within the ordinary skill of the art and requires no more than routine experimentation.

As used herein, the terms "additional pharmaceutical agent" or "additional therapeutic agent" or "additional therapeutically active agent" with respect to the compounds described herein refers to an active agent other than the Compound I or Compounds 1-12, or a pharmaceutically acceptable salt or ester thereof, which is administered to elicit a therapeutic effect. The pharmaceutical agent(s) may be directed to a therapeutic effect related to the condition that the compounds of the present disclosure is intended to treat or ameliorate (e.g., cancer) or, the pharmaceutical agent may be intended to treat or ameliorate a symptom of the underlying condition (e.g., tumor growth, hemorrhage, ulceration, pain, enlarged lymph nodes, cough, jaundice, swelling, weight loss, cachexia, sweating, anemia, paraneoplastic phenomena, thrombosis, etc.) or to further reduce the appearance or severity of side effects of the compounds of the present disclosure.

As used herein, the phrase "a disorder characterized by cell proliferation" or "a condition characterized by cell proliferation" include, but are not limited to, cancer, benign and malignant tumors. Examples of cancer and tumors include, but are not limited to, cancers or tumor growth of the colorectum, breast (including inflammatory breast cancer), lung, liver, pancreas, lymph node, colon, prostate, brain, head and neck, skin, kidney, osteosarcoma, blood and heart (e.g., leukemia, lymphoma, and carcinoma).

The term "treating" means one or more of relieving, alleviating, delaying, reducing, improving, or managing at least one symptom of a condition in a subject. The term "treating" may also mean one or more of arresting, delaying the onset (i.e., the period prior to clinical manifestation of the condition) or reducing the risk of developing or worsening a condition.

The term "patient" or "subject" as used herein, includes humans and animals, preferably mammals.

As used herein, the terms "inhibiting" or "reducing" cell proliferation is meant to slow down, to decrease, or, for example, to stop the amount of cell proliferation, as measured using methods known to those of ordinary skill in the art, by, for example, 10%, 20%, 30%, 40%, 50%, 60%, 70%, 80%, 90%, 95%, or 100%, when compared to proliferating cells that are not subjected to the methods and compositions of the present application.

As used herein, the term "apoptosis" refers to an intrinsic cell self-destruction or suicide program. In response to a triggering stimulus, cells undergo a cascade of events including cell shrinkage, blebbing of cell membranes and chromatic condensation and fragmentation. These events culminate in cell conversion to clusters of membrane-bound particles (apoptotic bodies), which are thereafter engulfed by macrophages.

Unless otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the present specification and attached claims are approximations that can vary depending upon the desired properties sought to be obtained by the present application.
Compound I Compound I is a synthetically derived small molecule, which can selectively binds and stabilizes DNA G-quadruplex (G4) structures. Key attributes of Compound I include induction of DNA damage through G4 stabilization which is dependent on intact BRCA1/2 and other homologous recombination mediated pathways for resolution. Cumulative mutations affecting BRCA1/2 and homologous recombination (HR) deficient tumor cells result in synthetic lethality.

Compound I showed specific toxicity against BRCA1/2 deficient cells in a number of cell lines of different genetic backgrounds (colon, breast and ovary) and different specifies origin (mouse and human). Compound I exhibited a wide therapeutic index of activity in BRCA2 knockout tumor cells in a xenograft model, when compared with isogenic wild type control cells. Without bound to any theory, the data to date attribute the anti-tumor activity of Compound I to bind and stabilize G4 DNA structure and impede the progression of DNA replication complexes and induces single stranded DNA gaps or breaks. The BRCA pathway is required for the repair of Compound I induced DNA damage, and that compromised DNA damage repair in the absence of BRCA genes will lead to lethality. BRCA deficient cells can be killed by Compound I at low drug concentration which are not effective at inhibiting rDNA transcription which suggests, without bound to any theory, that the dose used to treat BRCA deficient cancers is lower than that required to inhibit RNA Polymerase I and disrupt nucleons function.

Compound I exhibited antiproliferation activity against a variety of cancer cell lines. See Example 11.
Lyophilized Solid Form of Compound I and Compositions Thereof In one embodiment, the present invention provides a solid lyophilized form of Compound I (free base). In another embodiment, the present invention provides a solid lyophilized form of a pharmaceutically acceptable salt and/or solvate of Compound I.

In one embodiment, the present invention provides a solid lyophilized form of Compound I, or a pharmaceutically acceptable salt and/or solvate thereof, wherein the composition, upon reconstitution with diluent, has a pH from about 4 to about 6. In some embodiments, the reconstituted solution of a solid lyophilized form of compound I, or a pharmaceutically acceptable salt and/or solvate thereof has a pH from about 4 to about 5.5. In some embodiments, the diluent utilized for reconstitution is 5% dextrose in water or 5% glucose in water.

A non-lyophilized Compound I formulated as ready-to-use solution (25 mg/mL in 50 mM monobasic sodium phosphate, pH 6.0) has shown to have limited stability and as a result, required frequent (e.g., every 6 months) and repeated manufacturing to maintain supplies. See Example 1. The ready-to-use solution stored at 25° C./60% RH for 3 months and 6 months showed more than 1% impurities by HPLC. Further, the ready-to-use solution stored at 40° C./75% RH for 3 months showed more than 2% impurities by HPLC and more than 3% impurities when stored at 40° C./75% RH for 6 months (Tables 1 and 2).

In one embodiment, the present invention provides a solid lyophilized form of Compound I, or a pharmaceutically acceptable salt and/or solvate thereof, wherein the solid lyophilized form has a superior shelf life when compared to a conventional ready-to-use formulation comprising Compound I, or a pharmaceutically acceptable salt and/or solvate thereof. In another embodiment, the present invention provides a solid lyophilized form of Compound I, or a pharmaceutically acceptable salt and/or solvate thereof, wherein the solid lyophilized form is more stable during storage when compared to a conventional ready-to-use formulation comprising Compound I, or a pharmaceutically acceptable salt and/or solvate thereof. Inventors discovered that maintaining soluble oxygen content ≤1.0 ppm during the process of preparing the solid lyophilized form of Compound I, or a pharmaceutically acceptable salt and/or solvate thereof, is critical in improving stability.

In one embodiment, the solid lyophilized composition comprising Compound I, or a pharmaceutically acceptable salt and/or solvate thereof, wherein the composition comprises less than 0.5% impurities. In another embodiment, the composition comprises less than 0.3% impurities.

In one embodiment, the solid lyophilized composition comprises less than 0.7% impurities after the composition is stored at room temperature for 6 months. In another embodiment, the solid lyophilized composition comprises less than 0.5% impurities after the composition is stored at room temperature for 3 months. In some embodiments, the solid lyophilized composition comprises less than about 0.5% impurities resulting from oxidation of Compound I after the composition is stored at room temperature for 6 months.

In one embodiment, the present disclosure provides a composition comprising a solid lyophilized Compound I, or a pharmaceutically acceptable salt and/or solvate thereof, wherein the composition comprises less than about 3% impurities. In one embodiment, the present disclosure provides a composition comprising a solid lyophilized Compound I, or a pharmaceutically acceptable salt and/or solvate thereof, wherein the composition comprises less than about 2% impurities. In one embodiment, the present disclosure provides a composition comprising a solid lyophilized Compound I, or a pharmaceutically acceptable salt and/or solvate thereof, wherein the composition comprises less than about 1% impurities. In one embodiment, the present disclosure provides a composition comprising a solid lyophilized Compound I, or a pharmaceutically acceptable salt and/or solvate thereof, wherein the composition comprises less than about 0.5% impurities. In some embodiments, the purity and impurities of Compound I are measured as area % by high-performance liquid chromatography (HPLC). In another embodiment, the HPLC is reverse-phase HPLC. In another embodiment, the determination of the impurities of Compound I is by running the reconstituted composition over reverse-phase HPLC using the following parameters:

| RP-HPLC Chromatography Parameters (Acid Mobile Phase) | |
| --- | --- |
| Parameter | Conditions |
| Column | Agilent Zorbax SB-CN, 4.6 × 150 mm, 5 μm |
| Mobile Phase A | 950/50/2 Water/Acetonitrile/Perchloric Acid |
| Mobile Phase B/ Needle Wash | 50/50 Methanol/Acetonitrile |
| Diluent | 0.1% Trifluoroacetic Acid in Water |
| Injection volume | 20 μL |
| Run Time | 40 min |
| Detection Wavelength | 240 nm |

| RP-HPLC Chromatography Parameters (Base Mobile Phase) | |
| --- | --- |
| Parameter | Conditions |
| Column | Waters XBridge Phenyl, 150 mm (L) × 4.6 mm (ID), 3.5 μM |
| Mobile Phase A | 10 mM $Na_2HPO_4$, pH 11.0 |
| Mobile Phase B/Needle Wash | Methanol |
| Diluent | 0.1% Trifluoroacetic Acid in Water |
| Injection volume | 10 μL |
| Run Time | 58 min |
| Detection Wavelength | 240 nm |

In one embodiment, the purity and impurity of any one of the compounds and composition as disclosed herein is determined using the above described RP-HPLC Chromatography conditions with acid mobile phase. In one embodiment, the purity and impurity of any one of the compounds and composition as disclosed herein is determined in accordance to Example 5.

In one embodiment, the purity and impurity of any one of the compounds and composition as disclosed herein is determined using the above described RP-HPLC Chromatography conditions with base mobile phase. In one embodiment, the purity and impurity of any one of the compounds and composition as disclosed herein is determined in accordance to Example 10.

In another embodiment, the composition comprising the solid lyophilized Compound I, or a pharmaceutically acceptable salt and/or solvate thereof, comprises less than about 3% impurities after the composition is stored at room temperature for 28 days. In another embodiment, the composition comprising the solid lyophilized Compound I, or a pharmaceutically acceptable salt and/or solvate thereof, comprises less than about 2% impurities after the composition is stored at room temperature for 28 days. In another embodiment, the composition comprising the solid lyophilized Compound I, or a pharmaceutically acceptable salt and/or solvate thereof, comprises less than about 1% impurities after the composition is stored at room temperature for 28 days. In another embodiment, the composition comprising the solid lyophilized Compound I, or a pharmaceutically acceptable salt and/or solvate thereof, comprises less than about 0.5% impurities after the composition is stored at room temperature for 28 days.

In another embodiment, the composition comprising the solid lyophilized Compound I, or a pharmaceutically acceptable salt and/or solvate thereof, comprises less than about 3% impurities after the composition is stored at room temperature for 1 month. In another embodiment, the composition comprising the solid lyophilized Compound I, or a pharmaceutically acceptable salt and/or solvate thereof, comprises less than about 2% impurities after the composition is stored at room temperature for 1 month. In another embodiment, the composition comprising the solid lyophilized Compound I, or a pharmaceutically acceptable salt and/or solvate thereof, comprises less than about 1% impurities after the composition is stored at room temperature for 1 month. In another embodiment, the composition comprising the solid lyophilized Compound I, or a pharmaceutically acceptable salt and/or solvate thereof, comprises less than about 0.5% impurities after the composition is stored at room temperature for 1 month.

In another embodiment, the composition comprising the solid lyophilized Compound I, or a pharmaceutically acceptable salt and/or solvate thereof, comprises less than about 3% impurities after the composition is stored at room temperature for less than or equal to 28 days. In another embodiment, the composition comprising the solid lyophilized Compound I, or a pharmaceutically acceptable salt and/or solvate thereof, comprises less than about 2% impurities after the composition is stored at room temperature for less than or equal to 28 days. In another embodiment, the composition comprising the solid lyophilized Compound I, or a pharmaceutically acceptable salt and/or solvate thereof, comprises less than about 1% impurities after the composition is stored at room temperature for less than or equal to 28 days. In another embodiment, the composition comprising the solid lyophilized Compound I, or a pharmaceutically acceptable salt and/or solvate thereof, comprises less than about 0.5% impurities after the composition is stored at room temperature for less than or equal to 28 days.

In another embodiment, the composition comprising the solid lyophilized Compound I, or a pharmaceutically acceptable salt and/or solvate thereof, comprises less than about 3%, less than about 2%, less than about 1% impurities, or less than about 0.5% after the composition is stored at room temperature for at least 24 months and any subranges therebetween. In another embodiment, the composition comprising the solid lyophilized Compound I, or a pharmaceutically acceptable salt and/or solvate thereof, comprises less than about 3% impurities after the composition is stored at room temperature for up to 24 months and any subranges therebetween. In another embodiment, the composition comprising the solid lyophilized Compound I, or a pharmaceutically acceptable salt and/or solvate thereof, comprises less than about 2% impurities after the composition is stored at room temperature for up to 24 months and any subranges therebetween. In another embodiment, the composition comprising the solid lyophilized Compound I, or a pharmaceutically acceptable salt and/or solvate thereof, comprises less than about 1% impurities after the composition is stored at room temperature for up to 24 months and any subranges therebetween. In another embodiment, the composition comprising the solid lyophilized Compound I, or a pharmaceutically acceptable salt and/or solvate thereof, comprises less than about 0.5% impurities after the composition is stored at room temperature for up to 24 months and any subranges therebetween.

In some embodiments, the composition comprising the solid lyophilized Compound I, or a pharmaceutically acceptable salt and/or solvate thereof, comprises less than about 1% impurities after the composition is stored at room temperature for at least about 7 days, at least about 14 days, at least about 28 days, at least about 42 days, or at least about 96 days. In some embodiments, the composition comprising the solid lyophilized Compound I, or a pharmaceutically acceptable salt and/or solvate thereof, comprises less than about 1% impurities after the composition is stored at room temperature for about 7 days, about 14 days, about 28 days, about 42 days, or about 96 days.

In some embodiments, the composition comprising the solid lyophilized Compound I, or a pharmaceutically acceptable salt and/or solvate thereof, comprises less than about 1% impurities after the composition is stored at room temperature for at least about 1 week, at least about 2 weeks, at least about 3 weeks, at least about 4 weeks, at least about 5 weeks, at least about 6 weeks, at least about 7 weeks, at least about 8 weeks, at least about 9 weeks, at least about 10 weeks, at least about 11 weeks, at least about 12 weeks, at least about 13 weeks, at least about 14 weeks, or at least about 15 weeks. In some embodiments, the composition comprising the solid lyophilized Compound I, or a pharmaceutically acceptable salt and/or solvate thereof, comprises less than about 1% impurities after the composition is stored at room temperature for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, or about 15 weeks.

In other embodiments, the composition comprising the solid lyophilized Compound I, or a pharmaceutically acceptable salt and/or solvate thereof, comprises less than about 1% impurities after the composition is stored at room temperature for at least about 1 month, at least about 2 months, at least about 3 months, at least about 4 months, at least about 5 months, at least about 6 months, at least about 7 months, at least about 8 months, at least about 9 months, at least about 10 months, at least about 11 months, at least about 12 months, at least about 13 months, at least about 14 months, at least about 15 months, at least about 16 months, at least about 17 months, at least about 18 months, at least about 19 months, at least about 20 months, at least about 21 months, at least about 22 months, at least about 23 months, or at least about 24 months. In other embodiments, the composition comprising the solid lyophilized Compound I, or a pharmaceutically acceptable salt and/or solvate thereof, comprises less than about 1% impurities after the composition is stored at room temperature for about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months.

In another embodiment, the composition comprising the solid lyophilized Compound I, or a pharmaceutically acceptable salt and/or solvate thereof, comprises less than about 0.3% impurities after the composition is stored at about −20° C. for up to 24 months and any subranges therebetween. In another embodiment, the composition comprising the solid lyophilized Compound I, or a pharmaceutically acceptable salt and/or solvate thereof, comprises less than about 0.2% impurities after the composition is stored at about −20° C. for up to 24 months and any subranges therebetween. In another embodiment, the composition comprising the solid lyophilized Compound I, or a pharmaceutically acceptable salt and/or solvate thereof, comprises less than about 0.1% impurities after the composition is stored at about −20° C. for up to 24 months and any subranges therebetween. In one embodiment, the composition is stored for about 1 month, about 2 months, or about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months, or any subranges therebetween.

In another embodiment, the composition comprising the solid lyophilized Compound I, or a pharmaceutically acceptable salt and/or solvate thereof, comprises less than about 0.3% impurities after the composition is stored at about 5° C. for up to 24 months and any subranges therebetween. In another embodiment, the composition comprising the solid lyophilized Compound I, or a pharmaceutically acceptable salt and/or solvate thereof, comprises less than about 0.2% impurities after the composition is stored at about 5° C. for up to 24 months and any subranges therebetween. In another embodiment, the composition comprising the solid lyophilized Compound I, or a pharmaceutically acceptable salt and/or solvate thereof, comprises less than about 0.1% impurities after the composition is stored at about 5° C. for up to 24 months and any subranges therebetween. In one embodiment, the composition is stored for about 1 month, about 2 months, or about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months, or any subranges therebetween.

In another embodiment, the composition comprising the solid lyophilized Compound I, or a pharmaceutically acceptable salt and/or solvate thereof, comprises less than about 3% impurities after the composition is stored at a temperature in the range of about 2 to about 8° C. for at least 36 months and any subranges therebetween. In another embodiment, the composition comprising the solid lyophilized Compound I, or a pharmaceutically acceptable salt and/or solvate thereof, comprises less than about 3% impurities after the composition is stored at a temperature in the range of about 2 to about 8° C. for up to 36 months and any subranges therebetween. In another embodiment, the composition comprising the solid lyophilized Compound I, or a pharmaceutically acceptable salt and/or solvate thereof, comprises less than about 2% impurities after the composition is stored at a temperature in the range of about 2 to about 8° C. for up to 36 months and any subranges therebetween. In another embodiment, the composition comprising the solid lyophilized Compound I, or a pharmaceutically acceptable salt and/or solvate thereof, comprises less than about 1.5% impurities after the composition is stored at a temperature in the range of about 2 to about 8° C. for up to 36 months and any subranges therebetween. In another embodiment, the composition comprising the solid lyophilized Compound I, or a pharmaceutically acceptable salt and/or solvate thereof, comprises less than about 1% impurities after the composition is stored at a temperature in the range of about 2 to about 8° C. for up to 36 months and any subranges therebetween. In one embodiment, the composition is stored for about 1 month, about 2 months, or about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, about 24 months, about 25 months, about 26 months, about 27 months, about 28 months, about 29 months, about 30 months, about 31 months, about 32 months, or about 33 months, about 34 months, about 35 months, or about 36 months. In one embodiment, when the composition is stored at about 2 to about 8° C., it is under ambient relative humidity. In one embodiment, the composition is stored at about 2° C., at about 3° C., at about 4° C., at about 5° C., at about 6° C., at about 7° C., or at about 8° C. under ambient relative humidity. In one embodiment, the composition is stored at about 5° C. under ambient relative humidity.

In another embodiment, the composition comprising the solid lyophilized Compound I, or a pharmaceutically acceptable salt and/or solvate thereof, comprises less than about 3% impurities after the composition is stored at about 25° C./60% relative humidity (RH) for at least 36 months and any subranges therebetween. In another embodiment, the composition comprising the solid lyophilized Compound I, or a pharmaceutically acceptable salt and/or solvate thereof, comprises less than about 3% impurities after the composition is stored at about 25° C./60% relative humidity (RH) for up to 36 months and any subranges therebetween. In another embodiment, the composition comprising the solid lyophilized Compound I, or a pharmaceutically acceptable salt and/or solvate thereof, comprises less than about 2% impurities after the composition is stored at about 25° C./60% RH for up to 36 months and any subranges therebetween. In another embodiment, the composition comprising the solid lyophilized Compound I, or a pharmaceutically acceptable salt and/or solvate thereof, comprises less than about 1.5% impurities after the composition is stored at about 25° C./60% RH for up to 36 months and any subranges therebetween. In another embodiment, the composition comprising the solid lyophilized Compound I, or a pharmaceutically acceptable salt and/or solvate thereof, comprises less than about 1% impurities after the composition is stored at about 25° C./60% RH for up to 36 months and any subranges therebetween. In some embodiments, the composition is stored at about 25° C./60% RH for up to 24 months. In one embodiment, the composition is stored for about 1 month, about 2 months, or about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, about 24 months, about 25 months, about 26 months, about 27 months, about 28 months, about 29 months, about 30 months, about 31 months, about 32 months, or about 33 months, about 34 months, about 35 months, or about 36 months.

In another embodiment, the composition comprising the solid lyophilized Compound I, or a pharmaceutically acceptable salt and/or solvate thereof, comprises less than about 3% impurities after the composition is stored at about 30° C./65% RH for at least 3 months and any subranges therebetween. In another embodiment, the composition comprising the solid lyophilized Compound I, or a pharmaceutically acceptable salt and/or solvate thereof, comprises less than about 3% impurities after the composition is stored at about 30° C./65% RH for up to 3 months and any subranges therebetween. In another embodiment, the composition comprising the solid lyophilized Compound I, or a pharmaceutically acceptable salt and/or solvate thereof, comprises less than about 2% impurities after the composition is stored at about 30° C./65% RH for up to 3 months and any subranges therebetween. In another embodiment, the composition comprising the solid lyophilized Compound I, or a pharmaceutically acceptable salt and/or solvate thereof, comprises less than about 1.5% impurities after the composition is stored at about 30° C./65% RH for up to 3 months and any subranges therebetween. In another embodiment, the composition comprising the solid lyophilized Compound I, or a pharmaceutically acceptable salt and/or solvate thereof, comprises less than about 1% impurities after the composition is stored at about 30° C./65% RH for up to 3 months and any subranges therebetween. In one embodiment, the composition is stored for about 1 month, about 2 months, or about 3 months.

In another embodiment, the composition comprising the solid lyophilized Compound I, or a pharmaceutically acceptable salt and/or solvate thereof, comprises less than about 3% impurities after the composition is stored at about 40° C./75% RH for at least 3 months and any subranges therebetween. In another embodiment, the composition comprising the solid lyophilized Compound I, or a pharmaceutically acceptable salt and/or solvate thereof, comprises less than about 3% impurities after the composition is stored at about 40° C./75% RH for up to 3 months and any subranges therebetween. In another embodiment, the composition comprising the solid lyophilized Compound I, or a pharmaceutically acceptable salt and/or solvate thereof, comprises less than about 2% impurities after the composition is stored at about 40° C./75% RH for up to 3 months and any subranges therebetween. In another embodiment, the composition comprising the solid lyophilized Compound I, or a pharmaceutically acceptable salt and/or solvate thereof, comprises less than about 1.5% impurities after the composition is stored at about 40° C./75% RH for up to 3 months and any subranges therebetween. In one embodiment, the composition is stored for about 1 month, about 2 months, or about 3 months.

In some embodiments, the composition comprising the solid lyophilized Compound I, or a pharmaceutically acceptable salt and/or solvate thereof, comprises less than about 1% impurities after the composition is stored at 50° C. for at least about 7 days, at least about 14 days, at least about 28 days, at least about 42 days, or at least about 96 days. In some embodiments, the composition comprising the solid lyophilized Compound I, or a pharmaceutically acceptable salt and/or solvate thereof, comprises less than about 1% impurities after the composition is stored at 50° C. for about 7 days, about 14 days, about 28 days, about 42 days, or about 96 days. In some embodiments, the composition comprising the solid lyophilized Compound I, or a pharmaceutically acceptable salt and/or solvate thereof, comprises less than about 1% impurities after the composition is stored at 50° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, or about 15 weeks. In other embodiments, the composition comprising the solid lyophilized Compound I, or a pharmaceutically acceptable salt and/or solvate thereof, comprises less than about 1% impurities after the composition is stored at 50° C. for about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months.

In some embodiments, the composition comprising the solid lyophilized Compound I, or a pharmaceutically acceptable salt and/or solvate thereof, comprises less than about 1% impurities after the composition is stored at 5° C. for at least about 7 days, at least about 14 days, at least about 28 days, at least about 42 days, or at least about 96 days. In some embodiments, the composition comprising the solid lyophilized Compound I, or a pharmaceutically acceptable salt and/or solvate thereof, comprises less than about 1% impurities after the composition is stored at 5° C. for about 7 days, about 14 days, about 28 days, about 42 days, or about 96 days. In some embodiments, the composition comprising the solid lyophilized Compound I, or a pharmaceutically acceptable salt and/or solvate thereof, comprises less than about 1% impurities after the composition is stored at 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, or about 15 weeks. In other embodiments, the composition comprising the solid lyophilized Compound I, or a pharmaceutically acceptable salt and/or solvate thereof, comprises less than about 1% impurities after the composition is stored at 5° C. for about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months.

In one embodiment, the composition comprising the solid lyophilized Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% impurities resulting from oxidation of Compound I after the composition is stored at room temperature for 28 days. In some embodiments, the composition comprising the solid lyophilized Compound I, or a pharmaceutically acceptable salt and/or solvate thereof, comprises less than about 0.4%, less than about 0.3%, or less than about 0.2% impurities resulting from oxidation of Compound I after the composition is stored at room temperature for 28 days.

In one embodiment, the composition comprising the solid lyophilized Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% impurities resulting from oxidation of Compound I after the composition is stored at room temperature for less than or equal to 28 days. In some embodiments, the composition comprising the solid lyophilized Compound I, or a pharmaceutically acceptable salt and/or solvate thereof, comprises less than about 0.4%, less than about 0.3%, or less than about 0.2% impurities resulting from oxidation of Compound I after the composition is stored at room temperature for less than or equal to 28 days.

In one embodiment, the composition comprising the solid lyophilized Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% impurities resulting from oxidation of Compound I after the composition is stored at room temperature for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, or about 15 weeks.

In another embodiment, the composition comprising the solid lyophilized Compound I, or a pharmaceutically acceptable salt and/or solvate thereof, is substantially free of an oxidization product of a Compound I, or a pharmaceutically acceptable salt and/or solvate thereof. In one embodiment, maintaining soluble oxygen ≤1.0 ppm during the process of preparing the solid lyophilized Compound I, or a pharmaceutically acceptable salt and/or solvate thereof is critical in providing the composition that is substantially free of an oxidization product of a Compound I, or a pharmaceutically acceptable salt and/or solvate thereof. In one embodiment, maintaining soluble oxygen <1 ppm during the process of preparing the solid lyophilized Compound I, or a pharmaceutically acceptable salt and/or solvate thereof is critical in providing the composition that is substantially free of an oxidization product of a Compound I, or a pharmaceutically acceptable salt and/or solvate thereof.

In one embodiment, the oxidation product of Compound I is selected from:

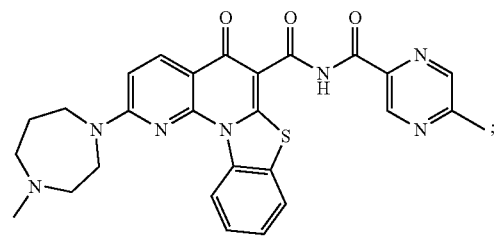

(10)

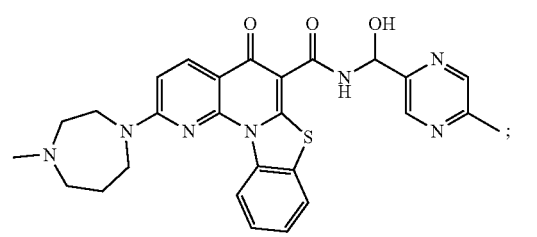

(4)

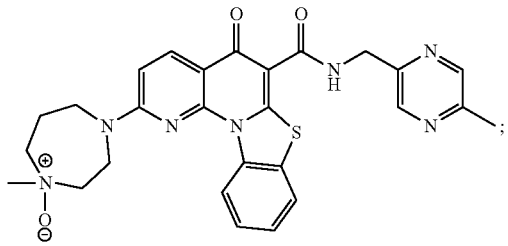

(9)

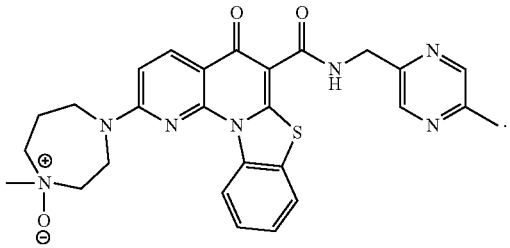

(9)

In some embodiments, the composition comprising the solid lyophilized Compound I, or a pharmaceutically acceptable salt and/or solvate thereof, comprises less than about 0.1% of

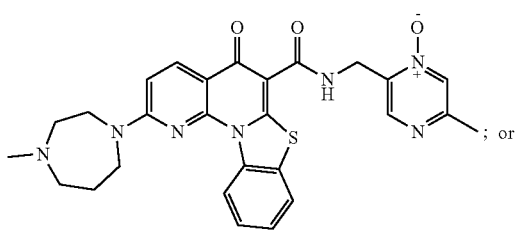

(2)

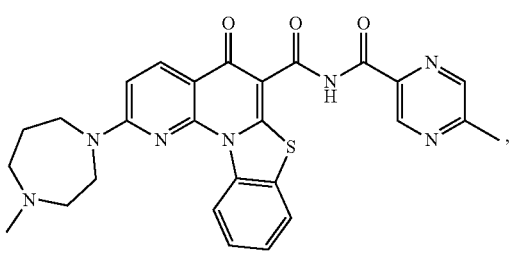

(10)

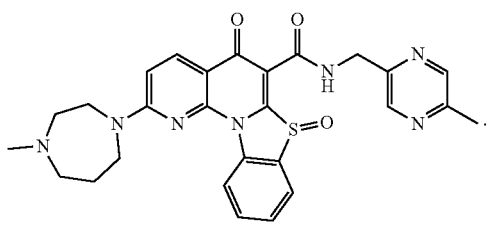

(3)

In one embodiment, the oxidation product is a ketone product. In some embodiments, the oxidation product is an N-oxide product. In one embodiment, the ketone product is Compound 10. In one embodiment, the N-oxide product is Compound 9.

In one embodiment, the solid lyophilized composition comprises less than 0.1% of

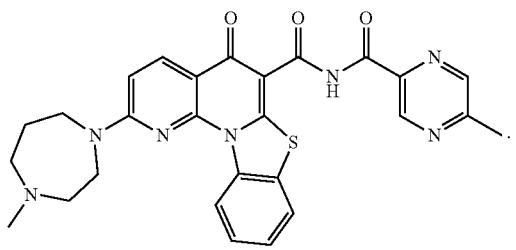

(10)

In another embodiment, the solid lyophilized composition comprises less than 0.2% impurities resulting from oxidation of Compound I, wherein the oxidation of Compound I is a N-oxide of Compound I. In other embodiments, the solid lyophilized composition comprises less than 0.2% of after the composition is stored at room temperature for 28 days. In some embodiments, the composition comprising the solid lyophilized Compound I, or a pharmaceutically acceptable salt and/or solvate thereof, comprises less than about 0.1% of Compound 10, after the composition is stored at room temperature for 1 month. In some embodiments, the composition comprising the solid lyophilized Compound I, or a pharmaceutically acceptable salt and/or solvate thereof, comprises less than about 0.2% of Compound 10, after the composition is stored at room temperature for 28 days or for 1 month. In some embodiments, the composition comprising the solid lyophilized Compound I, or a pharmaceutically acceptable salt and/or solvate thereof, comprises less than about 0.3% of Compound 10, after the composition is stored at room temperature for 28 days or for 1 month. In some embodiments, the composition is stored at room temperature for at least 28 days or for 1 month.

In some embodiments, the composition comprising the solid lyophilized Compound I, or a pharmaceutically acceptable salt and/or solvate thereof, comprises less than about 0.3% of Compound 10, after the composition is stored at 25° C./60% RH for 28 days or 1 month. In some embodiments, the composition comprising the solid lyophilized Compound I, or a pharmaceutically acceptable salt and/or solvate thereof, comprises less than about 0.2% of Compound 10, after the composition is stored at 25° C./60% RH for 28 days or 1 month. In some embodiments, the composition comprising the solid lyophilized Compound I, or a pharmaceutically acceptable salt and/or solvate thereof, comprises less than about 0.1% of Compound 10, after the composition is stored at 25° C./60% RH for 28 days or 1 month. In some embodiments, the composition is stored at room temperature for at least 28 days or 1 month. In some embodiments, the composition comprising the solid lyophilized Compound I, or a pharmaceutically acceptable salt and/or solvate thereof, comprises less than about 0.05% of Compound 10, after the composition is stored at 25° C./60% RH for 28 days or 1 month. In some embodiments, the composition is stored at room temperature for at least 28 days or 1 month.

In some embodiments, the composition comprising the solid lyophilized Compound I, or a pharmaceutically acceptable salt and/or solvate thereof, comprises less than about 0.3% of Compound 10, after the composition is stored at 25° C./60% RH for less than or equal 3 months. In some embodiments, the composition comprising the solid lyophilized Compound I, or a pharmaceutically acceptable salt and/or solvate thereof, comprises less than about 0.2% of Compound 10, after the composition is stored at 25° C./60% RH for less than or equal to 3 months. In some embodiments, the composition comprising the solid lyophilized Compound I, or a pharmaceutically acceptable salt and/or solvate thereof, comprises less than about 0.1% of Compound 10, after the composition is stored at 25° C./60% RH for less than or equal to 3 months. In some embodiments, the composition comprising the solid lyophilized Compound I, or a pharmaceutically acceptable salt and/or solvate thereof, comprises less than about 0.05% of Compound 10, after the composition is stored at 25° C./60% RH for less than or equal to 3 months.

In some embodiments, the composition comprising the solid lyophilized Compound I, or a pharmaceutically acceptable salt and/or solvate thereof, comprises less than about 0.3% of Compound 10, after the composition is stored at 25° C./60% RH for less than or equal to 12 months. In some embodiments, the composition comprising the solid lyophilized Compound I, or a pharmaceutically acceptable salt and/or solvate thereof, comprises less than about 0.2% of Compound 10, after the composition is stored at 25° C./60% RH for less than or equal to 12 months. In some embodiments, the composition comprising the solid lyophilized Compound I, or a pharmaceutically acceptable salt and/or solvate thereof, comprises less than about 0.1% of Compound 10, after the composition is stored at 25° C./60% RH for less than or equal to 12 months. In some embodiments, the composition comprising the solid lyophilized Compound I, or a pharmaceutically acceptable salt and/or solvate thereof, comprises less than about 0.3% of Compound 10, after the composition is stored at 25° C./60% RH for less than or equal to 24 months. In some embodiments, the composition comprising the solid lyophilized Compound I, or a pharmaceutically acceptable salt and/or solvate thereof, comprises less than about 0.2% of Compound 10, after the composition is stored at 25° C./60% RH for less than or equal to 24 months. In some embodiments, the composition comprising the solid lyophilized Compound I, or a pharmaceutically acceptable salt and/or solvate thereof, comprises less than about 0.1% of Compound 10, after the composition is stored at 25° C./60% RH for less than or equal to 24 months.

In some embodiments, the composition comprising the solid lyophilized Compound I, or a pharmaceutically acceptable salt and/or solvate thereof, comprises less than about 0.6% of Compound 10, after the composition is stored at 25° C./60% RH for up to 36 months and any subranges therebetween. In some embodiments, the composition comprising the solid lyophilized Compound I, or a pharmaceutically acceptable salt and/or solvate thereof, comprises less than about 0.6% of Compound 10, after the composition is stored at 25° C./60% RH for up to 24 months and any subranges therebetween. In some embodiments, the composition comprising the solid lyophilized Compound I, or a pharmaceutically acceptable salt and/or solvate thereof, comprises less than about 0.6% of Compound 10, after the composition is stored at 25° C./60% RH for up to 12 months and any subranges therebetween.

In some embodiments, the composition comprising the solid lyophilized Compound I, or a pharmaceutically acceptable salt and/or solvate thereof, comprises less than about 0.5% of Compound 10, after the composition is stored at 25° C./60% RH for up to 36 months and any subranges therebetween. In some embodiments, the composition comprising the solid lyophilized Compound I, or a pharmaceutically acceptable salt and/or solvate thereof, comprises less than about 0.4% of Compound 10, after the composition is stored at 25° C./60% RH for up to 36 months and any subranges therebetween. In some embodiments, the composition comprising the solid lyophilized Compound I, or a pharmaceutically acceptable salt and/or solvate thereof, comprises less than about 0.3% of Compound 10, after the composition is stored at 25° C./60% RH for up to 36 months and any subranges therebetween.

In some embodiments, the composition comprising the solid lyophilized Compound I, or a pharmaceutically acceptable salt and/or solvate thereof, comprises less than about 0.5% of Compound 10, after the composition is stored at a temperature in the range of about 2° C. to about 8° C. for up to 36 months and any subranges therebetween. In some embodiments, the composition comprising the solid lyophilized Compound I, or a pharmaceutically acceptable salt and/or solvate thereof, comprises less than about 0.5% of Compound 10, after the composition is stored at a temperature in the range of about 2° C. to about 8° C. for up to 24 months and any subranges therebetween. In some embodiments, the composition comprising the solid lyophilized Compound I, or a pharmaceutically acceptable salt and/or solvate thereof, comprises less than about 0.5% of Compound 10, after the composition is stored at a temperature in the range of about 2° C. to about 8° C. for up to 12 months and any subranges therebetween.

In some embodiments, the composition comprising the solid lyophilized Compound I, or a pharmaceutically acceptable salt and/or solvate thereof, comprises less than about 0.4% of Compound 10, after the composition is stored at a temperature in the range of about 2° C. to about 8° C. for up to 36 months and any subranges therebetween. In some embodiments, the composition comprising the solid lyophilized Compound I, or a pharmaceutically acceptable salt and/or solvate thereof, comprises less than about 0.3% of Compound 10, after the composition is stored at a temperature in the range of about 2° C. to about 8° C. for up to 36 months and any subranges therebetween.

In some embodiments, the composition comprising the solid lyophilized Compound I, or a pharmaceutically acceptable salt and/or solvate thereof, comprises less than about 0.1% of Compound 10, after the composition is stored at about 5° C. for up to 3 months and any subranges therebetween. In some embodiments, the composition comprising the solid lyophilized Compound I, or a pharmaceutically acceptable salt and/or solvate thereof, comprises less than about 0.05% of Compound 10, after the composition is stored at about 5° C. for up to 3 months and any subranges therebetween.

In one embodiment, the composition comprising the solid lyophilized Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% of N-oxides of Compound I after the composition is stored at room temperature for 14 days. In some embodiments, the composition comprising solid lyophilized Compound I, or a pharmaceutically acceptable salt and/or solvate thereof, comprises less than about 0.3%, less than about 0.2%, or less than about 0.1% of N-oxides of Compound I after the composition is stored at room temperature for 14 days. In some embodiments, the composition is stored at room temperature for at least 14 days.

In one embodiment, the composition comprising the solid lyophilized Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% N-oxides of the Compound I after the composition is stored at room temperature for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, or about 15 weeks.

In one embodiment, the composition comprising the solid lyophilized Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% N-oxides of the Compound I after the composition is stored at a temperature in the range of 2° C. to about 30° C., and at any subranges therebetween, for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, or about 15 weeks, or any subranges therebetween. In one embodiment, the composition comprising the solid lyophilized Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% N-oxides of the Compound I after the composition is stored at a temperature in the range of 2° C. to about 30° C., and at any subranges therebetween, for about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months, or any subranges therebetween.

In one embodiment, the composition comprising the solid lyophilized Compound I, or a pharmaceutically acceptable salt and/or solvate thereof, comprises less than about 0.1% impurities resulting from oxidation of Compound I after the composition is stored at room temperature, at about 5° C., or at 25° C./60% RH for up to 3 months, or any subranges therebetween. In one embodiment, the composition comprising the solid lyophilized Compound I, or a pharmaceutically acceptable salt and/or solvate thereof, comprises less than about 0.05% impurities resulting from oxidation of Compound I after the composition is stored at room temperature, at about 5° C., or at 25° C./60% RH for up to 3 months, or any subranges therebetween.

In one embodiment, the composition comprising the solid lyophilized Compound I, or a pharmaceutically acceptable salt and/or solvate thereof, comprises less than about 0.1% N-oxides of the Compound I after the composition is stored at room temperature, at about 5° C., or at 25° C./60% RH for up to 3 months, or any subranges therebetween. In one embodiment, the composition comprising the solid lyophilized Compound I, or a pharmaceutically acceptable salt and/or solvate thereof, comprises less than about 0.05% N-oxides of the Compound I after the composition is stored at room temperature, at about 5° C., or at 25° C./60% RH for up to 3 months, or any subranges therebetween.

In another embodiment, the composition comprising the solid lyophilized Compound I, or a pharmaceutically acceptable salt and/or solvate thereof, is substantially free of an N-oxide of a Compound I, or a pharmaceutically acceptable salt and/or solvate thereof.

In some embodiments, the composition comprising the solid lyophilized Compound I, or a pharmaceutically acceptable salt and/or solvate thereof, comprises less than about 0.2% of

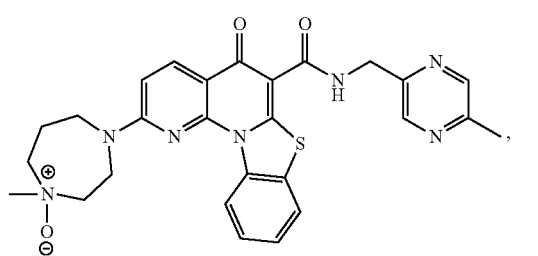

(9)

after the composition is stored at room temperature for 14 days.

In some embodiments, the composition comprising the solid lyophilized Compound I, or a pharmaceutically acceptable salt and/or solvate thereof, comprises less than about 0.3% of Compound 9, after the composition is stored at room temperature for 28 days or 1 month. In some embodiments, the composition comprising the solid lyophilized Compound I, or a pharmaceutically acceptable salt and/or solvate thereof, comprises less than about 0.2% of Compound 9, after the composition is stored at room temperature for 28 days or 1 month. In some embodiments, the composition comprising the solid lyophilized Compound I, or a pharmaceutically acceptable salt and/or solvate thereof, comprises less than about 0.3% of Compound 9, after the composition is stored at room temperature for less than or equal to 28 days or 1 month. In some embodiments, the composition comprising the solid lyophilized Compound I, or a pharmaceutically acceptable salt and/or solvate thereof, comprises less than about 0.2% of Compound 9, after the composition is stored at room temperature for less than or equal to 28 days or 1 month. In some embodiments, the composition is stored at room temperature for at least 28 days or at least 1 month.

In some embodiments, the composition comprising the solid lyophilized Compound I, or a pharmaceutically acceptable salt and/or solvate thereof, comprises less than about 0.3% of Compound 9, after the composition is stored at 25° C./60% RH for 28 days or 1 month. In some embodiments, the composition comprising the solid lyophilized Compound I, or a pharmaceutically acceptable salt and/or solvate thereof, comprises less than about 0.2% of Compound 9, after the composition is stored at 25° C./60% RH for 28 days or 1 month. In some embodiments, the composition comprising the solid lyophilized Compound I, or a pharmaceutically acceptable salt and/or solvate thereof, comprises less than about 0.3% of Compound 9, after the composition is stored at 25° C./60% RH for less than or equal to 28 days or 1 month. In some embodiments, the composition comprising the solid lyophilized Compound I, or a pharmaceutically acceptable salt and/or solvate thereof, comprises less than about 0.2% of Compound 9, after the composition is stored at 25° C./60% RH for less than or equal to 28 days or 1 month. In some embodiments, the composition is stored at room temperature for at least 28 days or at least 1 month.

In some embodiments, the composition comprising the solid lyophilized Compound I, or a pharmaceutically acceptable salt and/or solvate thereof, comprises less than about 0.5% of Compound 9, after the composition is stored at 25° C./60% RH for up to 36 months and any subranges therebetween. In some embodiments, the composition comprising the solid lyophilized Compound I, or a pharmaceutically acceptable salt and/or solvate thereof, comprises less than about 0.5% of Compound 9, after the composition is stored at 25° C./60% RH for up to 24 months and any subranges therebetween. In some embodiments, the composition comprising the solid lyophilized Compound I, or a pharmaceutically acceptable salt and/or solvate thereof, comprises less than about 0.5% of Compound 9, after the composition is stored at 25° C./60% RH for up to 12 months and any subranges therebetween. In some embodiments, the composition is stored at room temperature for at least 12 months.

In some embodiments, the composition comprising the solid lyophilized Compound I, or a pharmaceutically acceptable salt and/or solvate thereof, comprises less than about 0.4% of Compound 9, after the composition is stored at 25° C./60% RH for up to 36 months and any subranges therebetween. In some embodiments, the composition comprising the solid lyophilized Compound I, or a pharmaceutically acceptable salt and/or solvate thereof, comprises less than about 0.3% of Compound 9, after the composition is stored at 25° C./60% RH for up to 36 months and any subranges therebetween.

In some embodiments, the composition comprising the solid lyophilized Compound I, or a pharmaceutically acceptable salt and/or solvate thereof, comprises less than about 0.3% of Compound 9, after the composition is stored at 25° C./60% RH for less than or equal to 24 months. In some embodiments, the composition comprising the solid lyophilized Compound I, or a pharmaceutically acceptable salt and/or solvate thereof, comprises less than about 0.2% of Compound 9, after the composition is stored at 25° C./60% RH for less than or equal to 24 months. In some embodiments, the composition comprising the solid lyophilized Compound I, or a pharmaceutically acceptable salt and/or solvate thereof, comprises less than about 0.15% of Compound 9, after the composition is stored at 25° C./60% RH for less than or equal to 24 months.

In some embodiments, the composition comprising the solid lyophilized Compound I, or a pharmaceutically acceptable salt and/or solvate thereof, comprises less than about 0.5% of Compound 9, after the composition is stored at a temperature in the range of about 2° C. to about 8° C. for up to 36 months and any subranges therebetween. In some embodiments, the composition comprising the solid lyophilized Compound I, or a pharmaceutically acceptable salt and/or solvate thereof, comprises less than about 0.5% of Compound 9, after the composition is stored at a temperature in the range of about 2° C. to about 8° C. for up to 24 months and any subranges therebetween. In some embodiments, the composition comprising the solid lyophilized Compound I, or a pharmaceutically acceptable salt and/or solvate thereof, comprises less than about 0.5% of Compound 9, after the composition is stored at a temperature in the range of about 2° C. to about 8° C. for up to 12 months and any subranges therebetween. In some embodiments, the composition is stored at room temperature for at least 12 months.

In some embodiments, the composition comprising the solid lyophilized Compound I, or a pharmaceutically acceptable salt and/or solvate thereof, comprises less than about 0.4% of Compound 9, after the composition is stored at a temperature in the range of about 2° C. to about 8° C. for up to 36 months and any subranges therebetween. In some embodiments, the composition comprising the solid lyophilized Compound I, or a pharmaceutically acceptable salt and/or solvate thereof, comprises less than about 0.3% of Compound 9, after the composition is stored at a temperature in the range of about 2° C. to about 8° C. for up to 36 months and any subranges therebetween. In some embodiments, the composition comprising the solid lyophilized Compound I, or a pharmaceutically acceptable salt and/or solvate thereof, comprises less than about 0.2% of Compound 9, after the composition is stored at a temperature in the range of about 2° C. to about 8° C. for up to 36 months and any subranges therebetween.

In some embodiments, the composition comprising the solid lyophilized Compound I, or a pharmaceutically acceptable salt and/or solvate thereof, comprises less than about 0.3% of Compound 9, after the composition is stored at a temperature in the range of about 2° C. to about 30° C., and at any subranges therebetween, for less than or equal to 28 days or 1 month. In some embodiments, the composition comprising the solid lyophilized Compound I, or a pharmaceutically acceptable salt and/or solvate thereof, comprises less than about 0.2% of Compound 9, after the composition is stored at a temperature in the range of about 2° C. to about 30° C., and at any subranges therebetween, for less than or equal to 28 days or 1 month. In some embodiments, the composition is stored at room temperature for at least 28 days or at least 1 month.

In some embodiments, the composition comprising the solid lyophilized Compound I, or a pharmaceutically acceptable salt and/or solvate thereof, is substantially free of an antioxidant.

In other embodiments, the composition comprising the solid lyophilized Compound I, or a pharmaceutically acceptable salt and/or solvate thereof, is substantially free of ascorbic acid.

In one embodiment, the present invention provides a solid lyophilized form of Compound I, or a pharmaceutically acceptable salt and/or solvate thereof, wherein the pharmacokinetic properties and bioavailability do not significantly differ from Compound I, or a pharmaceutically acceptable salt and/or solvate thereof produced by different pathways. In another embodiment, the solid lyophilized form of Compound I, or a pharmaceutically acceptable salt and/or solvate thereof, when reconstituted as an IV infusion or solution, have substantially similar or identical bioavailability compared to a Compound I, or a pharmaceutically acceptable salt and/or solvate thereof produced by different pathways.

In one embodiment, the present invention provides a solid lyophilized form of Compound I, or a pharmaceutically acceptable salt and/or solvate thereof, wherein the solid lyophilized form comprises a bulking agent. In some embodiments, the bulking agent can be sucrose, mannitol, or trehalose. In one embodiment, the bulking agent is mannitol. In another embodiment, the bulking agent is sucrose.

In one embodiment of the present disclosure, the composition comprises a solid lyophilized form of Compound I, or a pharmaceutically acceptable salt and/or solvate thereof and a bulking agent in about 6:1, about 3:1, about 3:2, about 1:1, about 3:4, about 3:5, about 1:2, about 3:7, about 3:8, about 1:3, about 3:10, about 3:11, or about 1:4 ratio by weight, or any other value or range of values therein. In one embodiment, the composition comprises a solid lyophilized form of Compound I, or a pharmaceutically acceptable salt and/or solvate thereof and a bulking agent in about 3:2. In one embodiment, the composition comprises a solid lyophilized form of Compound I, or a pharmaceutically acceptable salt and/or solvate thereof and a bulking agent in about 3:10.

In one embodiment, the present invention provides a solid lyophilized form of Compound I, or a pharmaceutically acceptable salt and/or solvate thereof, wherein the water content of the solid lyophilized form is less than about 5%, less than about 4%, less than about 3%, less than about 2%, or less than about 1%. In one embodiment, the present invention provides a solid lyophilized form of Compound I, or a pharmaceutically acceptable salt and/or solvate thereof, wherein the water content of the solid lyophilized form is less than 1%. In some embodiments, the water content of the solid lyophilized form of Compound I, or a pharmaceutically acceptable salt and/or solvate thereof, is less than about 0.2% or less than about 0.1%. In other embodiments, the water content of the solid lyophilized form of the present disclosure is less than about 5%, about 4.5%, about 4%, about 3.5%, about 3%, about 2.5%, about 2%, about 1.5%, about 1%, about 0.9%, about 0.8%, about 0.7%, about 0.6%, about 0.5%, about 0.4%, about 0.3%, about 0.2%, about 0.1%, about 0.09%, about 0.08%, about 0.07%, about 0.06%, about 0.05%, about 0.04%, about 0.03%, about 0.02%, or about 0.01%, or any other value or range of values therein.

In one embodiment, the Compound I sample used to prepare the solid lyophilized form of Compound I comprises Compound I Polymorphs A and/or E or non-polymorphic form of Compound I. In one embodiment, the Compound I sample used to prepare the solid lyophilized form of Compound I comprises Compound I Polymorphs A and E. See WO 2017/105382, the contents of which are hereby incorporated in its entirety for all intended purposes.

In one embodiment, the solid lyophilized forms are characterized by Differential Scanning Calorimetry (DSC). The DSC thermogram is typically expressed by a diagram plotting the normalized heat flow in units of Watts/gram ("W/g") versus the measured sample temperature in degree C. The DSC thermogram is usually evaluated for extrapolated onset and end (outset) temperatures, peak temperature, and heat of fusion. A peak characteristic value of a DSC thermogram is often used as the characteristic peak to distinguish one form of a structure from others.

Those skilled in the art recognize that the measurements of the DSC thermogram for a given solid form of the same compound will vary within a margin of error. The values of a single peak characteristic value, expressed in degree C., allow appropriate error margins. Typically, the error margins are represented by "±". For example, the single peak characteristic value of about "53.09±2.0" denotes a range from about 53.09+2, i.e., about 55.09, to about 53.09-2, i.e., about 51.09. Depending on the sample preparation techniques, the calibration techniques applied to the instruments, human operational variations, and etc., those skilled in the art recognize that the appropriate error of margins for a single peak characteristic value can be ±2.5; ±2.0; ±1.5; ±1.0; ±0.5; or less.

In one embodiment, the storage of the solid lyophilized Compound I samples can take place at about −20° C., at a range of about 2° C. to about 8° C., at about 5° C., room temperature, at about 25° C., at about 30° C., at about 40° C., or at about 50° C. In one embodiment, the storage of the solid lyophilized Compound I samples can be for a duration of at least about 14 days after lyophilization, at least about 28 days after lyophilization, at least about 42 days after lyophilization, at least about 96 days after lyophilization, at least about 6 months after lyophilization, at least about 12 months after lyophilization, at least about 24 months after lyophilization, and/or at least about 36 months In one embodiment, the storage of the solid lyophilized Compound I samples can be for a duration of at least about 1 month after lyophilization, at least about 2 months after lyophilization, or at least about 3 months after lyophilization. In one embodiment, the storage of the solid lyophilized Compound I samples can be for a duration of about 14 days after lyophilization, about 28 days after lyophilization, about 42 days after lyophilization, about 96 days after lyophilization, about 6 months after lyophilization, about 12 months after lyophilization, about 24 months after lyophilization, and/or about 36 months. In one embodiment, the storage of the solid lyophilized Compound I samples can be for a duration of about 1 month after lyophilization, about 2 months after lyophilization, or about 3 months after lyophilization.

Process of Producing a Solid Lyophilized Form

In one embodiment, the present invention provides a process of producing a solid lyophilized form of a Compound I, or a pharmaceutically acceptable salt and/or solvate thereof.

In one embodiment, the present invention provides a process of producing a solid lyophilized form of a Compound I, or a pharmaceutically acceptable salt and/or solvate thereof where the solution comprising Compound I, or a pharmaceutically acceptable salt and/or solvate thereof is sparged with nitrogen prior to lyophilization. In one embodiment, all reagents and solutions used to prepare the solution comprising Compound I, or a pharmaceutically acceptable salt and/or solvate thereof is sparged with nitrogen. In one embodiment, all reagents and solutions used to prepare the solution comprising Compound I, or a pharmaceutically acceptable salt and/or solvate thereof is sparged with nitrogen at every step of the process of preparation of a lyophilized form of a Compound I, or a pharmaceutically acceptable salt and/or solvate thereof, up to the lyophilization step. In one embodiment, soluble oxygen (dissolved oxygen content) in all reagents and solutions used to prepare the solution comprising Compound I, or a pharmaceutically acceptable salt and/or solvate thereof in less than or equal to 1.0 ppm (≤1.0 ppm). In one embodiment, soluble oxygen in a solution comprising Compound I, or a pharmaceutically acceptable salt and/or solvate thereof prior to lyophilization in less than or equal to 1.0 ppm. In one embodiment, soluble oxygen is not higher than 1 ppm during the process of preparing a lyophilized form of a Compound I, or a pharmaceutically acceptable salt and/or solvate thereof. In one embodiment, soluble oxygen is measured using a dissolved oxygen meter equipped with a dissolved oxygen probe (e.g., Mettler Toledo M400; Mettler Toledo InPro6860i).

In one embodiment, a process of producing a solid lyophilized form of a Compound I, or a pharmaceutically acceptable salt and/or solvate thereof, comprises the following steps:
  a) adding a Compound I, or a pharmaceutically acceptable salt and/or solvate thereof, in about 5% to about 15% bulking agent solution;

b) adjusting pH of the solution of step a) between about 4 to about 5 with an aqueous acid, an aqueous base, and/or a buffer salt or solution;

c) freezing the solution of step b) between about −20° C. to about −60° C.;

d) optionally annealing between about −5° C. to about −50° C. then reducing temperature back to between about −30° C. to about −60° C.;

e) initiating vacuum to step c) or step d) at between about −30° C. to about −50° C.;

f) drying under reduced pressure at a first temperature between −10° C. to about −40° C.; and g) drying under reduced pressure at a second temperature between 0° C. to about 30° C.;

wherein aqueous acid is optionally added to step a) to facilitate dissolution, and step c) is optionally carried out in multiple stages at different temperatures and step f) is optionally repeated up to five times prior to step g) at a same or different temperature between −10° C. to about −40° C.

In one embodiment, water used in a preparation of solid lyophilized form of a Compound I, or a pharmaceutically acceptable salt and/or solvate thereof is degassed or sparged with nitrogen. In some embodiment, degassing or sparging with nitrogen takes place with stirring. In one embodiment, soluble oxygen in water used in a preparation of solid lyophilized form of a Compound I, or a pharmaceutically acceptable salt and/or solvate thereof is ≤1.0 ppm. In one embodiment, soluble oxygen in water used in a preparation of solid lyophilized form of a Compound I, or a pharmaceutically acceptable salt and/or solvate thereof is <1 ppm. In one embodiment, water is water for injection (WFI).

In one embodiment, about 5% to about 15% bulking agent solution is prepared using water which is degassed or sparged with nitrogen. In some embodiment, degassing or sparging with nitrogen takes place with stirring. In one embodiment, soluble oxygen in about 5% to about 15% bulking agent solution is ≤1.0 ppm. In one embodiment, soluble oxygen in about 5% to about 15% bulking agent solution is <1 ppm.

In one embodiment, an aqueous acid, an aqueous base, and/or a buffer salt or solution used in a preparation of solid lyophilized form of a Compound I, or a pharmaceutically acceptable salt and/or solvate thereof, is prepared using water which is degassed or sparged with nitrogen. In one embodiment, an aqueous acid, an aqueous base, and/or a buffer salt or solution used in a preparation of solid lyophilized form of a Compound I, or a pharmaceutically acceptable salt and/or solvate thereof, is degassed or sparged with nitrogen. In some embodiment, degassing or sparging with nitrogen takes place with stirring. In one embodiment, soluble oxygen in an aqueous acid, an aqueous base, and/or a buffer salt or solution used in a preparation of solid lyophilized form of a Compound I, or a pharmaceutically acceptable salt and/or solvate thereof is ≤1.0 ppm. In one embodiment, soluble oxygen in an aqueous acid, an aqueous base, and/or a buffer salt or solution used in a preparation of solid lyophilized form of a Compound I, or a pharmaceutically acceptable salt and/or solvate thereof is <1 ppm.

In one embodiment, about 5% to about 15% bulking agent solution comprising Compound I or a pharmaceutically acceptable salt and/or solvate thereof, is degassed or sparged with nitrogen. In some embodiment, degassing or sparging with nitrogen takes place with stirring. In some embodiment, degassing or sparging with nitrogen takes place after Compound I or a pharmaceutically acceptable salt and/or solvate thereof is dissolved in solution. In one embodiment, soluble oxygen in about 5% to about 15% bulking agent solution comprising Compound I or a pharmaceutically acceptable salt and/or solvate thereof is ≤1.0 ppm. In one embodiment, soluble oxygen in about 5% to about 15% bulking agent solution comprising Compound I or a pharmaceutically acceptable salt and/or solvate thereof is <1 ppm.

In one embodiment, the aqueous acid added to step a) and/or to adjust pH of the solution comprising Compound I, or a pharmaceutically acceptable salt and/or solvate thereof is HCl. In some embodiments, the concentration of HCl used to adjust pH is about 0.1 M to about 5 M. In other embodiments, the concentration of HCl used to adjust pH is about 0.1 M to about 2 M.

In some embodiments, the aqueous base used to adjust pH of the solution comprising Compound I, or a pharmaceutically acceptable salt and/or solvate thereof is NaOH. In some embodiments, the concentration of NaOH used to adjust pH is about 0.1 M to about 5 M. In other embodiments, the concentration of NaOH used to adjust H is about 0.1 M to about 2 M.

In some embodiments, buffer solutions are used to adjust pH of the solution. Buffer solutions commonly known in the art can be used.

In one embodiment, the solution comprising Compound I, or a pharmaceutically acceptable salt and/or solvate thereof is degassed or sparged with nitrogen after the pH of the solution is adjusted. In some embodiment, degassing or sparging with nitrogen takes place with stirring. In one embodiment, soluble oxygen in pH adjusted solution comprising Compound I, or a pharmaceutically acceptable salt and/or solvate thereof is ≤1.0 ppm. In one embodiment, soluble oxygen in pH adjusted solution comprising Compound I, or a pharmaceutically acceptable salt and/or solvate thereof is <1 ppm.

In one embodiment, the pH adjusted solution comprising Compound I, or a pharmaceutically acceptable salt and/or solvate thereof is transferred into lyophilization vials. In some embodiment, the pH adjusted solution comprising Compound I, or a pharmaceutically acceptable salt and/or solvate thereof is filled in 30 mL lyophilization vial at a fill volume of about 1 mL to about 20 mL (or in a different size lyophilization vial at a volume proportional as noted here). In one embodiment, the pH adjusted solution comprising Compound I, or a pharmaceutically acceptable salt and/or solvate thereof is filled in 30 mL lyophilization vial at a fill volume of about 5 mL or about 10 mL. In one embodiment, the pH adjusted solution comprising Compound I, or a pharmaceutically acceptable salt and/or solvate thereof is filled in 30 mL lyophilization vial at a fill volume of about 5 mL. In one embodiment, the pH adjusted solution comprising Compound I, or a pharmaceutically acceptable salt and/or solvate thereof has soluble oxygen content ≤1.0 ppm or <1 ppm.

The inventors discovered that reducing the fill volume of the lyophilization vials reduced the incident of vial breakage during lyophilization. For example, fill volume of about 5 mL can reduce vial breakage during lyophilization compared to fill volume of about 10 mL when using 30 mL lyophilization vials.

In one embodiment, freezing step c) is carried out in at least two stages. In some embodiments, a first freezing temperature is at between −20 to about −40° C. In one embodiment, the first freezing temperature is at between −25 to about −35° C. In another embodiment, the first freezing temperature is at −30° C. The ramp rate to the first freezing temperature, in one embodiment, is between about 0.1 and 0.5° C./min. The hold time at the first freezing temperature, in some embodiments, is between about 30 minutes and about 500 minutes. In one embodiment, the hold time at the first freezing temperature is between about 90 minutes and about 240 minutes.

In some embodiments, freezing is carried out at a second temperature. In one embodiment, the second freezing temperature is at between −30 to about −55° C. In one embodiment, the second freezing temperature is at between −35 to about −50° C. In another embodiment, the second freezing temperature is at −45° C. The ramp rate to the second freezing temperature, in one embodiment, is between about 0.1 and 0.5° C./min. The hold time at the second freezing temperature, in some embodiments, is between about 30 minutes and about 500 minutes. In one embodiment, the hold time at the second freezing temperature is between about 90 minutes and about 240 minutes.

In one embodiment, the an annealing process takes place subsequent to freezing the solution comprising a Compound I, or a pharmaceutically acceptable salt and/or solvate thereof. In one embodiment, the an annealing process takes place subsequent to freezing the solution comprising a Compound I, or a pharmaceutically acceptable salt and/or solvate thereof and buking agent. In some embodiments, the annealing temperature is at between about −5° C. to about −50° C. That is, in some embodiments, the annealing temperature is at about −5, −10, −15, −20, −25, −30, −35, −40, −45, or −50° C. In one embodiment, the annealing temperature is at between about −5° C. to about −25° C. In one embodiment, the annealing temperature is at about −10° C. The ramp rate to the annealing temperature, in one embodiment, is between about 0.1 and 0.5° C./min. The hold time at the annealing temperature, in some embodiments, is between about 30 minutes and about 500 minutes. In one embodiment, the hold time at the annealing temperature is between about 90 minutes and about 240 minutes.

In one embodiment, the bulking agent is used in about 600 mg, about 500 mg, about 400 mg, about 300 mg, about 200 mg, or about 100 mg per 150 mg of Compound I. In another embodiment, the bulking agent is used in about 150 mg, about 140 mg, about 130 mg, about 120 mg, about 110 mg, about 100 mg, about 90 mg, about 80 mg, about 70 mg, about 60 mg, or about 50 mg per 150 mg of Compound I. In one embodiment, the bulking agent is used in about 100 mg per 150 mg of Compound I, or any other value or range of values therein.

In one embodiment, about 200 mg, about 225 mg, about 150 mg, about 125 mg, or about 100 mg of Compound I, or any other value or range of values therein, is in every lyophilization vial. In one embodiment, about 150 mg of Compound I is in every lyophilization vial.

In one embodiment, the bulking agent is sucrose.

In one embodiment, the bulking agent is mannitol. In one embodiment, the annealing process subsequent to freezing the solution comprising a Compound I and mannitol is advantageous in promoting better crystallization of mannitol. In some embodiments, lack of annealing subsequent to freezing the solution comprising a Compound I and mannitol leads to partial crystallization of mannitol. In some embodiments, annealing subsequent to freezing the solution comprising a Compound I and mannitol at temperature between −15° C. to −20° C. leads to partial crystallization of mannitol.

In one embodiment, a drying process of the frozen solution comprising Compound I or a pharmaceutically acceptable salt and/or solvate thereof; or Compound I or a pharmaceutically acceptable salt and/or solvate thereof and a bulking agent, requires two separate temperatures. In one embodiment, the first drying temperature is between about −10° C. to about −40° C. That is, the first drying temperature is about −10, −15, −20, −25, −30, −35, or −40° C. In one embodiment, the first drying temperature is between about −10° C. to about −20° C. The ramp rate to the first drying temperature, in one embodiment, is between about 0.1 and 0.5° C./min.

In one embodiment, the first drying process requires about 1 hour to about 1 week. In some embodiments, the first drying process requires about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 36, about 60, about 84, about 108, about 132, or about 156 hours. In some embodiments, the first drying process requires about 1, about 2, about 3, about 4, about 5, about 6, or about 7 days. In one embodiment, the first drying process requires about 2 to about 4 days.

In one embodiment, the first drying process requires a pressure between about 300 mTorr to about 500 mTorr. That is, the first drying pressure is about 300, about 325, about 350, about 375, about 400, about 425, about 450, about 475, or about 500 mTorr. In one embodiment, the first drying process requires a pressure between about 300 mTorr to about 400 mTorr.

In one embodiment, the first drying process between about −10° C. to about −40° C. can be repeated at same or different temperatures prior to the second drying process.

In one embodiment, a process of producing a solid lyophilized form of Compound I or a pharmaceutically acceptable salt and/or solvate thereof requires a second drying step after the first drying step. In one embodiment, the second drying temperature is between about 0° C. to about 30° C. That is, the second drying temperature is about 0, 5, 10, 15, 20, 25, or 30° C. In one embodiment, the second drying temperature is between about 20° C. to about 30° C. The ramp rate to the second drying temperature, in one embodiment, is between about 0.1 and 0.5° C./min.

In one embodiment, the second drying process requires about 1 hour to about 1 week. In some embodiments, the second drying process requires about 1, about 2, about 3, about 4, about 5, about 6, about 7, about 8, about 9, about 10, about 11, about 12, about 13, about 14, about 15, about 16, about 17, about 18, about 19, about 20, about 21, about 22, about 23, about 24, about 36, about 60, about 84, about 108, about 132, or about 156 hours. In some embodiments, the second drying process requires about 1, about 2, about 3, about 4, about 5, about 6, or about 7 days. In one embodiment, the second drying process requires about 3 to about 24 hours.

In one embodiment, the second drying process requires a pressure between about 25 mTorr to about 100 mTorr. That is, the second drying pressure is about 25, about 30, about 35, about 40, about 45, about 50, about 55, about 60, about 65, about 70, about 75, about 80, about 85, about 90, about 95, or about 100 mTorr. In one embodiment, the first drying process requires a pressure between about 300 mTorr to about 400 mTorr.

In one embodiment, the second drying process between about 0° C. to about 30° C. can be repeated at same or different temperatures.

Exemplary process of obtaining a solid lyophilized form of Compound I is described in Examples 2 and 9. The examples further illustrate the present invention but should not be construed as in any way limiting its scope.

In one embodiment, the solid content (i.e., Compound I and bulking agent) in the lyophilization solution is less than about 10%, less than about 9%, less than about 8%, less than about 7%, less than about 6%, or less than about 5% by weight of a lyophilization solution. As used herein, the "lyophilization solution" refers to a solution containing Compound I, or a pharmaceutically acceptable salt and/or solvate thereof, prior to the solution being subjected to under the lyophilization conditions. In one embodiment, the solid content is about 6.5% by weight of the lyophilization solution. In another embodiment, the solid content is about 5% by weight of the lyophilization solution. For example, lyophilization solution can comprise 150 mg Compound I and 100 mg sucrose for total of 250 mg solid content with a 5 mL water for injection (5000 mg), which provides 6.5% solid content by weight of the lyophilization solution. In another example, lyophilization solution can comprise 150 mg Compound I and 500 mg mannitol for total of 650 mg solid content with a 10 mL water for injection (10,000 mg), which provides 6.1% solid content by weight of the lyophilization solution.

In one embodiment, the lyophilization solution comprises Compound I, or a pharmaceutically acceptable salt and/or solvate thereof, at a concentration greater than about 10 mg/mL, greater than about 11 mg/mL, greater than about 12 mg/mL, greater than about 13 mg/mL, greater than about 14 mg/mL, greater than about 15 mg/mL, greater than about 16 mg/mL, greater than about 17 mg/mL, greater than about 18 mg/mL, greater than about 19 mg/mL, greater than about 20 mg/mL, greater than about 21 mg/mL, greater than about 22 mg/mL, greater than about 23 mg/mL, greater than about 24 mg/mL, or greater than about 25 mg/mL, or any other value or range of values therein. In some embodiments, the lyophilization solution comprises Compound I, or a pharmaceutically acceptable salt and/or solvate thereof, at a concentration greater than about 15 mg/mL. In other embodiments, the lyophilization solution comprises Compound I, or a pharmaceutically acceptable salt and/or solvate thereof, at a concentration greater than about 25 mg/mL.

In one embodiment, the lyophilization is conducted in vial having a volume of about 50 cc, about 40 cc, about 30 cc, about 25 cc, about 20 cc or about 15 cc. In some embodiments, the lyophilization is conducted in a 20 cc vial. In one embodiment, the vial is de-pyrogenated glass vials.

In some embodiments, the lyophilization solution or the solid lyophilization composition does not comprise excipients that may facilitate oxidation or degradation of Compound I. In other embodiments, the lyophilization solution or the solid lyophilization composition is substantially free of excipients that may facilitate oxidation or degradation of Compound I.

Pharmaceutical Formulations

In one embodiment, the present invention provides a composition comprising Compound I, or a pharmaceutically acceptable salt and/or solvate. In one embodiment, the composition is in a solid form or a liquid form. In one embodiment, the present invention provides a composition comprising Compound I, or a pharmaceutically acceptable salt and/or solvate thereof, wherein the composition comprises less than about 1% impurities after the composition is stored at a temperature in the range of about 2° C. to about 30° C. for at least 28 days or at least 1 month.

In one embodiment, the present invention provides a liquid composition comprising Compound I, or a pharmaceutically acceptable salt and/or solvate. In some embodiments, the liquid composition is an aqueous solution. In some embodiments, the liquid composition comprising Compound I, or a pharmaceutically acceptable salt and/or solvate includes the composition just before lyophilization, as disclosed herein.

In one embodiment, the present invention provides a pharmaceutical formulation comprising Compound I, or a pharmaceutically acceptable salt and/or solvate thereof, wherein the formulation comprises less than about 3% impurities and wherein the formulation is a reconstituted solution from a solid lyophilized composition. In one embodiment, the present invention provides a pharmaceutical formulation comprising Compound I, or a pharmaceutically acceptable salt and/or solvate thereof, wherein the formulation comprises less than about 2% impurities and wherein the formulation is a reconstituted solution from a solid lyophilized composition. In one embodiment, the present invention provides a pharmaceutical formulation comprising Compound I, or a pharmaceutically acceptable salt and/or solvate thereof, wherein the formulation comprises less than about 1% impurities and wherein the formulation is a reconstituted solution from a solid lyophilized composition. In one embodiment, the present invention provides a pharmaceutical formulation comprising Compound I, or a pharmaceutically acceptable salt and/or solvate thereof, wherein the formulation comprises less than about 0.5% impurities and wherein the formulation is a reconstituted solution from a solid lyophilized composition.

In one embodiment, the formulation as described herein can be prepared by reconstituting the solid lyophilized composition of Compound I, or a pharmaceutically acceptable salt and/or solvate thereof, with any sterile diluent appropriate for human administration known in the art. Non-limiting examples of sterile diluent includes, water, glucose solution, dextrose solution, sucrose solution, and saline.

In some embodiments, the purity and impurities of the formulation comprising Compound I are measured as area % by high-performance liquid chromatography (HPLC).

In one embodiment, the present disclosure relates to a pharmaceutical formulation comprising a Compound I, or a pharmaceutically acceptable salt and/or solvate thereof, wherein the formulation comprises less than about 1% impurities; and wherein the formulation is a reconstituted solution from a solid lyophilized composition. In one embodiment, the pharmaceutical formulation comprises less than 0.5% impurities. In another embodiment, the pharmaceutical formulation comprises less than about 0.4% impurities resulting from oxidation of Compound I after the solid lyophilized composition is stored at room temperature for 28 days. In one embodiment, the pharmaceutical formulation comprises less than 0.1% impurities resulting from oxidation of Compound I after the solid lyophilized composition is stored at room temperature for 28 days, wherein the oxidation of Compound I is at one or more hydrocarbons. In another embodiment, the pharmaceutical formulation comprises less than about 0.4% impurities resulting from oxidation of Compound I after the solid lyophilized composition is stored at room temperature for less than or equal to 28 days or 1 month. In one embodiment, the pharmaceutical formulation comprises less than 0.1% impurities resulting from oxidation of Compound I after the solid lyophilized composition is stored at room temperature for less than or equal to 28 days or 1 month, wherein the oxidation of Compound I is at one or more hydrocarbons. In some embodiments, the composition is stored at room temperature for at least 28 days or 1 month.

In another embodiment, the pharmaceutical formulation comprises less than 0.1% of

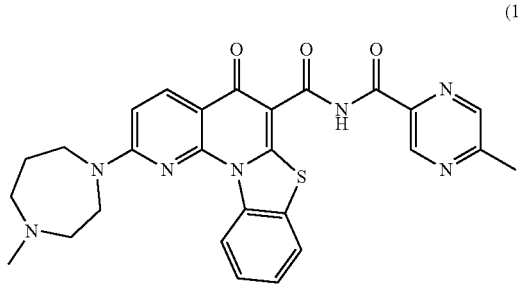

(10)

after the solid lyophilized composition is stored at room temperature for 28 days. In another embodiment, the pharmaceutical formulation comprises less than 0.1% of Compound 10 after the solid lyophilized composition is stored at room temperature for less than or equal to 28 days or 1 month. In some embodiments, the composition is stored at room temperature for at least 28 days or 1 month. In one embodiment, the pharmaceutical formulation comprises less than 0.2% impurities resulting from oxidation of Compound I after the composition is stored at room temperature for 14 days, wherein the oxidation of Compound I is a N-oxide of Compound I. In other embodiments, the pharmaceutical formulation comprises less than 0.2% of

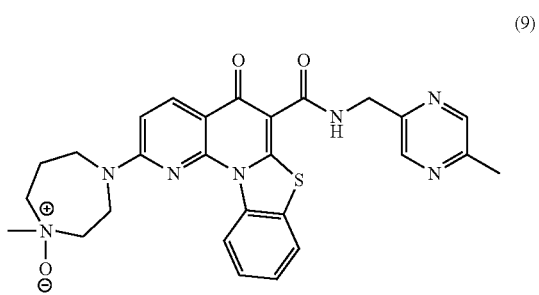

(9)

after the solid lyophilized composition is stored at room temperature for 14 days. In other embodiments, the pharmaceutical formulation comprises less than 0.2% of Compound 9 after the solid lyophilized composition is stored at room temperature for 1 month. In some embodiments, the pharmaceutical formulation comprises less than 0.3% impurities. In some embodiments, the composition is stored at room temperature for at least 14 days, at least 28 days, or at least 1 month.

In one embodiment, the composition comprising Compound I, or a pharmaceutically acceptable salt and/or solvate thereof, comprises less than about 0.1% impurities resulting from oxidation of Compound I after the composition is stored at room temperature, at about 5° C., or at 25° C./60% RH for up to 3 months, or any subranges therebetween. In one embodiment, the composition comprising Compound I, or a pharmaceutically acceptable salt and/or solvate thereof, comprises less than about 0.05% impurities resulting from oxidation of Compound I after the composition is stored at room temperature, at about 5° C., or at 25° C./60% RH for up to 3 months, or any subranges therebetween.

In one embodiment, the composition comprising Compound I, or a pharmaceutically acceptable salt and/or solvate thereof, comprises less than about 0.1% N-oxides of the Compound I after the composition is stored at room temperature, at about 5° C., or at 25° C./60% RH for up to 3 months, or any subranges therebetween. In one embodiment, the composition comprising Compound I, or a pharmaceutically acceptable salt and/or solvate thereof, comprises less than about 0.05% N-oxides of the Compound I after the composition is stored at room temperature, at about 5° C., or at 25° C./60% RH for up to 3 months, or any subranges therebetween.

In some embodiments, the composition comprising Compound I, or a pharmaceutically acceptable salt and/or solvate thereof, comprises less than about 0.2% of Compound 10, after the composition is stored at room temperature for 28 days or 1 month. In some embodiments, the composition comprising Compound I, or a pharmaceutically acceptable salt and/or solvate thereof, comprises less than about 0.1% of Compound 10, after the composition is stored at room temperature for 28 days or 1 month. In some embodiments, the composition comprising Compound I, or a pharmaceutically acceptable salt and/or solvate thereof, comprises less than about 0.2% of Compound 10, after the composition is stored at room temperature for 28 days or 1 month. In some embodiments, the composition comprising Compound I, or a pharmaceutically acceptable salt and/or solvate thereof, comprises less than about 0.2% or less than about 0.1% of Compound 10, after the composition is stored at room temperature for less than or equal to 28 days or 1 month. In one embodiment, the composition is an aqueous solution. In some embodiments, the composition is stored at room temperature for at least 28 days or at least 1 month.

In some embodiments, the composition comprising Compound I, or a pharmaceutically acceptable salt and/or solvate thereof, comprises less than about 0.3% of Compound 10, after the composition is stored at room temperature for up to about 3 months and any subranges therebetween. In some embodiments, the composition comprising Compound I, or a pharmaceutically acceptable salt and/or solvate thereof, comprises less than about 0.3% of Compound 10, after the composition is stored at room temperature for up to about 2 months and any subranges therebetween.

In some embodiments, the composition comprising Compound I, or a pharmaceutically acceptable salt and/or solvate thereof, comprises less than about 0.3% of Compound 10, after the composition is stored at 25° C./60% RH for up to about 3 months and any subranges therebetween. In some embodiments, the composition comprising Compound I, or a pharmaceutically acceptable salt and/or solvate thereof, comprises less than about 0.2% of Compound 10, after the composition is stored at 25° C./60% RH for up to about 3 months and any subranges therebetween. In some embodiments, the composition comprising Compound I, or a pharmaceutically acceptable salt and/or solvate thereof, comprises less than about 0.1% or less than about 0.05% of Compound 10, after the composition is stored at 25° C./60% RH for up to about 3 months and any subranges therebetween. In some embodiments, the composition comprising Compound I, or a pharmaceutically acceptable salt and/or solvate thereof, comprises less than about 0.3% of Compound 10, after the composition is stored at 25° C./60% RH for up to about 2 months and any subranges therebetween. In some embodiments, the composition comprising Compound I, or a pharmaceutically acceptable salt and/or solvate thereof, comprises less than about 0.2% of Compound 10, after the composition is stored at 25° C./60% RH for up to about 2 months and any subranges therebetween. In some embodiments, the composition comprising Compound I, or a pharmaceutically acceptable salt and/or solvate thereof, comprises less than about 0.3% of Compound 10, after the composition is stored at 25° C./60% RH for at least about 1 month and any subranges therebetween. In some embodiments, the composition comprising Compound I, or a pharmaceutically acceptable salt and/or solvate thereof, comprises less than about 0.3% of Compound 10, after the composition is stored at 25° C./60% RH for up to about 1 month and any subranges therebetween. In some embodiments, the composition comprising Compound I, or a pharmaceutically acceptable salt and/or solvate thereof, comprises less than about 0.2% of Compound 10, after the composition is stored at 25° C./60% RH for up to about 1 month and any subranges therebetween. In some embodiments, the composition comprising Compound I, or a pharmaceutically acceptable salt and/or solvate thereof, comprises less than about 0.1% of Compound 10, after the composition is stored at 25° C./60% RH for up to about 1 month and any subranges therebetween. In some embodiments, the composition comprising Compound I, or a pharmaceutically acceptable salt and/or solvate thereof, comprises less than about 0.05% of Compound 10, after the composition is stored at 25° C./60% RH for up to about 1 month and any subranges therebetween.

In some embodiments, the composition comprising Compound I, or a pharmaceutically acceptable salt and/or solvate thereof, comprises less than about 0.3% of Compound 10, after the composition is stored at 25° C./60% RH for less than or equal to 24 months. In some embodiments, the composition comprising Compound I, or a pharmaceutically acceptable salt and/or solvate thereof, comprises less than about 0.2% of Compound 10, after the composition is stored at 25° C./60% RH for less than or equal to 24 months. In some embodiments, the composition comprising Compound I, or a pharmaceutically acceptable salt and/or solvate thereof, comprises less than about 0.1% of Compound 10, after the composition is stored at 25° C./60% RH for less than or equal to 24 months.

In some embodiments, the composition comprising Compound I, or a pharmaceutically acceptable salt and/or solvate thereof, comprises less than about 0.6% of Compound 10, after the composition is stored at 25° C./60% RH for up to 36 months and any subranges therebetween. In some embodiments, the composition comprising Compound I, or a pharmaceutically acceptable salt and/or solvate thereof, comprises less than about 0.6% of Compound 10, after the composition is stored at 25° C./60% RH for up to 24 months and any subranges therebetween. In some embodiments, the composition comprising Compound I, or a pharmaceutically acceptable salt and/or solvate thereof, comprises less than about 0.6% of Compound 10, after the composition is stored at 25° C./60% RH for up to 12 months and any subranges therebetween.

In some embodiments, the composition comprising Compound I, or a pharmaceutically acceptable salt and/or solvate thereof, comprises less than about 0.3% of Compound 10, after the composition is stored at a temperature in the range of about 2° C. to about 8° C. for up to about 3 months and any subranges therebetween. In some embodiments, the composition comprising Compound I, or a pharmaceutically acceptable salt and/or solvate thereof, comprises less than about 0.2% of Compound 10, after the composition is stored at a temperature in the range of about 2° C. to about 8° C. for up to about 3 months and any subranges therebetween. In some embodiments, the composition comprising Compound I, or a pharmaceutically acceptable salt and/or solvate thereof, comprises less than about 0.1% of Compound 10, after the composition is stored at a temperature in the range of about 2° C. to about 8° C. for up to about 3 months and any subranges therebetween. In some embodiments, the composition comprising Compound I, or a pharmaceutically acceptable salt and/or solvate thereof, comprises less than about 0.05% of Compound 10, after the composition is stored at a temperature in the range of about 2° C. to about 8° C. for up to about 3 months and any subranges therebetween.

In some embodiments, the composition comprising Compound I, or a pharmaceutically acceptable salt and/or solvate thereof, comprises less than about 0.1% of Compound 10, after the composition is stored at about 5° C. for up to 3 months and any subranges therebetween. In some embodiments, the composition comprising Compound I, or a pharmaceutically acceptable salt and/or solvate thereof, comprises less than about 0.05% of Compound 10, after the composition is stored at about 5° C. for up to 3 months and any subranges therebetween.

In some embodiments, the composition comprising Compound I, or a pharmaceutically acceptable salt and/or solvate thereof, comprises less than about 0.3% of Compound 10, after the composition is stored at 30° C./65% RH for up to about 3 months and any subranges therebetween. In some embodiments, the composition comprising Compound I, or a pharmaceutically acceptable salt and/or solvate thereof, comprises less than about 0.2% of Compound 10, after the composition is stored at 30° C./65% RH for up to about 2 months and any subranges therebetween. In some embodiments, the composition comprising Compound I, or a pharmaceutically acceptable salt and/or solvate thereof, comprises less than about 0.1% of Compound 10, after the composition is stored at 30° C./65% RH for up to about 1 month and any subranges therebetween. In some embodiments, the composition is stored at room temperature for at least 1 month.

In some embodiments, the composition comprising Compound I, or a pharmaceutically acceptable salt and/or solvate thereof, comprises less than about 0.5% of Compound 10, after the composition is stored at 40° C./75% RH for up to about 3 months and any subranges therebetween. In some embodiments, the composition comprising Compound I, or a pharmaceutically acceptable salt and/or solvate thereof, comprises less than about 0.4% of Compound 10, after the composition is stored at 40° C./75% RH for up to about 2 months and any subranges therebetween. In some embodiments, the composition comprising Compound I, or a pharmaceutically acceptable salt and/or solvate thereof, comprises less than about 0.2% of Compound 10, after the composition is stored at 40° C./75% RH for up to about 1 month and any subranges therebetween. In some embodiments, the composition is stored at room temperature for at least 1 month.

In some embodiments, the composition comprising Compound I, or a pharmaceutically acceptable salt and/or solvate thereof, comprises less than about 0.2% of Compound 9, after the composition is stored at room temperature for 28 days or 1 month. In some embodiments, the composition comprising Compound I, or a pharmaceutically acceptable salt and/or solvate thereof, comprises less than about 0.1% of Compound 9, after the composition is stored at room temperature for 28 days or 1 month. In some embodiments, the composition comprising Compound I, or a pharmaceutically acceptable salt and/or solvate thereof, comprises less than about 0.05% of Compound 9, after the composition is stored at room temperature for 28 days or 1 month. In some embodiments, the composition comprising Compound I, or a pharmaceutically acceptable salt and/or solvate thereof, comprises less than about 0.2% of Compound 9, after the composition is stored at room temperature for 28 days or 1 month. In some embodiments, the composition comprising Compound I, or a pharmaceutically acceptable salt and/or solvate thereof, comprises less than about 0.2% or less than about 0.1% of Compound 9, after the composition is stored at room temperature for less than or equal to 28 days or 1 month. In one embodiment, the composition is an aqueous solution. In some embodiments, the composition comprising Compound I, or a pharmaceutically acceptable salt and/or solvate thereof, comprises less than about 0.05% of Compound 9, after the composition is stored at room temperature for less than or equal to 28 days or 1 month. In one embodiment, the composition is an aqueous solution. In some embodiments, the composition is stored at room temperature for at least 28 days or 1 month.

In some embodiments, the composition comprising Compound I, or a pharmaceutically acceptable salt and/or solvate thereof, comprises less than about 0.1% of Compound 9, after the composition is stored at room temperature for up to about 3 months and any subranges therebetween. In some embodiments, the composition comprising Compound I, or a pharmaceutically acceptable salt and/or solvate thereof, comprises less than about 0.0.5% of Compound 9, after the composition is stored at room temperature for up to about 3 months and any subranges therebetween.

In some embodiments, the composition comprising Compound I, or a pharmaceutically acceptable salt and/or solvate thereof, comprises less than about 0.2% of Compound 9, after the composition is stored at 25° C./60% RH for up to about 3 months and any subranges therebetween. In some embodiments, the composition comprising Compound I, or a pharmaceutically acceptable salt and/or solvate thereof, comprises less than about 0.1% of Compound 9, after the composition is stored at 25° C./60% RH for up to about 3 months and any subranges therebetween. In some embodiments, the composition comprising Compound I, or a pharmaceutically acceptable salt and/or solvate thereof, comprises less than about 0.05% of Compound 9, after the composition is stored at 25° C./60% RH for up to about 3 months and any subranges therebetween. In some embodiments, the composition is stored up to about 2 months or up to about 1 month. In some embodiments, the composition is stored at room temperature for at least 1 month.

In some embodiments, the composition comprising Compound I, or a pharmaceutically acceptable salt and/or solvate thereof, comprises less than about 0.3% of Compound 9, after the composition is stored at 25° C./60% RH for less than or equal to 24 months. In some embodiments, the composition comprising Compound I, or a pharmaceutically acceptable salt and/or solvate thereof, comprises less than about 0.2% of Compound 9, after the composition is stored at 25° C./60% RH for less than or equal to 24 months. In some embodiments, the composition comprising Compound I, or a pharmaceutically acceptable salt and/or solvate thereof, comprises less than about 0.15% of Compound 9, after the composition is stored at 25° C./60% RH for less than or equal to 24 months.

In some embodiments, the composition comprising Compound I, or a pharmaceutically acceptable salt and/or solvate thereof, comprises less than about 0.6% of Compound 9, after the composition is stored at 25° C./60% RH for up to 36 months and any subranges therebetween. In some embodiments, the composition comprising Compound I, or a pharmaceutically acceptable salt and/or solvate thereof, comprises less than about 0.6% of Compound 9, after the composition is stored at 25° C./60% RH for up to 24 months and any subranges therebetween. In some embodiments, the composition comprising Compound I, or a pharmaceutically acceptable salt and/or solvate thereof, comprises less than about 0.6% of Compound 9, after the composition is stored at 25° C./60% RH for up to 12 months and any subranges therebetween.

In some embodiments, the composition comprising Compound I, or a pharmaceutically acceptable salt and/or solvate thereof, comprises less than about 0.2% of Compound 9, after the composition is stored at a temperature in the range of about 2° C. to about 8° C. for up to about 3 months and any subranges therebetween. In some embodiments, the composition comprising Compound I, or a pharmaceutically acceptable salt and/or solvate thereof, comprises less than about 0.1% of Compound 9, after the composition is stored at a temperature in the range of about 2° C. to about 8° C. for up to about 3 months and any subranges therebetween. In some embodiments, the composition comprising Compound I, or a pharmaceutically acceptable salt and/or solvate thereof, comprises less than about 0.05% of Compound 9, after the composition is stored at a temperature in the range of about 2° C. to about 8° C. for up to about 3 months and any subranges therebetween. In some embodiments, the composition is stored up to about 2 months or up to about 1 month. In some embodiments, the composition is stored at room temperature for at least 1 month.

In some embodiments, the composition comprising Compound I, or a pharmaceutically acceptable salt and/or solvate thereof, comprises less than about 0.2% of Compound 9, after the composition is stored at 30° C./65% RH for up to about 3 months and any subranges therebetween. In some embodiments, the composition comprising Compound I, or a pharmaceutically acceptable salt and/or solvate thereof, comprises less than about 0.1% of Compound 9, after the composition is stored at 30° C./65% RH for up to about 3 months and any subranges therebetween. In some embodiments, the composition comprising Compound I, or a pharmaceutically acceptable salt and/or solvate thereof, comprises less than about 0.05% of Compound 9, after the composition is stored at 30° C./65% RH for up to about 3 months and any subranges therebetween. In some embodiments, the composition is stored up to about 2 months or up to about 1 month. In some embodiments, the composition is stored at room temperature for at least 1 month.

In some embodiments, the composition comprising Compound I, or a pharmaceutically acceptable salt and/or solvate thereof, comprises less than about 0.2% of Compound 9, after the composition is stored at 40° C./75% RH for up to about 3 months and any subranges therebetween. In some embodiments, the composition comprising Compound I, or a pharmaceutically acceptable salt and/or solvate thereof, comprises less than about 0.1% of Compound 9, after the composition is stored at 40° C./75% RH for up to about 3 months and any subranges therebetween. In some embodiments, the composition is stored up to about 2 months or up to about 1 month. In some embodiments, the composition is stored at room temperature for at least 1 month.

In some embodiments, the composition comprising Compound I, or a pharmaceutically acceptable salt and/or solvate thereof, comprises less than 0.15% of Compound 9, after the composition is stored at 5° C. for 28 days or 1 month. In some embodiments, the composition comprising Compound I, or a pharmaceutically acceptable salt and/or solvate thereof, comprises less than 0.15% of Compound 9, after the composition is stored at 5° C. in ambient relative humidity for 28 days or 1 month. In some embodiments, the composition comprising Compound I, or a pharmaceutically acceptable salt and/or solvate thereof, comprises less than 0.15% of Compound 9, after the composition is stored at 5° C. for 3 months. In some embodiments, the composition comprising Compound I, or a pharmaceutically acceptable salt and/or solvate thereof, comprises less than 0.15% of Compound 9, after the composition is stored at 5° C. in ambient relative humidity for 3 months. In some embodiments, the composition comprising Compound I, or a pharmaceutically acceptable salt and/or solvate thereof, comprises less than 0.13% of Compound 9, after the composition is stored at 5° C. in ambient relative humidity for 3 months. In some embodiments, the composition comprising Compound I, or a pharmaceutically acceptable salt and/or solvate thereof, comprises less than 0.05% of Compound 10, after the composition is stored at 5° C. for 3 months. In some embodiments, the composition comprising Compound I, or a pharmaceutically acceptable salt and/or solvate thereof, comprises less than 0.05% of Compound 10, after the composition is stored at 5° C. in ambient relative humidity for 3 months.

In some embodiments, the composition comprising Compound I, or a pharmaceutically acceptable salt and/or solvate thereof, comprises less than 1% of water content as measured by USP <921 Method 1c> after the composition is stored at 5° C. in ambient relative humidity for 28 days or 1 month. In some embodiments, the composition comprising Compound I, or a pharmaceutically acceptable salt and/or solvate thereof, comprises less than 0.5% of water content as measured by USP <921 Method 1c> after the composition is stored at 5° C. in ambient relative humidity for 28 days or 1 month. In some embodiments, the composition comprising Compound I, or a pharmaceutically acceptable salt and/or solvate thereof, comprises less than 0.25% of water content as measured by USP <921 Method 1c> after the composition is stored at 5° C. in ambient relative humidity for 28 days or 1 month. In some embodiments, the composition comprising Compound I, or a pharmaceutically acceptable salt and/or solvate thereof, comprises less than 0.1% of water content as measured by USP <921 Method 1c> after the composition is stored at 5° C. in ambient relative humidity for 28 days or 1 month.

In some embodiments, the composition comprising Compound I, or a pharmaceutically acceptable salt and/or solvate thereof, comprises less than 1% of water content as measured by USP <921 Method 1c> after the composition is stored at 5° C. in ambient relative humidity for 3 months. In some embodiments, the composition comprising Compound I, or a pharmaceutically acceptable salt and/or solvate thereof, comprises less than 0.5% of water content as measured by USP <921 Method 1c> after the composition is stored at 5° C. in ambient relative humidity for 3 months. In some embodiments, the composition comprising Compound I, or a pharmaceutically acceptable salt and/or solvate thereof, comprises less than 0.25% of water content as measured by USP <921 Method 1c> after the composition is stored at 5° C. in ambient relative humidity for 3 months. In some embodiments, the composition comprising Compound I, or a pharmaceutically acceptable salt and/or solvate thereof, comprises less than 0.1% of water content as measured by USP <921 Method 1c> after the composition is stored at 5° C. in ambient relative humidity for 3 months.

In some embodiments, the composition comprising Compound I, or a pharmaceutically acceptable salt and/or solvate thereof, comprises less than 0.15% of Compound 9, after the composition is stored at 25° C./60% RH for 3 months. In some embodiments, the composition comprising Compound I, or a pharmaceutically acceptable salt and/or solvate thereof, comprises less than 0.13% of Compound 9, after the composition is stored at 25° C./60% RH for 3 months. In some embodiments, the composition comprising Compound I, or a pharmaceutically acceptable salt and/or solvate thereof, comprises less than 0.05% of Compound 10, after the composition is stored at 25° C./60% RH for 3 months.

In some embodiments, the composition comprising Compound I, or a pharmaceutically acceptable salt and/or solvate thereof, comprises less than 1% of water content as measured by USP <921 Method 1c> after the composition is stored at 25° C./60% RH for 28 days or 1 month. In some embodiments, the composition comprising Compound I, or a pharmaceutically acceptable salt and/or solvate thereof, comprises less than 0.5% of water content as measured by USP <921 Method 1c> after the composition is stored at 25° C./60% RH for 28 days or 1 month. In some embodiments, the composition comprising Compound I, or a pharmaceutically acceptable salt and/or solvate thereof, comprises less than 0.25% of water content as measured by USP <921 Method 1c> after the composition is stored at 25° C./60% RH for 28 days or 1 month. In some embodiments, the composition comprising Compound I, or a pharmaceutically acceptable salt and/or solvate thereof, comprises less than 0.1% of water content as measured by USP <921 Method 1c> after the composition is stored at 25° C./60% RH for 28 days or 1 month.

In some embodiments, the composition comprising Compound I, or a pharmaceutically acceptable salt and/or solvate thereof, comprises less than 1% of water content as measured by USP <921 Method 1c> after the composition is stored at 25° C./60% RH for 3 months. In some embodiments, the composition comprising Compound I, or a pharmaceutically acceptable salt and/or solvate thereof, comprises less than 0.5% of water content as measured by USP <921 Method 1c> after the composition is stored at 25° C./60% RH for 3 months. In some embodiments, the composition comprising Compound I, or a pharmaceutically acceptable salt and/or solvate thereof, comprises less than 0.25% of water content as measured by USP <921 Method 1c> after the composition is stored at 25° C./60% RH for 3 months. In some embodiments, the composition comprising Compound I, or a pharmaceutically acceptable salt and/or solvate thereof, comprises less than 0.15% of water content as measured by USP <921 Method 1c> after the composition is stored at 25° C./60% RH for 3 months.

In one embodiment, the present invention provides a composition or a pharmaceutical composition comprising Compound I, or a pharmaceutically acceptable salt and/or solvate thereof, wherein the composition further comprises at least one of Compounds 1, 2, 3, 4, 5, 6, 7, 8, 9, 10, 11, and 12. In one embodiment, the present invention provides a composition or a pharmaceutical composition comprising Compound I, or a pharmaceutically acceptable salt and/or solvate thereof, wherein the composition further comprises at least one of Compounds 1, 7, 8, 9, and 10. In one embodiment, the present invention provides a composition or a pharmaceutical composition comprising Compound I, or a pharmaceutically acceptable salt and/or solvate thereof, wherein the composition further comprises at least one of Compounds 9 and 10. In one embodiment, the present invention provides a composition or a pharmaceutical composition comprising Compound I, or a pharmaceutically acceptable salt and/or solvate thereof, wherein the composition further comprises Compounds 9 and 10.

In one embodiment, the present disclosure provides a pharmaceutical composition comprising Compound I or a pharmaceutically acceptable salt and/or solvate thereof; wherein the composition further comprises Compound 1. In one embodiment, the present disclosure provides a pharmaceutical composition comprising Compound I or a pharmaceutically acceptable salt and/or solvate thereof; wherein the composition further comprises Compound 7. In one embodiment, the present disclosure provides a pharmaceutical composition comprising Compound I or a pharmaceutically acceptable salt and/or solvate thereof; wherein the composition further comprises Compound 8. In one embodiment, the present disclosure provides a pharmaceutical composition comprising Compound I or a pharmaceutically acceptable salt and/or solvate thereof; wherein the composition further comprises Compound 9. In one embodiment, the present disclosure provides a pharmaceutical composition comprising Compound I or a pharmaceutically acceptable salt and/or solvate thereof; wherein the composition further comprises Compound 10.

In one embodiment, the pharmaceutical composition comprises Compound I or a pharmaceutically acceptable salt and/or solvate thereof, and Compound 9 and Compound 10. In one embodiment, the pharmaceutical composition comprises Compound I or a pharmaceutically acceptable salt and/or solvate thereof, Compound 1, Compound 7, Compound 8, Compound 9 and Compound 10. In one embodiment, the pharmaceutical composition further comprises one or more compounds selected from the group consisting of Compound 2, Compound 3, Compound 4, Compound 5, Compound 6, Compound 11, and Compound 12. In one embodiment, the pharmaceutical composition comprises Compound I or a pharmaceutically acceptable salt and/or solvate thereof, and Compound 1-12.

In another embodiment, the formulation comprising Compound I, or a pharmaceutically acceptable salt and/or solvate thereof, comprises less than about 3% impurities after the solid lyophilized composition is stored at room temperature for 28 days. In another embodiment, the formulation comprising Compound I, or a pharmaceutically acceptable salt and/or solvate thereof, comprises less than about 2% impurities after the solid lyophilized composition is stored at room temperature for 28 days. In another embodiment, the formulation comprising Compound I, or a pharmaceutically acceptable salt and/or solvate thereof, comprises less than about 1% impurities after the solid lyophilized composition is stored at room temperature for 28 days. In another embodiment, the formulation comprising Compound I, or a pharmaceutically acceptable salt and/or solvate thereof, comprises less than about 0.5% impurities after the solid lyophilized composition is stored at room temperature for 28 days. In some embodiments, the composition is stored at room temperature for at least 28 days.

In another embodiment, the formulation comprising Compound I, or a pharmaceutically acceptable salt and/or solvate thereof, comprises less than about 3% impurities after the is stored at room temperature for less than or equal to 28 days or 1 month. In another embodiment, the formulation comprising Compound I, or a pharmaceutically acceptable salt and/or solvate thereof, comprises less than about 2% impurities after the solid lyophilized composition is stored at room temperature for less than or equal to 28 days or 1 month. In another embodiment, the formulation comprising Compound I, or a pharmaceutically acceptable salt and/or solvate thereof, comprises less than about 1% impurities after the solid lyophilized composition is stored at room temperature for 28 days or 1 month. In another embodiment, the formulation comprising Compound I, or a pharmaceutically acceptable salt and/or solvate thereof, comprises less than about 0.5% impurities after the solid lyophilized composition is stored at room temperature for less than or equal to 28 days or 1 month. In some embodiments, the composition is stored at room temperature for at least 28 days or 1 month.

In another embodiment, the formulation comprising Compound I, or a pharmaceutically acceptable salt and/or solvate thereof, comprises less than about 3% impurities after the formulation is stored at room temperature for less than or equal to 28 days or 1 month. In another embodiment, the formulation comprising Compound I, or a pharmaceutically acceptable salt and/or solvate thereof, comprises less than about 2% impurities after the formulation is stored at room temperature for less than or equal to 28 days or 1 month. In another embodiment, the formulation comprising Compound I, or a pharmaceutically acceptable salt and/or solvate thereof, comprises less than about 1% impurities after the formulation is stored at room temperature for 28 days or 1 month. In another embodiment, the formulation comprising Compound I, or a pharmaceutically acceptable salt and/or solvate thereof, comprises less than about 0.5% impurities after the formulation is stored at room temperature for less than or equal to 28 days or 1 month. In some embodiments, the composition is stored at room temperature for at least 28 days or at least 1 month.

In some embodiments, the formulation comprising Compound I, or a pharmaceutically acceptable salt and/or solvate thereof, comprises less than about 1% impurities after the solid lyophilized composition is stored at room temperature for at least about 7 days, at least about 14 days, at least about 28 days, at least about 42 days, or at least about 96 days. In some embodiments, the formulation comprising Compound I, or a pharmaceutically acceptable salt and/or solvate thereof, comprises less than about 1% impurities after the solid lyophilized composition is stored at room temperature for about 7 days, about 14 days, about 28 days, about 42 days, or about 96 days. In some embodiments, the formulation comprising Compound I, or a pharmaceutically acceptable salt and/or solvate thereof, comprises less than about 1% impurities after the solid lyophilized composition is stored at room temperature for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, or about 15 weeks. In other embodiments, the formulation comprising Compound I, or a pharmaceutically acceptable salt and/or solvate thereof, comprises less than about 1% impurities after the solid lyophilized composition is stored at room temperature for about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months.

In some embodiments, the formulation comprising Compound I, or a pharmaceutically acceptable salt and/or solvate thereof, comprises less than about 1% impurities after the formulation is stored at room temperature for at least about 7 days, at least about 14 days, at least about 28 days, at least about 42 days, or at least about 96 days. In some embodiments, the formulation comprising Compound I, or a pharmaceutically acceptable salt and/or solvate thereof, comprises less than about 1% impurities after the formulation is stored at room temperature for about 7 days, about 14 days, about 28 days, about 42 days, or about 96 days. In some embodiments, the formulation comprising Compound I, or a pharmaceutically acceptable salt and/or solvate thereof, comprises less than about 1% impurities after the formulation is stored at room temperature for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, or about 15 weeks. In other embodiments, the formulation comprising Compound I, or a pharmaceutically acceptable salt and/or solvate thereof, comprises less than about 1% impurities after the formulation is stored at room temperature for about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months.

In some embodiments, the formulation comprising Compound I, or a pharmaceutically acceptable salt and/or solvate thereof, comprises less than about 2% impurities after the formulation is stored at room temperature for at least about 7 days, at least about 14 days, at least about 28 days, at least about 42 days, or at least about 96 days, or any subranges therebetween. In some embodiments, the formulation comprising Compound I, or a pharmaceutically acceptable salt and/or solvate thereof, comprises less than about 2% impurities after the formulation is stored at room temperature for about 7 days, about 14 days, about 28 days, about 42 days, or about 96 days, or any subranges therebetween. In some embodiments, the formulation comprising Compound I, or a pharmaceutically acceptable salt and/or solvate thereof, comprises less than about 1% impurities after the formulation is stored at a temperature in the range of about 2° C. to about 30° C. for about 7 days, about 14 days, about 28 days, about 42 days, or about 96 days, or any subranges therebetween.

In some embodiments, the formulation comprising Compound I, or a pharmaceutically acceptable salt and/or solvate thereof, comprises less than about 2% impurities after the formulation is stored at a temperature in the range of about 2° C. to about 30° C. for at least about 7 days, at least about 14 days, at least about 28 days, at least about 42 days, or at least about 96 days, or any subranges therebetween. In some embodiments, the formulation comprising Compound I, or a pharmaceutically acceptable salt and/or solvate thereof, comprises less than about 2% impurities after the formulation is stored at a temperature in the range of about 2° C. to about 30° C. for about 7 days, about 14 days, about 28 days, about 42 days, or about 96 days, or any subranges therebetween. In some embodiments, the formulation comprising Compound I, or a pharmaceutically acceptable salt and/or solvate thereof, comprises less than about 1% impurities after the formulation is stored at a temperature in the range of about 2° C. to about 30° C. for about 7 days, about 14 days, about 28 days, about 42 days, or about 96 days, or any subranges therebetween.

In some embodiments, the formulation comprising Compound I, or a pharmaceutically acceptable salt and/or solvate thereof, comprises less than about 1% impurities after the solid lyophilized composition is stored at 50° C. for at least about 7 days, at least about 14 days, at least about 28 days, at least about 42 days, or at least about 96 days. In some embodiments, the formulation comprising Compound I, or a pharmaceutically acceptable salt and/or solvate thereof, comprises less than about 1% impurities after the solid lyophilized composition is stored at 50° C. for about 7 days, about 14 days, about 28 days, about 42 days, or about 96 days. In some embodiments, the formulation comprising Compound I, or a pharmaceutically acceptable salt and/or solvate thereof, comprises less than about 1% impurities after the solid lyophilized composition is stored at 50° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, or about 15 weeks. In other embodiments, the formulation comprising Compound I, or a pharmaceutically acceptable salt and/or solvate thereof, comprises less than about 1% impurities after the solid lyophilized composition is stored at 50° C. for about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months.

In some embodiments, the formulation comprising Compound I, or a pharmaceutically acceptable salt and/or solvate thereof, comprises less than about 1% impurities after the solid lyophilized composition is stored at 5° C. for at least about 7 days, at least about 14 days, at least about 28 days, at least about 42 days, or at least about 96 days. In some embodiments, the formulation comprising Compound I, or a pharmaceutically acceptable salt and/or solvate thereof, comprises less than about 1% impurities after the solid lyophilized composition is stored at 5° C. for about 7 days, about 14 days, about 28 days, about 42 days, or about 96 days. In some embodiments, the formulation comprising Compound I, or a pharmaceutically acceptable salt and/or solvate thereof, comprises less than about 1% impurities after the solid lyophilized composition is stored at 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, or about 15 weeks. In other embodiments, the formulation comprising Compound I, or a pharmaceutically acceptable salt and/or solvate thereof, comprises less than about 1% impurities after the solid lyophilized composition is stored at 5° C. for about 1 month, about 2 months, about 3 months, about 4 months, about 5 months, about 6 months, about 7 months, about 8 months, about 9 months, about 10 months, about 11 months, about 12 months, about 13 months, about 14 months, about 15 months, about 16 months, about 17 months, about 18 months, about 19 months, about 20 months, about 21 months, about 22 months, about 23 months, or about 24 months.

In some embodiments, the formulation comprising Compound I, or a pharmaceutically acceptable salt and/or solvate thereof, comprises less than about 3% impurities after the formulation is stored at 40° C./75% RH for at least about 7 days, at least about 14 days, at least about 28 days, at least about 42 days, or at least about 96 days, or any subranges therebetween. In some embodiments, the formulation comprising Compound I, or a pharmaceutically acceptable salt and/or solvate thereof, comprises less than about 3% impurities after the formulation is stored at 40° C./75% RH for about 7 days, about 14 days, about 28 days, about 42 days, or about 96 days, or any subranges therebetween. In some embodiments, the formulation comprising Compound I, or a pharmaceutically acceptable salt and/or solvate thereof, comprises less than about 1% impurities after the formulation is stored at 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, or about 15 weeks. In other embodiments, the formulation comprising Compound I, or a pharmaceutically acceptable salt and/or solvate thereof, comprises less than about 1% impurities after the formulation is stored at 40° C./75% RH for about 1 month, about 2 months, or about 3 months, or any subranges therebetween.

In some embodiments, the formulation comprising Compound I, or a pharmaceutically acceptable salt and/or solvate thereof, comprises less than about 3% impurities after the formulation is stored at 40° C./75% RH for at least about 7 days, at least about 14 days, at least about 28 days, at least about 42 days, or at least about 96 days, or any subranges therebetween. In some embodiments, the formulation comprising Compound I, or a pharmaceutically acceptable salt and/or solvate thereof, comprises less than about 3% impurities after the formulation is stored at 40° C./75% RH for about 7 days, about 14 days, about 28 days, about 42 days, or about 96 days, or any subranges therebetween. In some embodiments, the formulation comprising Compound I, or a pharmaceutically acceptable salt and/or solvate thereof, comprises less than about 1% impurities after the formulation is stored at 5° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, or about 15 weeks. In other embodiments, the formulation comprising Compound I, or a pharmaceutically acceptable salt and/or solvate thereof, comprises less than about 1% impurities after the formulation is stored at 40° C./75% RH for about 1 month, about 2 months, or about 3 months, or any subranges therebetween.

In one embodiment, the formulation comprising Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% impurities resulting from oxidation of Compound I after the solid lyophilized composition is stored at room temperature for 28 days. In some embodiments, the formulation comprising Compound I, or a pharmaceutically acceptable salt and/or solvate thereof, comprises less than about 0.4%, less than about 0.3%, or less than about 0.2% impurities resulting from oxidation of Compound I after the solid lyophilized composition is stored at room temperature for 28 days.

In one embodiment, the formulation comprising Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% impurities resulting from oxidation of Compound I after the solid lyophilized composition is stored at room temperature for less than or equal to 28 days. In some embodiments, the formulation comprising Compound I, or a pharmaceutically acceptable salt and/or solvate thereof, comprises less than about 0.4%, less than about 0.3%, or less than about 0.2% impurities resulting from oxidation of Compound I after the solid lyophilized composition is stored at room temperature for less than or equal to 28 days.

In one embodiment, the formulation comprising Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% impurities resulting from oxidation of Compound I after the formulation is stored at room temperature for less than or equal to 28 days. In some embodiments, the formulation comprising Compound I, or a pharmaceutically acceptable salt and/or solvate thereof, comprises less than about 0.4%, less than about 0.3%, or less than about 0.2% impurities resulting from oxidation of Compound I after the formulation is stored at room temperature for less than or equal to 28 days.

In one embodiment, the formulation comprising Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% impurities resulting from oxidation of Compound I after the solid lyophilized composition is stored at room temperature for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, or about 15 weeks.

In one embodiment, the formulation comprising Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% impurities resulting from oxidation of Compound I after the formulation is stored at room temperature for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, or about 15 weeks, or any subranges therebetween.

In one embodiment, the formulation comprising Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% impurities resulting from oxidation of Compound I after the solid lyophilized composition is stored at a temperature in the range of about 2° C. to about 30° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, or about 15 weeks, about 6 months, about 9 months, about 12 months, about 18 months, about 24 months, about 36 months, or any subranges therebetween.

In one embodiment, the formulation comprising Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% impurities resulting from oxidation of Compound I after the formulation is stored at a temperature in the range of about 2° C. to about 30° C. for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, or about 15 weeks, or any subranges therebetween.

In one embodiment, the formulation comprising Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% impurities resulting from oxidation of Compound I after the formulation is stored at room temperature for up to about 3 months. In some embodiments, the formulation comprising Compound I, or a pharmaceutically acceptable salt and/or solvate thereof, comprises less than about 0.4%, less than about 0.3%, or less than about 0.2% impurities resulting from oxidation of Compound I after the formulation is stored at room temperature for up to about 3 months.

In one embodiment, the formulation comprising Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% impurities resulting from oxidation of Compound I after the formulation is stored at room temperature for up to about 24 months. In some embodiments, the formulation comprising Compound I, or a pharmaceutically acceptable salt and/or solvate thereof, comprises less than about 0.4%, less than about 0.3%, or less than about 0.2% impurities resulting from oxidation of Compound I after the formulation is stored at room temperature for up to about 24 months.

In one embodiment, the formulation comprising Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% impurities resulting from oxidation of Compound I after the formulation is stored at room temperature for up to about 36 months. In some embodiments, the formulation comprising Compound I, or a pharmaceutically acceptable salt and/or solvate thereof, comprises less than about 0.4%, less than about 0.3%, or less than about 0.2% impurities resulting from oxidation of Compound I after the formulation is stored at room temperature for up to about 36 months.

In another embodiment, the formulation comprising Compound I, or a pharmaceutically acceptable salt and/or solvate thereof, is substantially free of an oxidization product of a Compound I, or a pharmaceutically acceptable salt and/or solvate thereof. In one embodiment, maintaining soluble oxygen ≤1.0 ppm during the process of preparing the solid lyophilized Compound I, or a pharmaceutically acceptable salt and/or solvate thereof is critical in providing the formulation that is substantially free of an oxidization product of a Compound I, or a pharmaceutically acceptable salt and/or solvate thereof. In one embodiment, maintaining soluble oxygen <1.0 ppm during the process of preparing the solid lyophilized Compound I, or a pharmaceutically acceptable salt and/or solvate thereof is critical in providing the formulation that is substantially free of an oxidization product of a Compound I, or a pharmaceutically acceptable salt and/or solvate thereof.

In one embodiment, maintaining soluble oxygen ≤1.0 ppm at the time of preparing a liquid formulation comprising Compound I, or a pharmaceutically acceptable salt and/or solvate thereof is critical in providing the formulation that is substantially free of an oxidization product of a Compound I, or a pharmaceutically acceptable salt and/or solvate thereof. In one embodiment, maintaining soluble oxygen <1.0 ppm during the process of preparing a liquid formulation comprising Compound I, or a pharmaceutically acceptable salt and/or solvate thereof is critical in providing the formulation that is substantially free of an oxidization product of a Compound I, or a pharmaceutically acceptable salt and/or solvate thereof.

In one embodiment, the oxidation product of Compound I is selected from: Compounds 2, 3, 4, 9, or 10. In one embodiment, the oxidation product is a ketone product. In some embodiments, the oxidation product is an N-oxide product.

In some embodiments, the formulation comprising Compound I, or a pharmaceutically acceptable salt and/or solvate thereof, comprises less than about 0.1% of Compound 10, after the solid lyophilized composition is stored at room temperature for 28 days. In some embodiments, the formulation comprising Compound I, or a pharmaceutically acceptable salt and/or solvate thereof, comprises less than about 0.1% of Compound 10, after the solid lyophilized composition is stored at room temperature for 1 month. In some embodiments, the formulation comprising Compound I, or a pharmaceutically acceptable salt and/or solvate thereof, comprises less than about 0.1% of Compound 10 after the formulation is stored at room temperature for 28 days or 1 month. In one embodiment, the formulation is an aqueous liquid formulation.

In one embodiment, the formulation comprising the solid lyophilized Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% of N-oxides of Compound I after the solid lyophilized composition is stored at room temperature for 14 days. In some embodiments, the formulation comprising Compound I, or a pharmaceutically acceptable salt and/or solvate thereof, comprises less than about 0.3%, less than about 0.2%, or less than about 0.1% of N-oxides of Compound I after the solid lyophilized composition is stored at room temperature for 14 days.

In one embodiment, the formulation comprising the solid lyophilized Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% of N-oxides of Compound I after the solid lyophilized composition is stored at room temperature for 1 month. In some embodiments, the formulation comprising Compound I, or a pharmaceutically acceptable salt and/or solvate thereof, comprises less than about 0.3%, less than about 0.2%, or less than about 0.1% of N-oxides of Compound I after the solid lyophilized composition is stored at room temperature for 1 month.

In one embodiment, the formulation comprising Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% of N-oxides of Compound I after the formulation is stored at room temperature for 14 days. In some embodiments, the formulation comprising Compound I, or a pharmaceutically acceptable salt and/or solvate thereof, comprises less than about 0.3%, less than about 0.2%, or less than about 0.1% of N-oxides of Compound I after the formulation is stored at room temperature for 14 days.

In one embodiment, the formulation comprising Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% of N-oxides of Compound I after the formulation is stored at room temperature for 1 month. In some embodiments, the formulation comprising Compound I, or a pharmaceutically acceptable salt and/or solvate thereof, comprises less than about 0.3%, less than about 0.2%, or less than about 0.1% of N-oxides of Compound I after the formulation is stored at room temperature for 1 month.

In one embodiment, the formulation comprising Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% N-oxides of the Compound I after the solid lyophilized composition is stored at room temperature for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, or about 15 weeks.

In one embodiment, the formulation comprising Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% N-oxides of the Compound I after the formulation is stored at room temperature for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, or about 15 weeks, or any subranges therebetween.

In one embodiment, the formulation comprising Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% N-oxides of the Compound I after the solid lyophilized composition is stored at room temperature for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, about 15 weeks, about 6 months, about 9 months, about 12 months, about 18 months, about 24 months, and about 36 months, or any subranges therebetween.

In one embodiment, the formulation comprising Compound I, or a pharmaceutically acceptable salt and/or solvate thereof, comprises less than about 1%, less than about 0.9%, less than about 0.8%, less than about 0.7%, less than about 0.6%, less than about 0.5%, less than about 0.4%, less than about 0.3%, less than about 0.2%, or less than about 0.1% N-oxides of the Compound I after the formulation is stored at room temperature for about 1 week, about 2 weeks, about 3 weeks, about 4 weeks, about 5 weeks, about 6 weeks, about 7 weeks, about 8 weeks, about 9 weeks, about 10 weeks, about 11 weeks, about 12 weeks, about 13 weeks, about 14 weeks, or about 15 weeks, about 6 months, about 9 months, about 12 months, about 18 months, about 24 months, and about 36 months, or any subranges therebetween.

In another embodiment, the formulation comprising Compound I, or a pharmaceutically acceptable salt and/or solvate thereof, is substantially free of an N-oxide of a Compound I, or a pharmaceutically acceptable salt and/or solvate thereof.

In some embodiments, the formulation comprising Compound I, or a pharmaceutically acceptable salt and/or solvate thereof, comprises less than about 0.2% of Compound 9, after the solid lyophilized composition is stored at room temperature for 14 days. In some embodiments, the formulation comprising Compound I, or a pharmaceutically acceptable salt and/or solvate thereof, comprises less than about 0.2% of Compound 9, after the solid lyophilized composition is stored at room temperature for 1 month. In some embodiments, the formulation comprising Compound I, or a pharmaceutically acceptable salt and/or solvate thereof, comprises less than about 0.2% of Compound 9 after the formulation is stored at room temperature for 14 days or for 1 month.

In some embodiments, the formulation comprising Compound I, or a pharmaceutically acceptable salt and/or solvate thereof, is substantially free of an antioxidant.

In other embodiments, the formulation comprising Compound I, or a pharmaceutically acceptable salt and/or solvate thereof, is substantially free of ascorbic acid.

In one embodiment, purity or impurity of the compounds of the present invention or any of the compositions or formulations thereof is determined by HPLC. In one embodiment, the HPLC method is any one of the methods disclosed herein. In one embodiment, the HPLC parameters are any one of the parameters as disclosed herein. In one embodiment, the HPLC condition is the basic method as described herein. In one embodiment, the HPLC condition is the acidic method as described herein In one embodiment, the storage of the formulation comprising Compound I, or a pharmaceutically acceptable salt and/or solvate thereof can take place at about −20° C., at a range of about 2° C. to about 8° C., at about 5° C., room temperature, at about 25° C., at about 30° C., at about 40° C., or at about 50° C. In one embodiment, the storage of the formulation comprising Compound I, or a pharmaceutically acceptable salt and/or solvate thereof can be for a duration of at least about 14 days after lyophilization, at least about 28 days after lyophilization, at least about 42 days after lyophilization, at least about 96 days after lyophilization, at least about 6 months after lyophilization, at least about 12 months after lyophilization, at least about 24 months after lyophilization, and/or at least about 36 months In one embodiment, the storage of the formulation comprising Compound I, or a pharmaceutically acceptable salt and/or solvate thereof can be for a duration of about 14 days after lyophilization, about 28 days after lyophilization, about 42 days after lyophilization, about 96 days after lyophilization, about 6 months after lyophilization, about 12 months after lyophilization, about 24 months after lyophilization, and/or about 36 months. In one embodiment, the storage of the formulation comprising Compound I, or a pharmaceutically acceptable salt and/or solvate thereof can be for a duration of at least about 1 month after lyophilization, at least about 2 months after lyophilization, or at least about 3 months after lyophilization.

In one embodiment, the formulation comprises Compound I, or a pharmaceutically acceptable salt and/or solvate thereof, at a concentration greater than about 10 mg/mL, greater than about 11 mg/mL, greater than about 12 mg/mL, greater than about 13 mg/mL, greater than about 14 mg/mL, greater than about 15 mg/mL, greater than about 16 mg/mL, greater than about 17 mg/mL, greater than about 18 mg/mL, greater than about 19 mg/mL, greater than about 20 mg/mL, greater than about 21 mg/mL, greater than about 22 mg/mL, greater than about 23 mg/mL, greater than about 24 mg/mL, or greater than about 25 mg/mL, or any other value or range of values therein. In some embodiments, the formulation comprises Compound I, or a pharmaceutically acceptable salt and/or solvate thereof, at a concentration greater than about 15 mg/mL. In other embodiments, the formulation comprises Compound 1, or a pharmaceutically acceptable salt and/or solvate thereof, at a concentration greater than about 25 mg/mL.

In one embodiment, the formulation comprising Compound I, or a pharmaceutically acceptable salt and/or solvate thereof, wherein the formulation is a reconstituted solution from a solid lyophilized composition comprises a bulking agent. In some embodiments, the bulking agent can be sucrose, mannitol, or trehalose. In one embodiment, the bulking agent is mannitol. In one embodiment, the bulking agent is sucrose.

In one embodiment, the formulation comprising Compound I, or a pharmaceutically acceptable salt and/or solvate thereof, wherein the formulation comprises a bulking agent. In some embodiments, the bulking agent can be sucrose, mannitol, or trehalose. In one embodiment, the bulking agent is mannitol. In one embodiment, the bulking agent is sucrose.

In one embodiment, the present invention provides a liquid composition comprising Compound I, or a pharmaceutically acceptable salt and/or solvate thereof, wherein the composition, has a pH from about 4 to about 6. In some embodiments, the liquid composition has a pH from about 4 to about 5. In some embodiments, the liquid composition has a pH of about 4.5. In some embodiments, the liquid composition has a pH of 4.5±0.1.

In one embodiment, the formulation comprising Compound I, or a pharmaceutically acceptable salt and/or solvate thereof, wherein the formulation is a reconstituted solution from a solid lyophilized composition has a pH from about 4 to about 6. In some embodiments, the formulation has a pH from about 4 to about 5.5. In some embodiments, the solution utilized for reconstitution is 5% dextrose in water or 5% glucose in water.

In one embodiment, the formulation comprises about 200 mg, about 225 mg, about 150 mg, about 125 mg, or about 100 mg of a Compound I, or a pharmaceutically acceptable salt and/or solvate thereof, wherein the formulation is a reconstituted solution from a solid lyophilized composition of Compound I. In one embodiment, the formulation comprises about 150 mg of Compound I.

In one embodiment, the formulation comprises about 200 mg, about 225 mg, about 150 mg, about 125 mg, or about 100 mg of a Compound I, or a pharmaceutically acceptable salt and/or solvate thereof. In one embodiment, the formulation comprises about 150 mg of Compound I.

In one embodiment, the formulation comprising Compound I, or a pharmaceutically acceptable salt and/or solvate thereof, wherein the formulation is a reconstituted solution from a solid lyophilized composition of Compound I is in a vial.

In one embodiment, the formulation comprising Compound I, or a pharmaceutically acceptable salt and/or solvate thereof, wherein the formulation is in a vial.

In one embodiment, the formulation comprising Compound I, or a pharmaceutically acceptable salt and/or solvate thereof, wherein the formulation is a reconstituted solution from a solid lyophilized composition of Compound I is further diluted in an I.V. (intravenous) solution or an I.V. fluid bag or in an I.V. solution line.

In one embodiment, the formulation comprising Compound I, or a pharmaceutically acceptable salt and/or solvate thereof, wherein the formulation is further diluted in an I.V. (intravenous) solution or an I.V. fluid bag or in an I.V. solution line.

In one embodiment, the following numbered embodiments are provided for reconstituted solution prepared from a solid lyophilized Compound I or a pharmaceutically acceptable salt and/or solvate thereof.

In one embodiment, the present invention provides a pharmaceutical composition comprising a therapeutically effective amount of Compound I, or a pharmaceutically acceptable salt and/or solvate thereof, as disclosed herein, as the active ingredient, combined with a pharmaceutically acceptable excipient or carrier. In another embodiment, the present invention provides a pharmaceutical composition comprising a therapeutically effective amount of a solid lyophilized form of Compound I, or a pharmaceutically acceptable salt and/or solvate thereof, as disclosed herein, as the active ingredient, combined with a pharmaceutically acceptable excipient or carrier. The excipients are added to the formulation for a variety of purposes.

In one embodiment, the present disclosure relates to an aqueous composition comprising Compound I, or a pharmaceutically acceptable salt and/or solvate thereof, wherein the composition comprises less than or equal to 1 ppm of dissolved oxygen. In one embodiment, the aqueous composition comprises less than 1 ppm of dissolved oxygen.

In one embodiment, the aqueous composition comprises a bulking agent. In some embodiment, the bulking agent is selected from one or more of the group consisting of sucrose, mannitol, and trehalose. In one embodiment, the bulking agent is mannitol. In one embodiment, the bulking agent is sucrose.

In one embodiment, the aqueous composition has a pH of 4.5±1. In another embodiment, the aqueous composition has a pH of 4.5±0.5. In some embodiments, the aqueous composition has a pH of 4.5±0.1.

In one embodiment, the aqueous composition is the composition prior to lyophilization to prepare the lyophilized composition as disclosed herein.

Pharmaceutically acceptable diluents may be added to the formulation of the present invention (any formulation comprising a compound of the present invention). As used herein "diluents" include, but are not limited to, water, aqueous solutions of saccharides and/or sugar alcohols (e.g., glucose solution, dextrose solution, lactose solution, maltose solution, fructose solution), saline solution, and other aqueous medium.

Bulking agent may be added to the formulations of the present invention. Bulking agents increase the bulk of a solid pharmaceutical composition, and may make a pharmaceutical dosage form containing the composition easier for the patient and care giver to handle. Bulking agents for solid compositions include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, sucrose, trehalose, polymethacrylates (e.g., EUDRAGIT®), potassium chloride, powdered cellulose, sodium chloride, sorbitol, and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g., carbopol), carboxymethylcellulose sodium, dextrin, ethyl cellulose, gelatin, guar gum, gum tragacanth, hydrogenated vegetable oil, hydroxyethyl cellulose, hydroxypropyl cellulose (e.g., KLUCEL), hydroxypropyl methyl cellulose (e.g., METHOCEL), liquid glucose, magnesium aluminum silicate, maltodextrin, methylcellulose, polymethacrylates, povidone (e.g., KOLLIDON, PLASDONE), pregelatinized starch, sodium alginate, and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g., AC-DI-SOL and PRIMELLOSE), colloidal silicon dioxide, croscarmellose sodium, crospovidone (e.g., KOLLIDON and POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB), potato starch, and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition of the present invention (any composition comprising a compound of the present invention) include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

A liquid pharmaceutical compositions may be prepared using Compound I or a pharmaceutically acceptable salt and/or solvate thereof, and any other solid excipients where the components are dissolved or suspended in a liquid carrier such as water, vegetable oil, alcohol, polyethylene glycol, propylene glycol, or glycerin.

A liquid pharmaceutical compositions may be prepared using the solid lyophilized forms of the present invention (one or more of compounds of the present invention in lyophilized form) and any other solid excipients where the components are dissolved or suspended in a liquid carrier such as water, vegetable oil, alcohol, polyethylene glycol, propylene glycol, or glycerin.

Liquid pharmaceutical compositions may contain emulsifying agents to disperse uniformly throughout the composition an active ingredient or other excipient that is not soluble in the liquid carrier. Emulsifying agents that may be useful in liquid compositions of the present invention (any liquid composition comprising a compound of the present invention) include, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as aspartame, lactose, sorbitol, saccharin, sodium saccharin, sucrose, aspartame, fructose, mannitol, and invert sugar may be added to improve the taste.

Preservatives, chelating agents, and antioxidants, such as alcohol, sodium benzoate, butylated hydroxyl toluene, butylated hydroxyanisole, and ethylenediamine tetraacetic acid may be added at levels safe for ingestion to improve storage stability. Non-limiting examples of pharmaceutically acceptable antioxidants include, ascorbic acid, monothioglycerol, L-cysteine, thioglycolic acid, sodium metabisulfite, sodium EDTA, di-sodium EDTA, monoethanolamine gentisate, sodium formaldehyde sulfoxylate and sodium bisulfite. In one embodiment, preservatives, chelating agents, and/or antioxidants are added to achieve improved storage stability of at least about 18 months or at least about 24 months. In one embodiment, preservatives, chelating agents, and/or antioxidants are added to achieve improved storage stability of at least about 36 months. In one embodiment, preservatives, chelating agents, and/or antioxidants are added to achieve improved storage stability of at about 12 months, about 18 months, about 24 months, or about 36 months.

A liquid composition may also contain a buffer such as gluconic acid, lactic acid, citric acid or acetic acid, sodium gluconate, sodium lactate, sodium citrate, or sodium acetate. Selection of excipients and the amounts used may be readily determined by the formulation scientist based upon experience and consideration of standard procedures and reference works in the field.

The solid compositions of the present invention (any solid composition comprising a compound of the present invention) include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, one preferred route of administering the compounds of the present invention is by oral administration. The dosages may be conveniently presented in unit dosage form and prepared by any of the methods well-known in the pharmaceutical arts.

In one embodiment, the present invention provides a lyophilized solid composition of Compound I, or a pharmaceutically acceptable salt and/or solvate thereof, as disclosed herein, to be used for intravenous administration upon reconstitution with an appropriate injection solution. In one embodiment, the present invention provides a kit comprising a lyophilized solid composition of Compound I, or a pharmaceutically acceptable salt and/or solvate thereof, as disclosed herein, and an injection solution.

In one embodiment, the present invention provides a liquid formulation comprising Compound I, or a pharmaceutically acceptable salt and/or solvate thereof, as disclosed herein, to be used for intravenous administration. In one embodiment, the present invention provides a kit comprising a liquid formulation of Compound I, or a pharmaceutically acceptable salt and/or solvate thereof, as disclosed herein, and an injection solution.

Dosage forms include solid dosage forms like tablets, powders, capsules, suppositories, sachets, troches and lozenges, as well as liquid syrups, suspensions, aerosols and elixirs.

The dosage form of the present invention (any dosage form comprising a compound of the present invention) may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water that causes the powders to clump into granules. The granulate is screened and/or milled, dried and then screened and/or milled to the desired particle size. The granulate may be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention (any capsule comprising a compound of the present invention) may comprise any of the aforementioned blends and granulates that were described with reference to tableting; however, they are not subjected to a final tableting step.

The active ingredient and excipients may be formulated into compositions and dosage forms according to methods known in the art.

In one embodiment, a dosage form may be provided as a kit comprising a solid lyophilized form of Compound I and pharmaceutically acceptable excipients and carriers as separate components. In some embodiments, the dosage form kit allow physicians and patients to formulate an oral solution or injection solution prior to use by dissolving, suspending, or mixing the solid lyophilized form of Compound I with pharmaceutically acceptable excipients and carriers. In one embodiment, a dosage form kit which provides solid lyophilized form of Compound I has improved stability of Compound I compared to pre-formulated liquid formulations of Compound I.

In one embodiment, the solid lyophilized form of Compound I or a pharmaceutically acceptable salt and/or solvate thereof is placed in a sterile glass vials at about 5 mg/mL to 50 mg/mL, which is readily used to reconstituted a liquid formulation by addition of a pharmaceutically acceptable diluent to the vial. In one embodiment, a sterile vial contains about 5, 10, 15, 20, 25, 30, 35, 40, 45, or 50 mg/mL. In one embodiment, a sterile 10 mL vial contains about 10, 15, 20, or 25 mg of Compound I or a pharmaceutically acceptable salt and/or solvate thereof.

In one embodiment, a liquid formulation comprising Compound I or a pharmaceutically acceptable salt and/or solvate thereof can be placed in a sterile glass vials at about 5 mg/mL to 50 mg/mL, which can be readily used via intravenous administration. In one embodiment, a sterile vial contains about 5, 10, 15, 20, 25, 30, 35, 40, 45, or 50 mg/mL. In one embodiment, a sterile 10 mL vial contains about 10, 15, 20, or 25 mg of Compound I or a pharmaceutically acceptable salt and/or solvate thereof.

In one embodiment, the solid lyophilized form of Compound I, or a pharmaceutically acceptable salt and/or solvate thereof, is reconstituted prior to administration in pharmaceutically acceptable carrier or solvent. In one embodiment, the reconstituted solution formulation comprising Compound I, or a pharmaceutically acceptable salt and/or solvate thereof, is administered by an IV.

In one embodiment, the liquid formulation comprising Compound I, or a pharmaceutically acceptable salt and/or solvate thereof, is diluted prior to administration. In one embodiment, the diluted liquid formulation comprising Compound I, or a pharmaceutically acceptable salt and/or solvate thereof, is administered by an IV.

The solid lyophilized forms of the present invention, as described herein, may be used in pharmaceutical formulations or compositions as single components or mixtures together with other forms of Compound I, or a pharmaceutically acceptable salt and/or solvate thereof. In one embodiment, pharmaceutical formulations or compositions of the present invention contain 25-100% or 50-100% by weight, of at least one of the solid lyophilized form of Compound I as described herein, in the formulation or composition.

Various formulations of the present invention can comprise about 25-100% or 50-100% by weight, of Compound I or a pharmaceutically acceptable salt and/or solvate thereof, as described herein.

Compounds 1-12 of the Invention

The present invention also provides Compounds 1-12, or pharmaceutically acceptable salt or ester thereof. In some embodiment, the present invention relates to isolated Compounds 1-12, or pharmaceutically acceptable salt or ester thereof. In another embodiment, the present invention relates to purified Compounds 1-12, or pharmaceutically acceptable salt or ester thereof. In one embodiment, the present invention relates to isolated and purified Compounds 1-12, or pharmaceutically acceptable salt or ester thereof. In other embodiments, the present invention relates to substantially pure Compounds 1-12, or pharmaceutically acceptable salt or este thereof.

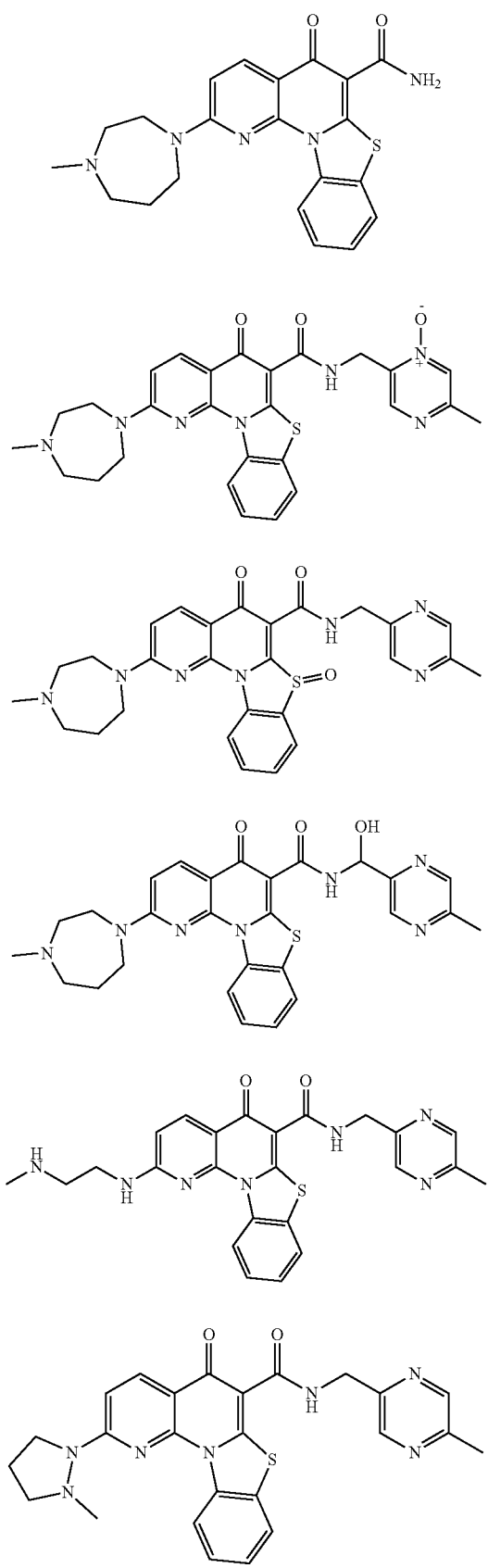

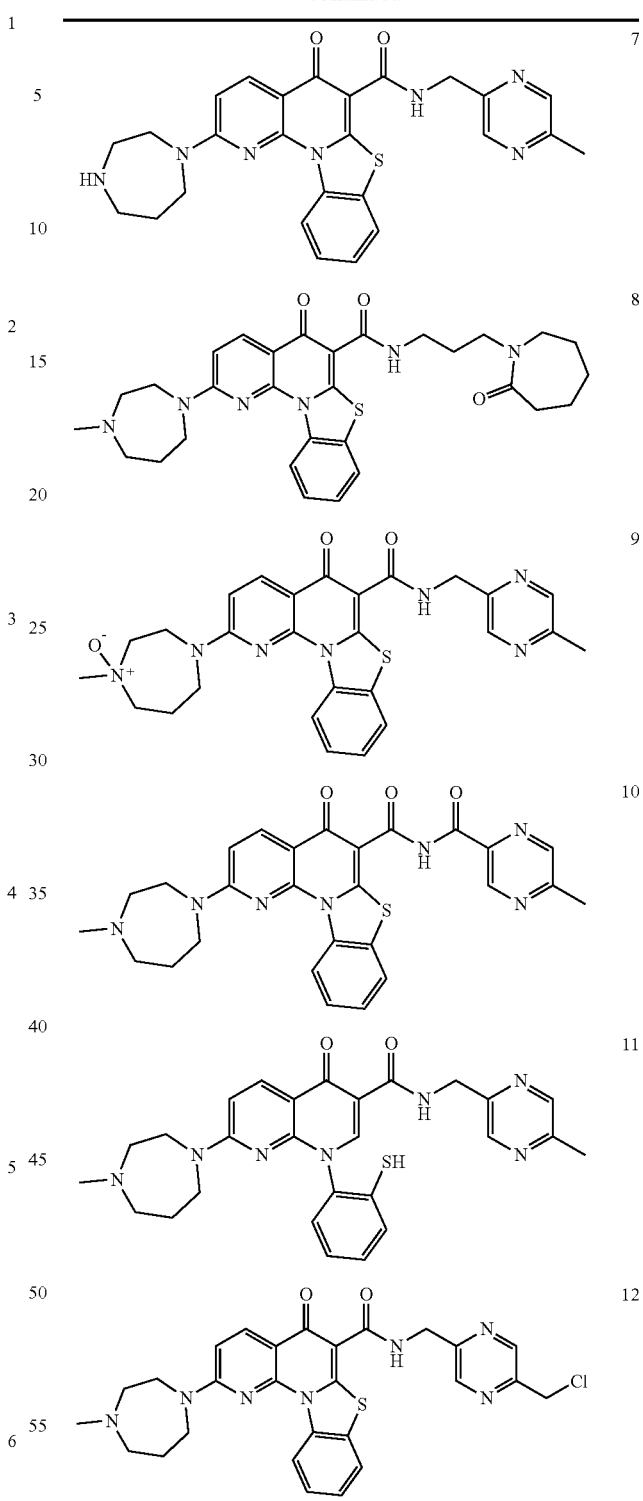

In one embodiment, the term "purified" refers to a compound that has been separated from other components of a reaction mixture and measures at least 90% (by area) by HPLC. The compound of the present disclosure can be purified by any known purification techniques, including but not limited to, chromatography and recrystallization. For example, purified Compound 1 is at least 90%, at least 91%, at least 92%, at least 93%, at least 94%, or at least 95% (by area) when analyzed by HPLC. In other embodiments, Compounds 1-12, or pharmaceutically acceptable salt or ester thereof can be purified. In another embodiment, the Compounds 1-12, or pharmaceutically acceptable salt or ester thereof can be isolated and purified.

In one embodiment, the term "substantially pure" refers to a compound that is at least about 95% pure (by area) as determined by HPLC. For example, substantially pure Compound 1 is at least about 95%, at least about 95.5%, at least about 96%, at least about 96.5%, at least about 97%, at least about 97.5%, at least about 98%, at least about 98.5%, at least about 99%, at least about 99.1%, at least about 99.2%, at least about 99.3%, at least about 99.4%, or at least about 99.5%, pure (by area) as determined by HPLC. In some embodiments, Compounds 1-12, or pharmaceutically acceptable salt or ester thereof can be substantially pure.

In one embodiment, Compounds 1, 7, 8, 9, and 10 has the following relative retention times in using the reverse-phase HPLC methods as disclosed herein.

| Compound | RRT (RP-HPLC basic mobile phase) | RRT (RP-HPLC acidic mobile phase) |
| --- | --- | --- |
| 1 | 0.62 | 0.88 |
| 7 | 0.75 | 1.00 |
| 10 | 1.12 | 1.07 |
| 9 | 0.35 | 1.05 |
| 8 | 1.24 | 1.05 |

In one embodiment, the present invention relates to Compounds 1-12, or pharmaceutically acceptable salt or ester thereof, which is substantially free of Compound I. In some embodiment, Compounds 1-12, or pharmaceutically acceptable salt or ester thereof comprises less than about 5%, less than about 4.5%, less than about 4%, less than about 3.5%, less than about 3%, less than about 2.5%, less than about 2%, less than about 1.5%, less than about 1%, less than about 0.9%, less than about 0.8%, less than about 0.7%, less than about 0.6%, less than about 0.5%, less than about 0.4%, less than about 0.3%, less than about 0.2%, or less than about 0.1% of Compound I.

In one embodiment, the present disclosure relates to Compounds 1-12, or a pharmaceutically acceptable salt or ester thereof, which demonstrates sensitivity to a BRCA2 null cell line relative to the parental cell line. In one embodiment, the sensitivity of the BRCA2 null cell line is at least two hundred fold greater than the BRCA2 wild type cell line.

In other embodiments, the sensitivity is at least twenty fold higher. In some embodiments, the sensitivity is at least 200 fold higher. In other embodiment, the sensitivity is at least 2, 5, 10, 15, 20, 25, 30, 35, 40, 45, 50, 60, 70, 80, 90, 100, 125, 150, 175, 200 or 400 fold higher.

In one embodiment, the sensitivity to BRCA2 null cell lines can be determined through proliferation assay on DLD-1 Parental and BRCA2−/− isogenic cell lines as discussed in Example 24.

In one embodiment, Compounds 1-12, or pharmaceutically acceptable salt or ester thereof can be formed from Compound I via degradation or as impurities during the synthesis of Compound I.

Compositions with Compounds 1-12

In one embodiment, the present invention provides a pharmaceutical composition comprising at least one of Compounds 1-12, or a pharmaceutically acceptable salt or ester thereof, as disclosed herein as the active ingredient, with a pharmaceutically acceptable excipient or carrier. The excipients are added to the formulation for a variety of purposes.

Diluents may be added to any formulations described herein. Diluents increase the bulk of a solid pharmaceutical composition, and may make a pharmaceutical dosage form containing the composition easier for the patient and care giver to handle. Diluents for solid compositions include, for example, microcrystalline cellulose (e.g., AVICEL), microfine cellulose, lactose, starch, pregelatinized starch, calcium carbonate, calcium sulfate, sugar, dextrates, dextrin, dextrose, dibasic calcium phosphate dihydrate, tribasic calcium phosphate, kaolin, magnesium carbonate, magnesium oxide, maltodextrin, mannitol, polymethacrylates (e.g., EUDRAGIT®), potassium chloride, powdered cellulose, sodium chloride, sorbitol, and talc.

Solid pharmaceutical compositions that are compacted into a dosage form, such as a tablet, may include excipients whose functions include helping to bind the active ingredient and other excipients together after compression. Binders for solid pharmaceutical compositions include acacia, alginic acid, carbomer (e.g., carbopol), carboxymethylcellulose sodium, dextrin, ethyl cellulose, gelatin, guar gum, gum tragacanth, hydrogenated vegetable oil, hydroxyethyl cellulose, hydroxypropyl cellulose (e.g., KLUCEL), hydroxypropyl methyl cellulose (e.g., METHOCEL), liquid glucose, magnesium aluminum silicate, maltodextrin, methylcellulose, polymethacrylates, povidone (e.g., KOLLIDON, PLASDONE), pregelatinized starch, sodium alginate, and starch.

The dissolution rate of a compacted solid pharmaceutical composition in the patient's stomach may be increased by the addition of a disintegrant to the composition. Disintegrants include alginic acid, carboxymethylcellulose calcium, carboxymethylcellulose sodium (e.g., AC-DI-SOL and PRIMELLOSE), colloidal silicon dioxide, croscarmellose sodium, crospovidone (e.g., KOLLIDON and POLYPLASDONE), guar gum, magnesium aluminum silicate, methyl cellulose, microcrystalline cellulose, polacrilin potassium, powdered cellulose, pregelatinized starch, sodium alginate, sodium starch glycolate (e.g., EXPLOTAB), potato starch, and starch.

Glidants can be added to improve the flowability of a non-compacted solid composition and to improve the accuracy of dosing. Excipients that may function as glidants include colloidal silicon dioxide, magnesium trisilicate, powdered cellulose, starch, talc, and tribasic calcium phosphate.

When a dosage form such as a tablet is made by the compaction of a powdered composition, the composition is subjected to pressure from a punch and dye. Some excipients and active ingredients have a tendency to adhere to the surfaces of the punch and dye, which can cause the product to have pitting and other surface irregularities. A lubricant can be added to the composition to reduce adhesion and ease the release of the product from the dye. Lubricants include magnesium stearate, calcium stearate, glyceryl monostearate, glyceryl palmitostearate, hydrogenated castor oil, hydrogenated vegetable oil, mineral oil, polyethylene glycol, sodium benzoate, sodium lauryl sulfate, sodium stearyl fumarate, stearic acid, talc, and zinc stearate.

Flavoring agents and flavor enhancers make the dosage form more palatable to the patient. Common flavoring agents and flavor enhancers for pharmaceutical products that may be included in the composition of the present invention (any composition comprising a compound of the present invention) include maltol, vanillin, ethyl vanillin, menthol, citric acid, fumaric acid, ethyl maltol, and tartaric acid.

Solid and liquid compositions may also be dyed using any pharmaceutically acceptable colorant to improve their appearance and/or facilitate patient identification of the product and unit dosage level.

In liquid pharmaceutical compositions may be prepared using the crystalline forms of the present invention (any crystalline form of a compound of the present invention) and any other solid excipients where the components are dissolved or suspended in a liquid carrier such as water, vegetable oil, alcohol, polyethylene glycol, propylene glycol, or glycerin.

Liquid pharmaceutical compositions may contain emulsifying agents to disperse uniformly throughout the composition an active ingredient or other excipient that is not soluble in the liquid carrier. Emulsifying agents that may be useful in any liquid compositions described herein, including, for example, gelatin, egg yolk, casein, cholesterol, acacia, tragacanth, chondrus, pectin, methyl cellulose, carbomer, cetostearyl alcohol, and cetyl alcohol.

Liquid pharmaceutical compositions may also contain a viscosity enhancing agent to improve the mouth-feel of the product and/or coat the lining of the gastrointestinal tract. Such agents include acacia, alginic acid bentonite, carbomer, carboxymethylcellulose calcium or sodium, cetostearyl alcohol, methyl cellulose, ethylcellulose, gelatin guar gum, hydroxyethyl cellulose, hydroxypropyl cellulose, hydroxypropyl methyl cellulose, maltodextrin, polyvinyl alcohol, povidone, propylene carbonate, propylene glycol alginate, sodium alginate, sodium starch glycolate, starch tragacanth, and xanthan gum.

Sweetening agents such as aspartame, lactose, sorbitol, saccharin, sodium saccharin, sucrose, aspartame, fructose, mannitol, and invert sugar may be added to improve the taste.

Bulking agents can be included in a pharmaceutical composition. Non-limiting examples include mannitol, lactose, sucrose, sodium chloride, trehalose, dextrose, starch, hydroxyethylstarch (hetastarch), cellulose, cyclodextrins, glycine, or mixtures thereof.

Preservatives and chelating agents such as alcohol, sodium benzoate, butylated hydroxyl toluene, butylated hydroxyanisole, and ethylenediamine tetraacetic acid may be added at levels safe for ingestion to improve storage stability.

A liquid composition may also contain a buffer such as gluconic acid, lactic acid, citric acid or acetic acid, sodium gluconate, sodium lactate, sodium citrate, or sodium acetate. Selection of excipients and the amounts used may be readily determined by the formulation scientist based upon experience and consideration of standard procedures and reference works in the field.

The solid compositions of the present invention (any solid composition comprising a compound of the present invention) include powders, granulates, aggregates and compacted compositions. The dosages include dosages suitable for oral, buccal, rectal, parenteral (including subcutaneous, intramuscular, and intravenous), inhalant and ophthalmic administration. Although the most suitable administration in any given case will depend on the nature and severity of the condition being treated, one of the preferred route of administration of the compound of the present invention is oral. The dosages may be conveniently presented in unit dosage form and prepared by any of the methods well-known in the pharmaceutical arts.

Dosage forms include solid dosage forms like tablets, powders, capsules, suppositories, sachets, troches and lozenges, as well as liquid syrups, suspensions, aerosols and elixirs.

The dosage form of the present invention (any dosage form comprising a compound of the present invention) may be a capsule containing the composition, preferably a powdered or granulated solid composition of the invention, within either a hard or soft shell. The shell may be made from gelatin and optionally contain a plasticizer such as glycerin and sorbitol, and an opacifying agent or colorant.

A composition for tableting or capsule filling may be prepared by wet granulation. In wet granulation, some or all of the active ingredients and excipients in powder form are blended and then further mixed in the presence of a liquid, typically water that causes the powders to clump into granules. The granulate is screened and/or milled, dried and then screened and/or milled to the desired particle size. The granulate may be tableted, or other excipients may be added prior to tableting, such as a glidant and/or a lubricant.

A tableting composition may be prepared conventionally by dry blending. For example, the blended composition of the actives and excipients may be compacted into a slug or a sheet and then comminuted into compacted granules. The compacted granules may subsequently be compressed into a tablet.

As an alternative to dry granulation, a blended composition may be compressed directly into a compacted dosage form using direct compression techniques. Direct compression produces a more uniform tablet without granules. Excipients that are particularly well suited for direct compression tableting include microcrystalline cellulose, spray dried lactose, dicalcium phosphate dihydrate and colloidal silica. The proper use of these and other excipients in direct compression tableting is known to those in the art with experience and skill in particular formulation challenges of direct compression tableting.

A capsule filling of the present invention (any capsule comprising a compound of the present invention) may comprise any of the aforementioned blends and granulates that were described with reference to tableting; however, they are not subjected to a final tableting step.

The active ingredient and excipients may be formulated into compositions and dosage forms according to methods known in the art.

In one embodiment, a dosage form may be provided as a kit comprising at least one of Compounds 1-12, or a pharmaceutically acceptable salt or ester thereof, and pharmaceutically acceptable excipients and carriers as separate components. In some embodiments, the dosage form kit allow physicians and patients to formulate an oral solution or injection solution prior to use by dissolving, suspending, reconstituting, or mixing the crystalline form of at least one of Compounds 1-12, or a pharmaceutically acceptable salt or ester thereof, with pharmaceutically acceptable excipients and carriers.

It is not necessary that the formulations of the present invention contain only one of Compounds 1-12, or a pharmaceutically acceptable salt or ester thereof. Two or more compounds selected from Compounds 1-12, or a pharmaceutically acceptable salt or ester thereof may be used in pharmaceutical formulations or compositions as single components or mixtures. In one embodiment, pharmaceutical formulations or compositions of the present invention contain 25-100% or 50-100% by weight, at least one of Compounds 1-12, or a pharmaceutically acceptable salt or ester thereof, as described herein, in the formulation or composition.

In one embodiment, the pharmaceutical composition of the present disclosure comprising at least one of Compounds 1-12, or a pharmaceutically acceptable salt or ester thereof, further comprises one or more pharmaceutically active agent. In one embodiment, the one or more therapeutically active agent is an anticancer agent. In some embodiments, the one or more therapeutically active anticancer agents include, but are not limited to, paclitaxel, vinblastine, vincristine, etoposide, doxorubicin, herceptin, lapatinib, gefitinib, erlotinib, tamoxifen, fulvestrant, anastrazole, lectrozole, exemestane, fadrozole, cyclophosphamide, taxotere, melphalan, chlorambucil, mechlorethamine, chlorambucil, phenylalanine, mustard, cyclophosphamide, ifosfamide, carmustine (BCNU), lomustine (CCNU), streptozotocin, busulfan, thiotepa, cisplatin, carboplatin, dactinomycin (actinomycin D), doxorubicin (adriamycin), daunorubicin, idarubicin, mitoxantrone, plicamycin, mitomycin, C Bleomycin, combinations thereof, and the like. In another embodiment, the one or more therapeutically active anticancer agents include, but are not limited to, PARP (poly (DP-ribose)polymerase) inhibitors and CDK (cyclin-dependent kinase) inhibitors.

Suitable PARP inhibitors include, but are not limited to, 4-(3-(1-(cyclopropanecarbonyl)piperazine-4-carbonyl)-4-fluorobenzyl)phthalazin-1(2H)-one (olaparib, AZD2281, Ku-0059436), 2-[(2R)-2-methylpyrrolidin-2-yl]-1H-benzimidazole-4-carboxamide (veliparib, ABT-888), (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one (talazoparib, BMN 673), 4-iodo-3-nitrobenzamide (iniparib, BSI-201), 8-fluoro-5-(4-((methylamino)methyl)phenyl)-3,4-dihydro-2H-azepino[5,4,3-cd]indol-1(6H)-one phosphoric acid (rucaparib, AG-014699, PF-01367338), 2-[4-[(dimethylamino)methyl]phenyl]-5,6-dihydroimidazo[4,5,1-jk][1,4]benzodiazepin-7(4H)-one (AG14361), 3-aminobenzamide (INO-1001), 2-(2-fluoro-4-((S)-pyrrolidin-2-yl)phenyl)-3H-benzo[d]imidazole-4-carboxamide (A-966492), N-(5,6-dihydro-6-oxo-2-phenanthridinyl)-2-acetamide hydrochloride (PJ34, PJ34 HCl), MK-4827, 3,4-dihydro-4-oxo-3,4-dihydro-4-oxo-N-[(1S)-1-phenylethyl]-2-quinazolinepropanamide (ME0328), 5-(2-oxo-2-phenylethoxy)-1(2H)-isoquinolinone (UPF-1069), 4-[[4-fluoro-3-[(4-methoxy-1-piperidinyl)carbonyl]phenyl] methyl]-1(2H)-phthalazinone (AZD 2461), and the like. In another embodiment, the one or more therapeutically active agent is an immunotherapeutic agent. In some embodiments, the one or more immunotherapeutic agents includes, but are not limited to, a monoclonal antibody, an immune effector cell, adoptive cell transfer, an immunotoxin, a vaccine, a cytokine, and the like.

Suitable CDK inhibitors include, but are not limited to, AZD-5438, BMI-1040, BMS-032, BMS-387, CVT-2584, flavopyridol, GPC-286199, MCS-5A, PD0332991, PHA-690509, seliciclib (CYC202, R-roscovitine), ZK-304709 AT7519M, P276-00, SCH 727965, AG-024322, LEE011, LY2835219, P1446A-05, BAY 1000394, SNS-032, 5-((3-chlorophenyl)amino)benzo[c][2,6]naphthyridine-8-carboxylic acid (CX-4945), and the like.

Therapeutic Use

The present invention also provides treatment of disorders related to proliferation of cells. In one aspect, there is provided a method for selectively activating p53 protein comprising contacting a cell afflicted by disorder related to cell proliferation with Compound I, or a pharmaceutically acceptable salt and/or solvate thereof. In one embodiment, the method comprises contacting cancer and/or tumor cells with the solid lyophilized form of Compound I, or a pharmaceutically acceptable salt and/or solvate thereof, as disclosed herein. In another embodiment, the method of contacting cancer and/or tumor cells with the solid lyophilized form of Compound I, or a pharmaceutically acceptable salt and/or solvate thereof, as disclosed herein, may induce cell apoptosis or alleviate or delay the progression of the disorder.

In one aspect, there is provided a method for selectively activating p53 protein comprising contacting a cell afflicted by disorder related to cell proliferation with at least one of Compounds 1-12, or a pharmaceutically acceptable salt or ester thereof, as disclosed herein. In one aspect, there is provided a method for stabilizing G-quadruplex (G4) comprising contacting a cell afflicted by disorder related to cell proliferation with at least one of Compounds 1-12, or a pharmaceutically acceptable salt or ester thereof, as disclosed herein. In one embodiment, the method comprises contacting cancer and/or tumor cells with at least one of Compounds 1-12, or a pharmaceutically acceptable salt or ester thereof, as disclosed herein. In another embodiment, the method of contacting cancer and/or tumor cells with at least one of Compounds 1-12, or a pharmaceutically acceptable salt or ester thereof, as disclosed herein, may induce cell apoptosis or alleviate or delay the progression of the disorder.

Additionally, disclosed are methods for treating cancers, cancer cells, tumors, or tumor cells. Non limiting examples of cancer that may be treated by the methods of this disclosure include cancer or cancer cells of: colorectum, breast, lung, liver, pancreas, lymph node, colon, prostate, brain, head and neck, skin, ovary, cervical, thyroid, bladder, kidney, osteosarcoma, blood and heart (e.g., leukemia, lymphoma, and carcinoma), uterine, gastrointestinal malignancies, and carcinomas of the larynx and oral cavity. Non limiting examples of tumors that may be treated by the methods of this disclosure include tumors and tumor cells of: colorectum, breast, lung, liver, pancreas, lymph node, colon, prostate, brain, head and neck, skin, kidney, osteosarcoma, blood and heart (e.g., leukemia, lymphoma, and carcinoma), uterine, gastrointestine, larynx, and oral cavity.

The present invention also provides methods of treating, delaying, ameliorating and/or alleviating the progression of disorders or conditions characterized by cell proliferation in a subject. More particularly, the methods of the present invention, as described herein, can involve administration of an effective amount of the solid lyophilized form of the quinolone compounds described herein, in a subject to treat a disorder or a condition characterized by cell proliferation. In one embodiment, the methods of the present invention, as described herein, can involve administration of an effective amount of any one of the compounds of the present invention, in a subject to treat a disorder or a condition characterized by cell proliferation. A formulation or a composition reconstituted from the solid lyophilized form can be administered in an amount effective selectively activate p53 proteins in cancer and/or tumor cells, which may lead to cell death or apoptosis. The terms "subject" and "patient" are used interchangeably throughout the present application.

Compounds 1-12, or a pharmaceutically acceptable salt or ester thereof, as disclosed herein, can be administered in an amount effective to stabilize G4 in cancer and/or tumor cells, which may lead to cell death or apoptosis.

In one embodiment, disorders or conditions characterized by cell proliferation is cancer. In another embodiment, the present invention provides methods of treating or ameliorating cancer, comprising administering a therapeutically effective amount of the formulation which is a reconstituted solution from a solid lyophilized Compound I, or a pharmaceutically acceptable salt or ester thereof as disclosed herein, to a subject in need thereof. In another embodiment, the present invention provides methods of treating or ameliorating cancer, comprising administering a therapeutically effective amount of at least one of Compounds 1-12, or a pharmaceutically acceptable salt or ester thereof, to a subject in need thereof.

In one embodiment, the method disclosed herein comprises injecting the formulation which is a reconstituted solution from a solid lyophilized Compound I, or a pharmaceutically acceptable salt or ester thereof, directly into a subject. In one embodiment, the formulation which is a reconstituted solution from a solid lyophilized Compound I, or a pharmaceutically acceptable salt or ester thereof, is further diluted in an I.V. solution/fluid bag or I.V. line then administration to the subject.

In one embodiment, cancer treated or ameliorated by the method as disclosed herein may be selected from one or more of the group consisting of Acute Lymphoblastic Leukemia, Acute Myeloid Leukemia, Adrenocortical Carcinoma, AIDS-Related Cancers, Kaposi Sarcoma, Lymphoma, Anal Cancer, Appendix Cancer, Astrocytomas, Childhood Atypical Teratoid/Rhabdoid Tumor, Basal Cell Carcinoma, Skin Cancer (Nonmelanoma), Childhood Bile Duct Cancer, Extrahepatic Bladder Cancer, Bone Cancer, Ewing Sarcoma Family of Tumors, Osteosarcoma and Malignant Fibrous Histiocytoma, Brain Stem Glioma, Brain Tumors, Embryonal Tumors, Germ Cell Tumors, Craniopharyngioma, Ependymoma, Bronchial Tumors, Burkitt Lymphoma (Non-Hodgkin Lymphoma), Carcinoid Tumor, Gastrointestinal Carcinoma of Unknown Primary, Cardiac (Heart) Tumors, Lymphoma, Primary, Cervical Cancer, Childhood Cancers, Chordoma, Chronic Lymphocytic Leukemia, Chronic Myelogenous Leukemia, Chronic Myeloproliferative Neoplasms Colon Cancer, Colorectal Cancer, Cutaneous T-Cell Lymphoma, Ductal Carcinoma In Situ, Endometrial Cancer, Ependymoma, Esophageal Cancer, Esthesioneuroblastoma, Ewing Sarcoma, Extracranial Germ Cell Tumor, Extragonadal Germ Cell Tumor, Extrahepatic Bile Duct Cancer, Eye Cancer, Intraocular Melanoma, Retinoblastoma, Fibrous Histiocytoma of Bone, Malignant, and Osteosarcoma, Gallbladder Cancer, Gastric (Stomach) Cancer, Gastrointestinal Carcinoid Tumor, Gastrointestinal Stromal Tumors, Extragonadal Cancer, Ovarian Cancer, Testicular Cancer, Gestational Trophoblastic Disease, Glioma, Brain Stem Cancer, Hairy Cell Leukemia, Head and Neck Cancer, Heart Cancer, Hepatocellular (Liver) Cancer, Histiocytosis, Langerhans Cell Cancer, Hodgkin Lymphoma, Hypopharyngeal Cancer, Intraocular Melanoma, Islet Cell Tumors, Pancreatic Neuroendocrine Tumors, Kaposi Sarcoma, Kidney Cancer, Renal Cell Cancer, Wilms Tumor and Other Childhood Kidney Tumors, Langerhans Cell Histiocytosis, Laryngeal Cancer, Leukemia, Chronic Lymphocytic Cancer, Chronic Myelogenous Cancer, Hairy Cell Cancer, Lip and Oral Cavity Cancer, Liver Cancer (Primary), Lobular Carcinoma In Situ (LCIS), Lung Cancer, Non-Small Cell Cancer, Small Cell Cancer, Lymphoma, Cutaneous T-Cell (Mycosis Fungoides and Sézary Syndrome), Hodgkin Cancer, Non-Hodgkin Cancer, Macroglobulinemia, Waldenström, Male Breast Cancer, Malignant Fibrous Histiocytoma of Bone and Osteosarcoma, Melanoma, Intraocular (Eye) Cancer, Merkel Cell Carcinoma, Mesothelioma, Malignant, Metastatic Squamous Neck Cancer with Occult Primary, Midline Tract Carcinoma Involving NUT Gene, Mouth Cancer, Multiple Endocrine Neoplasia Syndromes, Multiple Myeloma/Plasma Cell Neoplasm, Mycosis Fungoides, Myelodysplastic Syndromes, Myelodysplastic/Myeloproliferative Neoplasms, Myelogenous Leukemia, Chronic, Myeloid Leukemia, Acute, Myeloma Multiple, Chronic Myeloproliferative Neoplasms, Nasal Cavity and Paranasal Sinus Cancer, Nasopharyngeal Cancer, Neuroblastoma, Non-Hodgkin Lymphoma, Non-Small Cell Lung Cancer, Oral Cancer, Oral Cavity Cancer, Lip and Oropharyngeal Cancer, Osteosarcoma and Malignant Fibrous Histiocytoma of Bone, Epithelial Cancer, Low Malignant Potential Tumor, Pancreatic Cancer, Pancreatic Neuroendocrine Tumors (Islet Cell Tumors), Papillomatosis, Paraganglioma, Parathyroid Cancer, Penile Cancer, Pharyngeal Cancer, Pheochromocytoma, Pituitary Tumor, Plasma Cell Neoplasm/Multiple Myeloma, Pleuropulmonary Blastoma, Primary Central Nervous System Lymphoma, Rectal Cancer, Renal Cell (Kidney) Cancer, Retinoblastoma, Rhabdomyosarcoma, Salivary Gland Cancer, Sarcoma, Ewing Cancer, Kaposi Cancer, Osteosarcoma (Bone Cancer), Soft Tissue Cancer, Uterine Cancer, Sézary Syndrome, Skin Cancer, Childhood Melanoma, Merkel Cell Carcinoma, Nonmelanoma, Small Cell Lung Cancer, Small Intestine Cancer, Soft Tissue Sarcoma, Squamous Cell Carcinoma, Skin Cancer (Nonmelanoma), Childhood Squamous Neck Cancer with Occult Primary, Metastatic Cancer, Stomach (Gastric) Cancer, T-Cell Lymphoma, Cutaneous Cancer, Testicular Cancer, Throat Cancer, Thymoma and Thymic Carcinoma, Thyroid Cancer, Transitional Cell Cancer of the Renal Pelvis and Ureter, Unknown Primary, Carcinoma of Childhood, Unusual Cancers of Childhood, Urethral Cancer, Uterine Cancer, Endometrial Cancer, Uterine Sarcoma, Vaginal Cancer, Vulvar Cancer, Waldenström Macroglobulinemia, Wilms Tumor, and Women's Cancers In one embodiment, cancer treated or ameliorated by any one of the methods as disclosed herein may be selected from the group consisting of: heme cancer, colorectum cancer, breast cancer, lung cancer, liver cancer, ovarian cancer, cervical cancer, Ewing's sarcoma, pancreatic cancer, cancer of the lymph nodes, colon cancer, prostate cancer, brain cancer, cancer of the head and neck, skin cancer, kidney cancer, cancer of the heart, uterine cancer, gastrointestinal malignancies, and carcinomas of the larynx and oral cavit. In some embodiments, the cancer treated or ameliorated by the said method is selected from the group consisting of uterine cancer, gastrointestinal malignancies, and carcinomas of the larynx and oral cavity. In one embodiment, cancer treated or ameliorated by the said method is heme cancer which is selected from the group consisting of: leukemia, lymphoma, myeloma, and multiple myeloma. In one embodiment, cancer treated or ameliorated by any one of the methods as disclosed herein may be selected from the group consisting of: heme cancer, colorectal cancer, breast cancer, lung cancer, liver cancer, ovarian cancer, cervical cancer, Ewing's sarcoma, pancreatic cancer, cancer of the lymph nodes, colon cancer, prostate cancer, brain cancer, cancer of the head and neck, skin cancer, kidney cancer, osteosarcoma, and cancer of the heart. In one embodiment, cancer treated or ameliorated by the said method is heme cancer which is selected from the group consisting of: leukemia, lymphoma, myeloma, and multiple myeloma.

In one embodiment, cancer treated or ameliorated by any one of the methods as disclosed herein can be wherein the subject has a mutation in a DNA repair gene. In a specific embodiment, the DNA repair gene is a homologous recombinant gene. In another embodiment, the DNA repair gene is a gene in the homologous recombination (HR) dependent deoxyribonucleic acid (DNA) double strand break (DSB) repair pathway. In a specific embodiment, the DNA repair gene is a homologous recombinant (HR) or non-homologous end joining (NHEJ) gene. In another embodiment, the DNA repair gene is a gene in the homologous recombination (HR) or non-homologous end joining (NHEJ) dependent deoxyribonucleic acid (DNA) double strand break (DSB) repair pathway. In another method, the DNA repair gene is one or more genes selected from the group consisting of BRCA-1, BRCA-2, ATM, ATR, CHK1, CHK2, Rad51, RPA and XRCC3.

In another embodiment, cancer treated or ameliorated by the said method comprises cancer cells harboring defects in BRCA1 gene (breast cancer type 1), BRCA2 (breast cancer type 2), and/or other members of the homologous recombination pathway. In another embodiment, the cancer cells are deficient in BRCA1 and/or BRCA2. In another embodiment, the cancer cells are homozygous for a mutation in BRCA1 and/or BRCA2. In another embodiment, the cancer cells are heterozygous for a mutation in BRCA1 and/or BRCA2.

In one embodiment, cancer treated or ameliorated by any one of the methods as disclosed herein is BRCA2 deficient. In another embodiment, the Compound I, or a pharmaceutically acceptable salt and/or solvate thereof in the formulation, induces more apoptotic cell death in BRCA2 deficient or BRCA2 knockout cells relative to BRCA2 proficient or BRCA2 wild type cells. In one embodiment, the solid lyophilized form of Compound I, or a pharmaceutically acceptable salt and/or solvate thereof, are selectively toxic to BRCA2 deficient or BRCA2 knockout cells over BRCA2 proficient or BRCA2 wild type cells. In other embodiments, BRCA2 deficient or BRCA2 knockout cells exhibit higher sensitivity to the solid lyophilized form of Compound I, or a pharmaceutically acceptable salt and/or solvate thereof, as compared to BRCA2 proficient or BRCA2 wild type cells. In another embodiment, Compounds 1-12, or a pharmaceutically acceptable salt or ester thereof, induces more apoptotic cell death in BRCA2 deficient or BRCA2 knockout cells relative to BRCA2 proficient or BRCA2 wild type cells. In one embodiment, Compounds 1-12, or a pharmaceutically acceptable salt or ester thereof, are selectively toxic to BRCA2 deficient or BRCA2 knockout cells over BRCA2 proficient or BRCA2 wild type cells. In other embodiments, BRCA2 deficient or BRCA2 knockout cells exhibit higher sensitivity to Compounds 1-12, or a pharmaceutically acceptable salt or ester thereof, as compared to BRCA2 proficient or BRCA2 wild type cells.

In one embodiment, cancer treated or ameliorated by any one of the methods as disclosed herein is BRCA mutant or BRCA-like mutant cancer. In some embodiments, the BRCA mutant or BRCA-like mutant cancer is a BRCA2-mutated cancer. In other embodiments, the BRCA mutant or BRCA-like mutant cancer is breast cancer, ovarian cancer, pancreatic cancer, or prostate cancer. In one embodiment, the BRCA mutant or BRCA-like mutant cancer is breast cancer or prostate cancer. In one embodiment, cancer treated or ameliorated by any one of the methods as disclosed herein is BRCA mutant cancer. In some embodiment, the BRCA mutant cancer is a BRCA2-mutated cancer. In other embodiments, the BRCA mutant cancer is breast cancer, ovarian cancer, pancreatic cancer, or prostate cancer. In one embodiment, the BRCA mutant cancer is breast cancer or prostate cancer.

In one embodiment, the present disclosure relates to a method for treating or ameliorating cell proliferation disorder in a human subject, comprising administering to a subject in need thereof a therapeutically effective amount of a formulation which is a reconstituted solution from a solid lyophilized form of Compound I, or a pharmaceutically acceptable salt and/or solvate thereof as disclosed herein. In some embodiments, the human subject carries a BRCA mutation. In other embodiments, the human subject carries a BRCA2 mutation. In another embodiment, the human subject is homozygous for a mutation in BRCA2.

In one embodiment, the present disclosure relates to a method for treating or ameliorating cell proliferation disorder in a human subject, comprising administering to a subject in need thereof a therapeutically effective amount of any one of Compounds 1-12, or a pharmaceutically acceptable salt or ester thereof, or a pharmaceutical composition comprising at least one of Compounds 1-12, or a pharmaceutically acceptable salt or ester thereof. In some embodiments, the human subject carries a BRCA mutation. In other embodiments, the human subject carries a BRCA2 mutation. In another embodiment, the human subject is homozygous for a mutation in BRCA2.

Additionally, the present disclosure relates to methods for treating cancers, cancer cells, tumors, or tumor cells comprising administering a therapeutically effective amount of a formulation which is a reconstituted solution from a solid lyophilized form of Compound I, or a pharmaceutically acceptable salt and/or solvate thereof as disclosed herein. The present disclosure also relates to methods for treating cancers, cancer cells, tumors, or tumor cells comprising administering a therapeutically effective amount of at least one of Compounds 1-12, or a pharmaceutically acceptable salt or ester thereof, to a subject in need thereof. Non limiting examples of cancer that may be treated by the methods of this disclosure include cancer or cancer cells of: colorectum, breast, ovary, cervix, lung, liver, pancreas, lymph node, colon, prostate, brain, head and neck, skin, kidney, osteosarcoma, bone (e.g., Ewing's sarcoma), blood and heart (e.g., leukemia, lymphoma, carcinoma), uterine, gastrointestinal malignancies, and carcinomas of the larynx and oral cavity. Non limiting examples of tumors that may be treated by the methods of this disclosure include tumors and tumor cells of: colorectum, breast, ovary, cervix, lung, liver, pancreas, lymph node, colon, prostate, brain, head and neck, skin, kidney, osteosarcoma, bone (e.g., Ewing's sarcoma), blood and heart (e.g., leukemia, lymphoma, carcinoma), uterine, gastrointestinal malignancies, and carcinomas of the larynx and oral cavity.

The present invention also provides methods of decreasing Pol I transcription comprising administering a formulation which is a reconstituted solution from a solid lyophilized form of Compound I, or a pharmaceutically acceptable salt and/or solvate thereof as disclosed herein, to a subject in need. In some embodiments, the inhibition of Pol I transcription is in peripheral blood mononuclear cells (PBMC). In other embodiments, the inhibition of Pol I transcription can be observed in PBMC at one hour post-IV infusion of a dose comprising a Compound I, or a pharmaceutically acceptable salt and/or solvate thereof. In one embodiment, the dose comprises a therapeutically effective amount of a Compound I, or a pharmaceutically acceptable salt and/or solvate thereof.

In one embodiment, the inhibition of Pol I transcription in PBMC 1 hour post-infusion is at an average level of about 15% inhibition or greater. In another embodiment, the Pol I transcription in PBMC 1 hour post-infusion is at an average level of about 5% inhibition or greater, about 10% inhibition or greater, about 15% inhibition or greater, about 20% inhibition or greater, about 25% inhibition or greater, about 30% inhibition or greater, about 35% inhibition or greater, about 40% inhibition or greater, about 45% inhibition or greater, about 50% inhibition or greater, about 55% inhibition or greater, about 65% inhibition or greater, or about 70% inhibition or greater.

In one embodiment of the present methods disclosed herein, the inhibition of Pol I transcription can be observed in MACS (magnetic-activated cell sorting) sorted tumor cells.

As used herein, administering can be effected or performed using any of the various methods known to those skilled in the art. Compound I or Compounds 1-12, or a pharmaceutically acceptable salt or ester thereof, or a composition comprising thereof, can be administered, for example, subcutaneously, intravenously, parenterally, intraperitoneally, intradermally, intramuscularly, topically, enteral (e.g., orally), rectally, nasally, buccally, sublingually, vaginally, by inhalation spray, by drug pump or via an implanted reservoir in dosage formulations containing conventional non-toxic, physiologically acceptable carriers or vehicles. A formulation or a composition reconstituted from the solid lyophilized form can be administered, for example, subcutaneously, intravenously, parenterally, intraperitoneally, intradermally, intramuscularly, topically, enteral (e.g., orally), rectally, nasally, buccally, sublingually, vaginally, by inhalation spray, by drug pump or via an implanted reservoir in dosage formulations containing conventional non-toxic, physiologically acceptable carriers or vehicles. In one embodiment, the composition of the present disclosure is administered intravenously.

Further, Compound I or Compounds 1-12, or a pharmaceutically acceptable salt or ester thereof, or a composition comprising thereof, can be administered to a localized area in need of treatment. For example, a formulation or a composition reconstituted from the presently disclosed lyophilized forms can be administered to a localized area in need of treatment. Administration to a localized area can be achieved by, for example, and not by way of limitation, local infusion during surgery, topical application, transdermal patches, by injection, by catheter, by suppository, or by implant (the implant can optionally be of a porous, non-porous, or gelatinous material), including membranes, such as sialastic membranes or fibers.

The form of Compound I or Compounds 1-12, or a pharmaceutically acceptable salt or ester thereof, a composition comprising thereof, or the formulation or the composition in which the solid lyophilized form is administered (e.g., syrup, elixir, capsule, tablet, foams, emulsion, gel, etc.) will depend in part on the route by which it is administered. For example, for mucosal (e.g., oral mucosa, rectal, intestinal mucosa, bronchial mucosa) administration, nose drops, aerosols, inhalants, nebulizers, eye drops or suppositories can be used. Compound I or Compounds 1-12, or a pharmaceutically acceptable salt or ester thereof, or a composition comprising thereof, and the solid lyophilized form can also be used to coat bioimplantable materials to enhance neurite outgrowth, neural survival, or cellular interaction with the implant surface. Compound I or Compounds 1-12, or a pharmaceutically acceptable salt or ester thereof, or a composition comprising thereof; or the solid lyophilized forms disclosed herein can be administered together with other biologically active agents, such as anticancer agents, analgesics, anti-inflammatory agents, anesthetics and other agents which can control one or more symptoms or causes of a disorder or a condition characterized by cell proliferation.

In one embodiment, the solid lyophilized form of Compound I, or pharmaceutically acceptable salt and/or solvate of Compound I, as disclosed herein, can be administered in combination with one or more therapeutically active agent. In one embodiment, the one or more therapeutically active agent is an anticancer agent. In some embodiments, the one or more therapeutically active anticancer agents include, but are not limited to, paclitaxel, vinblastine, vincristine, etoposide, doxorubicin, hercepztin, lapatinib, gefitinib, erlotinib, tamoxifen, fulvestrant, anastrazole, lectrozole, exemestane, fadrozole, cyclophosphamide, taxotere, melphalan, chlorambucil, mechlorethamine, chlorambucil, phenylalanine, mustard, cyclophosphamide, ifosfamide, carmustine (BCNU), lomustine (CCNU), streptozotocin, busulfan, thiotepa, cisplatin, carboplatin, dactinomycin (actinomycin D), doxorubici(adriamycin), daunorubicin, idarubicin, mitoxantrone, plicamycin, mitomycin, C Bleomycin, combinations thereof, and the like. In another embodiment, the one or more therapeutically active anticancer agents include, but are not limited to, PARP (poly (DP-ribose)polymerase) inhibitors. Suitable PARP inhibitors include, but are not limited to, 4-(3-(1-(cyclopropanecarbonyl)piperazine-4-carbonyl)-4-fluorobenzyl)phthalazin-1(2H)-one (olaparib, AZD2281, Ku-0059436), 2-[(2R)-2-methylpyrrolidin-2-yl]-1H-benzimidazole-4-carboxamide (Veliparib, ABT-888), (8S,9R)-5-fluoro-8-(4-fluorophenyl)-9-(1-methyl-1H-1,2,4-triazol-5-yl)-8,9-dihydro-2H-pyrido[4,3,2-de]phthalazin-3(7H)-one (talazoparib, BMN 673), 4-iodo-3-nitrobenzamide (iniparib, BSI-201), 8-fluoro-5-(4-((methylamino)methyl)phenyl)-3,4-dihydro-2H-azepino[5,4,3-cd]indol-1(6H)-one phosphoric acid (Rucaparib, AG-014699, PF-01367338), 2-[4-[(dimethylamino)methyl]phenyl]-5,6-dihydroimidazo[4,5,1-jk][1,4]benzodiazepin-7(4H)-one (AG14361), 3-aminobenzamide (INO-1001), 2-(2-fluoro-4-((S)-pyrrolidin-2-yl)phenyl)-3H-benzo[d]imidazole-4-carboxamide (A-966492), N-(5,6-dihydro-6-oxo-2-phenanthridinyl)-2-acetamide hydrochloride (PJ34, PJ34 HCl), MK-4827, 3,4-dihydro-4-oxo-3,4-dihydro-4-oxo-N-[(1S)-1-phenylethyl]-2-quinazolinepropanamide (ME0328), 5-(2-oxo-2-phenylethoxy)-1(2H)-isoquinolinone (UPF-1069), 4-[[4-fluoro-3-[(4-methoxy-1-piperidinyl)carbonyl]phenyl]methyl]-1(2H)-phthalazinone (AZD 2461), 5-((3-chlorophenyl)amino)benzo[c][2,6]naphthyridine-8-carboxylic acid (CX-4945), and the like. In another embodiment, the one or more therapeutically active agent is an immunotherapeutic agent. In some embodiments, the one or more immunotherapeutic agents includes, but are not limited to, a monoclonal antibody, an immune effector cell, adoptive cell transfer, an immunotoxin, a vaccine, a cytokine, and the like.

In one embodiment, Compound I or Compounds 1-12, or a pharmaceutically acceptable salt or ester thereof, or a composition comprising thereof can be administered in combination with radiotherapy. In another embodiment, the solid lyophilized form of Compound 1, or a pharmaceutically acceptable salt and/or solvate of Compound I, as disclosed herein, can be administered in combination with radiotherapy.

Additionally, administration can comprise administering to the subject a plurality of dosages over a suitable period of time. Such administration regimens can be determined according to routine methods, upon a review of the instant disclosure.

Compound I or Compounds 1-12, or a pharmaceutically acceptable salt or ester thereof, of the invention are generally administered in a dose of about 0.01 mg/kg/dose to about 100 mg/kg/dose. Alternately the dose can be from about 0.1 mg/kg/dose to about 10 mg/kg/dose; or about 1 mg/kg/dose to 10 mg/kg/dose. Time release preparations may be employed or the dose may be administered in as many divided doses as is convenient. When other methods are used (e.g. intravenous administration), solid lyophilized forms are administered to the affected tissue at a rate from about 0.05 to about 10 mg/kg/hour, alternately from about 0.1 to about 1 mg/kg/hour. Such rates are easily maintained when these solid lyophilized forms are intravenously administered as discussed herein. Generally, topically administered formulations are administered in a dose of about 0.5 mg/kg/dose to about 10 mg/kg/dose range. Alternately, topical formulations are administered at a dose of about 1 mg/kg/dose to about 7.5 mg/kg/dose or even about 1 mg/kg/dose to about 5 mg/kg/dose.

Lyophilized forms of the invention are generally administered in a dose of about 0.01 mg/kg/dose to about 100 mg/kg/dose. Alternately the dose can be from about 0.1 mg/kg/dose to about 10 mg/kg/dose; or about 1 mg/kg/dose to 10 mg/kg/dose. Time release preparations may be employed or the dose may be administered in as many divided doses as is convenient. When other methods are used (e.g. intravenous administration), solid lyophilized forms are administered to the affected tissue at a rate from about 0.05 to about 10 mg/kg/hour, alternately from about 0.1 to about 1 mg/kg/hour. Such rates are easily maintained when these solid lyophilized forms are intravenously administered as discussed herein. Generally, topically administered formulations are administered in a dose of about 0.5 mg/kg/dose to about 10 mg/kg/dose range. Alternately, topical formulations are administered at a dose of about 1 mg/kg/dose to about 7.5 mg/kg/dose or even about 1 mg/kg/dose to about 5 mg/kg/dose.

A range of from about 0.1 to about 100 mg/kg is appropriate for a single dose. Continuous administration is appropriate in the range of about 0.05 to about 10 mg/kg.

Drug doses can also be given in milligrams per square meter of body surface area rather than body weight, as this method achieves a good correlation to certain metabolic and excretionary functions. Moreover, body surface area can be used as a common denominator for drug dosage in adults and children as well as in different animal species (Freireich et al., (1966) Cancer Chemother Rep. 50, 219-244). Briefly, to express a mg/kg dose in any given species as the equivalent mg/sq m dose, the dosage is multiplied by the appropriate km factor. In an adult human, 100 mg/kg is equivalent to 100 mg/kg×37 kg/sq m=3700 mg/m².

A dosage form of the present invention may contain at least one of Compound I or Compounds 1-12, or a pharmaceutically acceptable salt or ester thereof, as disclosed herein, in an amount of about 5 mg to about 500 mg. A dosage form of the present invention may contain at least one of Compounds 1-12, or a pharmaceutically acceptable salt or ester thereof, as disclosed herein, in an amount of about 5 mg to about 500 mg. That is, a dosage form of the present invention may contain Compound I or Compounds 1-12, or a pharmaceutically acceptable salt or ester thereof, in an amount of about 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 125 mg, 130 mg, 140 mg, 150 mg, 160 mg, 170 mg, 175 mg, 180 mg, 190 mg, 200 mg, 210 mg, 220 mg, 225 mg, 230 mg, 240 mg, 250 mg, 260 mg, 270 mg, 275 mg, 280 mg, 290 mg, 300 mg, 310 mg, 320 mg, 325 mg, 330 mg, 340 mg, 350 mg, 360 mg, 370 mg, 375 mg, 380 mg, 390 mg, 400 mg, 410 mg, 420 mg, 425 mg, 430 mg, 440 mg, 450 mg, 460 mg, 470 mg, 475 mg, 480 mg, 490 mg, or 500 mg. In one embodiment, such dosage amount is administered to a patient as a daily dose either in a single dose or in divided portions served multiple times a day, such as twice, three times, or four times a day.

In one embodiment, the lyophilized forms of the invention are generally administered in a dose of about 1 mg/m² to about 2000 mg/m² of Compound I, or a pharmaceutically acceptable salt and/or solvate of Compound I, as disclosed herein. In one embodiment, the lyophilized forms of the invention are administered in a dose of about 10 mg/m² to about 1500 mg/m² of Compound I, or a pharmaceutically acceptable salt and/or solvate thereof. In another embodiment, the lyophilized forms of the invention are administered in a dose of about 200 mg/m² to about 800 mg/m² of Compound I, or a pharmaceutically acceptable salt and/or solvate thereof. In another embodiment, the lyophilized forms of the invention are administered in a dose of about 20 mg/m² to about 300 mg/m² of Compound I, or a pharmaceutically acceptable salt and/or solvate thereof. In some embodiments, the dose can vary dependent on the type of diseases or conditions which Compound I, or a pharmaceutically acceptable salt and/or solvate thereof is being administered for (e.g., cancer or solid tumor). In some embodiments, the dose can vary depending on the health of the patients or the patient's sensitivity to Compound I, or a pharmaceutically acceptable salt and/or solvate thereof.

In one embodiment, the lyophilized forms of the invention are administered in a dose of about 25 mg/m² to about 2000 mg/m² of Compound I, or a pharmaceutically acceptable salt and/or solvate thereof. In one embodiment, the lyophilized forms of the invention can be administered in a dose of about 25 mg/m², about 30 mg/m², about 35 mg/m², about 40 mg/m², about 45 mg/m², about 50 mg/m², about 55 mg/m², about 60 mg/m², about 65 mg/m², about 70 mg/m², about 75 mg/m², about 80 mg/m², about 85 mg/m², about 90 mg/m², about 95 mg/m², about 100 mg/m², about 110 mg/m², about 120 mg/m², about 125 mg/m², about 130 mg/m², about 140 mg/m², about 150 mg/m², about 160 mg/m², about 170 mg/m², about 175 mg/m², about 180 mg/m², about 190 mg/m², about 200 mg/m², about 210 mg/m², about 220 mg/m², about 225 mg/m², about 230 mg/m², about 240 mg/m², about 250 mg/m², about 260 mg/m², about 270 mg/m², about 275 mg/m², about 280 mg/m², about 290 mg/m², about 300 mg/m², about 310 mg/m², about 320 mg/m², about 325 mg/m², about 330 mg/m², about 340 mg/m², about 350 mg/m², about 360 mg/m², about 370 mg/m², about 375 mg/m², about 380 mg/m², about 390 mg/m², about 400 mg/m², about 410 mg/m², about 420 mg/m², about 425 mg/m², about 430 mg/m², about 440 mg/m², about 450 mg/m², about 460 mg/m², about 470 mg/m², about 475 mg/m², about 480 mg/m², about 490 mg/m², about 500 mg/m², about 510 mg/m², about 520 mg/m², about 525 mg/m², about 530 mg/m², about 540 mg/m², about 550 mg/m², about 560 mg/m², about 570 mg/m², about 575 mg/m², about 580 mg/m², about 590 mg/m², about 500 mg/m², about 610 mg/m², about 620 mg/m², about 625 mg/m², about 630 mg/m², about 640 mg/m², about 650 mg/m², about 660 mg/m², about 670 mg/m², about 675 mg/m², about 680 mg/m², about 690 mg/m², about 700 mg/m², about 710 mg/m², about 720 mg/m², about 725 mg/m², about 730 mg/m², about 740 mg/m², about 750 mg/m², about 760 mg/m², about 770 mg/m², about 775 mg/m², about 780 mg/m², about 790 mg/m², about 800 mg/m², about 810 mg/m², about 820 mg/m², about 825 mg/m², about 830 mg/m², about 840 mg/m², about 850 mg/m², about 860 mg/m², about 870 mg/m², about 875 mg/m², about 880 mg/m², about 890 mg/m², about 900 mg/m², about 910 mg/m², about 920 mg/m², about 925 mg/m², about 930 mg/m², about 940 mg/m², about 950 mg/m², about 960 mg/m², about 970 mg/m², about 975 mg/m², about 980 mg/m², about 990 mg/m², about 1000 mg/m², about 1010 mg/m², about 1020 mg/m², about 1025 mg/m², about 1030 mg/m², about 1040 mg/m², about 1050 mg/m², about 1060 mg/m², about 1070 mg/m², about 1075 mg/m², about 1080 mg/m², about 1090 mg/m², about 1100 mg/m², about 1110 mg/m², about 1120 mg/m², about 1125 mg/m², about 1130 mg/m², about 1140 mg/m², about 1150 mg/m², about 1160 mg/m², about 1170 mg/m², about 1175 mg/m², about 1180 mg/m², about 1190 mg/m², about 1200 mg/m², about 1210 mg/m², about 1220 mg/m², about 1225 mg/m², about 1230 mg/m², about 1240 mg/m², about 1250 mg/m², about 1260 mg/m², about 1270 mg/m², about 1275 mg/m², about 1280 mg/m², about 1290 mg/m², about 1300 mg/m², about 1310 mg/m², about 1320 mg/m², about 1325 mg/m², about 1330 mg/m², about 1340 mg/m², about 1350 mg/m², about 1360 mg/m², about 1370 mg/m², about 1375 mg/m², about 1380 mg/m², about 1390 mg/m², about 1400 mg/m², about 1410 mg/m², about 1420 mg/m², about 1425 mg/m², about 1430 mg/m², about 1440 mg/m², about 1450 mg/m², about 1460 mg/m², about 1470 mg/m², about 1475 mg/m², about 1480 mg/m², about 1490 mg/m², about 1500 mg/m², about 1510 mg/m², about 1520 mg/m², about 1525 mg/m², about 1530 mg/m², about 1540 mg/m², about 1550 mg/m², about 1560 mg/m², about 1570 mg/m², about 1575 mg/m², about 1580 mg/m², about 1590 mg/m², about 1500 mg/m², about 1610 mg/m², about 1620 mg/m², about 1625 mg/m², about 1630 mg/m², about 1640 mg/m², about 1650 mg/m², about 1660 mg/m², about 1670 mg/m², about 1675 mg/m², about 1680 mg/m², about 1690 mg/m², about 1700 mg/m², about 1710 mg/m², about 1720 mg/m², about 1725 mg/m², about 1730 mg/m², about 1740 mg/m², about 1750 mg/m², about 1760 mg/m², about 1770 mg/m², about 1775 mg/m², about 1780 mg/m², about 1790 mg/m², about 1800 mg/m², about 1810 mg/m², about 1820 mg/m², about 1825 mg/m², about 1830 mg/m², about 1840 mg/m², about 1850 mg/m², about 1860 mg/m², about 1870 mg/m², about 1875 mg/m², about 1880 mg/m², about 1890 mg/m², about 1900 mg/m², about 1910 mg/m², about 1920 mg/m², about 1925 mg/m², about 1930 mg/m², about 1940 mg/m², about 1950 mg/m², about 1960 mg/m², about 1970 mg/m², about 1975 mg/m², about 1980 mg/m², about 1990 mg/m², or about 2000 mg/m² of Compound I, or a pharmaceutically acceptable salt and/or solvate thereof.

In one embodiment, the lyophilized forms of the invention can be generally administered in a dose of about less than about 500 mg/m² of Compound I, or a pharmaceutically acceptable salt and/or solvate thereof. In another embodiment, the lyophilized forms of the invention are generally administered in a dose of less than about 500 mg/m², less than about 490 mg/m², less than about 480 mg/m², less than about 475 mg/m², less than about 470 mg/m², less than about 460 mg/m², less than about 450 mg/m², less than about 440 mg/m², less than about 430 mg/m², less than about 420 mg/m², less than about 410 mg/m², less than about 400 mg/m², less than about 390 mg/m², less than about 380 mg/m², less than about 375 mg/m², less than about 370 mg/m², less than about 360 mg/m², less than about 350 mg/m², less than about 340 mg/m², less than about 330 mg/m², less than about 320 mg/m², less than about 310 mg/m², less than about 300 mg/m², less than about 290 mg/m², less than about 280 mg/m², less than about 275 mg/m², less than about 270 mg/m², less than about 260 mg/m², less than about 250 mg/m², less than about 240 mg/m², less than about 230 mg/m², less than about 220 mg/m², less than about 210 mg/m², less than about 200 mg/m², less than about 190 mg/m², less than about 180 mg/m², or less than about 170 mg/m² of Compound I, or a pharmaceutically acceptable salt and/or solvate thereof.

In some embodiments, the lyophilized forms of the invention can be administered to a cancer patient in a dose of less than about 750 mg/m², less than about 700 mg/m², less than about 600 mg/m², less than about 500 mg/m², less than about 475 mg/m², less than about 400 mg/m², less than about 325 mg/m², less than about 300 mg/m², less than about 200 mg/m², less than about 170 mg/m², or any subranges therein, of Compound I, or a pharmaceutically acceptable salt and/or solvate thereof. In other embodiments, the lyophilized forms of the invention can be administered to a cancer patient in a dose of less than about 170 mg/m² of Compound I, or a pharmaceutically acceptable salt and/or solvate thereof, every three weeks. In one embodiment, the cancer patient is a heme cancer patient.

In some embodiments, the lyophilized forms of the invention can be administered to a cancer patient in about 50 mg/m² to about 1550 mg/m², about 150 mg/m² to about 1250 mg/m², about 250 mg/m² to about 1050 mg/m², about 350 mg/m² to about 950 mg/m², about 375 mg/m² to about 850 mg/m², about 425 mg/m² to about 850 mg/m², about 450 mg/m² to about 800 mg/m², or about 500 mg/m² to about 750 mg/m², or any subranges therein, of Compound I, or a pharmaceutically acceptable salt and/or solvate thereof. In some embodiments, the lyophilized forms of the invention can be administered to a cancer patient in a dose of less than about 750 mg/m² of Compound I, or a pharmaceutically acceptable salt and/or solvate thereof. In other embodiments, the lyophilized forms of the invention can be administered to a cancer patient in any of the dosing frequency, dosing cycle or dosing regimen described herein. In one embodiment, the treatment is for solid tumors.

In one embodiment, a dosage form of the present invention containing Compound I, or a pharmaceutically acceptable salt and/or solvate thereof, as disclosed herein, is administered once a week, once every two weeks, once every three weeks, once every four weeks, or once a month. In some embodiments, a dosage form of the present invention containing Compound I, or a pharmaceutically acceptable salt and/or solvate thereof, as disclosed herein, is administered in a four-week treatment cycle comprising one administration weekly (QW×4). In some embodiments, a dosage form of the present invention containing Compound I, or a pharmaceutically acceptable salt and/or solvate thereof, as disclosed herein, is administered in a four-week treatment cycle comprising one administration weekly for two weeks followed by two weeks of rest period (no treatment) (QW×2). In some embodiments, a dosage form of the present invention containing Compound I, or a pharmaceutically acceptable salt and/or solvate thereof, as disclosed herein, is administered in a three-week treatment cycle comprising one administration weekly for two weeks followed by one week of rest period. In another embodiment, a dosage form of the present invention containing Compound I, or a pharmaceutically acceptable salt and/or solvate thereof, as disclosed herein, is administered once every three weeks. In other embodiments, a dosage form of the present invention containing Compound I, or a pharmaceutically acceptable salt and/or solvate thereof, as disclosed herein, is administered once every three weeks by IV infusion.

In some embodiment, the treatment regimen with Compound I, or a pharmaceutically acceptable salt and/or solvate thereof, as disclosed herein, can last from 1 cycle to 20 cycles or greater period of time. An appropriate length of the treatment can be determined by a physician.

In one embodiment, $T_{max}$ of Compound I, or a pharmaceutically acceptable salt and/or solvate thereof for human subjects who received a first dose of IV infusion administration at about 25 mg/m² to about 1000 mg/m² of the lyophilized form of Compound I, or a pharmaceutically acceptable salt and/or solvate thereof is about 0.25 hour to about 1.25 hour. In another embodiment, $T_{max}$ is about 0.5 hour to about 1.0 hour.

In one embodiment, the mean elimination half-life ($T_{1/2}$) of Compound I, or a pharmaceutically acceptable salt and/or solvate thereof for human subjects who received a first dose of IV infusion administration at about 25 mg/m² to about 1000 mg/m² of the lyophilized form of Compound I, or a pharmaceutically acceptable salt and/or solvate thereof is about 20 hours to about 95 hours. In one embodiment, the mean elimination half-life ($T_{1/2}$) of Compound I, or a pharmaceutically acceptable salt and/or solvate thereof for human subjects who received a first dose of IV infusion administration at about 50 mg/m² to about 1000 mg/m² of the lyophilized form of Compound I, or a pharmaceutically acceptable salt and/or solvate thereof is about 20 hours to about 50 hours.

In one embodiment, the unbound Compound I in area under the concentration-time curve for each dosing interval every 168 hours after steady-state exposures have been achieved ($AUC_{ss\tau}$) is about 2 ng·hr/mL to about 300 ng·hr/mL for subjects who received Compound I, or a pharmaceutically acceptable salt and/or solvate thereof in about 50 mg/m² to about 1550 mg/m². In one embodiment, the $AUC_{ss\tau}$ is about 5 ng·hr/mL to about 200 ng·hr/mL for subjects who received Compound I, or a pharmaceutically acceptable salt and/or solvate thereof in about 150 mg/m² to about 1050 mg/m². In one embodiment, the $AUC_{ss\tau}$ is about 10 ng·hr/mL to about 150 ng·hr/mL for subjects who received Compound I, or a pharmaceutically acceptable salt and/or solvate thereof in about 250 mg/m² to about 950 mg/m². In one embodiment, the $AUC_{ss\tau}$ is about 15 ng·hr/mL to about 140 ng·hr/mL for subjects who received Compound I, or a pharmaceutically acceptable salt and/or solvate thereof in about 350 mg/m² to about 850 mg/m². In one embodiment, the $AUC_{ss\tau}$ is about 15 ng·hr/mL to about 150 ng·hr/mL for subjects who received Compound I, or a pharmaceutically acceptable salt and/or solvate thereof in about 450 mg/m² to about 750 mg/m². In one embodiment, the $AUC_{ss\tau}$ is about 20 ng·hr/mL to about 120 ng·hr/mL for subjects who received Compound I, or a pharmaceutically acceptable salt and/or solvate thereof in about 450 mg/m² to about 750 mg/m². In some embodiments, the subject is on QW×4 cycle dosing regimen.

In one embodiment, the $AUC_{ss\tau}$ is about 2 ng·hr/mL to about 250 ng·hr/mL for subjects who received Compound I, or a pharmaceutically acceptable salt and/or solvate thereof in about 50 mg/m² to about 1550 mg/m². In one embodiment, the $AUC_{ss\tau}$ is about 5 ng·hr/mL to about 150 ng·hr/mL for subjects who received Compound I, or a pharmaceutically acceptable salt and/or solvate thereof in about 150 mg/m² to about 1050 mg/m². In one embodiment, the $AUC_{ss\tau}$ is about 10 ng·hr/mL to about 150 ng·hr/mL for subjects who received Compound I, or a pharmaceutically acceptable salt and/or solvate thereof in about 250 mg/m² to about 950 mg/m². In one embodiment, the $AUC_{ss\tau}$ is about 15 ng·hr/mL to about 130 ng·hr/mL for subjects who received Compound I, or a pharmaceutically acceptable salt and/or solvate thereof in about 350 mg/m² to about 850 mg/m². In one embodiment, the $AUC_{ss\tau}$ is about 15 ng·hr/mL to about 130 ng·hr/mL for subjects who received Compound I, or a pharmaceutically acceptable salt and/or solvate thereof in about 450 mg/m² to about 750 mg/m². In one embodiment, the $AUC_{ss\tau}$ is about 20 ng·hr/mL to about 120 ng·hr/mL for subjects who received Compound I, or a pharmaceutically acceptable salt and/or solvate thereof in about 450 mg/m² to about 750 mg/m². In some embodiments, the subject is on QW×2 four-week cycle dosing regimen.

A dosage form of the present invention may contain Compound I, or a pharmaceutically acceptable salt and/or solvate thereof, as disclosed herein, in an amount of about 5 mg to about 500 mg. That is, a dosage form of the present invention may contain Compound I in an amount of about 5 mg, 10 mg, 15 mg, 20 mg, 25 mg, 30 mg, 35 mg, 40 mg, 45 mg, 50 mg, 55 mg, 60 mg, 65 mg, 70 mg, 75 mg, 80 mg, 85 mg, 90 mg, 95 mg, 100 mg, 110 mg, 120 mg, 125 mg, 130 mg, 140 mg, 150 mg, 160 mg, 170 mg, 175 mg, 180 mg, 190 mg, 200 mg, 210 mg, 220 mg, 225 mg, 230 mg, 240 mg, 250 mg, 260 mg, 270 mg, 275 mg, 280 mg, 290 mg, 300 mg, 310 mg, 320 mg, 325 mg, 330 mg, 340 mg, 350 mg, 360 mg, 370 mg, 375 mg, 380 mg, 390 mg, 400 mg, 410 mg, 420 mg, 425 mg, 430 mg, 440 mg, 450 mg, 460 mg, 470 mg, 475 mg, 480 mg, 490 mg, or 500 mg. A dosage form of the present invention may contain Compound I, or a pharmaceutically acceptable salt and/or solvate thereof, as disclosed herein, in an amount of about 500 mg to about 1000 mg. That is, a dosage form of the present invention may contain Compound I in an amount of about 500 mg, 510 mg, 520 mg, 525 mg, 530 mg, 540 mg, 550 mg, 560 mg, 570 mg, 575 mg, 580 mg, 590 mg, 600 mg, 610 mg, 620 mg, 625 mg, 630 mg, 640 mg, 650 mg, 660 mg, 670 mg, 675 mg, 680 mg, 690 mg, 700 mg, 710 mg, 720 mg, 725 mg, 730 mg, 740 mg, 750 mg, 760 mg, 770 mg, 775 mg, 780 mg, 790 mg, 800 mg, 810 mg, 820 mg, 825 mg, 830 mg, 840 mg, 850 mg, 860 mg, 870 mg, 875 mg, 880 mg, 890 mg, 900 mg, 910 mg, 920 mg, 925 mg, 930 mg, 940 mg, 950 mg, 960 mg, 970 mg, 975 mg, 980 mg, 990 mg, or 1000 mg. In one embodiment, such dosage amount is administered to a patient as a daily dose either in a single dose or in divided portions served multiple times a day, such as twice, three times, or four times a day.

A dosage form of the present invention may be administered, hourly, daily, weekly, or monthly. The dosage form of the present invention may be administered twice a day or once a day. The dosage form of the present invention may be administered with food or without food.

Insofar as the crystalline forms or the solid lyophilized forms disclosed herein can take the form of a mimetic or fragment thereof, it is to be appreciated that the potency, and therefore dosage of an effective amount can vary. However, one skilled in the art can readily assess the potency of a crystalline form or a solid lyophilized form of the type presently envisioned by the present application.

In settings of a gradually progressive disorder or condition characterized by cell proliferation, Compound I or Compounds 1-12, or a pharmaceutically acceptable salt or ester thereof, or a composition comprising thereof, of the present application is generally administered on an ongoing basis. In one embodiment, a gradually progressive disorder or condition characterized by cell proliferation, a formulation or a composition reconstituted from a solid lyophilized form of the present application is generally administered on an ongoing basis. In certain settings administration of a formulation or a composition reconstituted from a lyophilized form disclosed herein can commence prior to the development of disease symptoms as part of a strategy to delay or treat the disease. In other settings Compound I or Compounds 1-12, or a pharmaceutically acceptable salt or ester thereof, or a composition comprising thereof, is administered after the onset of disease symptoms as part of a strategy to slow or reverse the disease process and/or part of a strategy to improve cellular function and reduce symptoms. In other embodiments, a formulation or a composition reconstituted from a solid lyophilized form disclosed herein is administered after the onset of disease symptoms as part of a strategy to slow or reverse the disease process and/or part of a strategy to improve cellular function and reduce symptoms.

It will be appreciated by one of skill in the art that dosage range will depend on the particular composition comprising Compound I or Compounds 1-12, or a pharmaceutically acceptable salt or ester thereof, and its potency. For example, the dosage range will depend on the particular lyophilized form, and its potency. The dosage range is understood to be large enough to produce the desired effect in which the neurodegenerative or other disorder and the symptoms associated therewith are ameliorated and/or survival of the cells is achieved, but not be so large as to cause unmanageable adverse side effects. It will be understood, however, that the specific dose level for any particular patient will depend on a variety of factors including the activity of the specific composition comprising Compound I or Compounds 1-12, or a pharmaceutically acceptable salt or ester thereof employed; the age, body weight, general health, sex and diet of the individual being treated; the time and route of administration; the rate of excretion; other drugs which have previously been administered; and the severity of the particular disease undergoing therapy, as is well understood by those skilled in the art. In one embodiment, the specific composition comprises lyophilized form of Compound I. The dosage can also be adjusted by the individual physician in the event of any complication. No unacceptable toxicological effects are expected when Compound I or Compounds 1-12, or a pharmaceutically acceptable salt or ester thereof, as disclosed herein are used in accordance with the present application. Further, no unacceptable toxicological effects are expected when solid lyophilized forms disclosed herein are used in accordance with the present application.

An effective amount of Compound I or Compounds 1-12, or a pharmaceutically acceptable salt or ester thereof, disclosed herein comprise amounts sufficient to produce a measurable biological response. Actual dosage levels of active ingredients can be varied so as to administer an amount of Compound I or Compounds 1-12, or a pharmaceutically acceptable salt or ester thereof, that is effective to achieve the desired therapeutic response for a particular subject and/or application. For example, an effective amount of the solid lyophilized forms disclosed herein comprise amounts sufficient to produce a measurable biological response. Actual dosage levels of active ingredients in a therapeutic solid lyophilized form of the present application can be varied so as to administer an amount of the solid lyophilized form that is effective to achieve the desired therapeutic response for a particular subject and/or application. Preferably, a minimal dose is administered, and the dose is escalated in the absence of dose-limiting toxicity to a minimally effective amount. Determination and adjustment of a therapeutically effective dose, as well as evaluation of when and how to make such adjustments, are known to those of ordinary skill in the art.

Further with respect to the methods of the present application, a preferred subject is a vertebrate subject. A preferred vertebrate is warm-blooded; a preferred warm-blooded vertebrate is a mammal. The subject treated by the presently disclosed methods is desirably a human, although it is to be understood that the principles of the present application indicate effectiveness with respect to all vertebrate species which are included in the term "subject." In this context, a vertebrate is understood to be any vertebrate species in which treatment of a neurodegenerative disorder is desirable. As used herein, the term "subject" includes both human and animal subjects. Thus, veterinary therapeutic uses are provided in accordance with the present application.

As such, the present application provides for the treatment of mammals such as humans, as well as those mammals of importance due to being endangered, such as Siberian tigers; of economic importance, such as animals raised on farms for consumption by humans; and/or animals of social importance to humans, such as animals kept as pets or in zoos or farms. Examples of such animals include but are not limited to: carnivores such as cats and dogs; swine, including pigs, hogs, and wild boars; ruminants and/or ungulates such as cattle, oxen, sheep, giraffes, deer, goats, bison, and camels; and horses. Also provided is the treatment of birds, including the treatment of those kinds of birds that are endangered and/or kept in zoos, as well as fowl, and more particularly domesticated fowl, i.e., poultry, such as turkeys, chickens, ducks, geese, guinea fowl, and the like, as they are also of economic importance to humans. Thus, also provided are the treatment of livestock, including, but not limited to, domesticated swine, ruminants, ungulates, horses (including race horses), poultry, and the like.

The disclosures, including various methods of treatment, of WO 2017/087235 are hereby incorporated by reference in their entirety for all purposes.

The following examples further illustrate the present invention but should not be construed as in any way limiting its scope.

EXAMPLES

Materials

Commercially available materials were used as received, unless otherwise noted. Compound I, or a pharmaceutically acceptable salt, solvate, and/or prodrug can be synthesized by known synthetic routes or by chemistry known by one skilled in the art (see, e.g., U.S. Pat. Nos. 7,928,100 and 8,853,234).

Example 1. Stability of Ready-to-Use Formulation of Non-Lyophilized Compound I

Non-lyophilized Compound I was formulated into ready-to-use solution having the following composition:

| | |
|---|---|
| Compound I (non-lyophilized) | 250 mg |
| Monosodium Phosphate USP | 59.99 mg |
| 1M HCl (to adjust pH to 6) | 0.33 mg |
| Sterile Water for Injection | Fill to 10.0 mL |

Compound I was dissolved in monosodium phosphate buffer solution, the pH was adjusted to 6 with 1M HCl, and sterile filtration was carried out. The filtered solution was filled into 10 mL vials and sealed with stoppers and flip-off seals.

Samples were stored under ICH (International Conference on Harmonisation) stability conditions:

| Long Term: | 25° C. ± 2° C. at 60% ± 5% relative humidity (RH) |
|---|---|
| Accelerated: | 40° C. ± 2° C. at 75% ± 5% relative humidity (RH) |

The ready-to-use samples subjected to the stability conditions were analyzed by HPLC for purity of Compound I and impurities (HPLC area %) using below conditions:

Instrument: Cambridge Major Laboratories method TM594.

Aqueous mobile phase (A): water/ACN/perchloric acid: (950/50/2).

Organic mobile phase (B): methanol/ACN: (50/50).

The method consists of a 10% (B) held for 5 minutes, then a gradient from 10-75% (B) in 30 minutes and a return to 10% (B) at 35.1 minutes and equilibration at 10% (B) for another 5 minutes (total run time=40 minutes). The method utilizes a Zorbax SB-CN, 3 μm, 4.6 mm ID×150 mm column equilibrated at 30° C. and run at 1.5 mL/minute. Detection is at 240 nm. The samples were prepared in a 50:50 mixture of water and acetonitrile. The injection volume was 20 μL.

TABLE 1

Stability Data over 6 months at 40° C./75% RH

| Sample Description | Appearance | pH | Purity by HPLC (%) | Total Impurities by HPLC (%) |
|---|---|---|---|---|
| The day formulation was prepared | Clear, pale yellow solution | 5.9 | 99 | 1.03 |
| 1 Month 40° C./75% RH Upright | Clear, pale yellow solution | 6.0 | 98 | 1.53 |
| 1 Month 40° C./75% RH Inverted | Clear, pale yellow solution | 6.0 | 98 | 1.55 |
| 3 Months 40° C./75% RH Upright | Clear, pale yellow solution | 6.1 | 97 | 2.49 |
| 3 Months 40° C./75% RH Inverted | Clear, pale yellow solution | 6.1 | 97 | 2.58 |
| 6 Months 40° C./75% RH Upright | Clear, pale yellow solution | 6.0 | 96 | 3.91 |
| 6 Months 40° C./75% RH Inverted | Clear, pale yellow solution | 6.0 | 96 | 3.94 |

TABLE 2

Stability Data over 6 months at 25° C./60% RH

| Sample Description | Appearance | pH | Purity by HPLC (%) | Total Impurities by HPLC (%) |
|---|---|---|---|---|
| The day formulation was prepared | Clear, pale yellow solution | 5.9 | 99 | 1.03 |
| 3 Months 40° C./75% RH Upright | Clear, pale yellow solution | 6.0 | 99 | 1.16 |
| 3 Months 40° C./75% RH Inverted | Clear, pale yellow solution | 6.1 | 99 | 1.16 |
| 6 Months 40° C./75% RH Upright | Clear, pale yellow solution | 6.0 | 99 | 1.26 |
| 6 Months 40° C./75% RH Inverted | Clear, pale yellow solution | 6.0 | 99 | 1.28 |

As shown in Tables 1 and 2, the ready-to-use formulation prepared with non-lyophilized Compound I showed more than 1% impurity under the tested storage conditions. Under the accelerated conditions (Table 1), the impurities increased to about 1.5% in one month, to about 2.5% at 3 months, and about 4% by 6 months. The non-lyophilized Compound I was determined to not have adequate stability at 25° C. and at 40° C.

Example 2. Formation of a Solid Lyophilized Form of Compound I with Mannitol as a Bulking Agent without Buffering Agent To a tared bottle containing a magnetic stirrer and covered with aluminum foil, 150 g of mannitol, 1000 mL water, and 15 mL of a 2 M hydrochloric acid (HCl) solution were added and the solution was stirred for approximately 10 minutes. Then the solution was sparged with nitrogen with stirring for approximately 15 minutes or until the dissolved oxygen content was <1 ppm. Nitrogen sparging continued throughout the remaining process. Compound I (free base) (45.345 g) was transferred to the beaker containing mannitol and HCl with nitrogen sparged water (10 mL×5). The headspace of the bottle was blanketed with nitrogen for 3 minutes and sealed with a lid. Stir solution to dissolve Compound I and if necessary add 2 M HCl solution and/or water to facilitate dissolution to obtain clear solution. Once compound I is completely dissolved, the solution was sparged with nitrogen with stirring for approximately 15 minutes or until the dissolved oxygen was <1 ppm. The pH of the solution was measured and then adjusted to pH 4.5±0.1 using 0.1-2 M HCl or 0.1-2 M NaOH as necessary. The volume of the solution was then adjusted to 500 mL with degassed water and sparged with nitrogen with stirring for approximately 15 minutes or until the dissolved oxygen was <1 ppm. The headspace of the bottle was blanketed with nitrogen for 3 minutes and sealed with a lid. The final pH was measured (pH 4.52). The solution was filtered through a filter chain (1×0.45 μm and 2×0.2 μm in series). The filtered solution was pumped into 30 mL vials (approximately 5 g or 5 mL each), partially stoppered and placed in the freeze dryer chamber. The freeze dry cycle used is shown in Table 3.

TABLE 3

Freeze Dry Cycle

| Step | Process | Temp. (° C.) | Ramp rate (° C./min) | Ramp time (min) | Hold time (min) | Pressure (mTorr) |
|---|---|---|---|---|---|---|
| 1 | Load | 5 | 1 | 20 | 60 | n/a |
| 2 | Freezing | −30 | 0.3 | 116.66 | 180 | n/a |
| 3 | Freezing | −45 | 0.3 | 50 | 180 | n/a |
| 4 | Annealing | −15 | 0.3 | 100 | 180 | n/a |
| 5 | Freezing | −45 | 0.3 | 100 | 180 | n/a |

TABLE 3-continued

Freeze Dry Cycle

| Step | Process | Temp. (° C.) | Ramp rate (° C./min) | Ramp time (min) | Hold time (min) | Pressure (mTorr) |
|---|---|---|---|---|---|---|
| 6 | Initiate vacuum | −45 | 0 | 0 | 30 | 350 |
| 7 | Primary drying | −15 | 0.3 | 100 | 3360 | 350 |
| 8 | Secondary drying | 25 | 0.3 | 133.33 | 500 | 50 |
| 9 | Finish | Vials closed under 90-95% pure nitrogen | | | | |

Total cycle time = 5290 minutes (3.7 days)

In some embodiments, the primary drying process is complete after 4900 minutes. In some embodiments, the total cycle time is about 4.4 days.

At the end of the freeze dry cycle, a white homogeneous plug was observed in the vials which showed little signs of shrinkage or cracking.

Example 3. Effect of Annealing by Freeze Drying Microscope

Free drying microscope (FDM) was used to determine the collapse temperature of the solid lyophilized form of Compound I as prepared according to Example 2. Analysis was performed with and without an annealing step. Each analysis was performed using a 10× objective lens with bright field transmitted light. A summary of the key observations from each analysis performed are shown in Table 4. Two runs were performed; run 1 with an annealing step (−15° C.) and run 2 without the annealing step.

TABLE 4

Thermal Observations by FDM of the Solid Lyophilized Form of Compound I as prepared according to Example 2

| Run | Annealing | Freezing (° C.) | Onset (° C.) | Collapse (° C.) |
|---|---|---|---|---|
| 1 | No | −22.6 | −9.3 | −5.1 |
| 2 | Yes | −26.4 | −6.9 | −4.0 |

Subtle changes in sample structure, e.g. ill-defined drying front, were noted as the first indications of sample collapse, followed by the appearance of bright spots. These visual observations were interpreted as the onset of collapse. Further loss of structure was evident as larger bright regions developed which spread across the sample. These regions subsequently formed a rip, resulting in gross collapse. This development of inter-connected bright regions/rips was taken as collapse of the product.

Example 4. Effect of Annealing by Differential Scanning Calorimetry

The solution containing the solid lyophilized form of Compound I as prepared according to Example 2 was analyzed by differential scanning calorimetry (DSC), with and without annealing, using the parameters shown in Table 5.

TABLE 5

DSC Parameters

| Parameter | Setting |
|---|---|
| Run 1 | 1. 25° C. to −50° C. at 1° C./min |
| | 2. hold −50° C. for 10 min |
| | 3. −50° C. to 25° C. at 1° C./min |
| Run 2 | 1. 25° C. to −50° C. at 2° C./min, hold for 10 min |
| | 2. annealing at −15° C., hold for 10 min |
| | 3. −15° C. to −50° C. at 2° C./min, hold for 10 min |
| | 4. −50° C. to 25° C. at 2° C./min |
| Run 3 | 1. 25° C. to −50° C. at 2° C./min, hold for 10 min |
| | 2. annealing at −20° C., hold for 10 min |
| | 3. −20° C. to −50° C. at 2° C./min, hold for 10 min |
| | 4. −50° C. to 25° C. at 2° C./min |
| Run 4 | 1. 25° C. to −50° C. at 2° C./min, hold for 10 min |
| | 2. annealing at −10° C., hold for 10 min |
| | 3. −15° C. to −50° C. at 2° C./min |
| | 4. −50° C. to 25° C. at 2° C./min |
| Crucible | Sealed 100 μL aluminum |
| Reference sample | Empty crucible |
| Purge gas | 60 mL/min $N_2$ |
| Dry gas | 170 mL/min $N_2$ |

Figure 2:
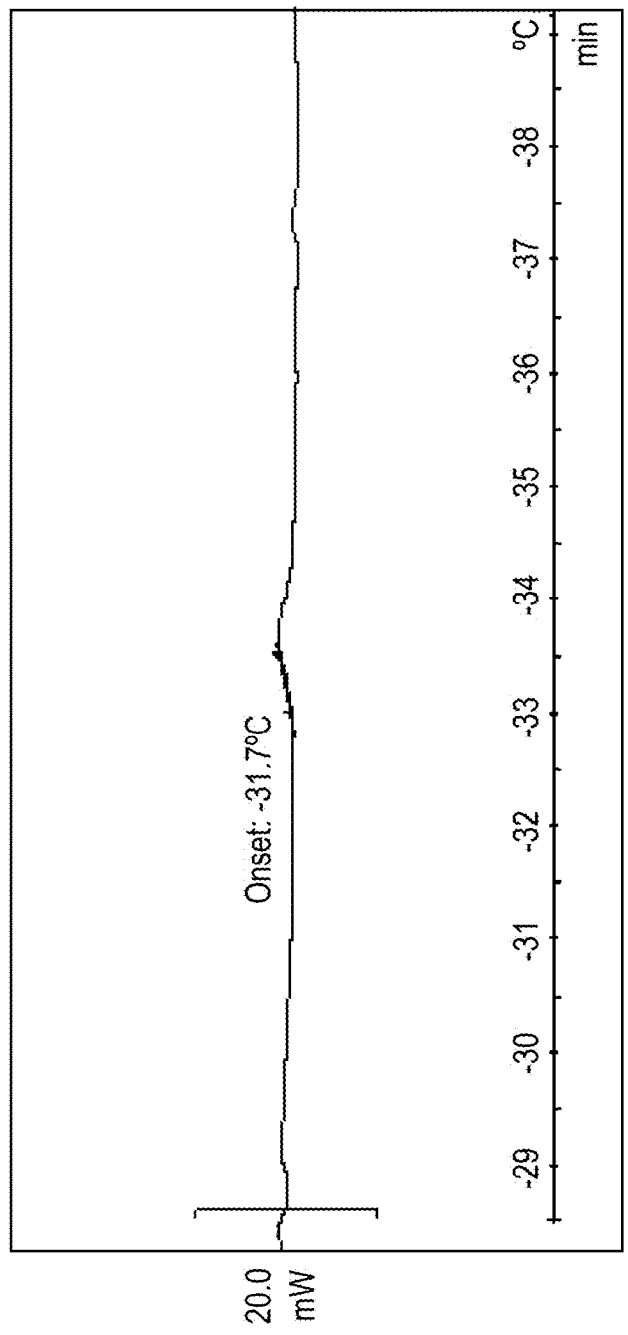
FIG. 2 is a magnification of the differential scanning calorimetry (DSC) thermogram of Run 1 as described in Example 4.
Figure 3:
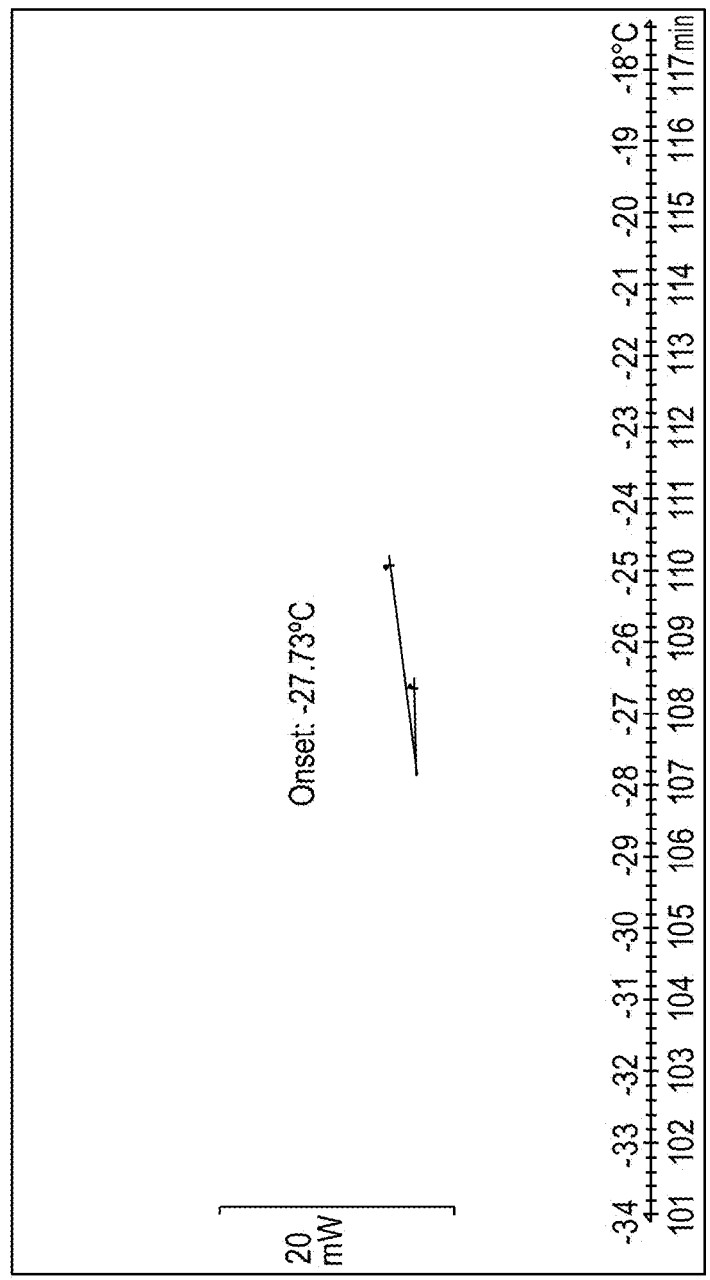
FIG. 3 is a magnification of the differential scanning calorimetry (DSC) thermogram of Run 1 as described in Example 4.
Figure 4:
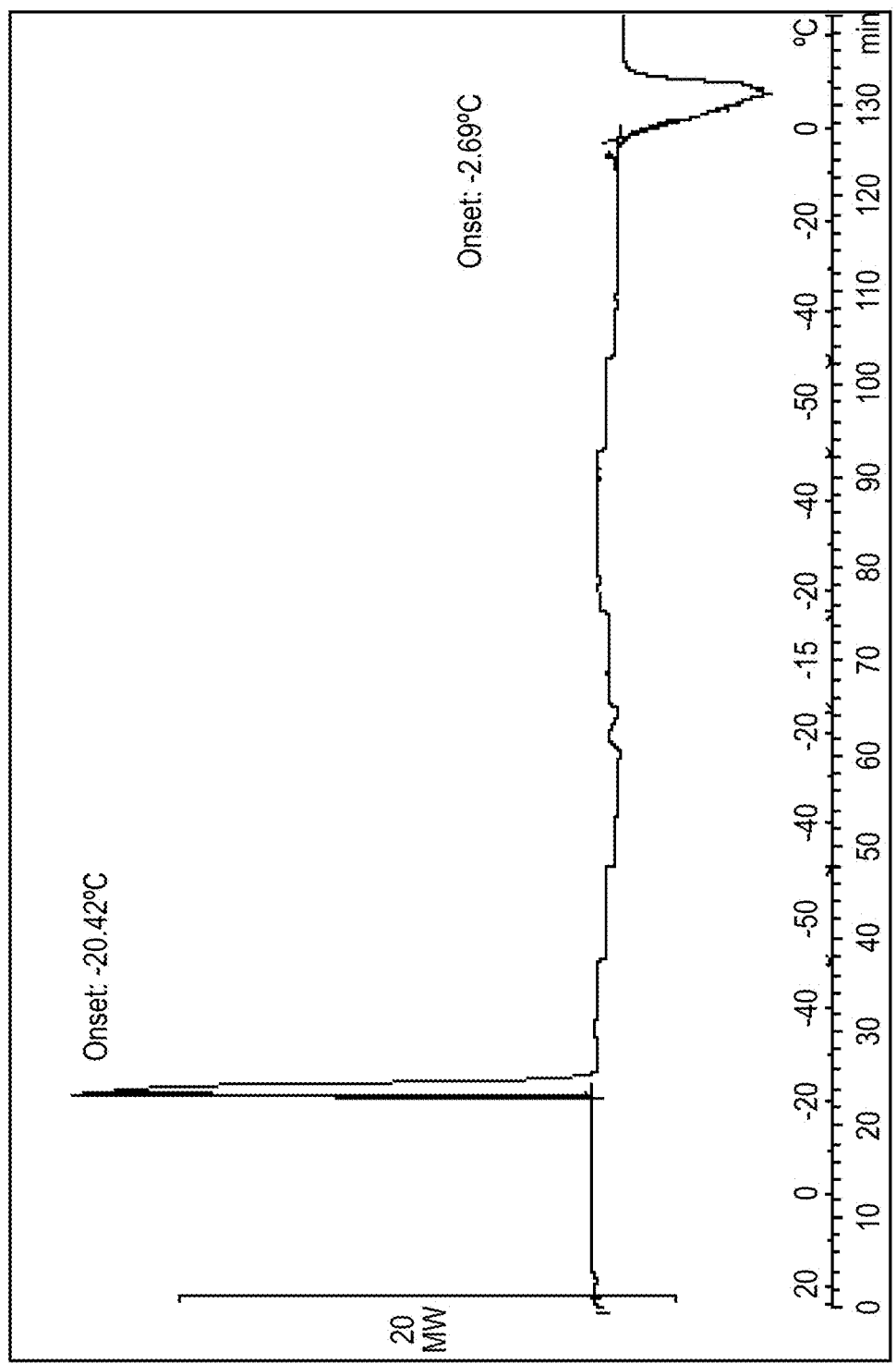
FIG. 4 is a differential scanning calorimetry (DSC) thermogram of Run 2 as described in Example 4.
Figure 5:
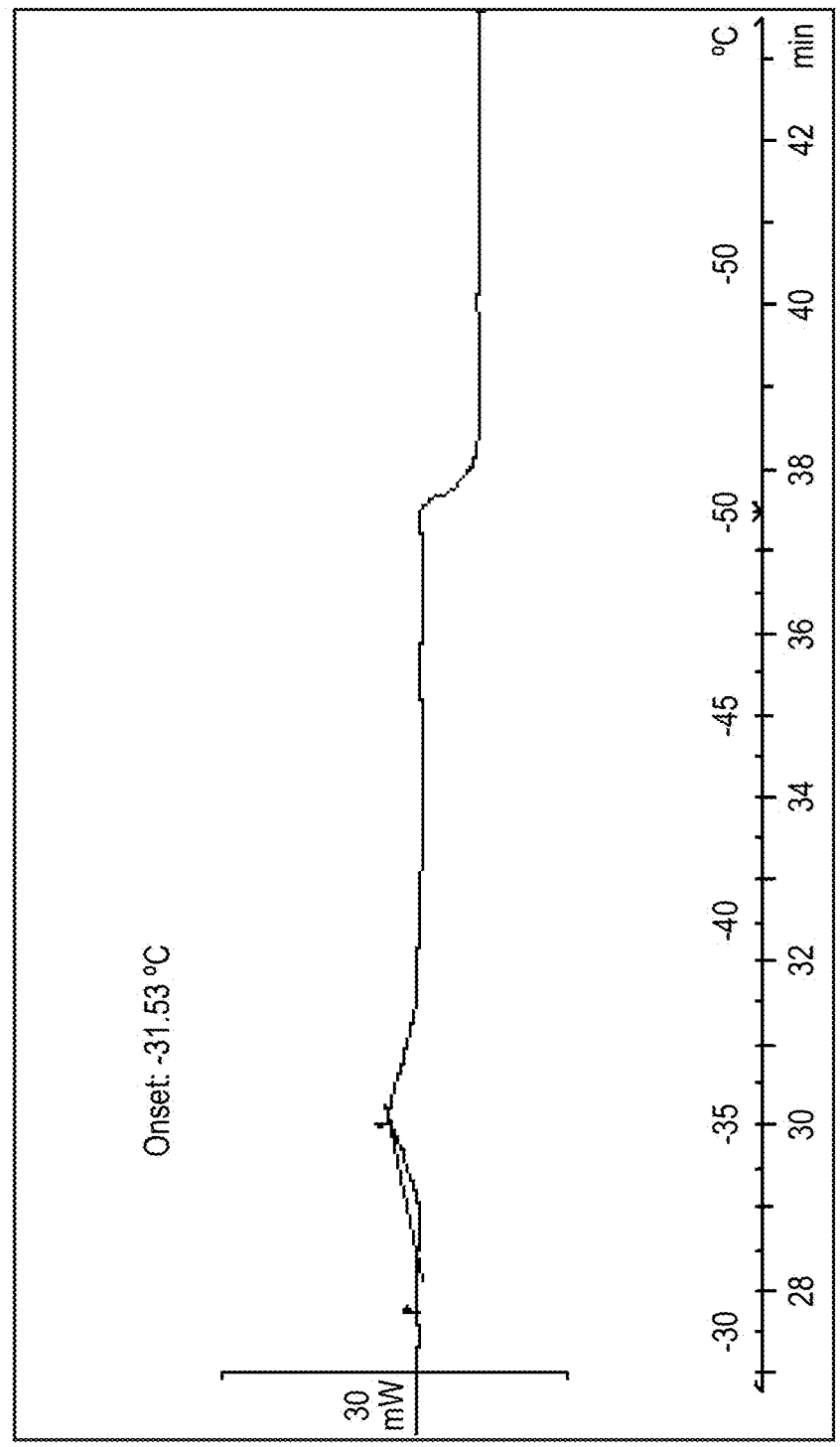
FIG. 5 is a magnification of the differential scanning calorimetry (DSC) thermogram of Run 2 as described in Example 4.
Figure 6:
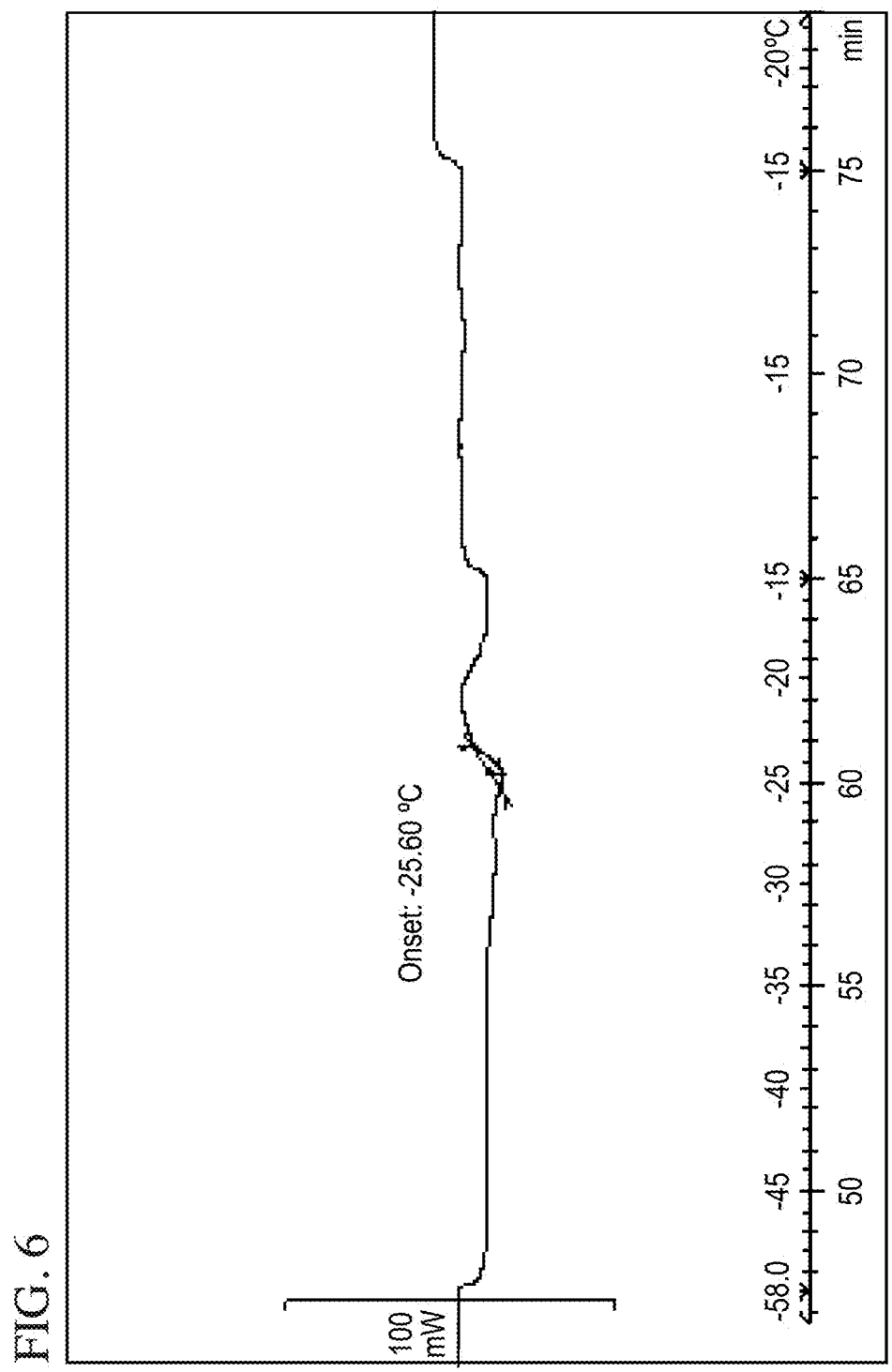
FIG. 6 is a magnification of the differential scanning calorimetry (DSC) thermogram of Run 2 as described in Example 4.
Figure 7:
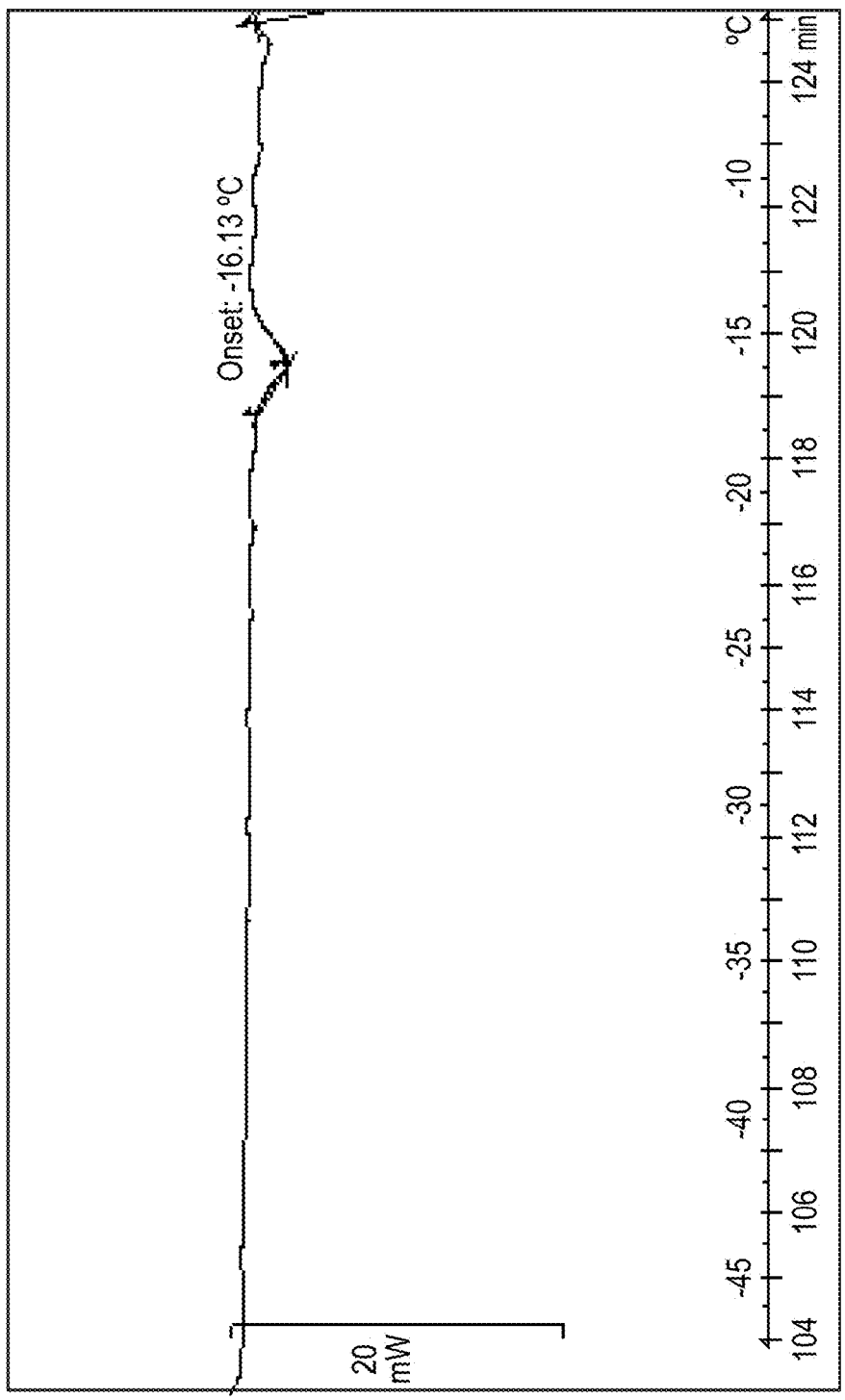
FIG. 7 is a magnification of the differential scanning calorimetry (DSC) thermogram of Run 2 as described in Example 4.

Run 1: Run 1 was conducted without an annealing step. On cooling, a large well defined freezing exotherm (−15.59° C.) and a second smaller exotherm was detected (−31.7° C.). Without bound to any theory, the second exotherm is thought to be a result of the partial crystallization of mannitol. On warming, a small exotherm was observed at approximately −25° C. before reaching the large broad melting endoderm which had an onset temperature at −2.43° C. DSC thermogram of Run 1 is shown in FIGS. 1-3.

Run 2: Run 2 was conducted with an annealing step at −15° C., which was held for 10 minutes. The observations from the DSC thermogram were similar to Run 1. On cooling, a large well defined freezing exotherm and a secondary smaller exotherm were observed at −20.42° C. and −31.53° C., respectively. On warming, a small exotherm, thought to represent mannitol crystallization, was detected at −26° C. Following annealing at −15° C. the crystallization exotherm is not observed. A small endotherm was observed at −16° C. Without bound to any theory, this endotherm was thought to be a result of a small melt. With continued heating, a larger broad melting endoderm was observed which had an onset temperature at −2.69° C. DSC thermogram of Run 2 is shown in FIGS. 4-7.

Figure 8:
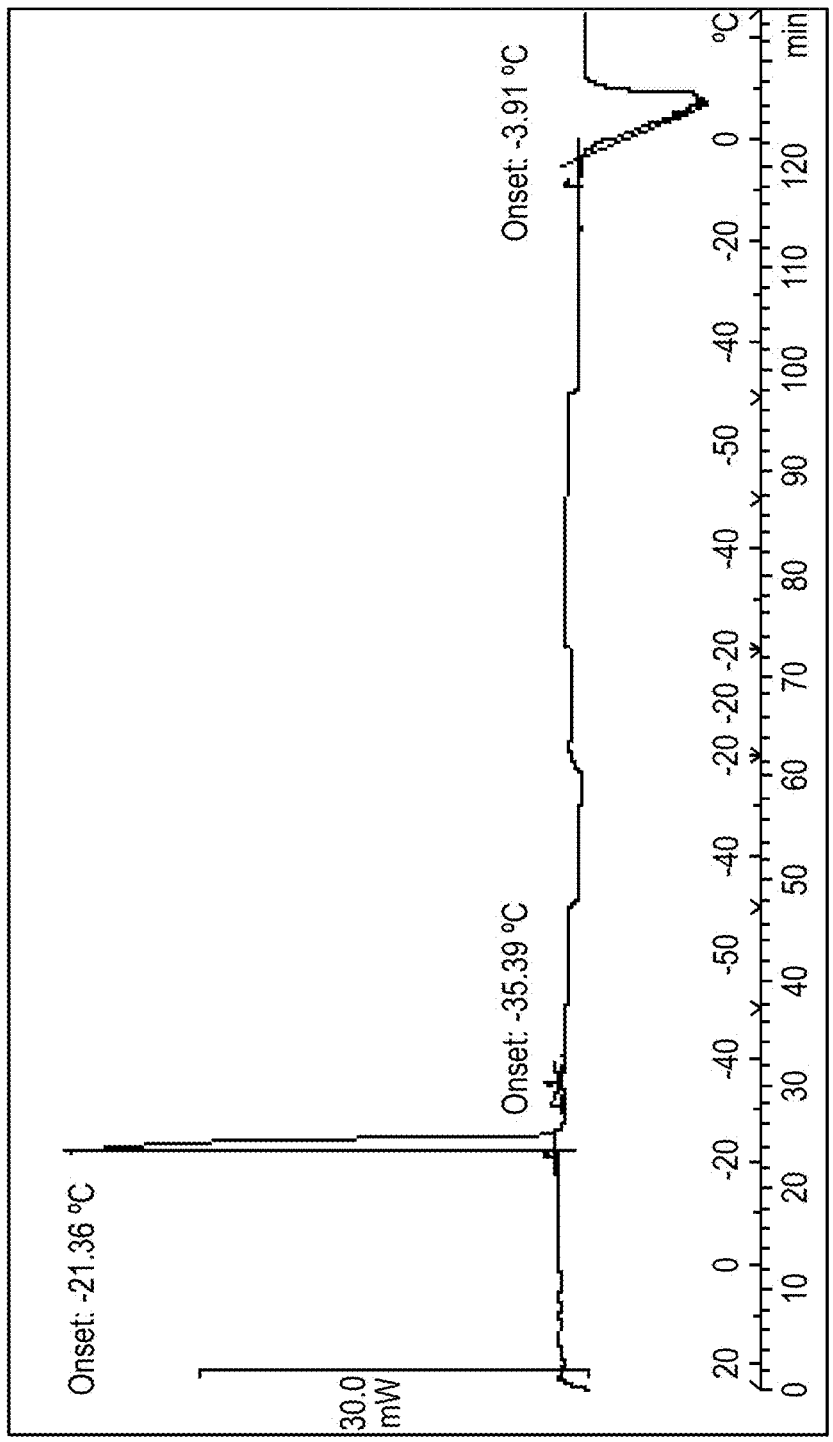
FIG. 8 is a differential scanning calorimetry (DSC) thermogram of Run 3 as described in Example 4.
Figure 9:
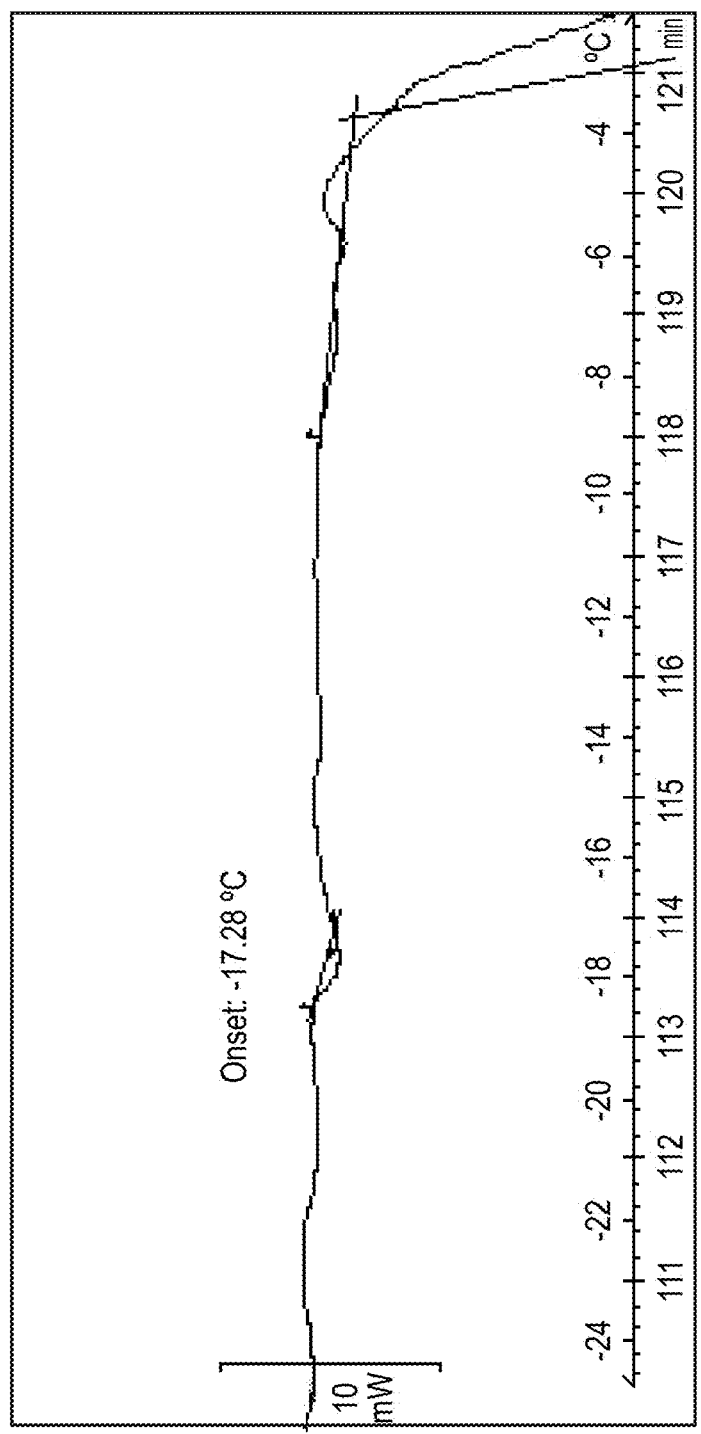
FIG. 9 is a magnification of the differential scanning calorimetry (DSC) thermogram of Run 3 as described in Example 4.

Run 3: Run 3 was conducted with an annealing step at −20° C., which was held for 10 minutes. On cooling, a large well defined freezing exotherm and a secondary smaller exotherm were observed at −21.36° C. and −35.39° C., respectively. After annealing, a small endotherm was observed at −17.28° C. before the major melt at −3.91° C. DSC thermogram of Run 3 is shown in FIGS. 8 and 9.

Figure 10:
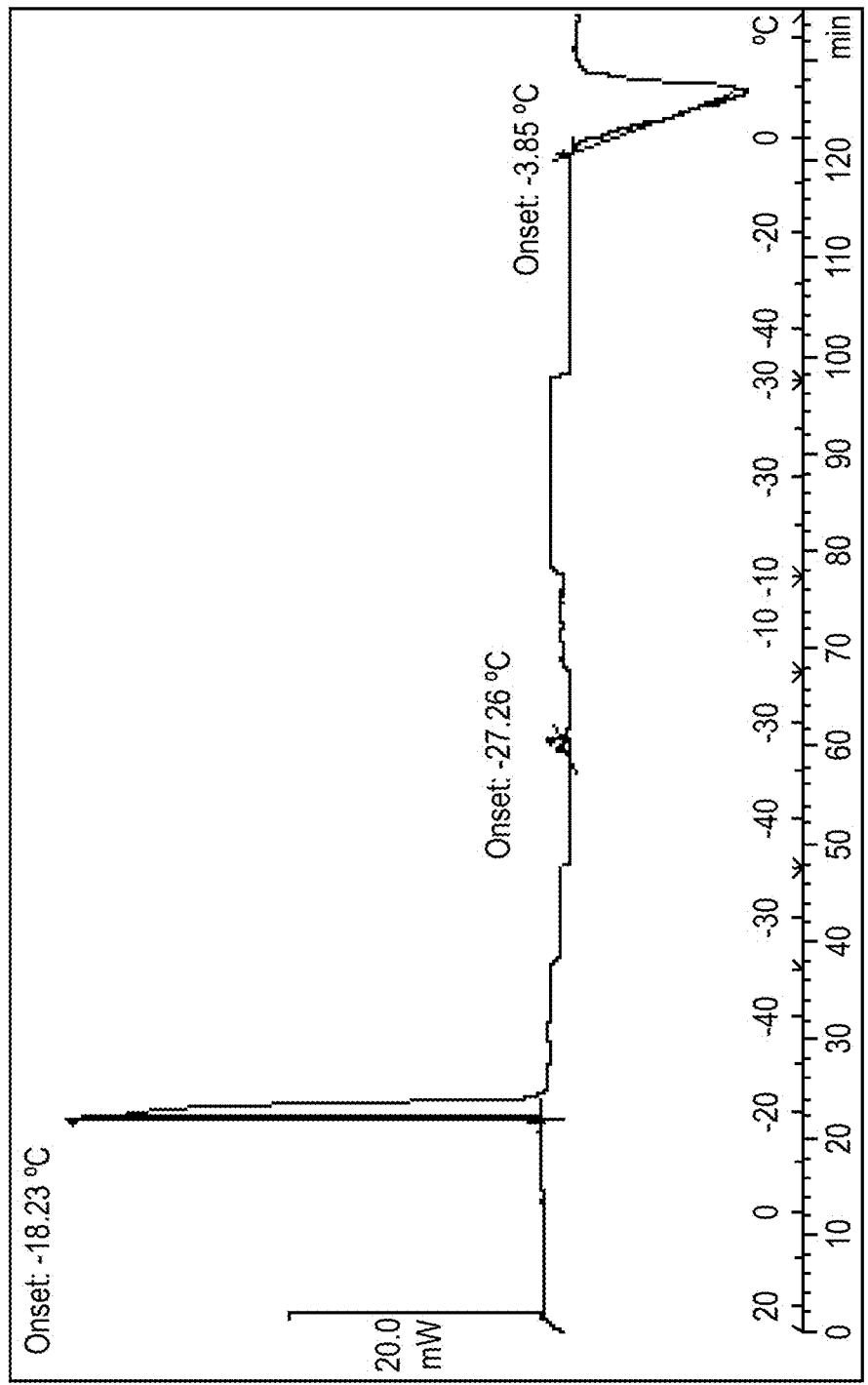
FIG. 10 is a differential scanning calorimetry (DSC) thermogram of Run 4 as described in Example 4.
Figure 11:
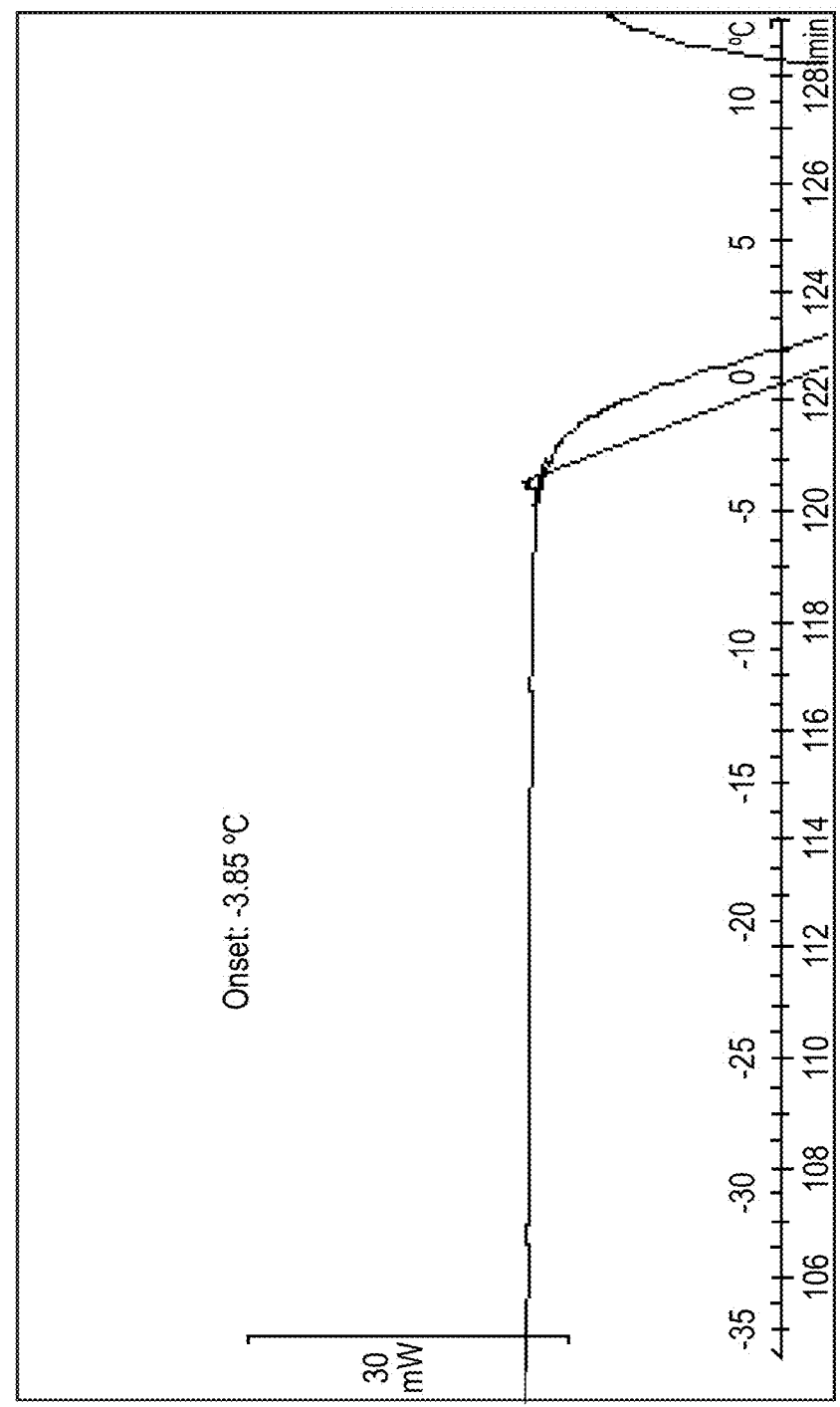
FIG. 11 is a magnification of the differential scanning calorimetry (DSC) thermogram of Run 4 as described in Example 4.

Run 4: Run 4 was conducted with an annealing step at −10° C., which was held for 10 minutes. On cooling, a large well defined freezing exotherm and a secondary smaller exotherm were observed at −18.23° C. and −27.26° C., respectively. The exotherm observed at approximately −28° C. before annealing could no longer be observed on heating after the annealing step. The endotherms, previously found in Runs 1-3 (at approximately −16° C.) that were, without bond to any theory, thought to be due to minor melts of mannitol were no longer observed. This suggests that annealing at −10° C. could promote better crystallization of mannitol, and therefore remove this minor melting event. DSC thermogram of Run 4 is shown in FIGS. 10 and 11.

On the basis of the above findings, it is suggested that during the process of freeze drying to obtain the solid lyophilized form of Compound I, the formulation should be cooled to at least −40° C. during freezing and the temperature should be kept below −16° C. during first drying step. In one embodiment, an annealing temperature of about −10° C. is also recommended to prevent the endotherm at approximately −16° C.

Example 5. Formation of a Solid Lyophilized Form of Compound I with Mannitol as a Bulking Agent with Buffer To evaluate the effects of buffer solutions in the lyophilized form of Compound I, lyophilization cycle (conservative cycle, e.g., each stage of lyophilization was conducted for a greater period of time to assure that it goes to completion before the next stage was initiated) was repeated for the formulation as described in Table 6.

Lyophilization with mannitol and acetate buffer gave acceptable cakes without any collapse or melt back. Breakage of vials was also not observed at the laboratory scale. Reconstitution of the cakes was quick and a clear homogenous solution was obtained for all the formulations containing mannitol. However, formulations without any mannitol (bulking agent) formed a biphasic solution system with an oily layer at the bottom.

It is hypothesized that the presence of mannitol was able to keep the acetate in the product during lyophilization and it was noted that at least 2% of mannitol was required for successful lyophilization and reconstitution. A clear homogenous solution was obtained upon reconstitution of formulation #1 (Table 6) that did not contain mannitol with citrate buffer. Thus, without any mannitol, without bound to any theory, it seems that the acetate buffer volatilizes during lyophilization resulting in upward pH shift and fails to keep the drug in solution upon reconstitution whereas, citrate buffer is not detrimental to the product. Due to unpredictable behavior of acetate buffer during lyophilization due to volatilization, subsequent formulations were carried out using citrate buffer which is also a suitable buffer for the target pH range around 4.5. It was also observed that most of the cakes prepared according to Table 6 turned pale yellowish upon storage indicative of oxidation.

TABLE 6

Selection of Buffer for Lyophilization of Compound I solutions

| # | Compound I (%) | Mannitol (%) | Citrate (mM) | Acetate (mM) | Cake Appearance | Recon. Time | Appearance of reconstituted solution |
|---|---|---|---|---|---|---|---|
| 1 | 3 | — | 50 | — | Good-NS | Fast | Homogenous |
| 2 | 3 | 2 | 50 | — | Good-NS | Immediate | Homogenous |
| 3 | 3 | 5 | 50 | — | Good-NS | Immediate | Homogenous |
| 4 | 3 | — | — | 50 | Good-NS | Slow | Biphasic, oily layer |
| 5 | 3 | 2 | — | 50 | Good-NS | Slow | Homogenous |
| 6 | 3 | 5 | — | 50 | Good-NS | Slow | Homogenous |

TABLE 7

Stability Assay Results at Room Temperature Showing % by Area (HPLC)

| RRT (min) | Citrate, No Mannitol | | | Citrate, 2% Mannitol | | | Acetate, 2% Mannitol | | |
|---|---|---|---|---|---|---|---|---|---|
| | RT Pre-lyo 0 d | RT Lyo 7 d | RT Lyo 14 d | RT Pre-lyo 0 d | RT Lyo 7 d | RT Lyo 14 d | RT Pre-lyo 0 d | RT Lyo 7 d | RT Lyo 14 d |
| 0.89 | | | | | | | | | |
| 0.90 | | | 0.062 | | 0.047 | 0.09 | | | |
| 0.91 | | | | | | | | | |
| 0.92 | | 0.071 | | | | | | | |
| 0.93 | | | | | | 0.076 | | | |
| 0.95 | | | | | | | | | |
| 0.96 | | | | | | | | | 0.048 |
| 0.97 | | | | | 0.057 | 0.045 | | 0.057 | 0.049 | 0.051 |
| 0.98 | | | | | | 0.046 | | | |
| 1.00* | 99.41 | 99.531 | 99.16 | 99.45 | 99.41 | 99.084 | 99.588 | 99.517 | 99.542 |
| 1.04 | | 0.048 | 0.265 | | | | | | |
| 1.05 | 0.136 | 0.105 | | 0.134 | 0.181 | 0.247 | 0.138 | 0.155 | 0.167 |
| 1.07 | 0.152 | 0.096 | 0.231 | 0.178 | 0.142 | 0.261 | 0.077 | 0.082 | 0.09 |
| 1.21 | | | | | | | | | |
| 1.23 | | 0.055 | 0.062 | | | | | | |
| 1.29 | | | | | | | | | |
| Total Imp.** | 0.59 | 0.469 | 0.84 | 0.55 | 0.59 | 0.916 | 0.412 | 0.483 | 0.458 |

TABLE 7-continued

Stability Assay Results at Room Temperature Showing % by Area (HPLC)

| | Citrate 5% Mannitol | | | Acetate 5% Mannitol | | |
|---|---|---|---|---|---|---|
| RRT (min) | RT Pre-lyo 0 d | RT Lyo 7 d | RT Lyo 14 d | RT Pre-lyo 0 d | RT Lyo 7 d | RT Lyo 14 d |
| 0.89 | | | 0.042 | | | |
| 0.90 | | | 0.082 | | | |
| 0.91 | | | | | | |
| 0.92 | | | 0.045 | | | |
| 0.93 | | | 0.037 | | | |
| 0.95 | | | | | | |
| 0.96 | | | | | 0.056 | 0.062 |
| 0.97 | 0.057 | | 0.043 | | | 0.068 |
| 0.98 | | | 0.086 | | | |
| 1.00* | 99.553 | 99.371 | 99.064 | 99.515 | 99.526 | 99.074 |
| 1.04 | | 0.063 | | | 0.053 | |
| 1.05 | 0.138 | 0.109 | 0.267 | 0.14 | 0.117 | 0.383 |
| 1.07 | 0.086 | 0.204 | 0.217 | 0.14 | 0.073 | 0.092 |
| 1.21 | | | | | | 0.07 |
| 1.23 | | | 0.035 | | | |
| 1.29 | | | | | | 0.056 |
| Total Imp.** | 0.447 | 0.629 | 0.936 | 0.485 | 0.474 | 0.926 |

*Compound I elution time; indicates purity of Compound I.
**Total impurities by area % by HPLC.

The mannitol formulations were assayed in stability test at room temperature before lyophilization ("Pre-lyo"), 7 days after lyophilization, and 14 days after lyophilization (Table 7). Each formulation was analyzed via reverse-phase (RP) HPLC using parameters shown below.

| RP-HPLC Chromatography Parameters (Acid Mobile Phase) | |
|---|---|
| Parameter | Conditions |
| Column | Agilent Zorbax SB-CN, 4.6 × 150 mm, 5 μm |
| Mobile Phase A | 95/50/2 Water/Acetonitrile/Perchloric Acid |
| Mobile Phase B/Needle Wash | 50/50 Methanol/Acetonitrile |
| Diluent | 0.1% Trifluoroacetic Acid in Water |
| Injection volume | 20 μL |
| Run Time | 40 min |
| Detection Wavelength | 240 nm |

Compound 1, 7, 8, 9, and 10 has the following relative retention times when using RP-HPLC method discussed directly above.

| Compound | RRT (RP-HPLC acidic mobile phase) |
|---|---|
| 1 | 0.88 |
| 7 | 1.00 |
| 10 | 1.07 |
| 9 | 1.05 |
| 8 | 1.05 |

Two key impurities, determined by the HPLC method discussed above, are identified to have relative retention times (RRT) 1.05 min (Compound 9) and at 1.07 min (Compound 10). The RRT for Compounds 9 and 10 as determined are relevant to Examples 5-7.

Example 6. Antioxidant Formulation of a Solid Lyophilized Form of Compound I

Di-sodium EDTA at 0.1% w/v and Ascorbic acid at 2% w/v and 5% w/w were evaluated to control oxidation via conservative lyophilization cycle (Table 8). Samples were analyzed randomly at room temperature and at 50° C. for 3 weeks using RP-HPLC. The results are summarized in Table 8.

TABLE 8

Selection of antioxidant for Lyophilization of Compound I

| # | Compound I (%) | Mannitol (%) | Citrate | Ascorbic Acid (%) | EDTA (mM) | Assay at 3 Weeks RT | Assay at 3 Weeks 50° C. |
|---|---|---|---|---|---|---|---|
| 1 | 3 | 2 | 50 mM, pH 4.0 | — | 0.1 | 96.18 | — |
| 2 | 3 | 2 | 50 mM, pH 4.5 | — | 0.1 | 98.02 | — |
| 3 | 3 | 2 | 50 mM, pH 4.0 | 2 | — | 99.41 | — |
| 4 | 3 | 2 | 50 mM, pH 4.5 | 2 | — | 97.94 | — |
| 5 | 3 | 2 | 50 mM, pH 4.5 | 5 | — | 99.5 | 98.89 |

The EDTA containing formulations showed more than 2% degradation within three weeks at RT at either pH. All the formulation cakes had a distinct yellow color. The impurity at RRT 1.07 for these formulations was correspondingly higher (greater than 0.5%). The pH did not seem to affect the behavior of the formulations containing EDTA.

There was no yellowing of the cakes in the case of formulations containing ascorbic acid. However, there was a considerable vial to vial variability (largely in the impurity at RRT 1.05) in the stability of these formulations at different time points at either pH and/or different concentrations of ascorbic acid.

Overall, the ascorbic acid formulations with mannitol (Table 9) exhibited better stability compared to the EDTA formulations (Table 10). Each formulation was analyzed via reverse-phase (RP) HPLC using parameters as discussed in Example 5 at room temperature before lyophilization ("Pre-lyo"), 14 days after lyophilization, and 21 days after lyophilization, and at 50° C. at 7 days after lyophilization.

Example 7. Bulking Agent Study

Sucrose and trehalose were evaluated as alternative bulking agent to mannitol. These two sugars are essentially disaccharides and do not contain reducing functions that may possibly react with amines as in the case of mannitol which may contain traces of reducing functions present during its manufacture. Initially, trehalose was evaluated at 2% w/v and 5% w/v in the presence of citrate buffer and ascorbic acid as antioxidant. The stability of these formulations was evaluated at RT and 50° C. and the results are summarized in Table 11.

TABLE 9

Stability Assay Results at Room Temperature and at 50° C. Showing % by Area (HPLC)

| | Mannitol + 2% Ascorbic, pH 4.0 | | | | Mannitol + 2% Ascorbic acid, pH 4.5 | | | | Mannitol + 5% Ascorbic acid, pH 4.5 | | | | | |
|---|---|---|---|---|---|---|---|---|---|---|---|---|---|---|
| Days | Pre-lyo 0 d | 50° C. 7 d | RT Lyo 14 d | RT Lyo 21 d | RT pre-lyo 0 d | 50° C. 7 d | RT Lyo 14 d | RT Lyo 21 d | RT pre-lyo 0 d | RT Lyo 4 d | RT Lyo 10 d | RT Lyo 21 d | RT Lyo 28 d | 50° C. Lyo 28 d |
| RRT (min) | | | | | | | | | | | | | | |
| 0.13 | | | | | | | | 0.052 | | | | | | |
| 0.14 | | | | 0.056 | | | | 0.098 | | | | | | |
| 0.16 | | | 0.141 | | | | 0.602 | | | | | | | |
| 0.95 | | | | 0.05 | | | | | | | | | | |
| 0.96 | | | | | | | | | | | | | 0.05 | 0.05 |
| 1.00* | 99.68 | 99.7 | 97.5 | 99.52 | 99.61 | 99.66 | 99.05 | 97.937 | 99.67 | 99.67 | 99.66 | 99.4 | 99.478 | 98.89 |
| 1.04 | | | | 0.113 | | | | | | | | | | |
| 1.05 | 0.151 | 0.14 | 0.64 | 0.107 | 0.11 | 0.147 | | 1.6 | 0.134 | 0.141 | 0.133 | 0.239 | 0.324 | 0.881 |
| 1.07 | | 0.036 | 0.022 | | | | 0.148 | 0.072 | | | | | | |
| 1.09 | | | | | | | | | | | | | 0.063 | |
| Total Imp.** | 0.32 | 0.3 | 0.5 | 0.48 | 0.39 | 0.34 | 0.95 | 2.063 | 0.33 | 0.33 | 0.34 | 0.6 | 0.522 | 1.11 |

*Compound I elution time; indicates purity of Compound I.
**Total impurities by area % by HPLC.

TABLE 10

Stability Assay Results at Room Temperature and at 50° C. Showing % by Area (HPLC)

| | Mannitol + EDTA, pH 4.0 | | | | Mannitol + EDTA, pH 4.5 | | | |
|---|---|---|---|---|---|---|---|---|
| RRT (min) | Pre-lyo 0 d | 50° C. Lyo 7 d | RT Lyo 14 d | RT Lyo 21 d | Pre-lyo 0 d | 50° C. Lyo 7 d | RT Lyo 14 d | RT Lyo 21 d |
| 0.887 | | | | 0.373 | | | | |
| 0.90 | | 0.209 | 0.386 | 0.12 | | | 0.052 | 0.06 |
| 0.91 | | 0.098 | | 0.36 | | | 0.061 | 0.068 |
| 0.92 | | | 0.236 | 0.11 | | | | |
| 0.93 | | 0.046 | 0.117 | | | | 0.045 | |
| 0.95 | | | | 0.06 | | | | |
| 0.96 | | 0.084 | | | | | | |
| 0.97 | | | | | | 0.051 | 0.056 | |
| 0.98 | | | 0.528 | 0.623 | | | 0.06 | 0.07 |
| 1.00* | 99.64 | 98.43 | 97.1 | 96.184 | 99.67 | 99.45 | 99.04 | 97.82 |
| 1.04 | | 0.438 | | | | | | |
| 1.05 | 0.142 | | 0.537 | 0.623 | 0.137 | 0.185 | 0.253 | 0.364 |
| 1.07 | 0.043 | 0.451 | 0.754 | 1.03 | 0.052 | 0.126 | 0.237 | 0.511 |
| 1.11 | | | 0.046 | | | | | |
| 1.12 | | | 0.041 | 0.103 | | | | |
| 1.15 | | 0.084 | | | | | | |
| 1.20 | | | | 0.135 | | | 0.056 | |
| Total Imp.** | 0.36 | 1.57 | 2.9 | 3.816 | 0.33 | 0.55 | 0.96 | 1.98 |

*Compound I elution time; indicates purity of Compound I.
**Total impurities by area % by HPLC.

TABLE 11

Trehalose based formulations for Lyophilization of Compound I

|   | Compound I (%) | Trehalose (%) | Ascorbic Acid (%) | Citrate | Assay at 10 Weeks RT | 50° C. |
|---|---|---|---|---|---|---|
| 1 | 3 | 2 | 2 | 50 mM, pH 4.0 | 99.26 | 99.26 |
| 2 | 3 | 2 | 2 | 50 mM, pH 4.5 | 99.64 | 99.64 |
| 3 | 3 | 2 | 5 | 50 mM, pH 4.5 | N/A | |

The trehalose/ascorbic acid formulations were found to be stable at RT for three weeks (Tables 12 and 13). Each formulation was analyzed via reverse-phase (RP) HPLC using parameters as discussed in Example 5 at room temperature before lyophilization ("Pre-lyo"), 4 days after lyophilization, 10 days after lyophilization, 21 days after lyophilization, and 28 days after lyophilization, and at 50° C. at 28 days after lyophilization.

The impurity at RRT 1.05 was <0.15 and negligible at RRT 1.07. However, after four weeks, some of these formulations turned reddish brown at 50° C. When these formulations were analyzed by RT-HPLC, N-oxide peak at RRT 1.05 was seen as increased but no change in the ketone peak at RRT 1.07. The browning in the vials was random and was considerably high at 50° C. For trehalose formulations with 5% ascorbic acid, within four weeks the N-oxide impurity increased significantly from 0.134% to 0.631% at both RT and 50° C. It does seem that ascorbic acid reacts with the drug at higher temperatures which results in poor stability of the formulation. Additionally, the vial-to-vial variability may have been due to moisture variability within the individual vials.

To further explore these effects, sucrose and trehalose formulations were lyophilized with 0, 0.5, and 1% ascorbic acid without any buffer (pH was adjusted with either HCl or NaOH). Additionally, formulations without any bulking agent, buffer or antioxidant were also lyophilized (to see if the yellow color formation was due to the excipients). These formulations are summarized in Table 14.

TABLE 12

Stability Assay Results at Room Temperature and at 50° C. Showing % by Area (HPLC)

| | Trehalose + 2% Ascorbic, pH 4.0 | | | | | | Trehalose + 2% Ascorbic, pH 4.5 | | | | | |
|---|---|---|---|---|---|---|---|---|---|---|---|---|
| RRT (min) | Pre-lyo 0 d | RT Lyo 4 d | RT Lyo 10 d | RT lyo 21 d | RT Lyo 28 d | 50° C. Lyo 28 d | Pre-lyo 0 d | RT Lyo 4 d | RT Lyo 10 d | RT Lyo 21 d | 50° C. Lyo 28 d | RT Lyo 28 d |
| 0.14 | | | 0.28 | | | | | | 0.26 | | | |
| 0.96 | | | | | 0.04 | | | | | | | |
| 0.97 | | | | | | | | | | | 0.083 | |
| 1.00* | 99.63 | 99.56 | 99.37 | 99.67 | 99.61 | 98.5 | 99.65 | 99.67 | 99.44 | 99.68 | 96.075 | 99.66 |
| 1.05 | 0.134 | 0.14 | 0.098 | 0.133 | 0.105 | 1.347 | 0.133 | 0.106 | 0.097 | 0.135 | 3.511 | 0.135 |
| 1.07 | | | | | | | | | | | | |
| 1.23 | | 0.055 | 0.062 | | 0.061 | | | | | | 0.056 | |
| Total Imp.** | 0.37 | 0.44 | 0.63 | 0.33 | 0.39 | 1.5 | 0.35 | 0.327 | 0.56 | 0.32 | 3.925 | 0.34 |

*Compound I elution time; indicates purity of Compound I.
**Total impurities by area % by HPLC.

TABLE 13

Stability Assay Results at Room Temperature and at 50° C. Showing % by Area (HPLC)

| | Trehalose + 5% Ascorbic, pH 4.5 | | | | | |
|---|---|---|---|---|---|---|
| RRT (min) | Pre-lyo 0 d | RT Lyo 4 d | RT Lyo 10 d | RT Lyo 21 d | RT Lyo 28 d | 50° C. Lyo 28 d |
| 0.14 | | | | 0.075 | | |
| 0.96 | 0.058 | 0.053 | 0.054 | | | |
| 0.97 | | | | | | 0.049 |
| 1.00* | 99.65 | 99.736 | 99.65 | 99.15 | 99.181 | 99.01 |
| 1.05 | 0.134 | 0.06 | 0.135 | 0.54 | 0.631 | 0.758 |
| 1.07 | | | | | | |
| 1.23 | | | | | | |
| Total Imp.** | 0.35 | 0.264 | 0.35 | 0.85 | 0.819 | 0.99 |

*Compound I elution time; indicates purity of Compound I.
**Total impurities by area % by HPLC.

TABLE 14

Formulations Containing Various Excipients for Short-term Stability of Compound I for Injection

| Formulation ID | Compound I (%) | Sucrose (%) | Trehalose (%) | Ascorbic acid (%) | 2M HCl/NaOH |
|---|---|---|---|---|---|
| SC0 | 3 | 2 | — | — | pH adjusted to 4.5 |
| SC05 | 3 | 2 | — | 0.5 | pH adjusted to 4.5 |
| SC1 | 3 | 2 | — | 1 | pH adjusted to 4.5 |
| SCB | — | 2 | — | 2 | pH adjusted to 4.5 |
| TC0 | 3 | — | 2 | — | pH adjusted to 4.5 |
| TC1 | 3 | — | 2 | 1 | pH adjusted to 4.5 |
| TCB | — | — | 2 | 2 | pH adjusted to 4.5 |
| HOM | 3 | — | — | — | pH adjusted to 4.5 |

Formulations SC05, SC1, and TC1 as discussed in Table 14 were analyzed via reverse-phase (RP) HPLC using parameters as discussed in Example 5 at room temperature and at 50° C., 4 days after lyophilization, 14 days after lyophilization, and 28 days after lyophilization.

TABLE 15

Stability Assay Results at Room Temperature and at 50° C. Showing % by Area (HPLC)

| | SC05 | | | | | | SC1 | | |
|---|---|---|---|---|---|---|---|---|---|
| | RT Lyo 7 days | 50° C. Lyo 7 days | RT Lyo 14 days | 50° C. Lyo 14 days | RT Lyo 28 days | 50° C. Lyo 28 days | RT Lyo 7 days | 50° C. Lyo 7 days | RT Lyo 14 days |
| 0.96 | | | | | | | | | |
| 1.00* | 99.7 | 99.7 | 99.7 | 99.6 | 99.5 | 99.1 | 99.71 | 99.6 | 99.6 |
| 1.05 | 0.14 | 0.14 | 0.14 | 0.15 | 0.13 | 0.34 | 0.14 | 0.14 | 0.14 |
| 2.00 | 0.03 | 0.03 | 0.02 | 0.03 | 0.02 | 0.05 | 0.025 | 0.02 | 0.02 |
| 1.23 | | | | 0.08 | | | | 0.05 | |
| 1.24 | | | | | | | | | |
| Total Imp.** | 0.3 | 0.29 | 0.3 | 0.33 | 0.46 | 0.88 | 0.289 | 0.36 | 0.33 |

| | SC1 | | | TC1 | | | | | |
|---|---|---|---|---|---|---|---|---|---|
| | 50° C. Lyo 14 days | RT Lyo 28 days | 50° C. Lyo 28 days | RT Lyo 7 days | 50° C. Lyo 7 days | RT Lyo 14 days | 50° C. Lyo 14 days | RT Lyo 28 days | 50° C. Lyo 28 days |
| 0.96 | | | | 0.06 | | | | | |
| 1.00* | 99.7 | 99.1 | 99.3 | 99.5 | 99.66 | 98.0 | 99.1 | 99.5 | 99.1 |
| 1.05 | 0.14 | 0.54 | 0.17 | 0.14 | 0.141 | 1.72 | 0.44 | 0.13 | 0.24 |
| 2.00 | 0.02 | 0.02 | 0.02 | 0.03 | 0.023 | 0.02 | | 0.02 | |
| 1.23 | | | | | | | | | |
| 1.24 | | | | | | | 0.09 | | |
| Total Imp.** | 0.3 | 0.83 | 0.64 | 0.46 | 0.338 | 1.91 | 0.88 | 0.42 | 0.86 |

*Compound I elution time; indicates purity of Compound I.
**Total impurities by area % by HPLC.

The lyophilized dry vials of compositions in Table 14 were evaluated for cake quality by appearance, and the reconstituted solution was tested for Compound I by RP-HPLC. The results of these studies are summarized in Table 16.

TABLE 16

Short-term Stability Results for Compound I Lyophilized Formulation

| Formulation ID | Age of Sample at test | Appearance of the cake | KF | Recon. Time | Recon. description | Assay by RP-HPLC RT | 50° C. |
|---|---|---|---|---|---|---|---|
| SC0 | 63 days | Good-NS* | 0.78 | 6 | Clear to pale yellow | 99.51 | 99.49 |
| SC05 | 42 Days | Good-NS | — | 8 | Clear to pale yellow | * | * |
| SC1 | 42 Days | Good-NS | — | 8 | Clear to pale yellow | * | * |
| TC0 | 35 Days | Good-NS | 0.86 | 8 | Clear to pale yellow | 99.47 | 99.45 |
| TC1 | 28 Days | Good-NS | — | 6 | Clear to pale yellow | * | * |
| HOM | 42 Days | Good-NS | 0.81 | 20 | Clear to pale yellow | 95.41 | 98.46 |

*vial to vial variability was found with inconsistent colored samples which may have been due to excessive moisture.

All the samples were found to be stable at 2-8° C. However, behavior of the ascorbic acid samples for both sucrose and trehalose formulations were found to be quite variable. Even the formulation with 0.5% ascorbic acid showed inconsistency. Some vials from either of the bulking agents turned pale brown at 50° C. But the blank formulations (i.e., formulation containing ascorbic acid and bulking agent with no Compound I) showed no color reaction indicating that the ascorbic acid does react with the drug at higher temperature. Without being bound by any theory, it may be possible that N-oxide impurity in the drug itself catalyzes the degradation of ascorbic acid and the by-products of this reaction further react with the drug making the formulation unstable and imparts yellow color.

Interestingly, the formulations without any antioxidant (i.e., SC0 and TC0 samples, Tables 14, and 16-18) were found to be the most stable. For sucrose containing samples, the impurity levels at 1.05 RRT fluctuated between 0.143 and 0.281% and those at RRT 1.07 fluctuated between 0.025 and 0.078. The trehalose samples were also found to be similar in behavior to that of sucrose. The formulation without any bulking agent or antioxidant (HOM, Tables 16 and 18) was unstable at both RT and 50° C. and these developed a pale yellow color with time with corresponding increase in impurity levels at RRT 1.07.

Formulations HOM, SC0, and TC0 as discussed in Tables 14 and 16 were analyzed via reverse-phase (RP) HPLC using parameters as discussed in Example 5 at room temperature and at 50° C., 14 days after lyophilization, 28 days after lyophilization, 42 days after lyophilization, and/or 96 days after lyophilization (Tables 17a and 17b).

TABLE 17a

Stability Assay Results at Room Temperature and at 50° C. Showing % by Area (HPLC)

| | TC0 | | | | | |
| --- | --- | --- | --- | --- | --- | --- |
| | Temperature | | | | | |
| | RT Lyo 14 days | 50° C. Lyo 14 days | RT Lyo 42 days | 50° C. Lyo 42 days | RT Lyo 96 days | 50° C. Lyo 96 days |
| RRT (min) | | | | | | |
| 0.87 | | | | | | |
| 0.88 | | | | | | |
| 0.90 | | 0.07 | | | | |
| 0.91 | | 0.08 | | | | |
| 0.92 | | | | | | |
| 0.93 | | | | | | |
| 0.95 | | 0.08 | | | | |
| 0.97 | | | | | | |
| 0.98 | | | | | | |
| 1.00* | 99.67 | 99.2 | 99.5 | 99.45 | 99.54 | 99.31 |
| 1.05 | 0.136 | 0.23 | 0.13 | 0.15 | 0.143 | 0.17 |
| 1.07 | 0.04 | 0.25 | 0.05 | 0.08 | 0.08 | 0.92 |
| 1.11 | | | | | | |
| 1.15 | | | | 0.04 | | 0.68 |
| 1.29 | | | | | | |
| 1.40 | | | 0.04 | | | |
| Total Impurities** | 0.33 | 0.8 | 0.5 | 0.55 | 0.46 | 0.69 |

*Compound I elution time; indicates purity of Compound I.
**Total impurities by area % by HPLC.

TABLE 17b

Stability Assay Results at Room Temperature and at 50° C. Showing % by Area (HPLC)

| | Formulation | | | | | | | | | | | |
| --- | --- | --- | --- | --- | --- | --- | --- | --- | --- | --- | --- | --- |
| | HOM | | | | | SC0 | | | | | | |
| | Temperature | | | | | | | | | | | |
| | RT Lyo 14 days | 50° C. Lyo 14 days | RT Lyo 28 days | 50° C. Lyo 28 days | RT Lyo 42 days | RT Lyo 14 days | 50° C. Lyo 14 days | RT Lyo 28 days | 50° C. Lyo 28 days | RT Lyo 42 days | 50° C. Lyo 42 days | RT Lyo 96 days | 50° C. Lyo 96 days |
| days | | | | | | | | | | | | |
| 0.87 | | | 0.10 | | 0.05 | | | | | | | | |
| 0.88 | | | 0.08 | 0.063 | 0.63 | | | | | 0.05 | | | |
| 0.90 | 0.06 | 0.24 | | | | | | | | | | | |
| 0.91 | | 0.30 | 0.30 | | | | | | | | | | |
| 0.92 | | | | | 1.06 | | | | | | | | |
| 0.93 | 0.05 | | | | | | | | | | | | |
| 0.95 | | | | | 0.19 | | | | | | | | |
| 0.97 | | | | | | 0.04 | | | | | | | |
| 0.98 | 0.05 | 0.26 | 0.51 | | 0.92 | | | | | | | | |
| 1.00* | 99.3 | 98.3 | 97.89 | 99.46 | 95.41 | 99.67 | 99.49 | 99.6 | 99.46 | 99.55 | 99.49 | 99.43 | 99.32 |
| 1.05 | 0.13 | 0.19 | 0.16 | 0.14 | 0.19 | 0.14 | 0.25 | 0.2 | 0.31 | 0.18 | 0.16 | 0.14 | 0.18 |
| 1.07 | 0.11 | 0.52 | 0.30 | 0.138 | 1.34 | 0.02 | 0.05 | 0.039 | 0.053 | 0.1 | 0.08 | 0.076 | 0.081 |
| 1.11 | | 0.06 | | | | | | | | | | | |
| 1.15 | | | | | 0.05 | | | | | | | | |
| 1.29 | 0.08 | | | | | | | | | | | | |
| 1.40 | | | | 0.24 | | | | | | | | | |
| Total Impurities** | 0.72 | 1.7 | 2.11 | 0.54 | 4.59 | 0.313 | 0.51 | 0.4 | 0.532 | 0.45 | 0.51 | 0.57 | 0.68 |

*Compound I elution time; indicates purity of Compound I.
**Total impurities by area % by HPLC.

It does seem that sucrose and trehalose remain amorphous in the interstitial freeze concentrate and impart stability to the drug from oxidation, possibly by matrix dilution effect. Although above studies were run to identify a stable formulation that contained ascorbic acid as an antioxidant, its effectiveness was not very evident especially considering the inconsistent protection even at the lowest concentration of 0.5% of ascorbic acid.

Example 8. Stability Study of Lyophilized Form of Compound I with Mannitol

The lyophilized forms of Compound I prepared with mannitol (without buffer or antioxidants) were subjected to stability study at −20° C., 5° C., and 25° C./60% RH for a period of 6 months. Each 30 mL Type I, clear glass sample vial with 20 mm Freeze Dry Stoppers (Flurotech™ coated) contained 150 mg of Compound I.

At each time point, a vial was removed from the stored condition and reconstituted with 10 mL of D5W and analyzed by HPLC method as discussed in Example 5 at 1 month, 2 months, 3 months, and/or 6 months. Stability results are shown in Tables 18a-18e. In Tables 18-18e, RRT matches the Compounds as shown below.

| Compound | RRT (RP-HPLC acidic mobile phase) |
| --- | --- |
| 1 | 0.88 |
| 7 | 1.00 |
| 10 | 1.07 |
| 9 | 1.05 |
| 8 | 1.05 |

Sample Preparation—Method A: 10% Mannitol solution was prepared by weighing 200 g±1.0 g of mannitol into glass beaker, adding approximately 1500 mL of WFI (water for injection) to the beaker and stirring until mannitol was dissolved. The mannitol solution was transferred to a 2 L volumetric flask and made to volume with WFI, then poured back to the original beaker to sir and mix further. 1M HCl solution was prepared by adding 16.4 mL of HCl (37%) to a 200 mL volumetric flask containing approximately 100 mL of WFI, adding WFI to make 200 mL in volume, and inverting to mix the prepared solution.

To a tared 2 L Schott bottle containing a magnetic stirrer and wrapped in aluminum foil, 1020 g±1.0 g of the 10% mannitol solution was added. Then, 58.4 g±0.05 g of the 1M HCl solution was added to the 2 L Schott bottle and stirred for approximately 10 minutes. The solution prepared in the 2 L Schott bottle was purged with nitrogen which was continued throughout the manufacturing process. 30.22 g of Compound I (free base) was weighed then added to the 2 L Schott bottle containing 10% mannitol solution and 1 M HCl solution with continual magnetic stirring. The container used to weigh Compound I was rinsed with 3×10 mL of WFI and added to the Schott bottle. After Compound I dissolved (approximately 40 minutes), additional 650 g of WFI was added to the Schott bottle and the solution was stirred for approximately 10 minutes. The pH of the Compound I solution (in Schott bottle) was measured then adjusted to pH 4.5±0.1 using 1 M HCl solution. After each addition of 1 M HCl solution, the solution was stirred for several minutes prior to verifying the pH. Once the pH was adjusted, nitrogen purging was stopped. The pH adjusted Compound I solution was further diluted with WFI to a target weight of 2040 g±1.0 g and stirred. The final solution was clear, colorless, and free from any visible particles.

The final solution (pH adjusted and diluted) was filtered (chain including PVD Fmembrane filter 0.45 μm and 0.22 μm; peristaltic filtration pump by Watson Marlow) in the Bigneat and the bottle containing the filtered solution was sealed. The filtered solution was pumped (Watson Marlow Flexicon PF6-B pump; 100 RPM) into 30 mL Schott Clear Glass vials (10.0 mL filtered solution each). The glass vials were partially stoppered with 20 mm Freeze Dry Stopper Flurotec (Daikyo Seiko) one vial at a time with sterilized utensils inside a fume hood (Envair B101+1.5R) and placed on freeze dryer trays. The freeze dryer trays were transferred into freeze dry chamber and vial probe was positioned (Lyostar II; FTS Kinetics). Lyophilization was performed using the lyophilization cycle listed below. After lyophilization cycle finished, the vials were back filled with $N_2$ and the stopper was placed in situ, wiped down with isopropanol in the fume hood once removed from the freeze dryer, reconciled, then crimped. Seven vials out of 186 sample vials placed under the lyophilization cycle had smashed in the freeze dryer. Stability data for samples prepared by Method A is shown in Tables 18a and 18b.

| | | Freeze Dry Cycle for Method A | | | | |
|---|---|---|---|---|---|---|
| Step | Process | Temp. (° C.) | Ramp rate (° C./min) | Ramp time (min) | Hold time (min) | Pressure (mTorr) |
| 1 | Load | 5 | 0 | 0 | 60 | n/a |
| 2 | Freezing | −45 | 1.08 | 46 | 90 | n/a |
| 3 | Annealing | −15 | 0.33 | 90 | 60 | n/a |
| 4 | Freezing | −45 | 0.33 | 90 | 90 | n/a |
| 5 | Initiate vacuum | −45 | 0 | 0 | 30 | 350 |
| 6 | Primary drying | −15 | 0.33 | 90 | 4960 | 350 |
| 7 | Secondary drying | 25 | 0.18 | 222 | 519 | 50 |
| 8 | Finish | Vials closed under 90-95% pure nitrogen | | | | |

Total cycle time = 6287 minutes (4.4 days)

Sample Preparation—Method B (dissolved oxygen content ≤1 ppm): 2 L WFI was poured into a Schott bottled and degassed for 30 minutes with $N_2$ until dissolved oxygen content was ≤1 ppm (dissolved oxygen meter and probe; Mettler Toledo). 10% Mannitol solution was prepared by adding 150 g±1.0 g of mannitol and 1000 mL of degassed WFI to a tared 2 L Schott bottle containing a magnetic stirrer and wrapped in aluminum foil. To the Schott bottle containing mannitol, 15 mL of 2M HCl was added and stirred for approximately 10 minutes. The resulting solution was sparged with $N_2$ while stirring until dissolved oxygen content was ≤1 ppm (approx. 30 min). The headspace of the Schott bottle containing mannitol and HCl was purged with $N_2$ for 3 minutes and the bottle was sealed.

45.335 g of Compound I (free base) was weighed then added to the 2 L Schott bottle containing mannitol and HCl solution with continual magnetic stirring inside the Big Neat and CTS cabinets. After ~55 minutes of stirring once Compound I was added, a suspension was observed. About 30 mL of 2M HCl was added and stirred for ~25 minutes but the suspension persisted. About 5 mL of 2M HCl was added and stirred for ~15 minutes then about 100 mL of degassed WFI was added and stirred for ~5 minutes to provide a clear solution. Once a clear solution was obtained, the solution was sparged with $N_2$ while stirring until dissolved oxygen content was ≤1 ppm (approx. 40 min).

The pH of the Compound I solution (in Schott bottle) was measured then adjusted to pH 4.5±0.1 using 2 M HCl and 2 M NaOH solutions in a stepwise manner. After each addition of HCl or NaOH solutions, the solution was stirred for several minutes prior to verifying the pH. The pH adjusted Compound I solution was transferred to a 1000 mL volumetric flask and to a 500 mL volumetric flask and the flasks were filled with degassed WFI to the mark. Diluted solutions were transferred back to the original 2 L Schott bottle and sparged $N_2$ while stirring until dissolved oxygen content was ≤1 ppm (approx. 30 min). The headspace of the Schott bottle was purged with $N_2$ for 3 minutes and the bottle was sealed.

The final solution (pH adjusted and diluted) was filtered (chain including PVDF membrane filter 1×0.45 μm and 2×0.22 μm in series; peristaltic filtration pump) in the Big Neat and CTS cabinets and the bottle containing the filtered solution was sealed (The peristalitic pump filtration steps were not performed under $N_2$). The filtered solution was pumped (Watson Marlow Flexicon PF6-B pump; 100 RPM) into 30 mL Schott Clear Glass vials (5.0 mL filtered solution each). The glass vials were partially stoppered with 20 mm Freeze Dry Stopper Flurotec (West Pharma) one vial at a time with sterilized utensils inside a fume hood and placed on freeze dryer trays. The freeze dryer trays were transferred into freeze dry chamber and vial probe was positioned. Lyophilization was performed using the lyophilization cycle according to Table 3, Example 2. After lyophilization cycle finished, the vials were back filled with $N_2$ and the stopper was placed in situ, wiped down with isopropanol in the fume hood once removed from the freeze dryer, reconciled, then crimped. No vials failed (out of 258 sample vials) during the lyophilization cycle (e.g., no vials smashed in the freeze dryer).

TABLE 18a

Stability Assay Results at 2-8° C./ambient % RH (Sample - Method A).

|  | Specification | Initial | 1 month | 2 months | 3 months | 6 months |
|---|---|---|---|---|---|---|
| Appearance | White to off-white powder | White powder | White powder | White powder | White powder | White powder |
| Compound I by HPLC assay | 90.0-110.0% | 101.5% | 101% | 101% | 102% | 100% |
| Related Substances | Report individual related substances ≥ 0.05% All individual related substances ≤ 1.0% Total related substances ≤ 2.0% | RRT 1.05: 0.18% RRT 1.06: 0.08% RRT 1.08: 0.06% Total: 0.3% | RRT 0.83: 0.41% RRT 0.88: 0.05% RRT 0.95A: 0.10% RRT 0.95B: 0.06% RRT 1.05: 0.18% RRT 1.08: 0.17% Total: 1.0% | RRT 0.88: 0.06% RRT 0.95B: 0.06% RRT 1.05: 0.17% RRT 1.07: 0.15% Total: 0.4% | RRT 0.88: 0.05% RRT 0.95A: 0.05% RRT 0.95B: 0.06% RRT 0.96: 0.06% RRT 1.05: 0.16% RRT 1.07: 0.20% Total: 0.6% | RRT 0.88: 0.09% RRT 0.89: 0.05% RRT 0.95B: 0.08% RRT 0.96: 0.07% RRT 1.05: 0.17% RRT 1.07: 0.28% Total: 0.7% |
| Appearance (Reconstituted Solution) | Clear, colorless to yellow solution, free of foreign particles | Clear, colorless solution, free of foreign particles | Clear, colorless solution, free of foreign particles | Clear, colorless solution, free of foreign particles | Clear, colorless solution, free of foreign particles | Clear, colorless solution, free of foreign particles |
| pH | Report Result | 4.45 | 4.56 | 4.51 | 4.45 | 4.25 |
| Reconstitution Time | Report Result | 1 min 8 sec | 54 sec | 55 sec | 41 sec | 1 min 16 sec |
| Water Content | Report Result to 2 decimal places | 0.14% | 0.16% | 0.20% | 0.16% | 0.64% |

|  | Specification | 9 months | 12 months | 18 months | 24 months | 36 months |
|---|---|---|---|---|---|---|
| Appearance | White to off-white powder | White powder | White powder | White powder | White powder | White powder |
| Compound I by HPLC assay | 90.0-110.0% | 100% | 101% | 98% | 99% | 101% |
| Related Substances | Report individual related substances ≥ 0.05% All individual related substances ≤ 1.0% Total related substances ≤ 2.0% | RRT 0.88: 0.06% RRT 0.95B: 0.06% RRT 0.96: 0.05% RRT 0.97: 0.07% RRT 1.05: 0.17% RRT 1.07: 0.27% Total: 0.7% | RRT 0.88: 0.09% RRT 0.89: 0.07% RRT 0.95B: 0.05% RRT 0.96: 0.10% RRT 0.97: 0.11% RRT 1.05: 0.17% RRT 1.07: 0.45% Total: 1.0% | RRT 0.88: 0.05% RRT 0.95B: 0.05% RRT 0.96: 0.06% RRT 0.97: 0.07% RRT 1.04: 0.05% RRT 1.05: 0.17% RRT 1.07: 0.20% Total: 0.6% | RPT 0.88: 0.06% RRT 0.89: 0.05% RPT 0.95B: 0.05% RPT 0.96: 0.06% RPT 0.97: 0.08% RRT 1.05: 0.17% RRT 1.07: 0.29% Total: 0.8% | RRT 0.88: 0.06% RRT 0.96: 0.06% RRT 0.97: 0.06% RRT 1.05: 0.18% RRT 1.07: 0.24% Total: 0.6% |
| Appearance (Reconstituted Solution) | Clear, colorless to yellow solution, free of foreign particles | Clear, colorless solution, free of foreign particles | Clear, colorless solution, free of foreign particles | Clear, colorless solution, free of foreign particles | Clear, colorless solution, free of foreign particles | Clear, colorless solution, free of foreign particles |
| pH | Report Result | 4.46 | 4.47 | 4.23 | 4.37 | 4.48 |
| Reconstitution Time | Report Result | 1 min 14 sec | 1 min 6 sec | 1 min 37 sec | 1 min 9 sec | 1 min 40 sec |
| Water Content | Report Result to 2 decimal places | 0.17% | 0.20% | 0.24% | 0.21% | 0.28% |

TABLE 18b

Stability Assay Results at 25° C./60% RH (Sample - Method A).

|  | Initial | 1 month | 2 months | 3 months |
|---|---|---|---|---|
| Appearance | White powder | White powder | White powder | White powder |
| Compound I by HPLC assay | 101.5% | 100% | 100% | 101% |
| Related Substances | RRT 1.05: 0.18% RRT 1.07: 0.08% RRT 1.08: 0.06% Total: 0.3% | RRT 0.83: 0.40% RRT 0.88: 0.05% RRT 0.95: 0.10% RRT 0.96: 0.06% RRT 1.07: 0.17% RRT 1.08: 0.15% Total: 0.9% | RRT 0.88: 0.06% RRT 0.96: 0.06% RRT 1.05: 0.17% RRT 1.07: 0.15% Total: 0.4% | RRT 0.88: 0.06% RRT 0.89: 0.05% RRT 0.96: 0.06% RRT 0.97: 0.07% RRT 1.05: 0.17% RRT 1.07: 0.21% Total: 0.6% |
| Appearance (Reconstituted | Clear, colorless solution, free of | Clear, colorless solution, free of | Clear, colorless solution, free of | Clear, colorless solution, free of |

TABLE 18b-continued

Stability Assay Results at 25° C./60% RH (Sample - Method A).

| | | | | |
|---|---|---|---|---|
| Solution) | foreign particles | foreign particles | foreign particles | foreign particles |
| pH | 4.45 | 4.55 | 4.48 | 4.43 |
| Reconstitution Time | 1 min 8 sec | 52 sec | 1 min 32 sec | 46 sec |
| Water Content | 0.14% | 0.26% | 0.25% | 0.26% |

| | 6 months | 9 months | 12 months | 36 months |
|---|---|---|---|---|
| Appearance | White powder | White powder | White powder | White powder |
| Compound I by HPLC assay | 101% | 99% | 100% | 101% |
| Related Substances | RRT 0.88: 0.11% RRT 0.89: 0.06% RRT 0.95: 0.05% RRT 0.96: 0.09% RRT 0.97: 0.09% RRT 1.04: 0.05% RRT 1.05: 0.20% RRT 1.07: 0.32% Total: 1.0% | RRT 0.88: 0.07% RRT 0.96: 0.07% RRT 0.97: 0.07% RRT 1.05: 0.19% RRT 1.07: 0.26% Total: 0.7% | RRT 0.88: 0.11% RRT 0.89: 0.10% RRT 0.92: 0.05% RRT 0.95: 0.06% RRT 0.96: 0.10% RRT 0.97: 0.16% RRT 1.05: 0.20% RRT 1.07: 0.55% Total: 1.3% | RRT 0.88: 0.10% RRT 0.89: 0.06% RRT 0.95: 0.06% RRT 0.96: 0.09% RRT 0.97: 0.09% RRT 1.05: 0.25% RRT 1.07: 0.34% Total: 1.0% |
| Appearance (Reconstituted Solution) | Clear, colorless solution, free of foreign particles | Clear, colorless solution, free of foreign particles | Clear, colorless solution, free of foreign particles | Clear, colorless solution, free of foreign particles |
| pH | 4.25 | 4.48 | 4.43 | 4.25 |
| Reconstitution Time | 51 sec | 56 sec | 58 sec | 4 min 20 sec |
| Water Content | 0.43% | 0.28% | 0.33% | 0.47% |

*See Table 18a for specification of each measurement

TABLE 18c

Stability Assay Results at −20° C. (Sample-Method B).

| | Specification | Initial | 1 month | 3 months | 6 months |
|---|---|---|---|---|---|
| Appearance | White to off-white powder | White powder | White powder | Off-white powder | Off-white powder |
| Compound I by HPLC assay | 90.0-110.0% | 100.2% | 100.9% | 99.5% | 99.7% |
| Related Substances | Report individual related substances ≥0.05% All individual related substances ≤1.0% Total related substances ≤2.0% | RRT 0.96: 0.05% RRT 1.04: 0.05% RRT 1.06: 0.17% RRT 1.08: 0.06% Total: 0.3% | RRT 1.06: 0.16% RRT 1.08: 0.06% Total: 0.2% | RRT 1.04: 0.08% RRT 1.05: 0.18% Total: 0.3% | RRT 1.05: 0.13% Total: 0.1% |
| Appearance (Reconstituted Solution) | Clear, colorless to yellow solution, free of foreign particles | Clear, colorless solution, free of foreign particles | Clear, colorless solution, free of foreign particles | Clear, colorless solution, free of foreign particles | Clear, colorless solution, free of foreign particles |
| pH (USP<791>) | Report Result | 4.6 | 4.4 | 4.4 | 4.5 |
| Reconstitution Time | Report Result | 1 min 30 sec | 65 sec | 1 min 56 sec | 2 min 10 sec |
| Water Content USP<921 Method 1c> | Report Result to 2 decimal places | 1.12% | 1.13% | 1.33% | 1.24% |
| Appearance | Off-white powder | Off-white powder | Off-white powder | Off-white powder | Off-white powder |
| Compound I by HPLC assay | 90.0-110.0% | 100.8% | 101.9% | 101.3% | 98.1% |
| Related Substances | Report individual related substances ≥0.05% All individual related substances ≤1.0% Total related substances ≤2.0% | RRT 1.05: 0.13% Total: 0.1% | RRT 1.05: 0.13% Total: 0.1% | RRT 1.05: 0.12% Total: 0.1% | RRT 1.05: 0.10% Total: 0.1% |
| Appearance (Reconstituted Solution) | Clear, colorless to yellow solution, free of foreign particles | Clear, colorless solution, free of foreign particles | Clear, colorless solution, free of foreign particles | Clear, colorless solution, free of foreign particles | Clear, colorless solution, free of foreign particles |

TABLE 18c-continued

Stability Assay Results at −20° C. (Sample-Method B).

|  | Specification | Initial | 1 month | 3 months | 6 months |
|---|---|---|---|---|---|
| pH (USP<791>) | Report Result | 4.6 | 4.5 | 4.5 | 4.4 |
| Reconstitution Time | Report Result | 2 min 52 sec | 3 min 30 sec | 3 min 12 sec | 5 min 47 sec |
| Water Content USP<921> Method 1c> | Report Result to 2 decimal places | 1.30% | 1.29% | 1.10% | 1.10% |

TABLE 18d

Stability Assay Results at 5° C (Sample-Method B).

|  | Specification | Initial | 1 month | 3 months | 6 months |
|---|---|---|---|---|---|
| Appearance | White to off-white powder | White powder | White powder | Off-white powder | Off-white powder |
| Compound I by HPLC assay | 90.0-110.0% | 100.2% | 99.5% | 101.2% | 100.7% |
| Related Substances | Report individual related substances ≥0.05% All individual related substances ≤1.0% Total related substances ≤2.0% | RRT 0.96: 0.05% RRT 1.04: 0.05% RRT 1.06: 0.17% RRT 1.08: 0.06% Total:0.3% | RRT 1.06: 0.16% RRT 1.08: 0.06% RRT 1.22: 0.05% Total: 0.3% | RRT 1.04: 0.08% RRT 1.05: 0.19% RRT 0.17: 0.05% Total: 0.3% | RRT 1.05: 0.13% Total: 0.1% |
| Appearance (Reconstituted Solution) | Clear, colorless to yellow solution, free of foreign particles | Clear, colorless solution, free of foreign particles | Clear, colorless solution, free of foreign particles | Clear, colorless solution, free of foreign particles | Clear, colorless solution, free of foreign particles |
| pH (USP<791>) | Report Result | 4.6 | 4.4 | 4.5 | 4.5 |
| Reconstitution Time | Report Result | 1 min 30 sec | 60 sec | 2 min 10 sec | 2 min 35 sec |
| Water Content USP<921> Method 1c> | Report Result to 2 decimal places | 1.12% | 1.51% | 1.19% | 1.25% |
| Appearance | White to off-white powder | Off-white powder | Off-white powder | Off-white powder | Off-white powder |
| Compound I by HPLC assay | 90.0-110.0% | 101.7% | 101.3% | 100.3% | 99.1% |
| Related Substances | Report individual related substances ≥0.05% All individual related substances ≤1.0% Total related substances ≤2.0% | RRT 1.05: 0.14% RRT 1.07: 0.05% Total:0.2% | RRT 1.05: 0.13% Total: 0.1% | RRT 1.05: 0.13% Total: 0.1% | RRT 1.05: 0.11% Total: 0.1% |
| Appearance (Reconstituted Solution) | Clear, colorless to yellow solution, free of foreign particles | Clear, colorless solution, free of foreign particles | Clear, colorless solution, free of foreign particles | Clear, colorless solution, free of foreign particles | Clear, colorless solution, free of foreign particles |
| pH (USP<791>) | Report Result | 4.6 | 4.5 | 4.5 | 4.5 |
| Reconstitution Time | Report Result | 3 min 19 sec | 3 min 5 sec | 3 min 36 sec | 5 min 34 sec |
| Water Content USP<921> Method 1c> | Report Result to 2 decimal places | 1.37% | 1.29% | 1.05% | 1.25% |

TABLE 18e

Stability Assay Results at 25° C./60% RH (Sample - Method B).

| | Initial | 1 month | 2 months | 3 months | 6 months | 12 months | 24 months |
|---|---|---|---|---|---|---|---|
| Appearance | White powder | White powder | Off-white powder | Off-white powder | Off-white powder | Off-white powder | Off-white powder |
| Compound I by HPLC assay | 100.2% | 99.8% | 101.0% | 100.8% | 100.3% | 100.7% | 97.6% |
| Related Substances | RRT 0.96: 0.05% | RRT 1.06: 0.17% | RRT 1.04: 0.08% | RRT 1.04: 0.08% | RRT 0.88: 0.06% | RRT 1.05: 0.18% | RRT 0.88: 0.05% |
| | RRT 1.04: 0.05% | RRT 1.08: 0.06% | RRT 1.05: 0.17% | RRT 1.05: 0.19% | RRT 1.05: 0.16% | RRT 1.07: 0.09% | RRT 1.05: 0.16% |
| | RRT 1.06: 0.17% | Total: 0.2% | RRT 0.17: 0.08% | RRT 0.17: 0.09% | RRT 1.07: 0.10% | Total: 0.3% | RRT 1.06: 0.17% |
| | RRT 1.08: 0.06% | | Total: 0.3% | Total: 0.4% | Total: 0.3% | | Total: 0.4% |
| | Total: 0.3% | | | | | | |
| Appearance (Reconstituted Solution) | Clear, colorless solution, free of foreign particles | Clear, colorless solution, free of foreign particles | Clear, colorless solution, free of foreign particles | Clear, colorless solution, free of foreign particles | Clear, colorless solution, free of foreign particles | Clear, colorless solution, free of foreign particles | Clear, colorless solution, free of foreign particles |
| pH (USP<791>) | 4.6 | 4.4 | 4.6 | 4.6 | 4.5 | 4.5 | 4.4 |
| Reconstitution Time | 1 min 30 sec | 55 sec | 1 min 55 sec | 2 min 15 sec | 1 min 57 sec | 2 min 40 sec | 6 min 14 sec |
| Water Content USP<921 Method 1c> | 1.12% | 1.47% | 1.30% | 1.30% | 1.30% | 1.55% | 1.33% |

*See Tables 18c and 18d for specification of each measurement

As demonstrated in Tables 18a-18e, samples prepared using the process where dissolved oxygen level was maintained under 1.0 ppm (Tables 18c-18e) were more stable than samples prepared without steps to check dissolved oxygen levels (Tables 18a-18b) as evident by the differences in the total related substances identified during the stability tests (0.1-0.4% vs 0.4-1.0%, respectively). Thus, in one embodiment, maintaining a low level of dissolved oxygen in samples during the preparation of the lyophilized form of Compound I impacts the stability of the lyophilized forms. In one embodiment, maintaining dissolved oxygen level below 1.0 ppm during the process of preparing a lyophilized form of Compound I, or a pharmaceutically acceptable salt and/or solvate thereof provides the lyophilized form with improved stability.

Example 9. Composition for Lyophilized Form of Compound I with Sucrose and Properties of the Composition Based upon the finding from Examples 6 and 7, the formulation outlined in Table 19 was used as Compound I solution (30 mg/mL) for lyophilization studies.

TABLE 19

Composition for Lyophilization of Compound I

| Ingredient | Amount/mL | Rationale for use |
|---|---|---|
| Compound I | 30 mg | Active |
| Sucrose, USP/EP | 20 mg | Stabilizer |
| Hydrochloric acid, NF/EP (as 1N solution) | QS for pH | pH adjustment |
| Sodium Hydroxide, NF/EP (as 1N solution) | QS for pH | pH adjustment |
| Water for injection, USP* | QS to 1 mL | Vehicle |

*Removed during lyophilization

Figure 12A:
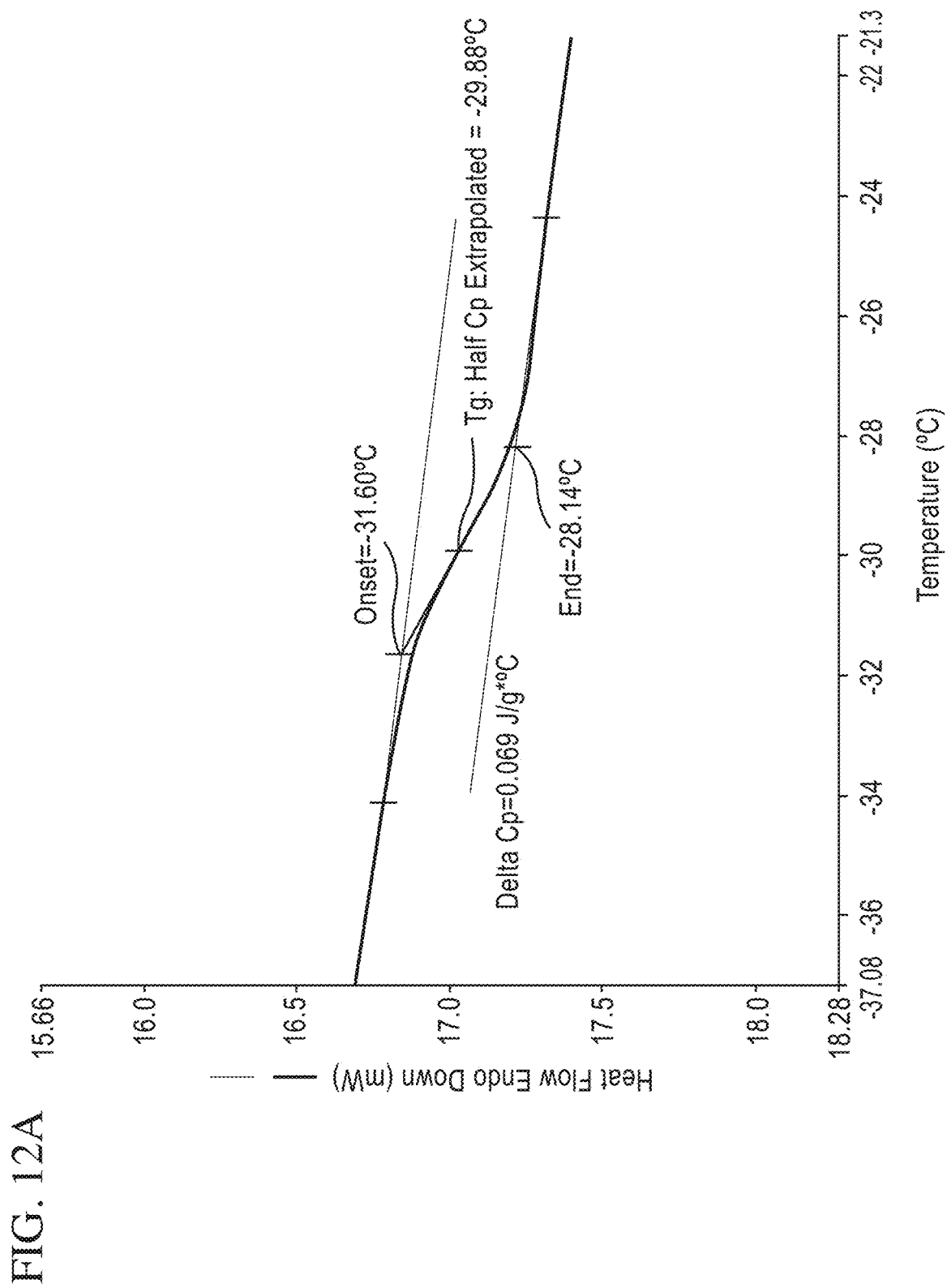
FIG. 12A is a DSC thermogram of warming curve of solution containing Compound I (no bulking agent or other excipients).
Figure 12B:
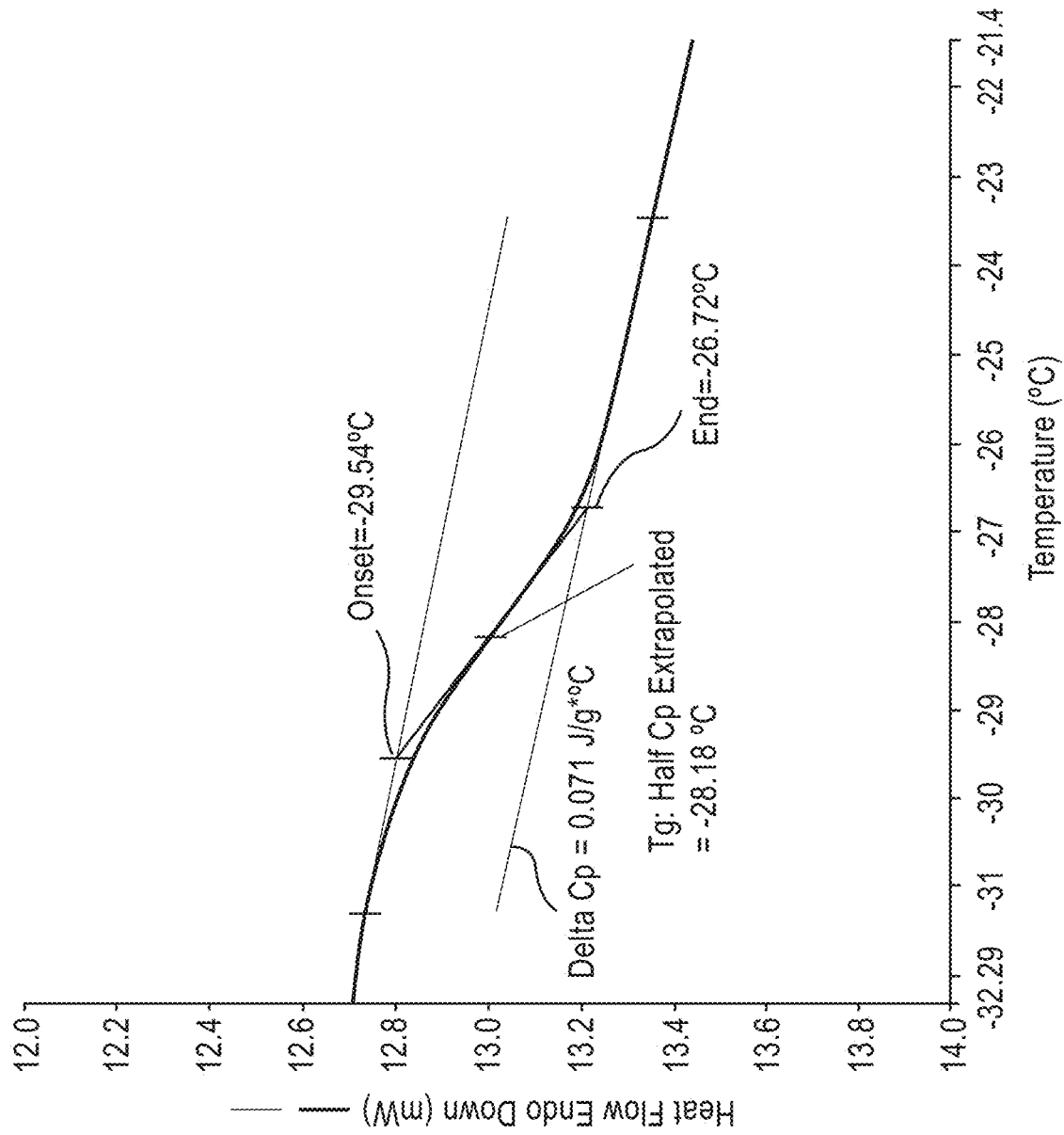
FIG. 12B is a DSC thermogram of warming curve for lyophilization solution of Compound I (solution of Table 19).

Glass Transition Temperature: The thermal properties of the frozen solution is largely dictated by the properties of the two main components, Compound I and sucrose, in their frozen state. The glass transition temperature (Tg') represents the maximum allowable product temperature during primary drying. If the product temperature exceeds Tg' while ice is still present, drying occurs from the liquid state and the product undergoes collapse/meltback. Therefore, accurate determination of Tg' of the frozen solution system is important for developing a reliable freeze-drying cycle. Tg' of the Compound I solution (as shown in Table 19) was determined using differential scanning calorimetry (Perkin Elmer, Model DSC 4000), where the solution was frozen below −50° C. at a rate of 10° C./minute, held at that temperature to ensure thermal equilibrium and subsequently warmed to room temperature at a rate of 5° C./minute. The data are shown in FIGS. 12A and 12B. Based on the warming curve, the Tg' of Compound I solution was determined to be approximately −28.16° C.

Lyophilization Cycle Parameters: The lyophilization parameters during the primary drying were chosen such that the product temperature remained below −30° C. during the sublimation phase of the drying. A thermal treatment step during freezing was included at −15° C. for approximately 1 hour to ensure consistent thermal behavior amongst the vials. Upon completion of the primary (sublimation) drying, the shelf temperature was raised to 0 and then to 25° C. and maintained at 25° C. during the rest of the drying cycle to ensure that the secondary (desorption) drying phase was complete and dry product was obtained with very low residual moisture level. The lyophilization process parameters are disclosed in Table 20.

TABLE 20

Lyophilization process parameters for Compound I

| Phase | Step | Rate/ Hold | Temp (° C. ± 3) | Time (Min.) | Pressure (mT) | Time (Hours) Cumulative |
|---|---|---|---|---|---|---|
| Freezing | 1 | Hold | 10 | — | Ambient | — |
|  | 2 | Rate | −45 | 120 | Ambient | 2 |
|  | 3 | Hold | −45 | 60 | Ambient | 3 |
| Annealing | 1 | Rate | −15 | 60 | Ambient | 4 |
|  | 2 | Hold | −15 | 60 | Ambient | 5 |
|  | 3 | Rate | −45 | 60 | Ambient | 6 |
| Prepare the vacuum pump, Cool the condenser to <−70° C. Open the pass-through valve between the chamber and condenser |
| Primary Drying | 1 | Hold | −45 | 30 | 75 ± 20 | 6.5 |
|  | 2 | Rate | −30 | 120 | 75 ± 20 | 8.5 |
|  | 3 | Hold | −30 | 2880 | 75 ± 20 | 56.5 |
| Secondary Drying | 4 | Rate | 0 | 240 | 75 ± 20 | 60.5 |
|  | 5 | Hold | 0 | 240 | 75 ± 20 | 64.5 |
|  | 6 | Rate | 25 | 240 | 75 ± 20 | 68.5 |
|  | 7 | Hold | 25 | 1080 | 75 ± 20 | 86.5 |
| Pre-Stoppering Hold: | If stoppering is not performed immediately after the end of secondary drying, shelf temperature and pressure should be held at +25° C. ± 3° C. and 75 ± 20 mT, respectively, for up to 24 hours until stoppering and unloading can be performed. |||||||
| Stoppering: | Back fill with $N_2$ to a pressure of approximately −3.6 psig and stopper vials. |||||||
| Post Stoppering Hold: | Stoppered vials may be held in the Lyophilizer at +25° C. ± 3° C. for up to 24 hours. |||||||

In addition to the cycle parameters in Table 20, an added specified loading time and an extended freezing time were included. Upon completion of the lyophilization process, the dried vials were fully stoppered inside the lyophilization chamber under vacuum and unloaded for sealing with aluminum crimps. The crimped vials were then subjected to 100% visual inspection and quality testing.

Due to the combination of the shelf temperatures and the chamber pressures, the product temperature did remain below its critical temperature of about −30° C. during the early part of the sublimation drying. The duration of the primary drying is longer due to the fact that the volume of the solution to be lyophilized is 5 mL. This is indicated by the rise in the temperature of the thermocouple containing vials once the ice was sublimed and the heat received was used to raise the temperature of the cake. The additional hold at the primary drying temperature was to ensure that the vials from the entire lot have completed the primary drying before the shelf temperature is raised to the secondary drying temperatures.

Example 10. Preparation of Liquid Formulation Comprising Compound I and Sucrose and Preparation of Lyophilized Form of Compound I with Sucrose for Injection 30 mg/mL (150 mg/vial)

Composition:

| | Quantity per mL |
|---|---|
| Compound I | 30.0 mg |
| Sucrose | 20.0 mg |
| HCl | As needed, for pH adjustment |

-continued

| | Quantity per mL |
|---|---|
| NaOH | As needed, for pH adjustment |
| Water for Injection (WFI) | q.s. |

Compounding: 37.5 kg of WFI was added to the compounding vessel at a temperature in the range of 15 to 30° C. Vigorously sparge WFI with nitrogen for no less than 30 minutes by placing the nitrogen sparging tubing at the bottom of the pressure vessel. Continue sparging in the vessel until dissolved oxygen content was ≤1 ppm. In a second pressure vessel was added 20.0 kg nitrogen sparged WFI and sucrose and mixed until dissolved while continuing nitrogen sparging, not less than 15 minutes. Nitrogen sparging continued as necessary until dissolved oxygen content was ≤1 ppm of the sucrose solution. To the sucrose solution, 813.8 g of 2 M HCl solution was slowly added and mixed for no less than 10 minutes after addition was complete. Add Compound I into the sucrose solution vessel and rinse container that contained Compound I with nitrogen sparged WFI. Mix solution until dissolved (no less than 15 min). Add 43.5 mL of 2 M HCl and mix for no less than 5 minutes. If solution is not visually dissolved, add another portion of 43.5 mL of 2M HCl and mix for no less than 5 minutes. Adjust pH, if necessary to 4.4-4.6 with 2M HCl or 1M NaOH solution prepared using nitrogen sparged WFI. Mix solution after each addition of 2M HCl or 1M NaOH. Adjust volume with nitrogen-sparged WFI as necessary. Pull a 10 mL sample to measure pH. If necessary, re-adjust pH to 4.4-4.6 using 2M HCl or 1M NaOH solution prepared using nitrogen sparged WFI. Filtration and filling directly proceeded this step. No material was stored overnight.

Sterilization through 0.22 μM membrane filters: A standard sterile filtration operation was designed to perform sterilization of the compounded bulk solution by membrane filtration through two 0.22 μM hydrophilic polyvinylidene fluoride (PVDF) membranes contained in a polycarbonate housing. The compounded bulk passed through the two sterilizing membranes in series, as is typical in sterile filtration operations, to provide redundant sterilizing capability.

Aseptic filling of the sterile solution: The Compound I sterile solution was filled into 20-cc clean, de-pyrogenated glass vials, with periodic weight checks to assure that the target fill quantity (5.05 g/vial) was maintained, and the vials were semi-stoppered with sterile elastomeric closures to provide a sample of Formulation A. The filled vials are then transferred onto the shelves of the lyophilizer chamber for lyophilization to provide a sample of lyophilized Formulation B. Samples of Formulation A and Formulation B were analyzed using the RP-HPLC Chromatography (base mobile phase) as shown below.

| RP-HPLC Chromatography Parameters (Base Mobile Phase) | |
|---|---|
| Parameter | Conditions |
| Column | Waters XBridge Phenyl, 150 mm(L) × 4.6 mm (ID), 3.5 μM |
| Mobile Phase A | 10 mM $Na_2HPO_4$, pH 11.0 |
| Mobile Phase B/Needle Wash | Methanol |
| Diluent | 0.1% Trifluoroacetic Acid in Water |
| Injection volume | 10 μL |
| Run Time | 58 min |
| Detection Wavelength | 240 nm |

The stability assay results for Formulations A and B are shown in Tables 21a-21e. In Tables 21a-21-e, RRT matches the Compounds as shown below.

| Compound | RRT (RP-HPLC basic mobile phase) |
|---|---|
| 1 | 0.62 |
| 7 | 0.75 |
| 10 | 1.12 |
| 9 | 0.35 |
| 8 | 1.24 |

TABLE 21a

Stability Assay Results at 5° C. for Formulation A

| | Initial | 1 month | 2 months | 3 months |
|---|---|---|---|---|
| Appearance | Clear, colorless solution, free of foreign particles | Clear, colorless solution, free of foreign particles | Clear, colorless solution, free of foreign particles | Clear, colorless solution, free of foreign particles |
| Compound I by HPLC assay | N/A | 100.3% | 100.3% | 99.3% |
| Related Substances | N/A | RRT 0.75: 0.31% RRT 1.24: 0.14% Total: 0.45% | RRT 0.75: 0.31% RRT 1.24: 0.14% Total: 0.45% | RRT 0.75: 0.30% RRT 1.24: 0.13% Total: 0.43% |
| pH (USP<791>) | 4.2 | 4.2 | 4.1 | 4.0 |

TABLE 21b

Stability Assay Results at 25° C./60% RH for Formulation A

| | Initial | 1 month | 2 months | 3 months |
|---|---|---|---|---|
| Appearance | Clear, colorless solution, free of foreign particles | Clear, colorless solution, free of foreign particles | Clear, colorless solution, free of foreign particles | Clear, colorless solution, free of foreign particles |
| Compound I by HPLC assay | N/A | 98.7% | 99.7% | 100% |
| Related Substances | N/A | RRT 0.75: 0.32% RRT 1.24: 0.14% RRT 1.12: 0.06% Total: 0.52% | RRT 0.75: 0.35% RRT 1.24: 0.14% RRT 1.12: 0.10% Total: 0.64% | RRT 0.75: 0.35% RRT 1.24: 0.13% RRT 1.12: 0.16% Total: 0.74% |
| pH (USP<791>) | 4.2 | 4.0 | 4.0 | 4.0 |

TABLE 21c

Stability Assay Results at 30° C./65% RH for Formulation A

|  | Initial | 1 month | 2 months | 3 months |
|---|---|---|---|---|
| Appearance | Clear, colorless solution, free of foreign particles | Clear, colorless solution, free of foreign particles | Clear, colorless solution, free of foreign particles | Clear, colorless solution, free of foreign particles |
| Compound I by HPLC assay | N/A | 100.3% | 100% | 98.3% |
| Related Substances | N/A | RRT 0.75: 0.34% RRT 1.24: 0.14% RRT 1.12: 0.08% Total: 0.56% | RRT 0.35: 0.05% RRT 0.75: 0.36% RRT 1.24: 0.14% RRT 1.12: 0.16% Total: 0.81% | RRT 0.35: 0.05% RRT 0.75: 0.35% RRT 1.24: 0.13% RRT 1.12: 0.23% Total: 0.88% |
| pH (USP<791>) | 4.2 | 4.1 | 4.0 | 4.0 |

TABLE 21d

Stability Assay Results at 5° C. (ambient RH) for Formulation B

|  | Initial | 1 month | 2 months | 3 months |
|---|---|---|---|---|
| Appearance | White lyophilized cake | White lyophilized cake | White fragmented lyophilized cake | White lyophilized cake |
| Compound I by HPLC assay | 101.5% | 101.8% | 101.8% | 100.9% |
| Related Substances | RRT 0.62: 0.05% RRT 0.75: 0.29% RRT 1.24: 0.12% Total: 0.46% | RRT 0.75: 0.32% RRT 1.24: 0.13% Total: 0.45% | RRT 0.75: 0.31% RRT 1.24: 0.12% Total: 0.43% | RRT 0.75: 0.30% RRT 1.24: 0.12% Total: 0.42% |
| Appearance (Reconstitued Solution) | Clear, colorless solution, free of foreign particles | Clear, colorless solution, free of foreign particles | Clear, colorless solution, free of foreign particles | Clear, colorless solution, free of foreign particles |
| pH (USP<791>) | 4.0 | 4.2 | 4.2 | 4.2 |
| Reconstitution Time | 1 min 20 sec | 40 sec | 49 sec | 40 sec |
| Water Content USP<921 Method 1c> | 0.05% | 0.05% | 0.05% | 0.05% |

TABLE 21e

Stability Assay Results at 25° C./60% RH for Formulation B

|  | Initial | 1 month | 2 months | 3 months |
|---|---|---|---|---|
| Appearance | White lyophilized cake | White lyophilized cake | White fragmented lyophilized cake | White lyophilized cake |
| Compound I by HPLC assay | 101.5% | 102.6% | 101.6% | 99.8% |
| Related Substances | RRT 0.62: 0.05% RRT 0.75: 0.29% RRT 1.24: 0.12% Total: 0.46% | RRT 0.75: 0.32% RRT 1.24: 0.13% Total: 0.45% | RRT 0.75: 0.31% RRT 1.24: 0.13% Total: 0.44% | RRT 0.75: 0.30% RRT 1.24: 0.12% Total: 0.42% |
| Appearance (Reconstitued Solution) | Clear, colorless solution, free of foreign particles | Clear, colorless solution, free of foreign particles | Clear, colorless solution, free of foreign particles | Clear, colorless solution, free of foreign particles |
| pH (USP<791>) | 4.0 | 4.2 | 4.2 | 4.2 |
| Reconstitution Time | 1 min 20 sec | 1 min | 34 sec | 49 sec |
| Water Content USP<921 Method 1c> | 0.05% | 0.07% | 0.09% | 0.10% |

Density of Compound I Bulk Solution for Lyophilization: The density of the Compound I bulk solution for lyophilization was determined using the Mettler Toledo Density meter (Densito 30 PX) at room temperature and was found to be 1.005 g/mL.

Determination of Lyophile Displacement Volume: The lyophile displacement volume is the volume of re-constituted solution in milliliters, displaced by 1.0 g of the lyophilized dry material (that contains the dried Compound I and excipients). The displacement volume is required for the determination of overfill necessary to achieve a 15 mg/mL solution upon reconstitution with exactly 10.0 mL of WFI (water for injection). The displacement volume for lyophilized Compound I for Injection was determined by placing 1000 mg of lyophilized material into a 10 mL volumetric flask and then adding 10.0 mL of water. The volume of the solution, in excess of 10.0 mL caused by displacement due to the solid content was then measured. Approximately 0.73 mL of water was found displaced when 1 gm of the lyophilized material was dissolved.

Using this relationship, the displacement value of the lyophilized cake was calculated as follows: The total weight of Compound I (150 mg) plus the added sucrose (100 mg) per vial is 250 mg. Therefore, for a 10.0 mL reconstitution volume to achieve concentration of 15.0 mg/mL of Compound I, the displacement value of the dried material will be 0.18 mL (250 mg×0.73) resulting in 10.18 mL total volume or 14.73 mg/mL of Compound 1. To account for this discrepancy caused by the displacement volume, one must fill about 5.1 mL of the solution to be lyophilized. The resulting dry product will then contain enough of Compound I in the reconstituted solution to deliver the targeted concentration of 15 mg/mL.

In one aspect of the present disclosure, the lyophilization composition prepared with sucrose can be beneficial compared to composition prepared with mannitol because the amount of solid content was significantly reduced from 500 mg mannitol to 100 mg sucrose (per 150 mg of Compound I). This significant reduction of solid content when using sucrose can be beneficial in reducing fill volumes of the lyophilization solution in lyophilization vials.

Furthermore, the lyophilized composition prepared with sucrose also demonstrated reduction in key impurities observable at RP-HPLC RRT 1.05 min and 1.07 min (see Example 6). Thus, in one embodiment, sucrose can be a useful bulking agent for preparing solid lyophilized forms of Compound I with good stability.

In addition, the lyophilized composition prepared with sucrose can also be beneficial compared to composition prepared with mannitol in reducing or eliminating vial breakage during the lyophilization cycle as, without bound to any theory, sucrose did not expand as much as mannitol, which was one cause in vial breakages.

Biological Assays and Examples

Example 11. Cell Viability Assessment and Cell Proliferation Assessment

The effect of Compound I on cell viability was assessed by Alamar Blue assay of metabolic activity in various cancer cell lines. Table 22 shows Compound I demonstrate broad spectrum antiproliferative activity in multiple cancer cell lines, while being significantly less active in normal cells.

TABLE 22

Compound I $EC_{50}$ in Cell Viability Assay

| Cell Line | Cancer Type | $EC_{50}$ (nM) |
| --- | --- | --- |
| EOL-1 | Leukemia | 3 |
| SR | Leukemia | 5 |
| MOLT-3 | Leukemia | 6 |
| MV 4;11 | Leukemia | 12 |
| SEM | Leukemia | 18 |
| A7 | Melanoma | 23 |
| NCI-H460 | Lung | 38 |
| THP-1 | Leukemia | 47 |
| NCI-H1299 | Lung | 55 |
| A375 | Melanoma | 58 |
| Jurkat | Leukemia | 64 |
| Ramos | Lymphoma | 66 |
| RPMI-8226 | Myeloma | 68 |
| NCI-H520 | Lung | 70 |
| MIA PaCa-2 | Pancreatic | 74 |
| SK-OV-3 | Ovarian | 78 |
| HL60 | Leukemia | 83 |
| MDA-MB-231 | Breast | 83 |
| BT-474 | Breast | 86 |
| COLO-205 | Colon | 96 |
| K562 | Leukemia | 104 |
| Hs 605.T | Breast | 116 |
| ZR-75-1 | Breast | 123 |
| Raji | Lymphoma | 133 |
| SKBr3 | Breast | 134 |
| MDA-MB-453 | Breast | 140 |
| Daudi | Lymphoma | 142 |
| HL60/MX2 | Leukemia | 147 |
| SK-MEL-24 | Melanoma | 147 |
| HCT-116 | Colon | 164 |
| NK92mi | Lymphoma | 165 |
| MDA-MB-468 | Breast | 171 |
| NCI-H2170 | Lung | 194 |
| U2OS | Osteosarcoma | 281 |
| BT-20 | Breast | 335 |
| MCF 7 | Breast | 347 |
| SUM 190PT | IBC* | 583 |
| BxPC-3 | Pancreatic | 664 |
| HT-29 | Colon | 741 |
| SUM 149PT | IBC* | 751 |
| PC-3 | Prostate | 1,100 |
| SK-MES-1 | Lung | 1,260 |
| Hs 578.T | Breast | 1,647 |
| UACC-812 | Breast | 1,830 |
| MDA-MB-361 | Breast | 2,100 |
| T47D | Breast | 2,337 |
| MDA-MB-175-VII | Breast | 2,780 |
| A549 | Lung | 4,900 |
| Saos-2 | Osteosarcoma | 5,000 |
| PANC-1 | Pancreatic | 5,000 |
| LNCaP | Prostate | 5,500 |
| CCD-1058Sk | Normal | 4,710 |
| CCD-1094Sk | Normal | 4,810 |
| CCD-1068Sk | Normal | 5,070 |
| BJ-hTERT | Normal | 5,174 |
| CD-1096Sk | Normal | 5,260 |

*IBC = Invasive ductal breast carcinoma (inflammatory)

Figure 14A:
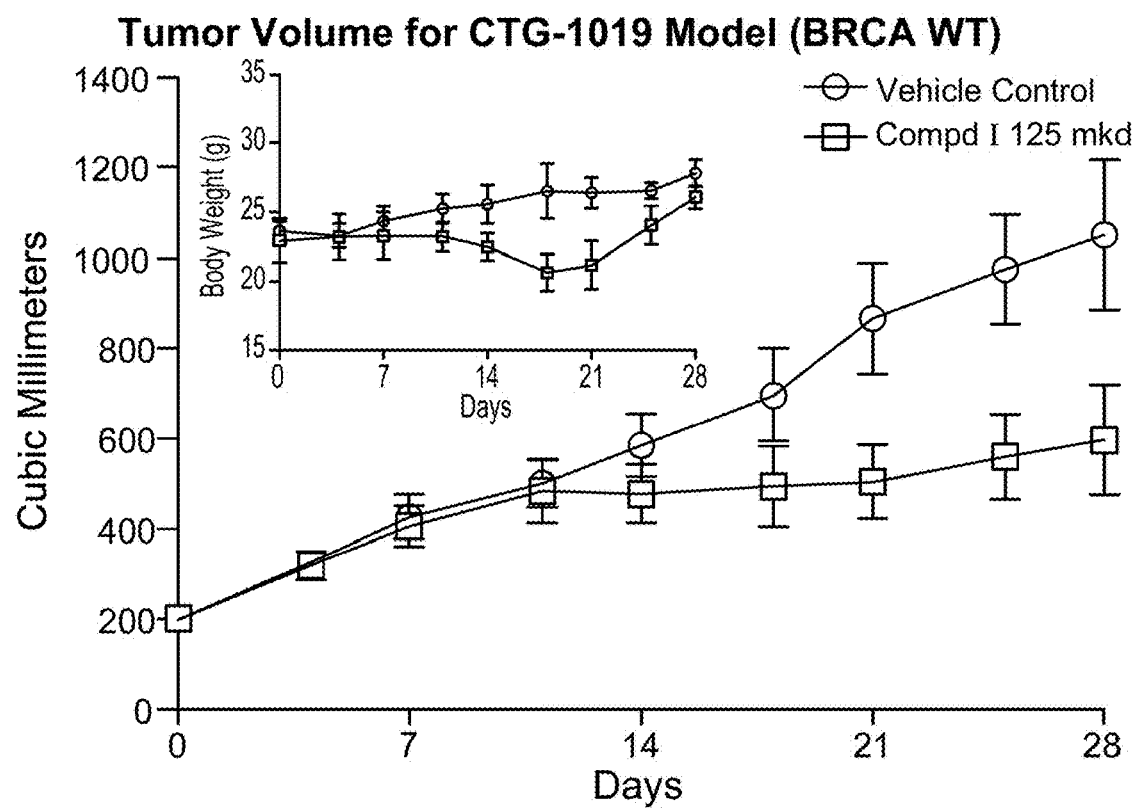
FIG. 14A shows the change in tumor volume in a mice (BRCA WT) receiving Compound I over the 28 day course of treatment. Vehicle control group (n=4); treatment group (n=8).

Example 12. In Vivo Validation of Compound I's Inhibition of BRCA2-Deficient Triple-Negative Breast Cancer Tumor Compound I significantly inhibited tumor growth of BRCA2-deficient triple-negative breast cancer (TNBC) patient-derived xenograft (PDX) model (FIGS. 14B and 14C), whereas Compound I does not inhibit tumor growth of BRCA2 proficient cells (FIG. 14A).

Example 13. Compound I in DLD1 and Isogenic BRCA2$^{-/-}$ Cell Lines

Compound I was tested at different concentrations for their anti-proliferative effects using Horizon's precisely engineered isogenic cell line pairs, DLD1 and isogenic BRCA2$^{-/-}$ cell lines. This study was conducted in vitro. Compound I has shown to be selectively toxic to BRCA2 deficient cancer cell lines (Compound I is selectively toxic to BRCA2 knockout cells but not to BRCA2 proficient wild type cells, e.g., BRCA2$^{+/+}$ and BRCA2$^{+/-}$). The sensitivity of DLD1 Parental and BRCA2$^{-/-}$ isogenic cell lines to Compound I as a single agent was also evaluated to look for evidence of synthetic lethality. The activity of Compound I was evaluated with short (48 hours) and long (6 days) endpoints using CellTiter-Glo® (Promega). Incubation times were 6 days (144 h) in the presence of Compound I. Test compounds were dissolved in NaH$_2$PO$_4$.

Figure 13:
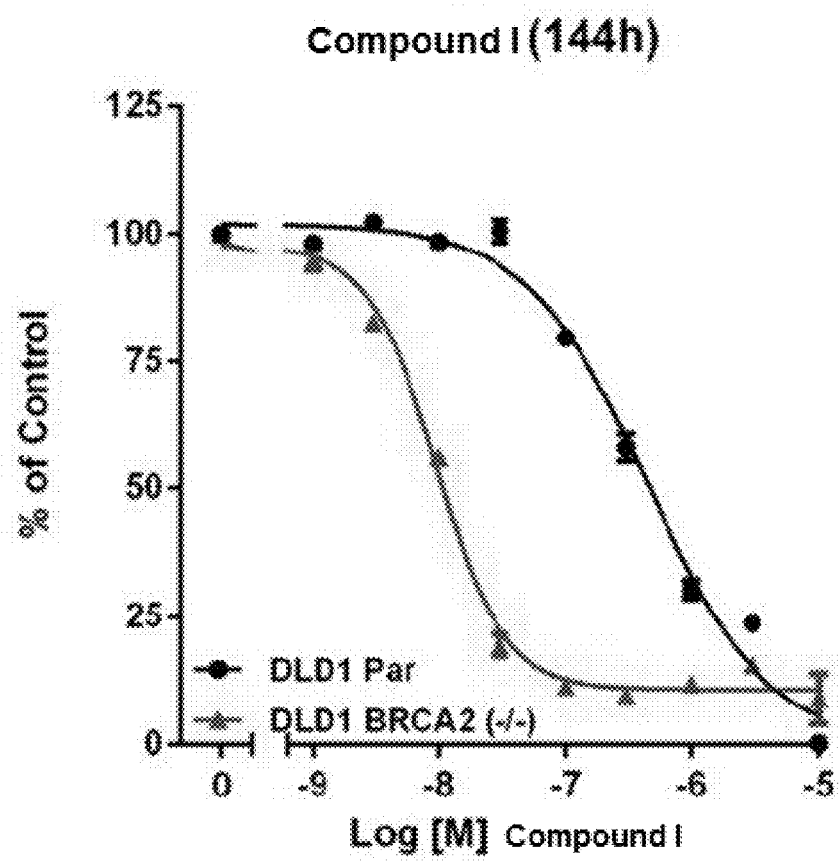
FIG. 13 shows cell proliferation assay results for Compound I in DLD1 and isogenic BRCA2$^{-/-}$ cell lines.

As shown in FIG. 13 and Table 23, the DLD1 BRCA2$^{-/-}$ line was significantly more sensitive to Compound I in the 6-day proliferation assay relative to the parental line, which is indicative of a synthetic lethal effect.

The relative IC$_{50}$ values are reported in Table 23. Where it was not possible to determine an IC$_{50}$ because of a partial response and/or the bottom of the curve not being well defined by the data, the % Inhibition at the top concentration is reported.

TABLE 23

The IC50 Values in DLD1 Parental and BRCA2$^{-/-}$ Isogenic Cell Lines

| Cell Background | Genotype | Assay Endpoint | IC$_{50}$ (μM) |
| --- | --- | --- | --- |
| DLD1 | Parental | 48 hours | 55% @ 10 μM |
|  | BRCA2$^{-/-}$ |  | 27% @ 10 μM |
| DLD1 | Parental | 6 days | 0.445 |
|  | BRCA2$^{-/-}$ | (144 hours) | 0.010 |

Example 14. Tumor Growth Inhibition in BRCA Deficient Patient-Derived Xenograft (PDX) Model Compound I was administered on 3 breast cancer patient's PDX models to assess therapeutic efficacy. Tumor growth inhibition (TGI) greater than 60% is considered predictive of clinical response (Wong, H. et al., Clinical Can Res, 2012). All 3 patients were treated with either taxane and/or anthracycline class chemotherapy prior to the tumor collection. The medical history of these three patients is described below (Table 24).

TABLE 24

BRCA Status of the Triple Negative Breast Cancer (TNBC) PDX Models

| ID | BRCA Status | Characterization |
| --- | --- | --- |
| CTG-1019 | gBRCA1m (K1183R; P871L) wtBRCA2 | The patient derived xenograft (PDX) tumor was derived from 53 year old Caucasian woman with Stage IV TNBC. Prior to the PDX tumor harvesting, the patient was treated with Cyclophosphamide/Doxorubicin/Paclitaxel for a duration of 28 months. Upon treatment failure, she was put on Docetaxel/Capecitabine for 10 months. The patient was then placed on treatments with Capecitabine, Eribulin and Doxil (each as a single agent) with progression of her cancer soon after. Next Generation Sequencing (NGS) revealed BRCA1 mutation (non-deleterious). |
| CTG-0012 | sBRCA1m (Y978*) gBRCA2m (N372H) | The PDX tumor was derived from a 36 year old Caucasian woman with Stage IV TNBC. Prior to the PDX tumor harvesting, she was treated with Docetaxel for a duration of 12 months before her disease progressed. The patient was subsequently treated with Capecitabine/Bevacizumab and Vinorelbine/Bevacizumab but failed both treatments. NGS Data revealed a deleterious somatic mutation in BRCA1 as well as a germline mutation in BRCA2. |
| CTG-0888 | sBRCA2m (X3030X-frameshift) gBRCA1m (K1183R; S1634G; P871L; E1038G) | The PDX tumor was derived from a 43 year old Caucasian woman with Stage III TNBC. Prior to PDX tumor harvesting, she was treated with Cyclophosphamide/Doxorubicin/Paclitaxel for a duration of 9 months. NGS data revealed a deleterious somatic mutation in BRCA2 and germline mutations in BRCA1. |

CTG-1019 Model: Stage IV TNBC gBRCA1m (Non-Deleterious Mutation), wtBRCA2

This study was conducted to evaluate the in vivo efficacy in Harlan nude mice (n=8). The CTG-1019 implanted mice received IV administration once a week (Q7D) of Compound I (not lyophilized) (125 mg/kg) for 3 weeks (3 doses). The response of CTG-1019 did not reach the defined threshold for a response (53.47% TGI compared to vehicle treated control). FIG. 14A shows the growth curve of CTG-1019 xenografts and changes in body weights over the 28 day course of treatment. Vehicle control group (n=4); treatment group (n=8).

CTG-0012 Model: Stage IV TNBC sBRCA1m (Deleterious Mutation)

Figure 14B:
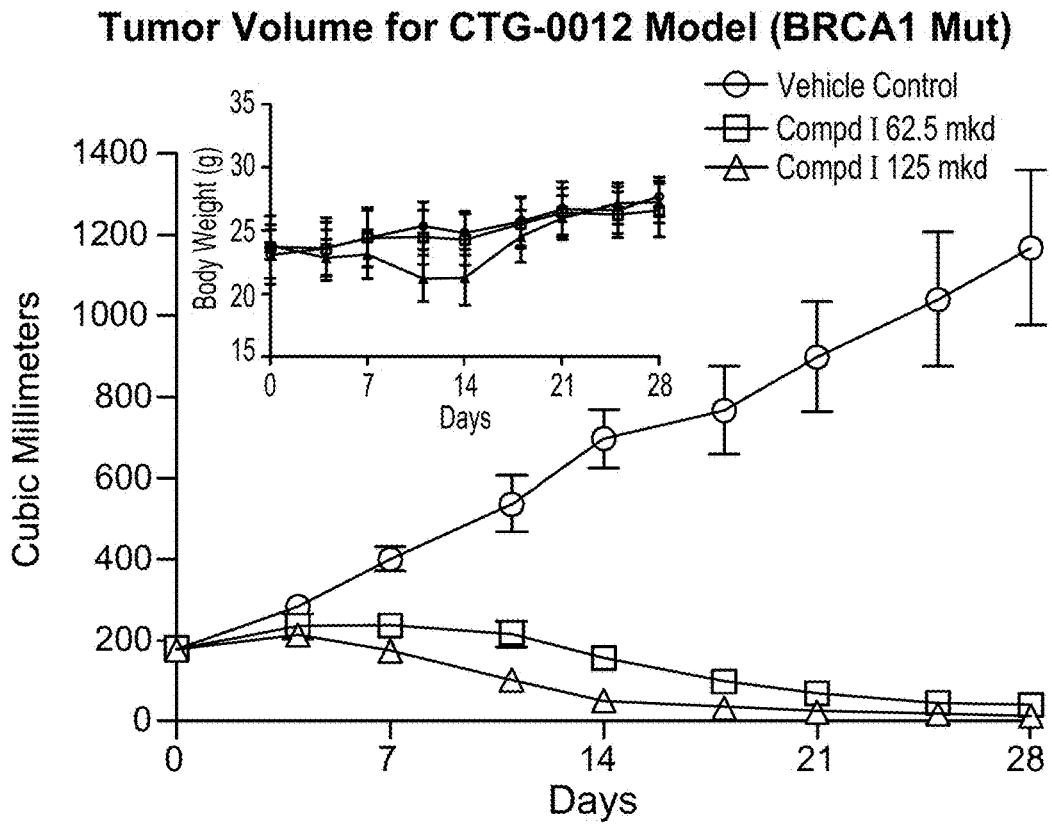
FIG. 14B shows the change in tumor volume in a mice (BRCA1 Mut) receiving Compound I over the 28 day course of treatment. Vehicle control group (n=4); treatment group (n=8).

This study was conducted to evaluate the in vivo efficacy in Harlan nude mice. Two dosing regimens were implemented for Compound I (not lyophilized), a once weekly for 2 weeks followed by 2 weeks recovery regimen (125 mg/kg IV weekly×2) and a weekly regimen for 4 weeks (62.5 mg/kg IV weekly×4). Both dosing regimens demonstrated TGI predictive of clinical response. The 62.5 mg/kg/dose and 125 mg/kg/dose regimens produced 114.49% and 116.53% TGI, respectively. Compound I treated animals also showed tumor regression, as indicated by a TGI value >100% (FIG. 14B). Vehicle control group (n=4); treatment group (n=8).

CTG-0888 Model: Stage III TNBC sBRCA2m (Deleterious Mutation)

Figure 14C:
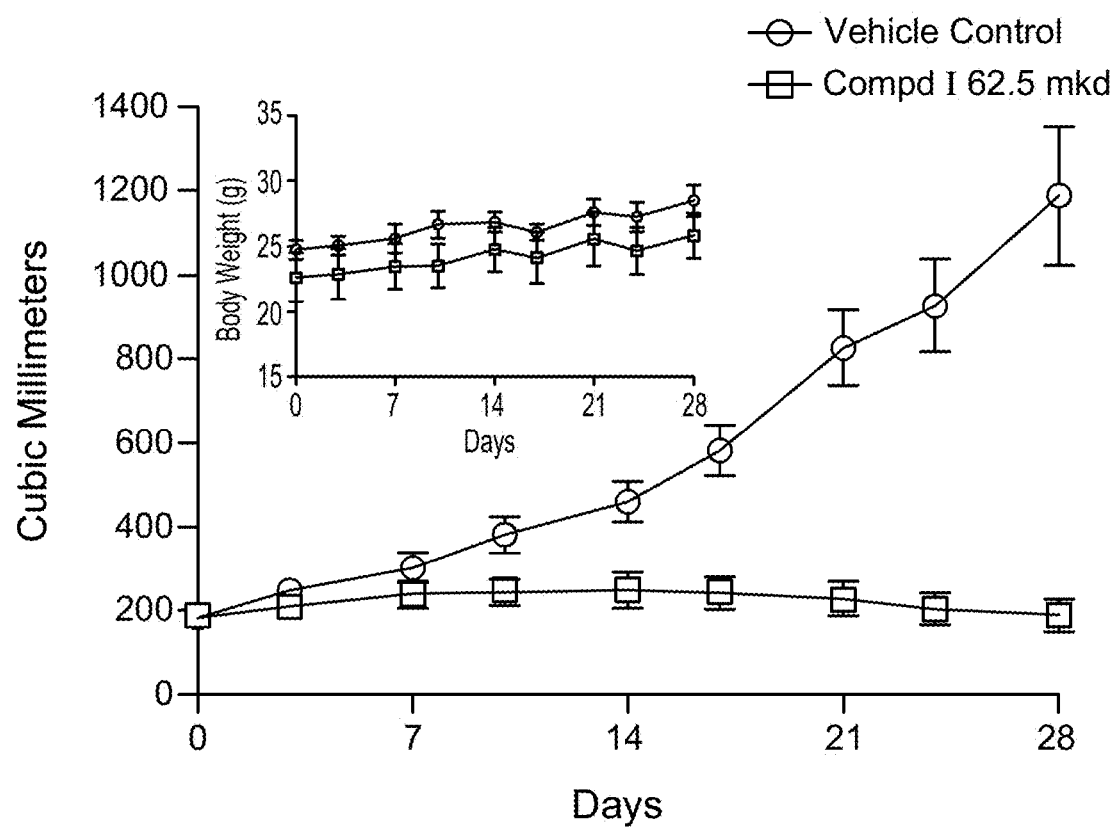
FIG. 14C shows the change in tumor volume in a mice (BRCA2 Mut) receiving Compound I over the 28 day course of treatment. Vehicle control group (n=4); treatment group (n=8).

The CTG-0888 implanted Harlan mice (n=8) received a once weekly for 4 weeks dosing regimen (62.5 mg/kg) The CTG-0888 implanted mice demonstrated 99.88% TGI compared to vehicle-treated control which is predictive for clinical response (FIG. 14C). Vehicle control group (n=4); treatment group (n=8).

TNBC is a particularly aggressive breast cancer and currently lacks effective treatment. The PDX data suggested that Compound I has an increased likelihood of eliciting a clinical response in TNBC patients with deleterious BRCA mutations who had received other chemotherapies. (FIGS. 14A-14C).

Example 15. Pharmacokinetic Parameters in Preclinical Species

A broad range of steady-state volumes of distribution ($V_{ss}$) were observed in the preclinical (mice, rats, dogs and monkeys) species (between 0.15-22 L/kg) which suggested low to high tissue distribution. See Table 25.

TABLE 25

Pharmacokinetic Parameters

| Species | Route | Dose (mg/kg) | $CI_s$ (mL/hr/kg) | $V_{ss}$ (mL/kg) | $T_{1/2}$ (hr) | $C_{max}$ (ng/mL) | $AUC_{24hr}$ (ng*hr/mL) |
|---|---|---|---|---|---|---|---|
| Mouse (ICR)* | IV | 5 | 29 | 145 | 6.0 | 34,288 | 186,235 |
| Rat (SD)* | IV | 5 | 192 | 1,087 | 9.0 | 12,429 | 26,584 |
| Dog* | IV | 5.8 | 1,896 | 11,726 | 9.0 | 861 | 2,947 |
| Monkey* | IV | 5.2 | 1,849 | 22,958 | 13.0 | 668 | 2,373 |

*Calculated mean of 3 animals

The plasma concentrations in the mouse are magnitude higher than in rat, dog and monkey. These trends are qualitatively similar to those seen in the plasma protein binding assays. Compound I is highly bound (>99%) to human plasma proteins, and this binding is independent of drug concentration. Compound I (1 μM) partitioning to blood cells compared to plasma was evaluated in human whole blood, and was determined to prefer plasma (~65%) to the cellular compartment (~30%).

Rats: Pharmacokinetic properties of Compound I were evaluated in a rat toxicity study across a range of IV doses: 5, 10, and 20 mg/kg/dose administered as ready-to-use formulation (see Example 1). Compound I was administered by intravenous infusion via a catheter placed into the lateral tail vein once per week over a period of 1 hour on Days 1, 8, and 15. Blood samples for toxicokinetic (TK) analysis were collected from treated TK animals predose, within 3 minutes of end of infusion, and at 1, 3, 5, 11, 23, and 47 hours post end of infusion on Day 1 and within 3 minutes of end of infusion and 47 hours post end of infusion on Day 15. The TK parameters were determined for Compound I from the mean plasma concentrations per gender and group, using a non-compartmental method. TK parameters derived for the first (Day 1) dose are tabulated in Table 26.

TABLE 26

Compound I TK Parameters from Day 1 (first dose)

| Dose (mg/kg/dose) | Sex | $T_{max}$ (hr) | $C_{max}$ (ng/mL) | $AUC_{inf}$ (ng * hr/mL) | $T_{1/2}$ (hr) |
|---|---|---|---|---|---|
| 5 | Male | 1.0 | 3,357 | 24,546 | 7.0 |
| 5 | Female | 1.0 | 2,517 | 20,849 | 9.3 |
| 10 | Male | 1.0 | 4,497 | 42,065 | 8.1 |
| 10 | Female | 2.0 | 3,810 | 44,795 | 7.6 |
| 20 | Male | 1.0 | 6,810 | 79,190 | 11.4 |
| 20 | Female | 6.0 | 4,957 | 80,608 | 16.8 |

$AUC_{0-inf}$ was found to be approximately dose proportional across the dose range, and terminal half-life determined across the doses ranged from approximately 7 to 16.8 hours.

Dogs: Pharmacokinetic properties of Compound I were evaluated in a dog toxicity study across a range of IV doses: 15, 30, and 45 mg/kg/dose. A ready-to-use solution of Compound I (see Example 1) was administered by intravenous infusion via a catheter placed into the cephalic vein once per week over a period of 1 hour on Days 1, 8, and 15. Blood samples for TK analysis were collected predose, 0.25, 0.5, and 1 hour (from the start of infusion), and then at 0.5, 1, 2, 3, 5, 7, 9, 11, 23, 35, and 47 hours post end of infusion on Day 1, and predose, 1 hour (end of infusion), and then at 47 hours post end of infusion on Day 15. The TK parameters were calculated for each animal, using individual plasma concentration-time data of Compound I. TK parameters derived for the first (Day 1) dose were tabulated and summarized by sex within dose group (Table 27).

Table 27. Mean TK Parameters of Compound 1 from Day 1 (First Dose)

TABLE 27

Mean TK Parameters of Compound 1 from Day 1 (first dose)

| Dose (mg/kg/dose) | Sex | $T_{max}$ (hr) | $C_{max}$ (ng/mL) | $AUC_{last}$ (ng * hr/mL) | $AUC_{last}$/Dose (ng * hr/mL/ (mg/kg)) |
|---|---|---|---|---|---|
| 15 | Male | 0.8 | 723 | 5,956 | 397 |
| 15 | Female | 0.8 | 690 | 5,533 | 369 |
| 30 | Male | 0.8 | 1,331 | 9,926 | 331 |
| 30 | Female | 0.5 | 1,011 | 8,354 | 278 |
| 45 | Male | 1.0 | 1,754 | 11,453 | 255 |
| 45 | Female | 0.8 | 1,654 | 13,385 | 297 |

As shown in Table 27, $AUC_{last}$ (area under the concentration-time curve from time 0 to the last observation postdose) increased with dose level. However the response was not dose proportional across the dose range, with higher values of $AUC_{last}$/dose at 15 mg/kg than at the 30 mg/kg and 45 mg/kg dose levels. Terminal half-life determined across the doses ranged from approximately 7 to 18.2 hours.

The non-clinical safety program included single and repeat dose toxicology studies in rats and dogs. These acute and subacute dose-ranging studies conducted in rats and dogs permitted the characterization of the toxicity of single and multiple doses of IV administration of Compound I using various dosing schedules, and also provided the rationale for the selection of doses to be studied in the single dose study with recovery after a 21-day non-dosing period in these species.

The dose limiting toxicity observed with single and multiple doses of IV administration of Compound I in rats and dogs was decreased blood cell count in leukocyte, erythrocyte and megakaryocyte cell lines. This toxicity is spontaneously reversible within three weeks following an IV dose of Compound I, and this influenced the selection of a clinical dosing schedule of once every three weeks. At higher dose exposures, a hypersensitivity-like reaction consistent with mast cell degranulation was also encountered. In dogs, this reaction resulted in urticarial or hive-like rash around the ears, eyes and muzzle, which resolved with antihistamine drug. This reaction was also noted to be transient, and had fully resolved by three hours following the dose, with or without antihistamine treatment.

Based on the observed tolerance of IV dose of Compound I, the rat appeared to be the most sensitive species on an mg/kg basis, and this predominated in the estimation of a human starting dose in the phase 1 study. This calculation concluded that patients should begin by receiving 25 mg/m² (approximately 50 mg per dose), via a one hour IV infusion once every 21 days.

Example 16. Development of a Population Pharmacokinetic (PK) and Tumor Growth Inhibition (TGI) Model in Mice The current population analysis utilized non-linear mixed effects modeling to quantify the PK and pharmacodynamics (PD) of Compound I. This approach involved estimation of fixed-effect (mean) parameters, together with inter-individual and residual variability for each of the models developed. Where relevant, covariate effects were incorporated to potentially explain the random sources of variability. An additional benefit of this modeling approach is the ability to appropriately handle sparse or unbalanced data, particularly where practical considerations prohibit intensive sampling. Finally, non-linear mixed effects modeling allows for the stochastic simulation of PK-PD to assist with dose recommendation in target populations of interest.

Two of the objectives of this analysis were to develop population models that 1) describe the PK of Compound I in non-tumor-bearing mice using data from different dosing and sampling regimens, and 2) characterize the PK-PD relationships between Compound I exposure and antitumor response in patient-derived mouse xenograft models.

A total of four non-clinical studies were used to characterize PK of Compound I in mice. The dosing regimens included both intravenous (IV) and oral (PO) routes of administration at various dosing schedules. Animal strains evaluated included wild-type ICR and athymic nude (nu/nu) mice (Table 28).

TABLE 28

Summary of Studies Included in the Mouse PK Analysis

| | Study Description | Dosing regimens | Number of mice | Total observations |
|---|---|---|---|---|
| 1 | A non-clinical single-dose PK study of Compoun I in female ICR mice | SD IV at 5 mg/kg or PO at 10 mg/kg | 3 (IV); 3 (PO) | 29 (IV); 25 (PO) |
| 2 | A non-clinical PK study of Compound I in ICR mice | SD IV at 25 and 75 mg/kg or PO at 25, 75, and 150 mg/kg | 3 (IV); 9 (PO) | 27 (IV); 81 (PO) |
| 3 | A non-clinical PK study of Compound I in nu/nu mice | SD IV of 25, 62.5, and 125 mg/kg | 9 (IV) | 45 (IV) |
| 4 | A non-clinical bioanalysis study of Compound I in A375 xenograft nu/nu mice | QD IV or PO for 3 days (4 consecutive doses) at 25 or 65 mg/kg | 8 (IV); 8 (PO) | 24 (IV); 24 (PO) |

IV = intravenous;
nu/nu = athymic nude;
PK = pharmacokinetics;
PO = oral;
QD = once daily;
SD = single dose.

The data from 4 additional studies (Table 29) were utilized to elucidate the relationships between Compound I exposure and antitumor activity in mice with patient-derived xenografts (PDX). These studies only included data from nu/nu immunocompromised mice in 5 different PDX models (CTG-0012, CTG0888, HBCx-10, HBCx-15, and HBCx-14). A summary of studies used in the population PK-PD analysis is provided in Table 29.

TABLE 29

Summary of Studies Included in the Mouse PK Analysis

| Study | Description | Dosing regimens | Number of mice | Total observations |
|---|---|---|---|---|
| 5 | Evaluation of the in vivo activity of Compound I in CTG-0012 Champions TumorGraft ™ models of human breast cancer in nu/nu mice | Control or IV Compound I at 62.5 mg/kg/dose (QW × 4) or 125 mg/kg/dose (QW × 2) | 3 (Control); 16 (Treatment) | 36 (Control); 144 (Treatment) |
| | Evaluation of the in vivo activity of Compound I in CTG-0888 Champions TumorGraft ™ models of human breast cancer in nu/nu mice | Control or IV Compound I at 62.5 mg/kg/dose (QW × 4) | 4 (Control); 8 (Treatment) | 36 (Control); 72 (Treatment) |
| 6 | Evaluation of the antitumor efficacy of Compound I in the HBCx-10 patient-derived breast xenograft model in nu/nu mice | Control or IV Compound I at 50 mg/kg/dose (QW × 2) | 8 (Control); 8 (Treatment) | 108 (Control); 241 (Treatment) |
| 7 | Evaluation of the antitumor efficacy of Compound I in the HBCx-15 patient-derived breast xenograft model in nu/nu mice | Control or IV Compound I at 62.5 mg/kg/dose (QW × 4) | 5 (Control); 5 (Treatment) | 53 (Control); 105 (Treatment) |
| 8 | Evaluation of the antitumor efficacy of Compound I in the HBCx-14 patient-derived breast xenograft model in nu/nu mice | Control or IV Compound I at 62.5 mg/kg/dose (QW × 4) | 4 (Control); 5 (Treatment) | 32 (Control); 144 (Treatment) |

IV = intravenous;
nu/nu = athymic nude;
QW × 2 = once weekly for 2 weeks;
QW × 4 = once weekly for 4 weeks.

Figure 15A:
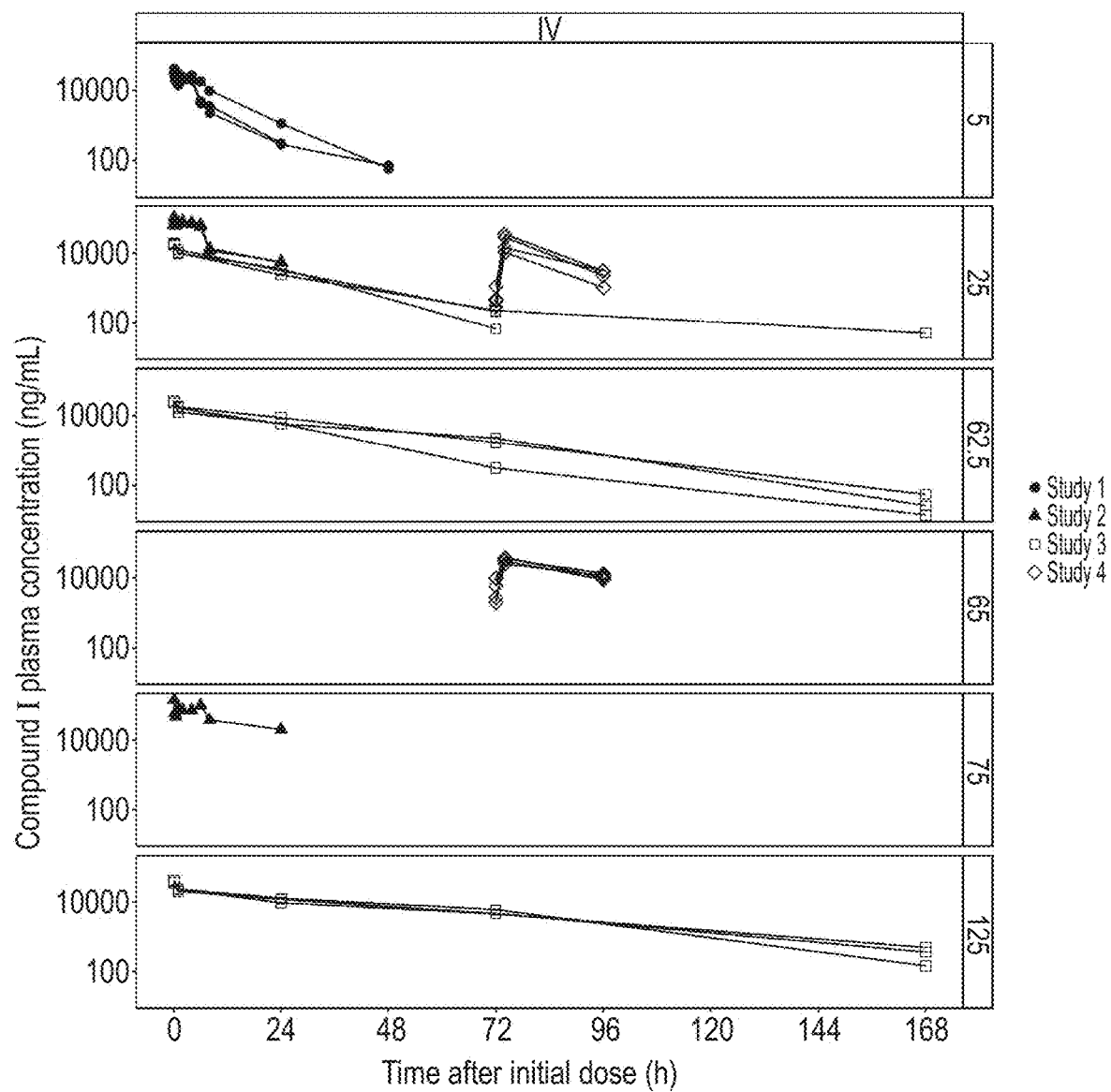
FIG. 15A shows composite display of the Compound I concentration-time data in mouse across dose regimen for IV administration in Study 1-4 of Example 16.
Figure 15B:
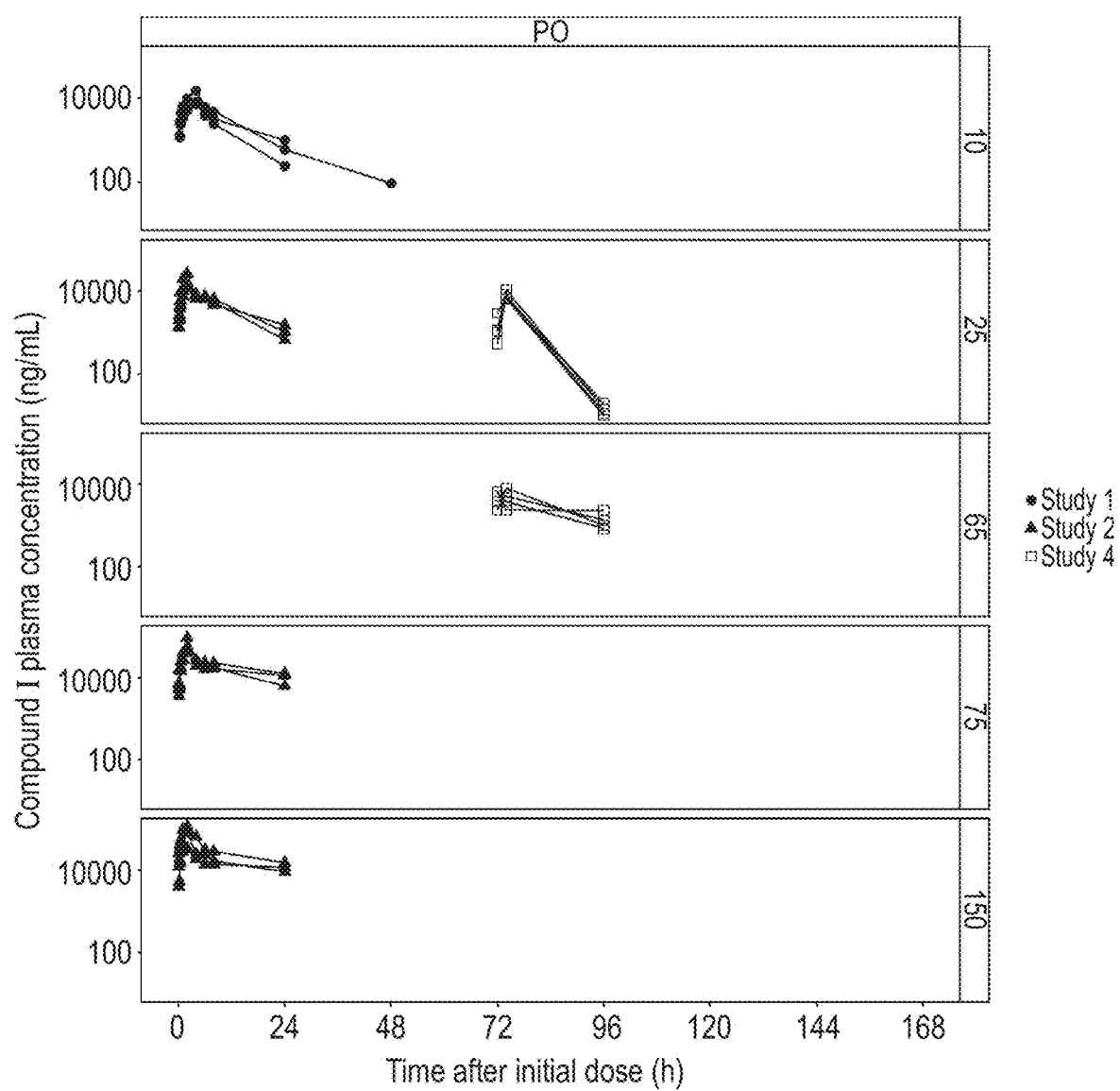
FIG. 15B shows composite display of the mouse Compound I concentration-time data across dose regimen for or administration in Study 1, 2, and 4 of Example 16.
Figure 16A:
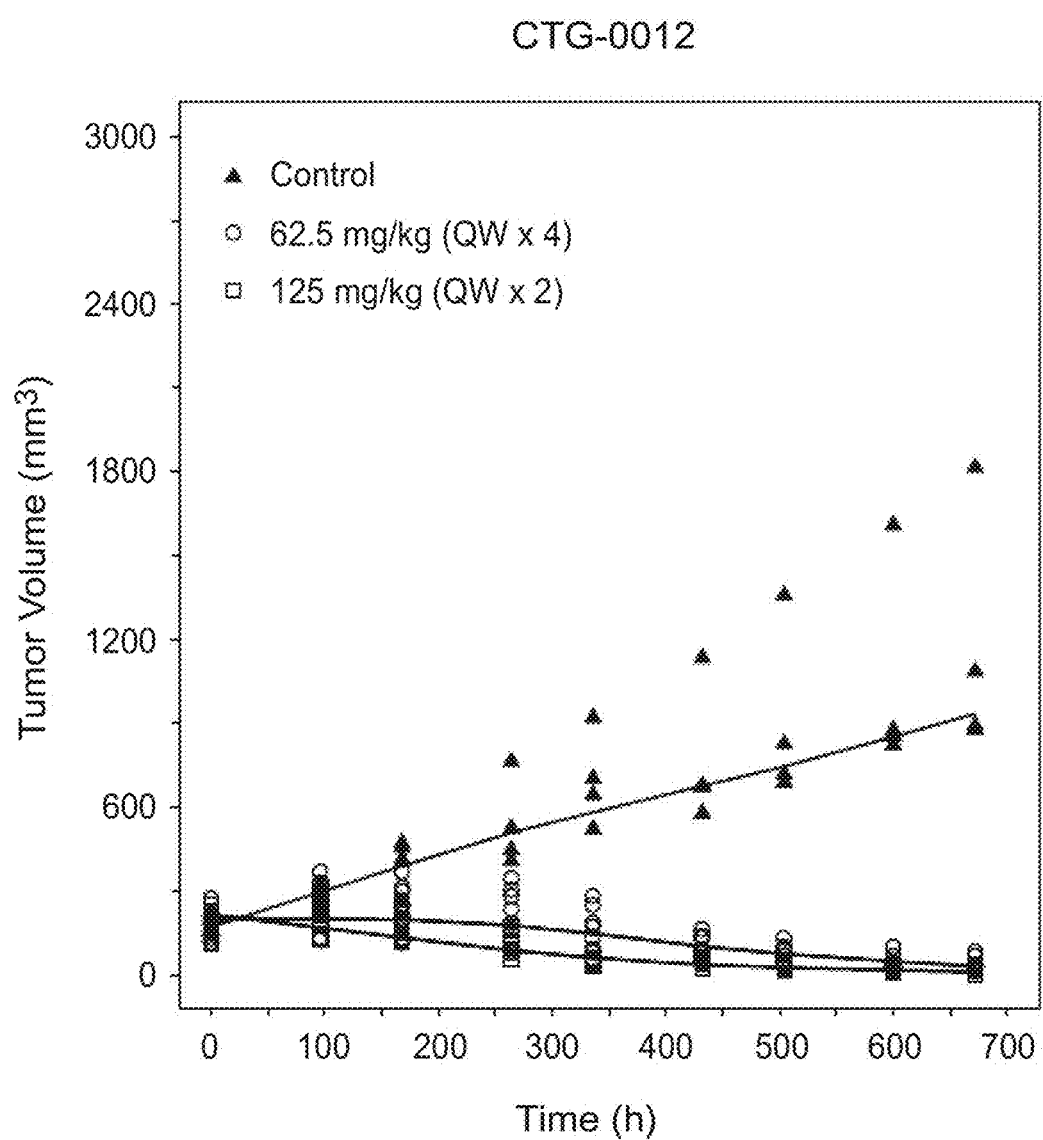
FIG. 16A shows observed time course of tumor volume following Compound I dosing to athymic nude mice further stratified by patient-derived xenograft model CTG-0012.
Figure 16B:
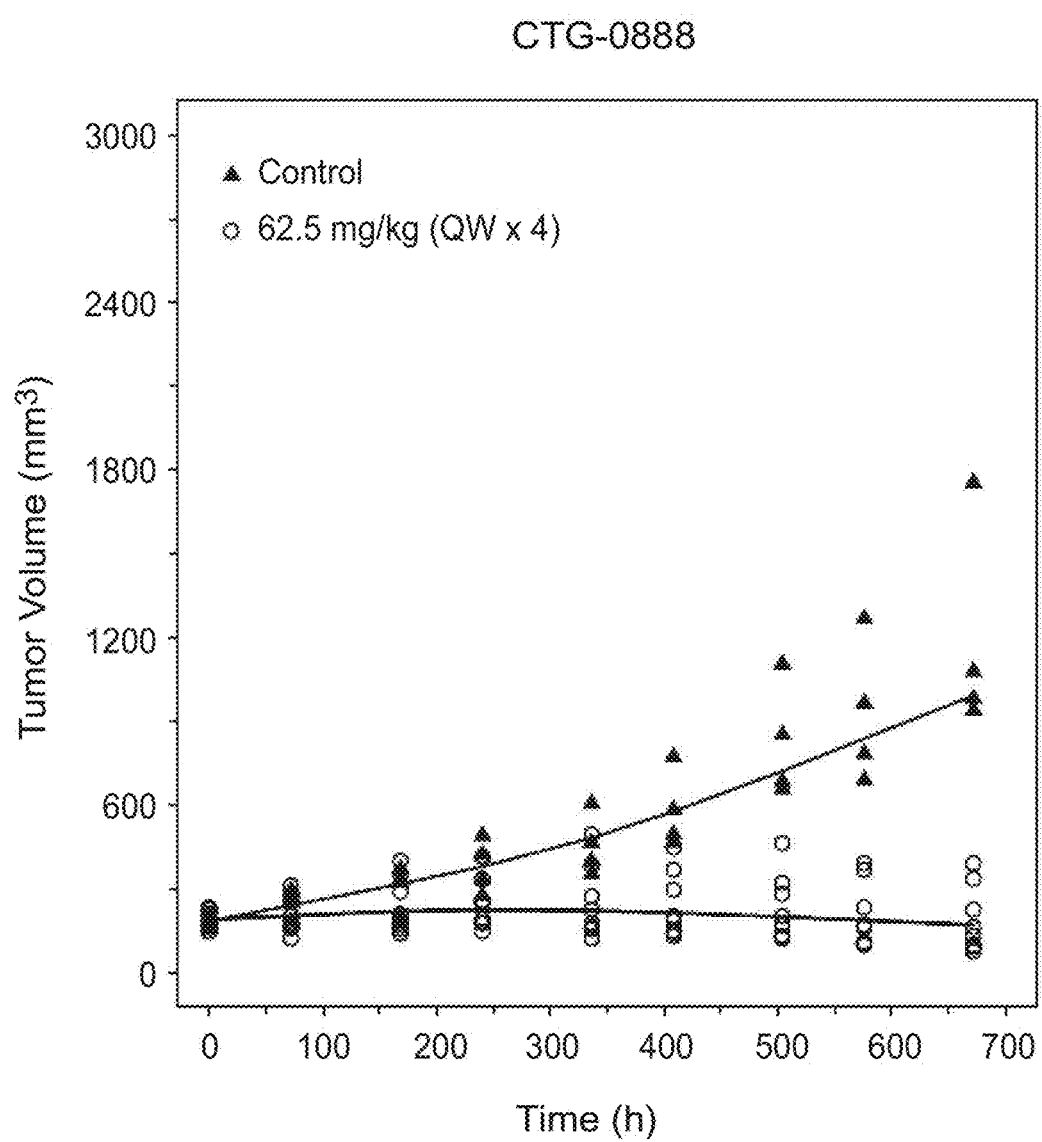
FIG. 16B shows observed time course of tumor volume following Compound I dosing to athymic nude mice further stratified by patient-derived xenograft model CTG-0888.
Figure 16C:
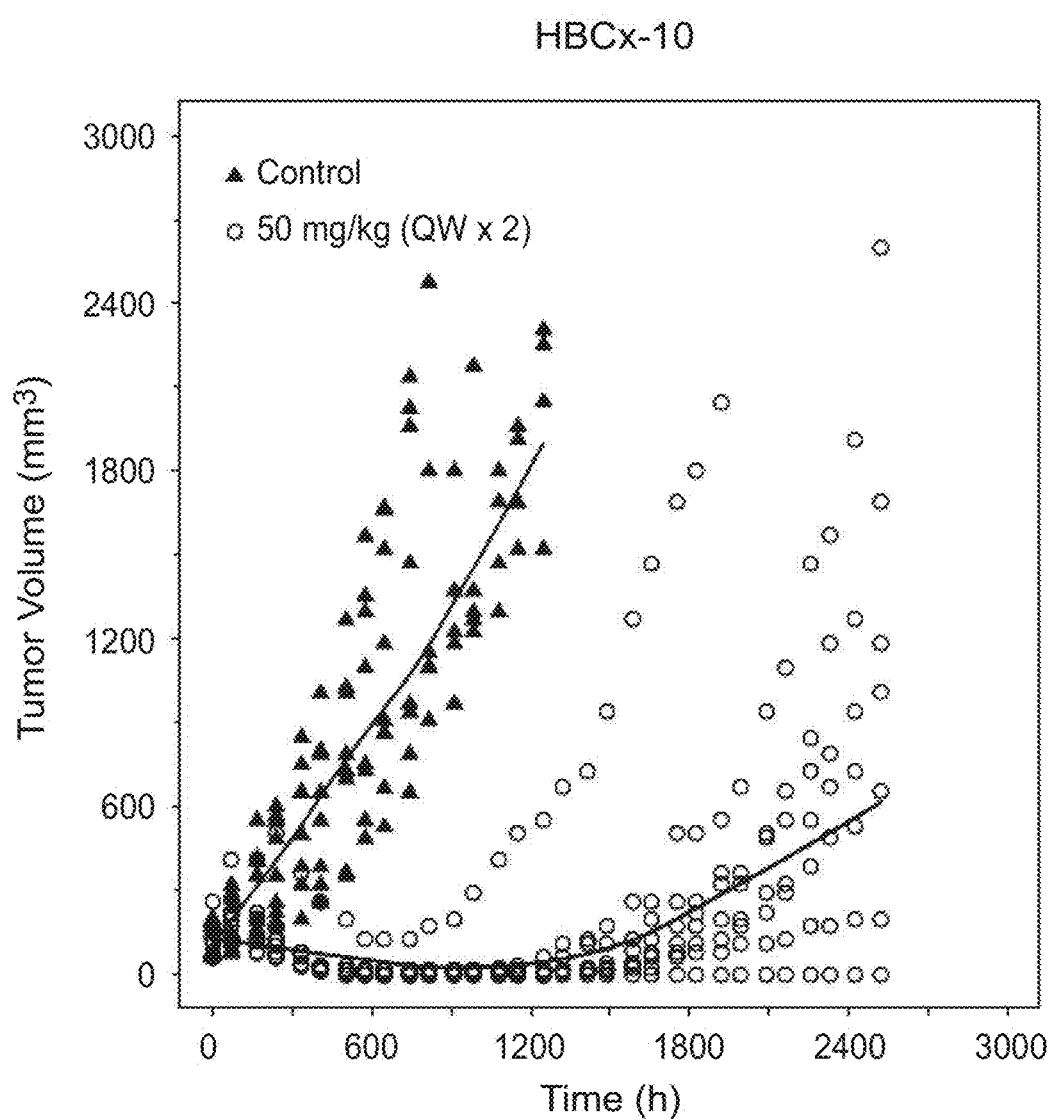
FIG. 16C shows observed time course of tumor volume following Compound I dosing to athymic nude mice further stratified by patient-derived xenograft model HBCx-10.
Figure 16D:
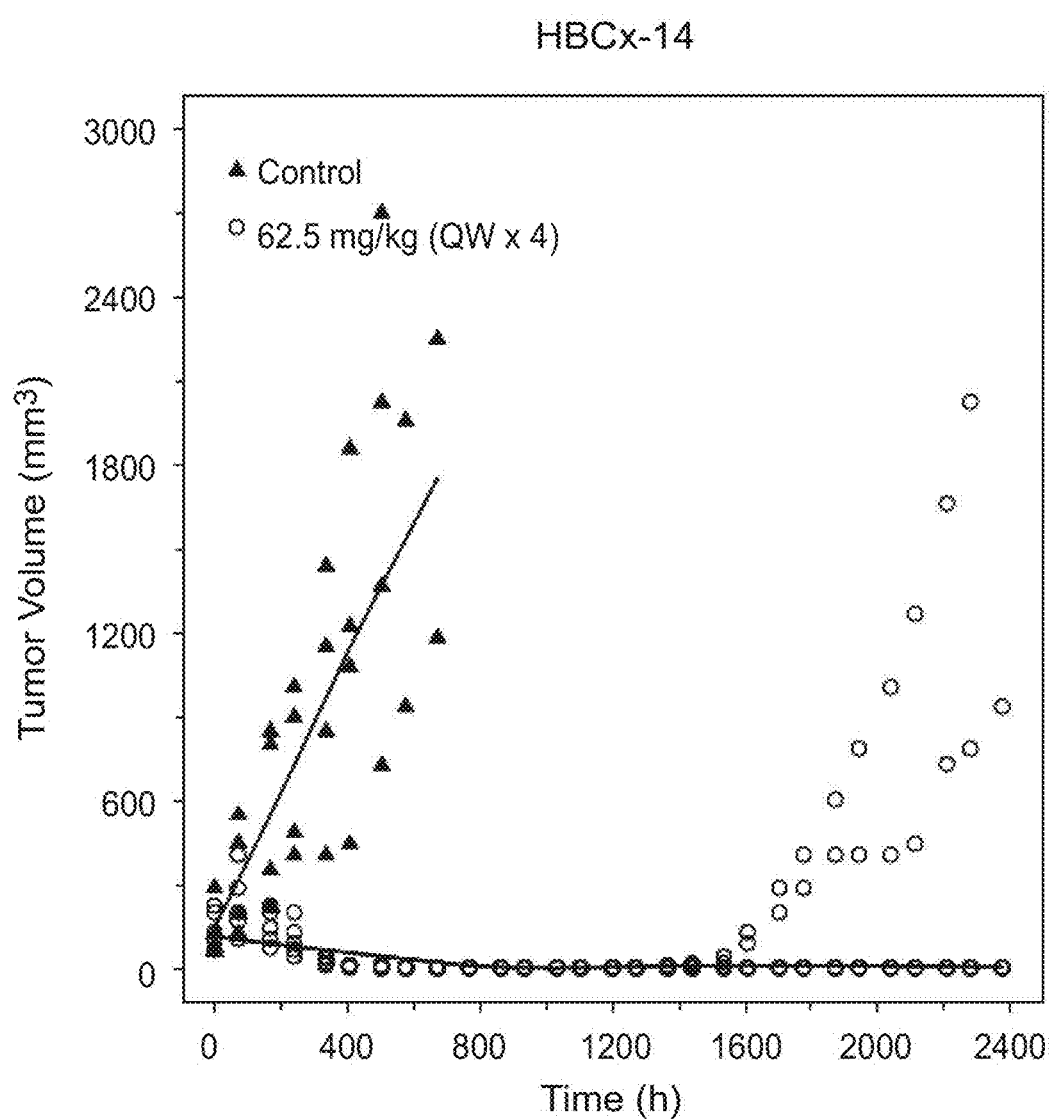
FIG. 16D shows observed time course of tumor volume following Compound I dosing to athymic nude mice further stratified by patient-derived xenograft model HBCx-14.
Figure 16E:
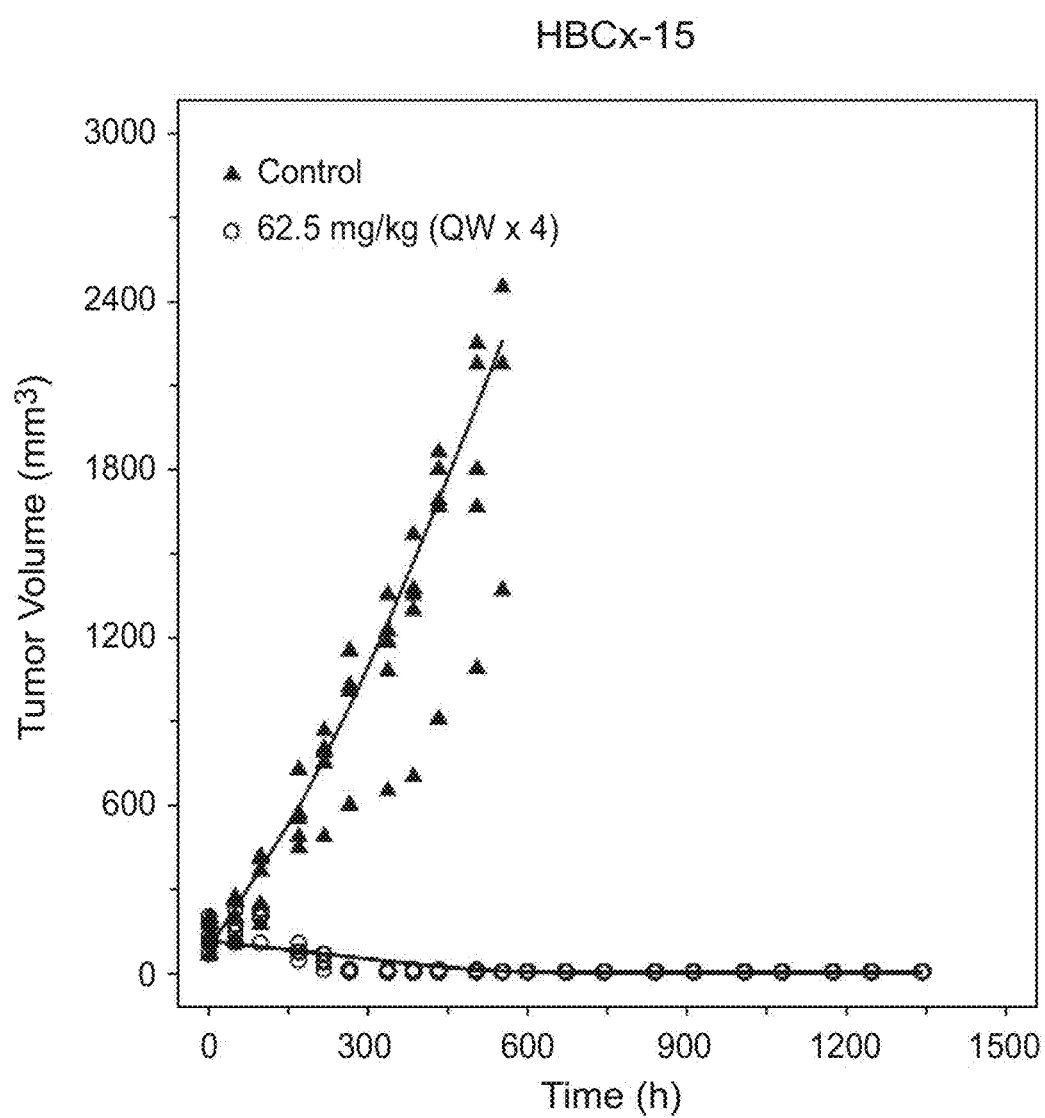
FIG. 16E shows observed time course of tumor volume following Compound I dosing to athymic nude mice further stratified by patient-derived xenograft model HBCx-15.

A composite display of the mouse Compound I concentration-time data across dose regimen and route of administration is presented in FIGS. 15A-15B for Study 1-4. In FIGS. 15A-15B, routes of administration included intravenous (IV, left panel) and oral (PO, right panel) dosing of Compound I to ICR or athymic nude mice. The panels are further stratified by dose at 5, 10, 25, 62.5, 65, 75, 125, or 150 mg/kg across Study 1-4 (Table 28). For the antitumor PK-PD studies (Study 5-8, Table 29), data across each of the PDX models are shown in FIGS. 16A-16E. In FIGS. 16A-16E, corresponding lines represent the median respective data.

Mouse P and mouse PK-PD data assemblies were performed using R (version 3.3.1) and a list of data items is tabulated in Table 30 (R: A Language and Environment for Statistical Computing. R Core Team, R Foundation for Statistical Computing, Vienna, Austria, 2014, http://www.R-project.org).

TABLE 30

Summary of Data Items Included in NONMEM Datasets

| Data item | Description | Descriptor identifiers |
|---|---|---|
| OMIT | Data exclusion identifier | '#' in row corresponding to excluded data |
| STUDY | Unique study identifier | Study 1-4 (Mouse PK) Study 5-8 (Mouse PK-PD) |
| ID | Unique analysis subject identifier | |
| SUBJ | Unique study subject identifier | |
| TIME | Time after initial dose/measurement | hours |
| DAY | Time after initial dose/measurement | days (only used in PK-PD data file) |
| SPECIES | Unique species identifier | 1 = Mouse; 2 = Human |
| STRAIN | Unique mouse strain identifier | 1 = ICR; 2 or 3 = nu/nu |
| DMGKG/DMGM2 | Dose administered | mg/kg (mouse) |
| AMT | Dose administered | mg |
| ROUTE | Dosing route identifier | 1 = IV; 2 = PO |
| RATE | Dose input identifier | 0 = bolus; −2 = IV infusion |

TABLE 30-continued

Summary of Data Items Included in NONMEM Datasets

| Data item | Description | Descriptor identifiers |
|---|---|---|
| CMT | Dose compartment identifier | 1 = PO (mouse); 2 = IV (mouse); 6 = tumor initialization (PK-PD only) |
| DVID | Dependent variable identifier | 0 = dose; 1 = concentration; 2 = tumor volume |
| DV | Dependent variable | μg/L concentration or mm³ tumor volume |
| LNDV | Natural log of dependent variable | μg/L concentration (PK only) |
| MDV | Missing dependent variable | 1 = missing; 0 = not missing |
| EVID | Event identification data item | 1 = missing; 0 = not missing |
| WT | Total bodyweight | kg |
| BSA | Body surface area | mg/m² |
| XENO | Xenograft identifier | 1 = CTG-0012; 2 = CTG-0888; 3 = HBCx-10; 4 = HBCx-14; 5 = HBCx-15 |
| SEX | Gender identifier | 1 = Male; 2 = Female |
| BLQ | Below quantitation limit identifier | 1 = BLQ; 0 = not BLQ |
| OCC | Dosing occasion identifier | 1 = 1st dose |

BLQ = below the quantitation limit;
IV = intravenous; nu/nu = athymic nude;
PD = pharmacodynamics;
PK = pharmacokinetics;
PO = oral.

Three independent datasets were created for each of the mouse PK and mouse PK-PD analysis objectives. Common or specific descriptor identifications for the datasets assembled are provided in Table 30.

Data Exclusion

All pre-dose concentrations and observations reported as 'N/A' were excluded from the analyses. The following outliers were excluded from the PK analysis in mice:

Data following 150 and 200 mg/kg IV dosing (Study 2, Table 28).

Data following 300 and 1000 mg/kg PO dosing (Study 2, Table 28).

Subjects not considered during non-compartmental analyses (N=2) due to implausibility.

Compound I concentrations reported as below the quantitation limit (BLQ) were excluded from the PK analyses due to their low proportion of the overall data (N=2 observations in mice).

All observations excluded from the analysis were retained in the data files and 'commented out' by inserting a '#' symbol in corresponding rows of the 'OMIT' column.

Population Analyses

A generalized stepwise approach was used to develop all PK or PK-PD models and included the following:

Initial characterization of the structural base model.

Incorporation of covariate effects that potentially explain random variability.

Structural Models

Mouse PK Model

Several PO absorption and disposition models were investigated to describe the PK of Compound I following IV or PO dosing to mice. In addition, the model included a pathway for enterohepatic recirculation, based on the known pharmacology of Compound I.

Total bodyweight was incorporated a priori into the structural base model to allow for parameter comparison between mice and humans. For this, the disposition parameters were allometrically scaled using Equation 1 below:

$$\theta_i = \theta_{pop} \cdot \left(\frac{\text{Weight(kg)}_i}{70}\right)^p \quad (1)$$

where weight $(kg)_i$ is the total weight for subject i, p is the allometric exponent, and 70 kg is a standardized human adult bodyweight. Exponents of ¾ and 1 were assumed for all clearances and volumes of distribution, respectively.

Figure 20:
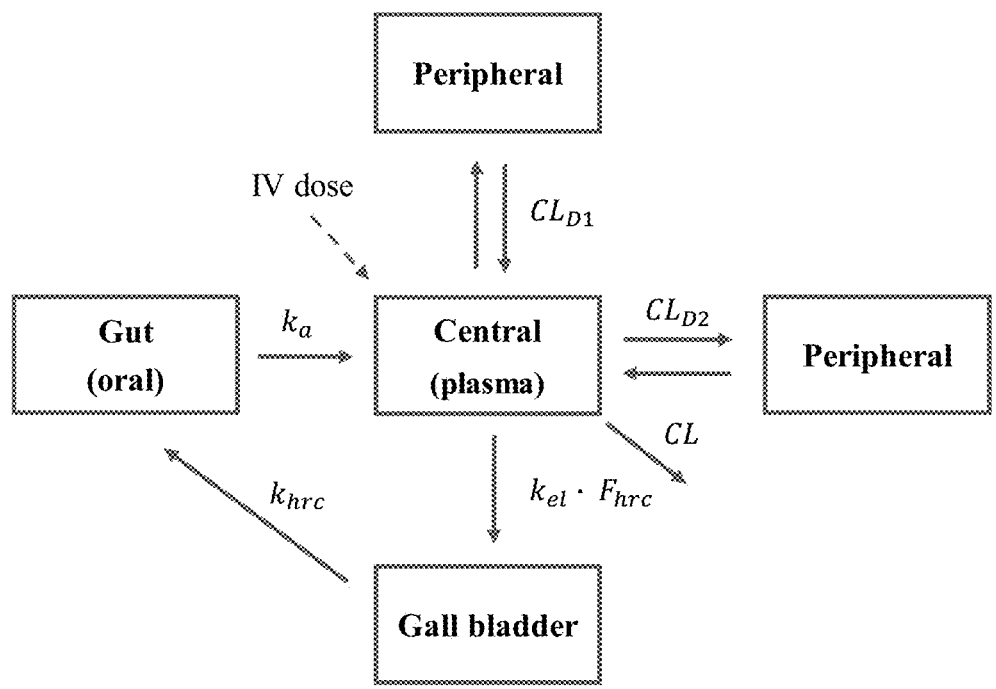
FIG. 20 shows the structure of the structural base PK model in mice.

The structure of the structural base PK model in mice is presented in FIG. 20.

The input after PO dosing was described by first-order absorption. Drug disposition was characterized by a 3 compartment model, with an additional pathway describing known enterohepatic recirculation. Abbreviations: CL=clearance from the central compartment; $CL_{D1}$=1st peripheral distribution clearance; $CL_{D2}$=2nd peripheral distribution clearance; $F_{hrc}$=fractional diversion to gall bladder; IV=intravenous; $k_a$=first-order rate constant for PO absorption; $k_{el}$=elimination constant; $k_{hrc}$=transfer rate from gall bladder to gut; PO=oral.

Differential equations for the above structural PK model are described by Equations 2 to 6.

$$\frac{dA_1}{dt} = -k_a \cdot A_1 + k_{HRC} \cdot A_5 \cdot \text{FLAG} \quad (2)$$

$$\frac{dA_2}{dt} = \quad (3)$$
$$k_a \cdot A_1 - \frac{CL_{D1}}{V_C} \cdot A_2 + \frac{CL_{D1}}{V_{P1}} \cdot A_3 - \frac{CL_{D2}}{V_C} \cdot A_2 + \frac{CL_{D2}}{V_{P2}} \cdot A_4 - \frac{CL}{V_C} \cdot A_2$$

$$\frac{dA_3}{dt} = \frac{CL_{D1}}{V_C} \cdot A_2 - \frac{CL_{D1}}{V_{P1}} \cdot A_3 \quad (4)$$

$$\frac{dA_4}{dt} = \frac{CL_{D2}}{V_C} \cdot A_2 - \frac{CL_{D2}}{V_{P2}} \cdot A_4 \quad (5)$$

$$\frac{dA_5}{dt} = k_{20} \cdot F_{HRC} \cdot A_2 - k_{HRC} \cdot A_5 \cdot \text{FLAG} \quad (6)$$

where compartments 1 to 5 represent the PO dosing, central (plasma), 1$^{st}$ peripheral, 2$^{nd}$ peripheral, and gall bladder, respectively. The FLAG component in Equations 2 and 6 is a reserved variable in the modeling software used that allows for estimation of the start and end times of enterohepatic recycling. All parameters are defined in Table 31.

TABLE 31

Population Parameter Estimates for Compound I PK in Mice

| Parameter (Units) | Parameter description | Population mean Estimate (% RSE) | % BSV Estimate (% RSE) |
|---|---|---|---|
| $F_{oral}$ | Absolute bioavailability after PO dosing | 0.248 (9.7) | — |
| $k_a$ (1/h) | First-order rate constant for PO absorption | 1.29 (11.5) | — |
| CL (L/h/70 kg) | Clearance from the central compartment | 0.330 (13.3) | — |
| $V_c$ (L/70 kg) | Central compartment distribution volume | 26.2 (15.1) | 44.5 (22.8) |
| $CL_{D1}$ (L/h/70 kg) | 1$^{st}$ peripheral distribution clearance | 0.145 (29.9) | — |
| $V_{P1}$ (L/70 kg) | 1$^{st}$ peripheral distribution volume | 7.51 (22.7) | — |
| $CL_{D2}$ (L/h/70 kg) | 2$^{nd}$ peripheral distribution clearance | 0.194 (33.7) | — |
| $V_{P2}$ (L/70 kg) | 2$^{nd}$ peripheral distribution volume | 149 (21.0) | — |
| $F_{hrc}$ | Fractional diversion to gall bladder | 1 FIX | — |
| $k_{hrc}$ (1/h) | Transfer rate from gall bladder to gut | 100 FIX | — |
| $HRC_{Time}$ (h) | Enterohepatic recirculation time | 3.66 (10.7) | — |
| FCL_NU | Fold change in clearance (nu/nu mice) | 3.99 (14.8) | — |
| FVC_NU | Fold change in central volume (nu/nu mice) | 4.78 (8.8) | — |
| $RUV_{prop}$ (CV) | Residual proportional error | 0.405 (6.6) | — |
| $RUV_{add}$ (ng/mL) | Residual additive error | 537 (44.8) | — |

Mouse PK-PD Model

A population analysis approach was used to simultaneous describe the kinetics of tumor growth (control) and drug inhibition effect (treatment) in nu/nu mice.11 The differential equation for the TGI model is described by Equation 7:

$$\frac{dXEN}{dt} = k_{growth} \cdot A_{XEN} + k_{drug} \cdot fcp \cdot A_{XEN} \quad (7)$$

where XEN represents the xenograft compartment, $k_{growth}$ is the rate constant for tumor growth, $k_{drug}$ is the rate constant for drug-induced antitumor inhibition, and fcp is the predicted unbound concentration of Compound I in plasma. In this model, the PD effect was driven using the free (not total) concentration of Compound I obtained using the developed mouse PK model. An averaged unbound fraction of 0.2% (99.8% bound) was used based on measured values for protein binding in mouse plasma. Five different xenograft types (CTG-0012, CTG-0888, HBCx-10, HBCx-14, and HBCx-15) were used in the development of the Compound I TGI model.

Modeling Assumptions

Several assumptions were required to accommodate pharmacological plausibility and/or allow for the development of parsimonious models. The following assumptions were incorporated:

Allometric scaling (Equation 1) was applied to all clearances and volumes of distribution in human mouse PK models.

Enterohepatic recirculation was included to support the known pharmacology of Compound I. However, only limited data were available to support the robust estimation of this kinetic pathway. Where necessary, parameters describing enterohepatic recirculation were fixed to allow for model convergence and to retain parsimony.

For PK-PD model development, Compound I concentration-time data from the same animal in mouse xenograft studies were unavailable. It was therefore assumed that all mice share equal exposures with no variability in the PK of Compound I. The parameters in these animals were fixed to the population mean values derived following development of the mouse PK model.

The unbound fraction to drive response in the PK-PD model was calculated using plasma protein binding data from mouse, dog and human species.

Parameter Estimation

The kinetics of Compound I concentration and xenograft volume was analyzed using non-linear mixed effects modeling (NONMEM® version 7.3; ICON Development Solutions, Maryland, USA). For PK model development, Compound I total drug concentrations were logarithmically transformed to efficiently accommodate the large range of magnitude in observed data. In contrast, xenograft volumes were modeled in the untransformed scale. All population analyses were performed using first-order conditional estimation with interaction, with the ADVAN13 subroutine (TOL=9) to solve the differential equations. For mouse PK model, the reserved FLAG term was used to define the start and end times of enterohepatic recycling using MTIME.

Model selection was based on the plausibility of parameter estimates, diagnostic scatter plots, and the Objective Function Value (OBJ; calculated using—2×log-likelihood). A $\chi 2$ distribution was used for comparison of nested models, where a decrease in the OBJ of 3.84 units ($\alpha<0.05$) was defined as statistically significant.

Parameter Variability

The between-subject variability (BSV) in parameter estimates was calculated using an exponential variance model that assumed a log-normal distribution (Equation 12):

$$\theta_i = \theta_{pop} \cdot \exp(\eta_{\theta,i}) \quad (12)$$

where $\theta_i$ represents the PK parameter for subject i, $\theta_{pop}$ is the population mean estimate, and $\eta_{\theta,i}$ is the subject-specific random effect. Initially, a diagonal variance-covariance structure was assumed for BSV parameters. Partial and full block matrix structures were additionally tested during model development.

The residual unexplained variability between observed and predicted data was investigated using a proportional, additive, or combined error model (Equation 13):

$$Y_{ij} = C_{ij}(1+\varepsilon_{1,ij}) + \varepsilon_{2,ij} \quad (13)$$

where $Y_{ij}$ is the j$^{th}$ observed value for the i$^{th}$ subject, $C_{ij}$ is the corresponding prediction, and $\varepsilon_{1,ij}$ and $\varepsilon_{2,ij}$ are the proportional and additive residual errors, respectively.

Examples of potential sources of residual variability include assay error, model misspecification, and incorrect dosing or sampling.

Covariate Testing

Categorical covariates (mouse strain, gender, or xenograft type) were assessed using the general equation:

$$TVP = P_{pop} \cdot \prod_{i=1}^{n} \theta_i$$

where $\theta_i$ is a direct proportionality constant. In this model, $\theta_i$ was fixed to 1 for a select reference subgroup and was estimated for other test subgroups. Reference groups for the above categorical covariates were ICR mouse strain, male gender, or CTG-0012 xenograft type.

Continuous scale covariates included bodyweight only and was applied a priori using allometric scaling to mouse PK model.

Handling of Censored Data

A statistical method to appropriately handle BLQ data was not incorporated in PK analyses due to their low proportion of the overall data (N=2 observations in mice).

Model Evaluation

A visual predictive check (VPC) was used to evaluate the predictive performance of PK and TGI models for Compound I. For this, 500 datasets were simulated using the final parameter estimates and original data as a template. The resulting prediction percentiles were then plotted and graphically compared to corresponding observed data. Non-parametric bootstrapping was not required because all developed PK and PK-PD models converged successfully and produced standard errors of the parameter estimates.

Mouse PK Model Summary

A total of 43 ICR wild-type and nu/nu mice were used to characterize the plasma PK of Compound I following IV and PO bolus administration. The absorption of Compound I after PO dosing was adequately described by a first-order input model. Absolute bioavailability via the PO route of drug administration was estimated as 24.8%. The disposition of Compound I was characterized by a 3-compartment model, with an additional enterohepatic recirculation pathway to accommodate its known pharmacology (FIG. 20). Estimated mean values for clearance and volume of the central compartment were 0.330 L/h/70 kg and 26.2 L/kg, respectively. A summary of population parameters is provided in Table 31.

Inclusion of a pathway to describe known enterohepatic circulation was particularly challenging due to the small number of mice available for population PK analysis. A further limitation was the lack of an apparent 'double-peak' in the concentration-time profiles for all mice. Consequently, to support the estimation of this pathway, it was assumed that:

Recirculation begins immediately after dosing with all of the Compound I clearance diverted to the gall bladder for the estimated duration of enterohepatic recycling;

The kinetics of transfer for gall bladder to gut is rapid.

Covariate analysis identified mouse strain as a significant demographic factor in describing the PK of Compound I. The estimated clearance and central volume were approximately 4- and 5-fold higher, respectively, in nu/nu relative to the ICR wild-type strain. Inclusion of the strain covariate reduced the BSV from 22% to 2% for clearance and 101% to 45% for volume ($\Delta$ OBJ=−60 units).

Good precision in parameter estimates and model convergence was achieved when assuming some of the population mean values describing enterohepatic recirculation. Eta shrinkage in the BSV of central volume was low and estimated as 9.4%.

Figure 17A:
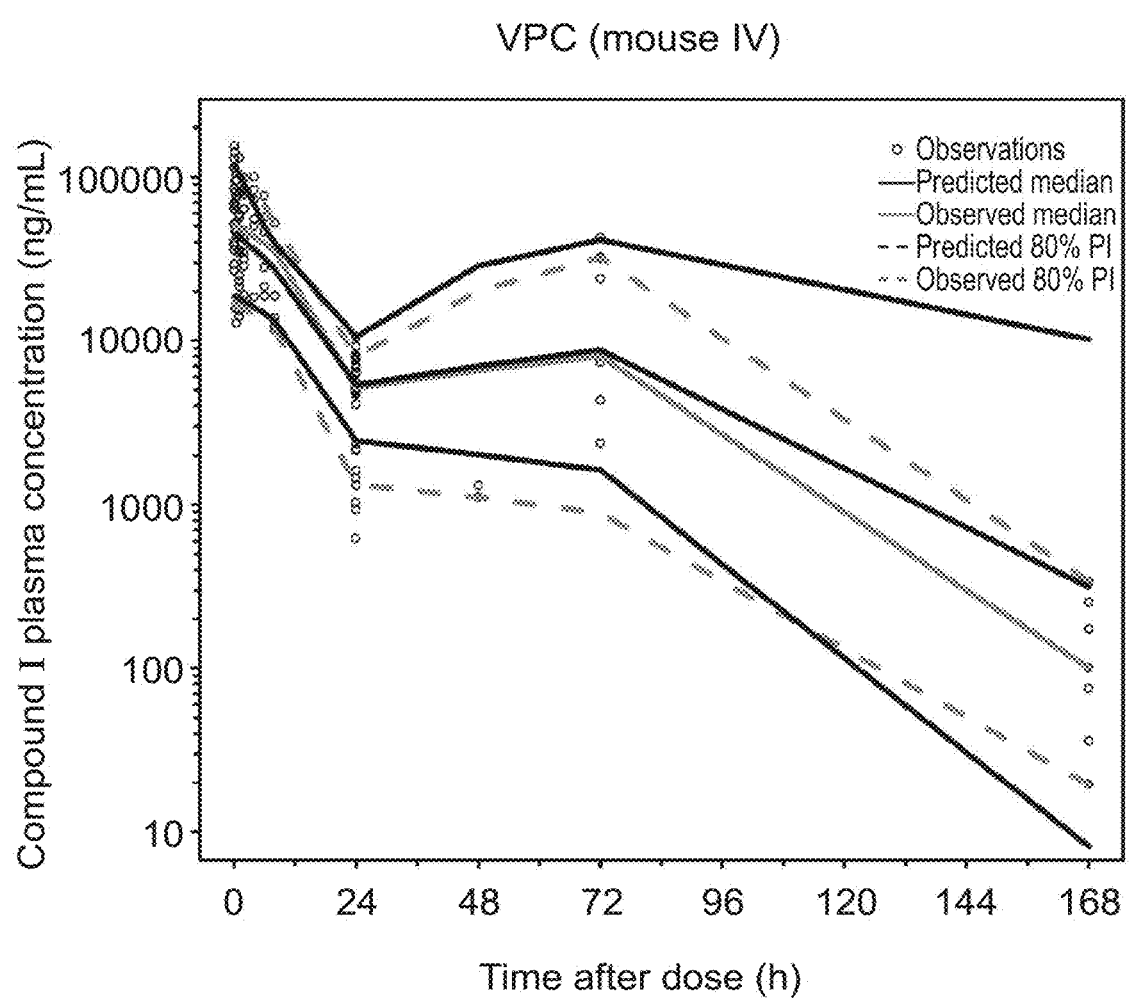
FIG. 17A shows visual predictive check evaluation of Compound I concentration-time in mouse after IV administration discussed in Example 16.
Figure 17B:
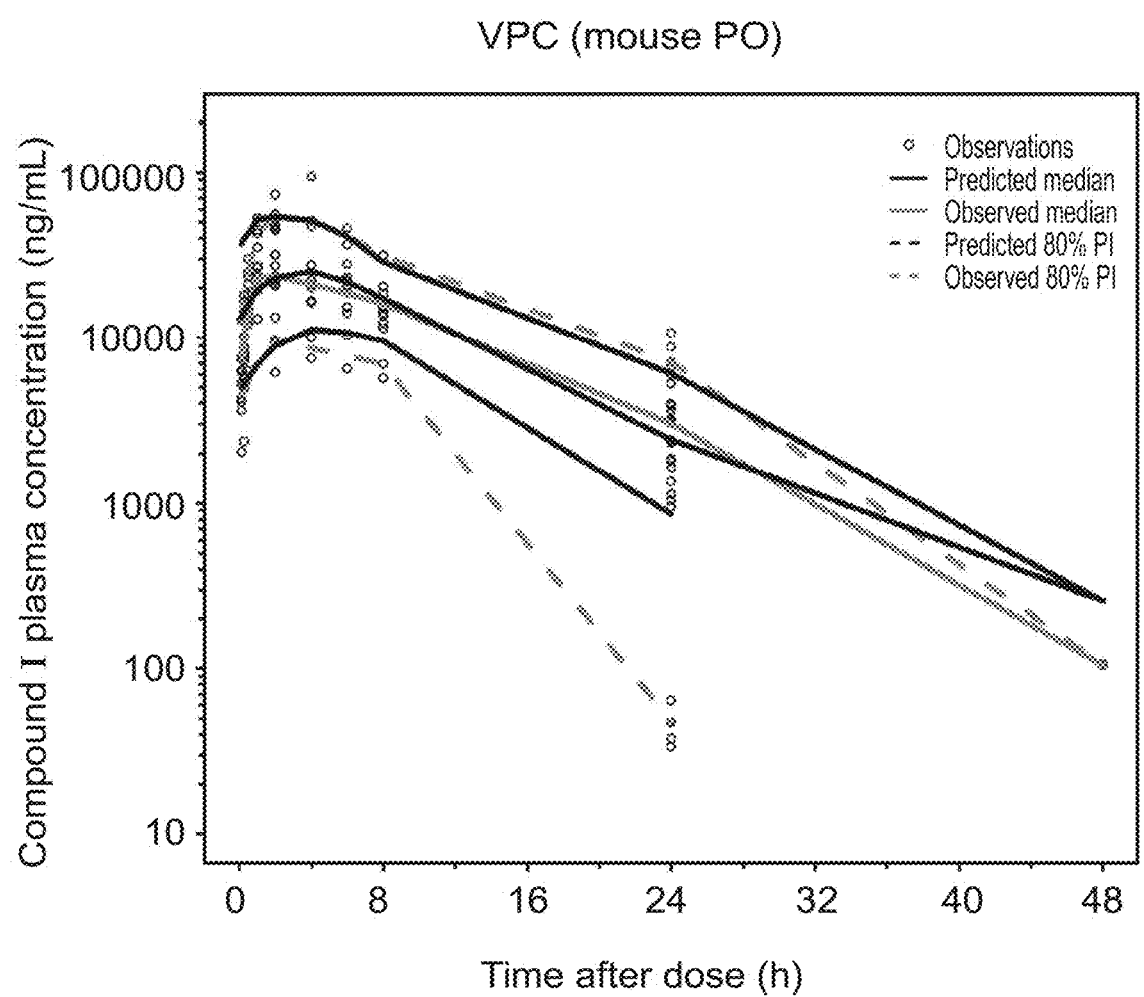
FIG. 17B shows visual predictive check evaluation of Compound I concentration-time in mouse after oral administration discussed in Example 16.
Figure 18:
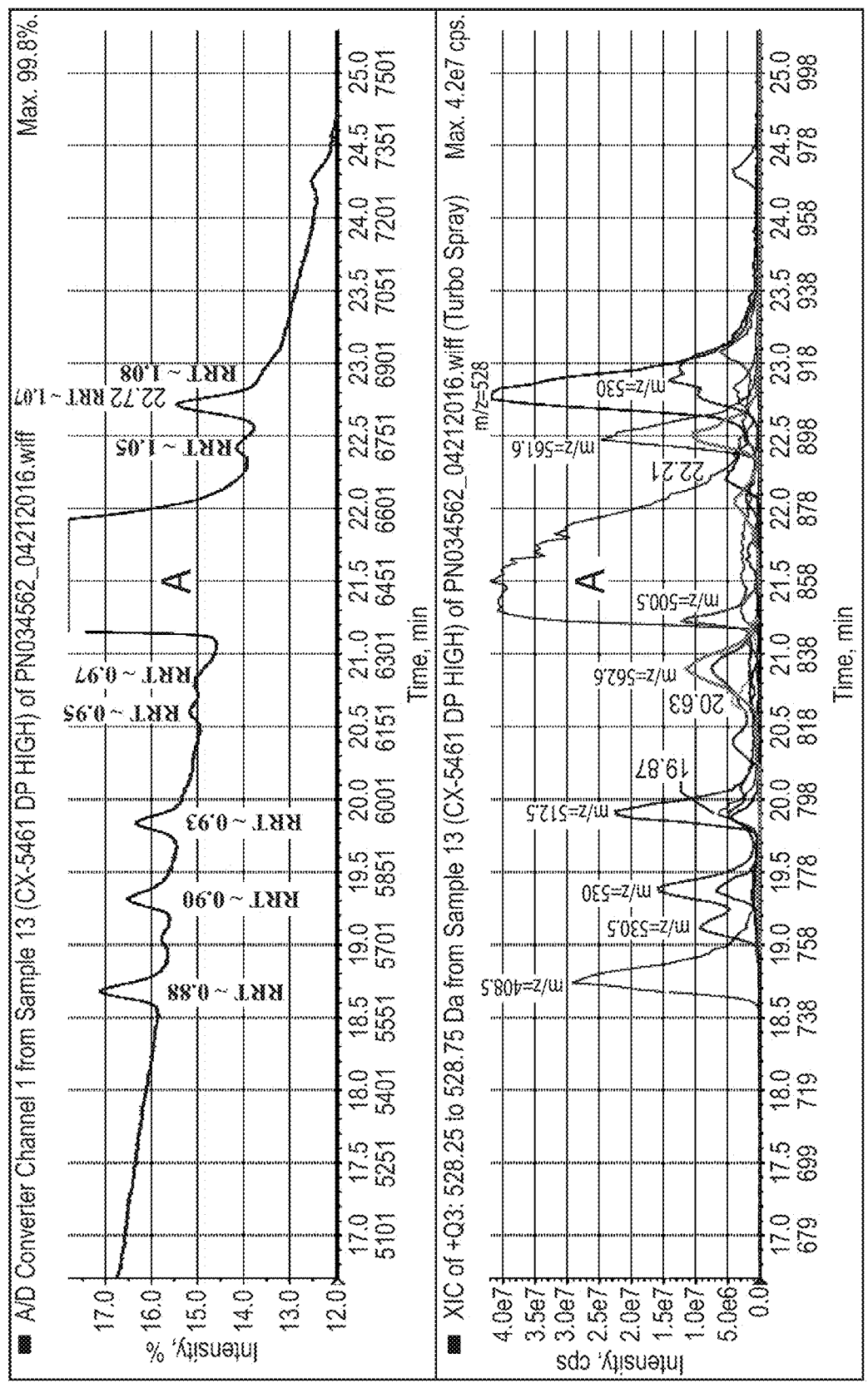
FIG. 18 UV chromatogram (top) and extracted ion chromatograms (bottom) performed on Compound I (A=Compound I) formulation product.
Figure 19A:
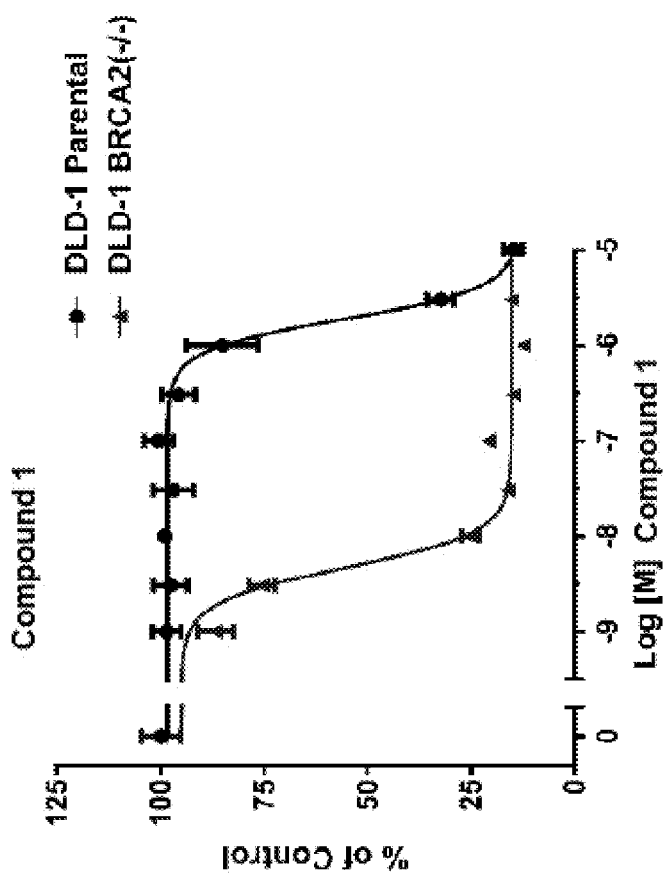
FIG. 19A shows dose response curve for Compound I in a cell proliferation assay.
Figure 19B:
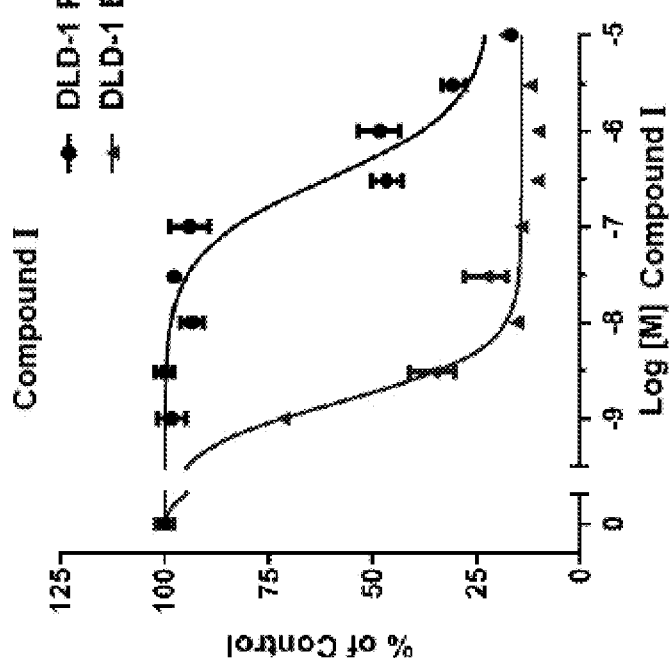
FIG. 19B shows dose response curve for Compound 1 in a cell proliferation assay.
Figure 19D:
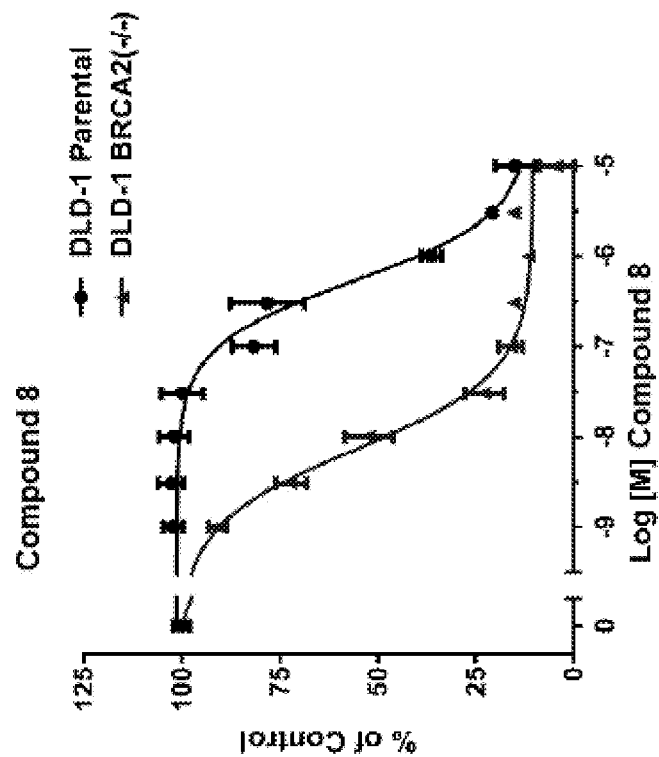
FIG. 19D shows dose response curve for Compound 8 in a cell proliferation assay.
Figure 19C:
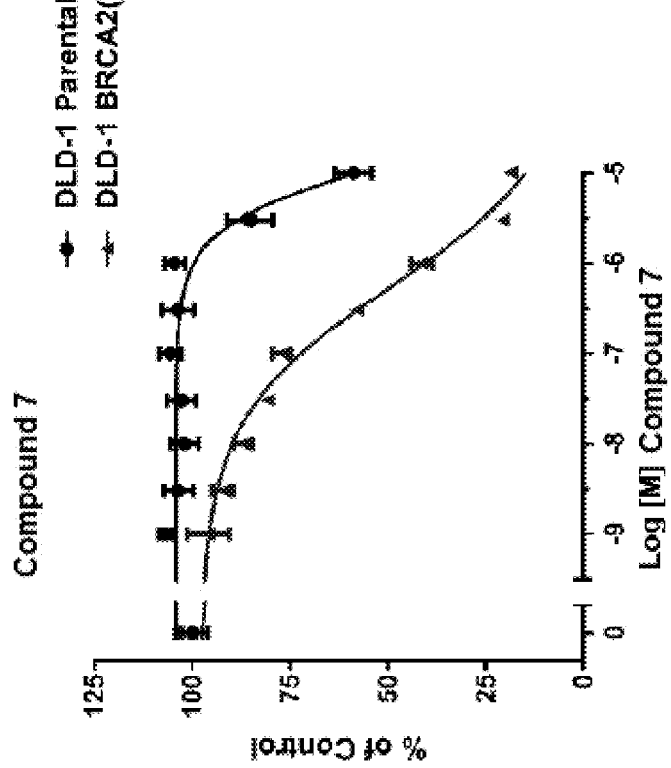
FIG. 19C shows dose response curve for Compound 7 in a cell proliferation assay.
Figure 19E:
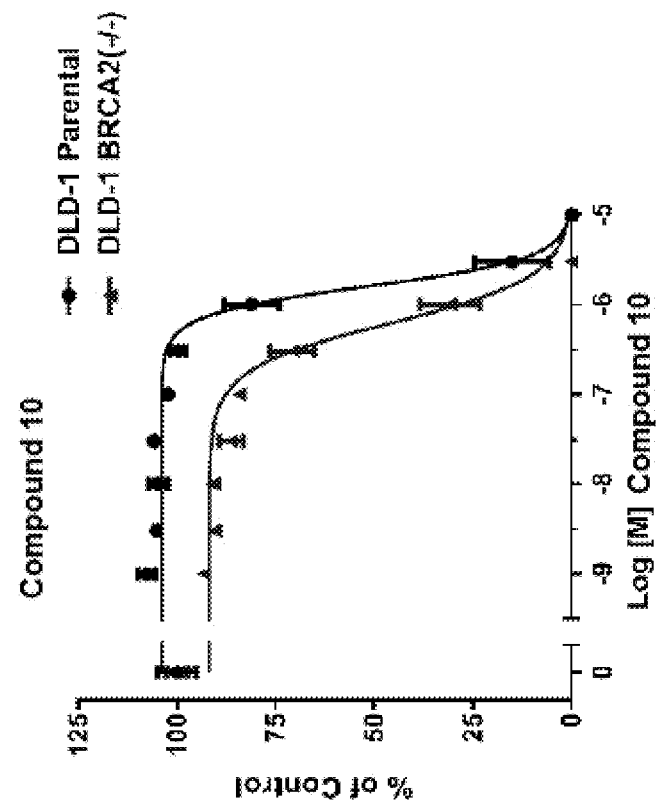
FIG. 19E shows dose response curve for Compound 9 in a cell proliferation assay.
Figure 19F:
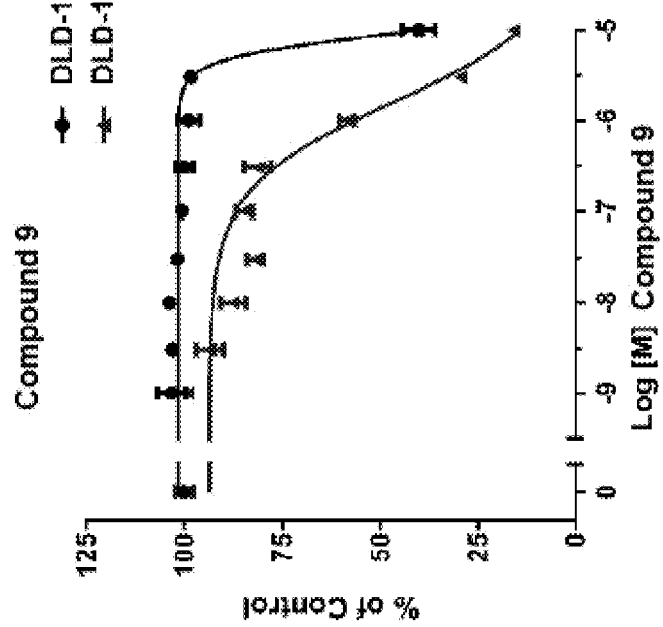
FIG. 19F shows dose response curve for Compound 10 in a cell proliferation assay.

Reasonable predictive performance of the final mouse covariate PK model was demonstrated when evaluating by VPC (FIGS. 17 and 17B). However, the upper percentile showed over-prediction of the model at the last sampling time (168 hours) following IV dosing. This discrepancy, without bound to any theory, likely reflects the inability of the model to capture both enterohepatic recycling and drug distribution, due to the small number of animal data available. This finding is expected since a clear 'double-peak' that represents the recycling of Compound I was only observed in 6 mice following IV dosing.

In FIG. 17A, the VPC is stratified to demonstrate the predictive performance following IV and in FIG. 17B, VPC is stratified to demonstrate the predictive performance following PO. Abbreviations: IV=intravenous; PI=prediction interval; PO=oral; VPC=visual predictive check.

Mouse PK-PD Model Summary

A population analysis approach was used to simultaneously model the kinetics of tumor growth (control xenografts) and drug-induced inhibition (treatment groups). Data from 67 nu/nu mice with implanted PDX were used for the development of the TGI model. The predicted plasma concentrations were obtained by fixing population mean values from the PK model developed in nu/nu mice. This assumption was required because drug concentrations were not available from the same animal in which tumor response was measured. Five different xenograft types (CTG-0012, CTG-0888, HBCx-10, HBCx-14, and HBCx-15) were used to characterize the TGI of Compound I.

The time course of xenograft growth in control mice was described by a first-order kinetic process ($k_{growth}$=0.002 h$^{-1}$). Drug-induced inhibition was driven using the predicted unbound concentration of Compound I in mice and had an estimated proportionality constant ($k_{drug}$) of 0.0006. The estimated initial tumor volume was 210 mm$^3$. Saturation of xenograft growth (control) was not included in the structural TGI model due to lack of data to support its estimation.

Covariate analysis was performed relative to CTG-0012 tumors and identified a xenograft effect for both $k_{growth}$ and $k_{drug}$ for all tumor types. Inclusion of a xenograft covariate reduced the BSV in $k_{growth}$ from 64% to 2% and that for $k_{drug}$ from 80% to 6%. A summary of population parameters for the mouse TGI model is provided in Table 32.

TABLE 32

| Population Parameter Estimates for Xenograft Growth Inhibition in Mice | | | |
|---|---|---|---|
| Parameter (Units) | Parameter description | Population mean Estimate (% RSE) | % BSV Estimate (% RSE) |
| TV$_0$ (mm$^3$) | Initial tumor volume | 210 (6.3) | 11.9(13.6) |
| $k_{growth}$ (1/h) | Rate constant for xenograft growth | 0.002 (14.6) | — |
| $k_{drug}$ (-) | Proportionality constant for drug inhibition | 0.0006 (7.8) | 5.8(42.5) |

TABLE 32-continued

Population Parameter Estimates for Xenograft Growth Inhibition in Mice

| Parameter (Units) | Parameter description | Population mean Estimate (% RSE) | % BSV Estimate (% RSE) |
|---|---|---|---|
| FTV0_CTG012 | Fold change in initial volume for CTG-0012 | 1.20 (10.2) | — |
| FGR_CTG0888 | Fold change in growth of CTG-0888 | 1.24 (17.3) | — |
| FGR_HBCx10 | Fold change in growth of HBCx-10 | 1.14 (16.1) | — |
| FGR_HBCx14 | Fold change in growth of HBCx-14 | 1.64 (17.7) | — |
| FGR_HBCx15 | Fold change in growth of HBCx-15 | 2.04 (16.3) | — |
| FDR_CTG0888 | Fold change in drug effect for CTG-0888 | 0.589 (23.6) | — |
| FDR_HBCx10 | Fold change in drug effect for HBCx-10 | 3.92 (17.7) | — |
| FDR_HBCx14 | Fold change in drug effect for HBCx-14 | 3.22 (19.8) | — |
| FDR_HBCx15 | Fold change in drug effect for HBCx-15 | 3.10 (9.8) | — |
| $RUV_{prop}$ (CV) | Residual proportional error | 0.154 (16.8) | — |
| $RUV_{add}$ (mm$^3$) | Residual additive error | 63.3 (12.5) | — |

BSV = between-subject variability; CV = coefficient of variation; RSE = relative standard error Relative to CTG-0012, the predicted rates of tumor growth for all other xenograft models ranged from 1.14- to 2.04-fold. Similarly, the proportionality constant for drug-induced inhibition ranged from 0.59- to 3.92-fold when compared with CTG-0012 reference tumors. Eta shrinkage in retained BSV parameters was acceptable and was 13.8% for initial tumor volume and 34.4% for $k_{drug}$.

Good predictive performance of the final mouse TGI model was demonstrated despite the paucity of data in each of the xenograft groups. For each tumor model, control data were generally only available in a total of 4 to 8 mice. Nonetheless, reasonable model predictions are illustrated when stratifying the VPC into control and treatment for each xenograft type.

The inhibition effect of Compound I was described using an immediate effect PK-PD model, which captured the re-growth of HBCx-10 tumors. Delayed effects (using an effect compartment) were investigated but produced model instability or implausibility in parameter estimates.

The mouse PK model and PK-PD model established herein can be combined with human PK model to simulate the effect of Compound I in human patients, which can be useful in predicting dosing, efficacy, and toxicity margins of Compound I. Such simulation is reasonable because the xenografts implanted in mice in this Example were derived from actual breast cancer tumors in human patients.

Example 17. Pharmacokinetic Studies in Human

Pharmacokinetic studies and dose escalation studies were conducted in adult patients with advanced hematologic cancers at 25, mg/m$^2$ (ready-to-use formulation), 50 mg/m$^2$ (ready-to-use formulation), 100 mg/m$^2$ (ready-to-use formulation), 170 mg/m$^2$ (lyophilized formulation), and 250 mg/m$^2$ (lyophilized formulation) dose levels of Compound I. Each patient received one dose over 1 hour by IV infusion, once every three weeks±2 days (Cohort 1).

Dose escalations were planned in 7 cohorts (25-450 mg/m2), in an accelerated design, with change to 3+3 design based on predefined toxicity criteria. 16 patients (6 myeloma, 2 Hodgkin lymphoma, 6 Non Hodgkin lymphoma (NHL), 1 TPLL, 1 CLL) were treated in 5 cohorts (25-250 mg/m2), for a median of 2 (1-18) cycles.

250 mg/m$^2$ dose of Compound I was prepared according to Example 2 (lyophilized composition with mannitol) and reconstituted with 5% glucose in sterile water for IV infusion.

Levels of Compound I in patient's plasma were analyzed by liquid chromatography tandem mass spectrometry (LC/MS/MS) assay. Experimental procedures of the validated methods are summarized below. The pharmacokinetic parameters after first dose in all dosage groups are shown in Table 33.

TABLE 33

Pharmacokinetic Parameters of Compound I from First Dose (First Cycle)

| Dose (mg/m$^2$) | N | $T_{max}$$^a$ (hr) | $AUC_{last}$ (ng*hr/mL) | $C_{max}$ (ng/mL) | $T_{1/2}$ (hr) |
|---|---|---|---|---|---|
| 25 | 3 | 1.00 (0.98; 1.00) | 2,056.7 ± 470.0 | 296.9 ± 46.4 | 23.20 ± 1.58 |
| 50 | 4 | 0.75 (0.25; 1.25) | 3,645.7 ± 2,221.8 | 384.3 ± 174.4 | 39.82 ± 16.92 |
| 100 | 4 | 0.5 (0.37; 1.00) | 10,146.3 ± 2493.6 | 636.0 ± 235.3 | 58.36 ± 12.89 |
| 170 | 3 | 0.52 (0.42; 1.00) | 16,792.2 ± 4,761.3 | 1,706.7 ± 454.6 | 45.47 ± 5.74 |
| 250 | 2 | 1.00 (1.00; 1.00) | 27,146.5 ± 438.9 | 1,358.0 ± 526.1 | 83.27 ± 12.92 |

Abbreviations: $AUC_{last}$ = area under the concentration-time curve from time 0 to the last observation postdose; Cmax = maximum observed concentration; $T_{1/2}$ = elimination half-life; $T_{max}$ = time to maximum observed concentration. $^a$Data are presented as median (min; max).

As shown in Table 32, preliminary pharmacokinetic data shows $AUC_{last}$ increased with increase dose of Compound I. However, these increases were not dose proportional across the dose range, with higher values of $AUC_{last}$/dose evident at the higher dose (100 mg/m$^2$, 170 mg/m$^2$, and 250 mg/m$^2$) than at the lower 25 mg/m$^2$ and 50 mg/m$^2$ dose levels. Mean elimination half-life determined across these dose levels ranged from approximately 23.2 to 83.3 hours.

The maximum tolerated dose was determined to be 170 mg/m$^2$.

Inhibition of Pol I transcription rates was measured via RNA-FISH quantitating the abundance of 47S pre-rRNA levels in peripheral blood mononuclear cells (PBMC) and tumor tissue, at various time points following the cycle 1. Skin biopsies from normal skin and rash areas were studied after the observation of photosensitivity in patients in cohort 1.

Significant decrease in Pol I transcription was observed at 1 hr post-infusion in PBMC. The average level of inhibition was 49.0% (22.9-69.9%), 51.1% (34.4-64.4%), 19.6% (−72.0-69.7%), 47.3% (46.5-48.0%) and 38.6% (6.8-70.4%) in cohorts 1-5 respectively (FIG. 22).

LC/MS/MS Validated Method of Measuring Compound I in Human Plasma

Sample Preparation

A reference standard stock solution of Compound I was prepared by weighing the reference standard and dissolving it in a solution of 50:50:0.1 (v/v) mixture of ACN:deionized water:formic acid, followed by vortex-mixing and sonication. This stock solution was used for preparation of the calibration standards. Another stock solution of Compound I was prepared following the same procedure and was used for preparation of the QC samples. Both stock solutions were prepared previously and stored at refrigeration (2° C. to 8° C.) prior to use on the day of assay. Compound I stock solution was found to be stable in this storage condition for 385 days. Both solutions were used within the established stability timeframe.

On the day of assay, each of the stock solutions was further diluted with a solution of 50:50:0.1 (v/v) mixture of ACN:deionized water:formic acid to provide a series of working solutions for spiking calibration standards and QC samples.

The internal standard stock solution was previously prepared by weighing Compound A (2-(4-Methyl-piperazin-1-yl)-5-oxo-5H-7-thia-1,11b-diaza-benzo[c]fluorene-6-carboxylic acid (5-methyl-pyrazin-2-ylmethyl)-amide) and dissolving it in a solution of 50:50:0.1 (v/v) mixture of ACN:deionized water:formic acid. This stock solution was stored at refrigeration (2° C. to 8° C.) prior to use. Compound A stock solution was found to be stable in this storage condition for 384 days. This solution was used within the established stability timeframe. On the day of assay, this solution was further diluted with a solution of 50:50:0.1 (v/v) mixture of ACN:deionized water:formic acid into a solution for spiking.

Calibration standards and QC samples were prepared by spiking the appropriate working solution and the internal standard spiking solution into blank human plasma (Na-Hep). Each sample was extracted with ACN and then centrifuged at 13700×g (12000 rpm) for 5 minutes. The extracted top layer was transferred to another disposable glass tube and evaporated to complete dryness in a water-bath at 40° C. under a stream of air or nitrogen. The dried sample was reconstituted with a solution of 50:50:0.1 (v/v) mixture of ACN:deionized water:formic acid. The reconstituted sample was transferred to a LC vial for LC/MS/MS analysis.

Each of the prospective test samples will be spiked with the internal standard solution, and then extracted, dried, and reconstituted following the same procedures for calibration standards and QC samples as described above. The reconstituted sample will be transferred to a LC vial for LC/MS/MS analysis along with calibration standards and QC samples Instrument Parameters The following two LC/MS/MS systems controlled by Micromass Masslynx® Version 4.0 were used to validate the assay method in this study:

Primary LC/MS/MS Instrument System (BRI Instrument Micro-2)

Micromass™ Quattro-Micro tandem triple quadrupole mass spectrometer (BRI ID: 553)

Agilent Model 1100 G1311A Quaternary Pump (BRI ID: 381)
Agilent Model 1100 G1329A Autosampler (BRI ID: 576)
Agilent Model 1100 G1330B Thermostat (BRI ID: 575)
Agilent Model 1100 G1316A Column Compartment (BRI ID: 491)

Alternate LC/MS/MS Instrument System Cross-Validated (BRI Instrument LC-2)

Micromass™ Quattro-LC tandem triple quadrupole mass spectrometer (BRI ID: 446)

Agilent Model 1100 G1312A Binary Pump (BRI ID: 443)
Agilent Model 1100 G1329A Autosampler (BRI ID: 459)
Agilent Model 1100 G1330B Thermostat (BRI ID: 460)
Agilent Model 1100 G1316A Column Compartment (BRI ID: 573)

The analytical method parameters are summarized below:

Isocratic elution using 7:3 (v/v) ACN: 75 mM Ammonium Formate (pH 2.5) as the mobile phase
Flow rate: 0.5 mL/min
Run time: Originally validated at 10 min; later validated at 6 min in this study
Column: Zorbax 300-SCX, 3×50 mm, 5 m
Injection volume: 5 µL
MS mode: ESI positive MRM mode This assay method was based on a nominal quantitation range of 5.00 ng/mL to 5000 ng/mL. Validation results met their acceptance criteria for the assessments of calibration range, assay accuracy and precision, hemolysis matrix effects, lipidemic matrix effects, selectivity and specificity, dilution integrity, and assay ruggedness with respect to changing analysts and instrument, and over the run time anticipated for a prospective test sample run. Chromatographic carryover was not observed. A 6-minute assay run time was validated. Compound I was found to be stable in sodium heparinised human plasma for 31 days at nominal −70° C. (−63° C. to −77° C.) and following 4 cycles of freeze/thaw.

Example 18. Analysis of Compound I Formulation Product

Compound I formulation product was analyzed by high performance liquid chromatography-mass spectrometry (HPLC-MS) to identify the presence of impurities and degradation products (Zorbax SB-CN; HPLC-UV/MS Method 1). Several peaks in the HPLC-MS were observed and the relative retention times and mass were identified as shown in Table 34.

TABLE 34

HPLC relative retention time (RRT) and corresponding observed mass

| RRT | MS (m/z) | RRT | MS (m/z) |
|---|---|---|---|
| 0.88 | 408.5 | 1.00 | 500.5; 514.7 |
| 0.89 | 530.5 | 1.05 | 561.5 |
| 0.90 | 530.5 | 1.07 | 528.4 |
| 0.93 | 530.5 | 1.08 | 530.5 |
| ~0.96 | 474.6; 486.6 | 1.085 | 516.5 |
| | | 1.095 | 548.5 |

In order to determine the structure of the impurities and degradation products, Compound I was subjected to stress conditions.

About one (1) gram of Compound I was transferred to a suitable clean beaker and suspended in about 100 ml of water for injection (Sterile Water for Injection, USP, B-BRAUN, REF L8500). Concentrated hydrochloric acid (34%-37%, TraceMetal Grade, Fisher Chemicals, A508-P212) was slowly added (dropwise to avoid overheating) under constant vigorous magnetic stirring until all the solid Compound I was dissolved and the pH of the solution checked to be 4.5-5.0 (pH paper, pH 0-14, colorpHast®, EMD, 9590). The solution of Compound I HCl salt was freeze dried (LABCONCO, FREEZONE6, Cat. No. 7753522, S. No. 070773948 A) yielding a light yellowish amorphous solid. Portions of the lyophilized material were transferred into crimped vials, purged with pure oxygen gas, and placed in an oven preset at 125° C. The sample placed under stress oxidation conditions were separated and/or analyzed using the various HPLC-UV/MS methods listed below and by Tandem Mass Spectrometry (MSMS).

Based on the mass spectrum, RRT=0.88 compound exhibiting a molecular ion [M+H]$^+$ m/z=408 was determined to be the product of Compound I undergoing hydrolysis to provide Compound 1. Independently verified, see Example 19.

Based on the MSMS spectrum, RRT=0.89 was proposed to be Compound 2 because of the evidence that the oxidation happened at the pyrazine moiety (observed fragments typical for an unchanged tetracyclic core and diazepane ring (m/z=391 and 365).

Based on the MSMS spectrum, RRT=0.90 was consistent with an oxidative transformation of Compound I (exhibits a molecular ion [M+H]$^+$ m/z=530). Since the oxidation of the diazepane ring (Compound 9) was already verified, this peak was proposed to due to Compound 3. MSMS spectrum also observed m/z 407, which could be attributed to fragmentation at the amide bond.

The MSMS spectrum of RRT=0.93 exhibited two strong ions at m/z=530 and 512. The peak at m/z=512 was consistent with loss of water from the oxidized molecular ion m/z=530. Due to the strong peak observed at m/z=391, it was reasoned that the oxidation likely took place in the pyrazine part of the molecule. Thus, Compound 4 was proposed for RRT=0.93.

The MSMS spectrum at about RRT=0.96 suggested two co-eluting impurities with [M+H]$^+$ m/z=474.6 and 486.6. The fragmentation pattern indicated that the structural modification was likely at the site of the diazepane ring in Compound I, related to impurities of the N-methyl-1,4-diazepane raw material. Compounds 5 and 6 were proposed based on the fragmentation patterns (amide bond fragmentation patterns observed).

The product observed at RRT=1.00 using HPLC-UV/MS Method 1 co-eluted with Compound 1. The resolution was enhanced with HPLC-UV/MS Method 2, Option 1. RRT=1.00 exhibiting [M+H]$^+$ m/z=500.5 was determined to be Compound 7 and independently verified (see Example 3).

RRT=1.05 exhibiting [M+H]$^+$ m/z=561 was determined to be compound 8 and independently verified (see Example 4). This impurity is a synthetic impurity likely resulted when intermediate 2-(4-methyl-1,4-diazepan-1-yl)-5-oxo-5H-benzo[4,5]thiazolo[3,2-a][1,8]naphthyridine-6-carboxylate reacted with N-(3-aminopropyl)-ε-caprolactam present in 1,8-Diazabicyclo[5.4.0]undec-7-ene (DBU).

Based on the MSMS spectrum, RRT=1.08 was consistent with Compound 9 and independently verified (see Example 5).

Based on the MSMS spectrum, RRT=1.07 was consistent with Compound 10 and independently verified (see Example 6).

Based on the MSMS spectrum, RRT=1.085 was exhibited fragmentation pattern consistent with having a thiol, thus Compound 11 was proposed.

The MSMS spectrum of RRT=1.095 exhibited fragmentation pattern which indicated the presence of a chlorine in the structure. Further, fragmentation pattern was consistent with the diazepane ring in tact (m/z=391 and 365). Thus, Compound 12 was proposed.

HPLC-UV/MS—Method 1
Mobile phase A: 20 mM ammonium formate:acetonitrile:methanol (90:5:5) (pH=3)
Mobile phase B: methanol/acetonitrile=1:1
Sample preparation in 0.1% trifluoroacetic acid in water.
Column: Agilent Zorbax SB-CN, 150 mm×3.0 mm, 3.5 μm.

| Time (min) | Flow (μL/min) | % A | % B |
|---|---|---|---|
| 0 | 650 | 95 | 5 |
| 2 | 650 | 95 | 5 |
| 35 | 650 | 25 | 75 |
| 36 | 650 | 95 | 5 |
| 42 | 650 | 95 | 5 |

Column: Synergi Polar-RP Column (4 μm, 2.0 mm×150 mm).

| Time (min) | Flow (μL/min) | % A | % B |
|---|---|---|---|
| 0 | 450 | 95 | 5 |
| 2 | 450 | 95 | 5 |
| 35 | 450 | 25 | 75 |
| 36 | 450 | 95 | 5 |
| 42 | 450 | 95 | 5 |

HPLC-UV/MS—Method 2
Mobile phase A: 3 ml of NH4OH in 1000 ml of HPLC Water (~0.1% wt)
Mobile phase B: Option 1—3 ml of NH4OH in 1000 ml of Acetonitrile (~0.1% wt); Option 2—3 ml of NH4OH in 1000 ml of Acetonitrile (~0.1% wt)
Column: XBridge Phenyl Column (5 μm, 4.6 mm×250 mm)—Option 1 Mobile phase B (semi-preparative column)

| Time (min) | Flow (μL/min) | % A | % B |
|---|---|---|---|
| 0 | 1200 | 85 | 15 |
| 2 | 1200 | 85 | 15 |
| 23 | 1200 | 22.5 | 77.5 |
| 24 | 1200 | 85 | 15 |
| 30 | 1200 | 85 | 15 |

Column: XBridge Phenyl Column (3.5 μm, 4.6 mm×100 mm)—Option 2 Mobile Phase B

| Time (min) | Flow (μL/min) | % A | % B |
|---|---|---|---|
| 0 | 1000 | 85 | 15 |
| 2 | 1000 | 85 | 15 |
| 23 | 1000 | 30 | 70 |
| 24 | 1000 | 30 | 70 |
| 25 | 1000 | 85 | 15 |
| 30 | 1000 | 85 | 15 |

HPLC-UV/MS—Method 3
Mobile phase A: 20 mM ammonium formate (pH=3)
Mobile phase B: 20 mM ammonium formate (pH=3) in water:acetonitrile:methanol (1:2:2)
Synthesis
Methods for (Examples 20-24)
Melting Point: Unless otherwise noted, melting points and range was determined according to USP <741>.
Mass Spectrometry: Sample prepared in 0.1% formic acid/50% methanol solution. Positive mode.

Purity: Unless otherwise noted, purity was determined by HPLC with the following parameters.

Mobile phase A: water/acetonitrile/perchloric acid=950/20/2 (v/v)

Mobile phase B: methanol/acetonitrile=50/50 (v/v)

Sample preparation in 0.1% trifluoroacetic acid in water. (20 mg of sample in 50 mL volumetric flask and diluted to volume. Then dilute 100 fold).

Column: Agilent Zorbax SB-CN, 150 mm (L)×4.6 mm (ID), 5 μm of particle size.

| Time (min) | Flow (mL/min) | % A | % B |
|---|---|---|---|
| 0.0 | 1.5 | 90.0 | 10.0 |
| 5.0 | 1.5 | 90.0 | 10.0 |
| 35.0 | 1.5 | 25.0 | 75.0 |
| 35.1 | 1.5 | 90.0 | 10.0 |
| 40.0 | 1.5 | 90.0 | 10.0 |

Run time: 40 minutes.

Sample Temperature: 25±3° C. Column Temperature: 30±3° C.

Detector: UV, 240 nm.

Injection volume: 20 μL.

Example 19: Synthesis of Compound 1

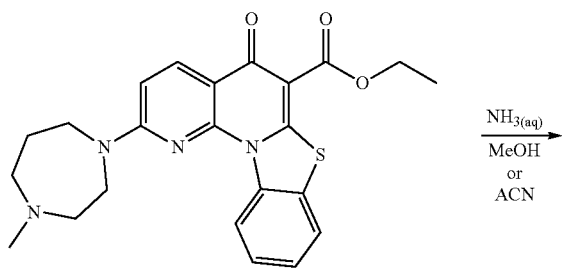

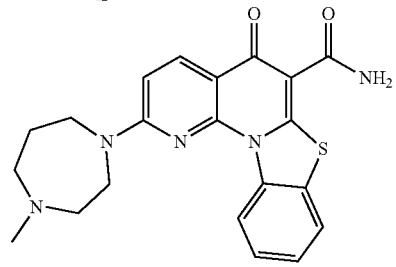

To a 5 L reactor was added ethyl 2-(4-methyl-1,4-diazepan-1-yl)-5-oxo-5H-benzo[4,5]thiazolo[3,2-a][1,8]naphthyridine-6-carboxylate (101 g, see WO 2009/046383 for synthesis) and acetonitrile (2 L). To the mixture was added 28-30% NH₃(aq) (1950 ml) then heated up to 60° C. (a lot of NH3 gas released) with condenser temperature at −13° C. The mixture was stirred for 4 days and additional 28-30% NH3(aq) (400 ml) was added. The mixture was stirred for 2 days and additional 28-30% NH3(aq) (200 ml) was added. The mixture was stirred for 1 day and additional 28-30% NH3(aq) (100 ml) was added. After 10 days of stirring, a lot of solid precipitated. The mixture was cooled to room temperature and stirred for 1 day. The mixture was filtered to get 92 g of crude Compound 1 in 53.8% yield with 94.66% purity and the loss on drying (LOD) was 42.1%.

To a 2 L reactor was added 38 g of crude Compound 1 and 800 ml of acetonitrile. The resulting mixture was heated to 60° C. and then added 800 ml of 28-30% NH₃(aq). The mixture was stirred for 3 hr, filtrated at 50-60° C. and washed with 350 ml of acetonitrile. The wet cake was dried at 40° C. overnight to get 34.8 g of Compound 1 (2-(4-methyl-1,4-diazepan-1-yl)-5-oxo-5H-benzo[4,5]thiazolo[3,2-a][1,8]naphthyridine-6-carboxamide) in 92% yield with 98.0% purity and the LOD was 2.30%. MS: m/z 408.136 [M+H]⁺. ¹H NMR and ¹³C NMR in CDCl₃ as shown below.

TABLE 35

| ¹H NMR and ¹³C NMR in CDCl₃ for Compound 1 ||
|---|---|
| Chemical shift (δ$_H$) | Chemical shift (δ$_C$) |
| — | 172.11, C |
| — | 110.70, C |
| — | 105.01, C |
| — | 158.21, C |
| — | 157.91, C |
| 7.030, d | 106.66, CH |
| 8.005, d | 136.55, CH |
| — | 149.15, C |
| — | 166.95, C |
| — | 136.81, C |
| 8.361, d | 122.28, CH |
| 7.558, dd | 126.28, CH |
| 7.466, dd | 125.54, CH |
| 7.611, d | 119.03, CH |
| — | 129.38, C |
| 2.769, brs | 39.50, CH₂ |
| 3.869, m | 56.54, CH₂ |
| 3.869, m | 56.30, CH₂ |
| 2.010, brs | 26.50, CH₂ |
| 2.769, brs | 45.91, CH₂ |
| 2.286, s | 47.42, CH₃ |
| 9.828, d | — |
| 9.816, d | — |

Example 20: Synthesis of Compound 7

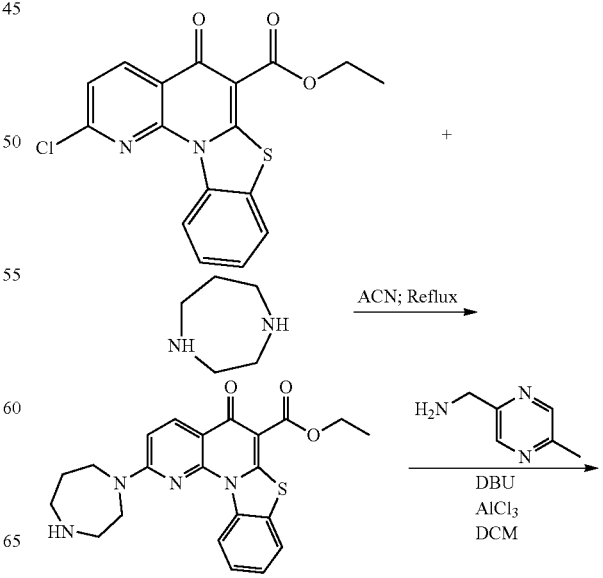

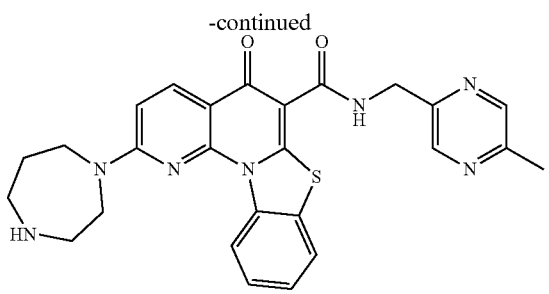

Step 1. To a mixture of ethyl 2-chloro-5-oxo-5H-benzo[4,5]thiazolo[3,2-a][1,8]naphthyridine-6-carboxylate (40 g, see WO 2009/046383 for synthesis) and homopiperazine (24 g, 2.1 eq.) were added acetonitrile (800 ml). The mixture was heated to 80° C. and stirred for 18 hr. The mixture was cooled to 20-25° C., filtered, washed with acetonitrile (160 ml), and vacuum dried at 40° C. for 24 hr. Ethyl 2-(1,4-diazepan-1-yl)-5-oxo-5H-benzo[4,5]thiazolo[3,2-a][1,8]naphthyridine-6-carboxylate (48.9 g) was obtained in approximately 100% yield with 98.0% purity.

Step 2. To a 2 L reactor was added ethyl 2-(1,4-diazepan-1-yl)-5-oxo-5H-benzo[4,5]thiazolo[3,2-a][1,8]naphthyridine-6-carboxylate (30 g) and DCM (600 ml). To the mixture was added DBU (32.35 ml) and 2-(aminomethyl)-5-methylpyrazine (17.67 g) then cooled to 5° C. AlCl$_3$ (11.39 g) was added while maintaining the temperature at no more than 10° C. and stirred for not less than 2 hr. 2 N NaOH(aq) (720 ml) was added for extraction. The aqueous layer was extracted with 100 ml of DCM. The combined organic layer was extracted with 850 ml of 0.7 N HCl(aq). The aqueous layer was added 900 ml of DCM. To the mixture was added 150 ml of 30% NaOH(aq) to adjust pH to 14. The organic layer was evaporated to dryness to get solid. The solid was added 240 ml of MeOH and 30 ml of H$_2$O for slurry. The mixture was filtrated and washed with 80 ml of MeOH/H$_2$O=8/1 (v/v). The wet cake was vacuum dried at 40° C. over a weekend to get Compound 7 (48.8 g; 2-(1,4-diazepan-1-yl)-N-((5-methylpyrazin-2-yl)methyl)-5-oxo-5H-benzo[4,5]thiazolo[3,2-a][1,8]naphthyridine-6-carboxamide) in approximately 59% yield with 98.4% purity. MS: m/z 500.164 [M+H]$^+$. MP: 238.0-239.6° C. $^1$H NMR and $^{13}$C NMR in CDCl$_3$ as shown below.

TBLE 36

| $^1$H NMR and $^{13}$C NMR in CDCl$_3$ for Compound 7 | |
|---|---|
| Chemical shift ($\delta_H$) | Chemical shift ($\delta_C$) |
| — | 173.02, C |
| — | 111.63, C |
| — | 149.61, C |
| — | 158.44, C |
| — | 158.26, C |
| 8.554, d | 121.64, CH |
| 9.528, d | 105.37, CH |
| — | 105.93, C |
| — | 166.49, C |
| — | 137.21, C |
| 7.745, d | 119.44, CH |
| 7.423, m | 125.47, CH |
| 7.423, m | 125.90, CH |
| 6.797, d | 129.81, CH |
| — | 137.32, C |
| 4.866, d | 51.71, CH$_2$ |
| — | 152.08, C |
| 8.579, s | 143.70, CH |
| — | 150.57, C |

TBLE 36-continued

| $^1$H NMR and $^{13}$C NMR in CDCl$_3$ for Compound 7 | |
|---|---|
| Chemical shift ($\delta_H$) | Chemical shift ($\delta_C$) |
| 8.449, s | 142.62, CH |
| 2.547, s | 21.17, CH$_3$ |
| 2.914, t | 48.38, CH$_2$ |
| 3.917, brs | 47.74, CH$_2$ |
| 3.917, brs | 42.60, CH$_2$ |
| 2.030, m | 29.05, CH$_2$ |
| 3.180, t | 48.12, CH$_2$ |

Example 21: Synthesis of Compound 8

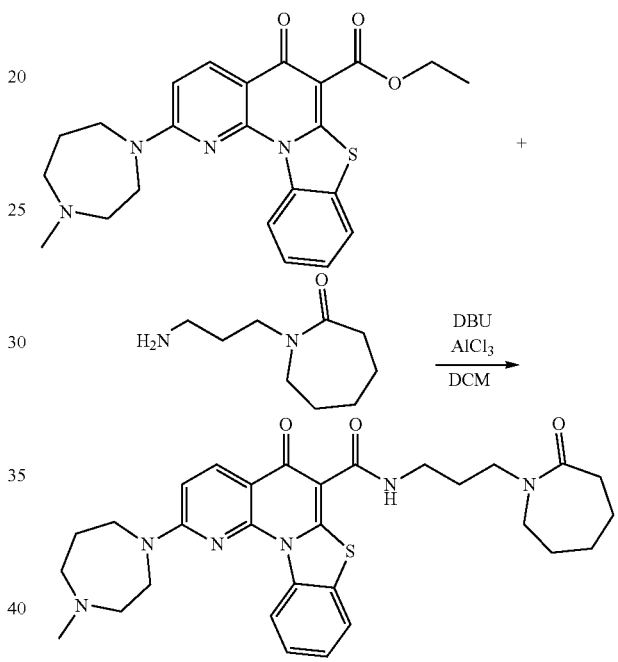

To a 5 L reactor was added ethyl 2-(4-methyl-1,4-diazepan-1-yl)-5-oxo-5H-benzo[4,5]thiazolo[3,2-a][1,8]naphthyridine-6-carboxylate (50.5 g) and DCM (1100 ml). To the mixture was added DBU (55 ml) and 1-(3-Aminopropyl)hexahydro-1H-azepin-2-one (41 g) then cooled to 0-5° C. AlCl$_3$ (20.3 g) was added slowly while maintaining the temperature at no more than 15° C. The mixture was warmed up to room temperature and stirred overnight. The mixture was added 1000 ml of 2 N NaOH(aq) for extraction. The aqueous layer was extracted with 300 ml of DCM. The combined organic layer was extracted with 1000 ml of HCl(aq) (pH=1). The organic layer was extracted again with 300 ml of HCl(aq) (pH=1). The combined aqueous layer was added 900 ml of DCM. The mixture was added 30% NaOH(aq) to adjust pH to 14. The aqueous layer was extracted with 300 ml of DCM. The combined organic layer was evaporated to dryness. The residue was added 500 ml of THF for slurry at 40° C. and then added 500 ml of n-heptane. The mixture was cooled to room temperature and filtrated. The wet cake was washed with 500 ml of THF/n-heptane=1/1 (v/v). The wet cake was vacuum dried at 40° C. overnight to get Compound 8 (54.5 g; 2-(4-methyl-1,4-diazepan-1-yl)-N-(3-(2-oxoazepan-1-yl)propyl)-5-oxo-5H-benzo[4,5]thiazolo[3,2-a][1,8]naphthyridine-6-carboxamide) in 84% yield with 98.3% purity. MS: m/z 561.242 [M+H]⁺. MP: 185.2-186.6° C. ¹H NMR and ¹³C NMR in CDCl₃ as shown below.

TABLE 37

¹H NMR and ¹³C NMR in CDCl₃ for Compound 8

| Chemical shift ($\delta_H$) | Chemical shift ($\delta_C$) |
|---|---|
| — | 172.80, C |
| — | 111.50, C |
| — | 149.23, C |
| — | 158.23, C |
| — | 158.00, C |
| 8.555, d | 121.43, CH |
| 9.506, d | 105.51, CH |
| — | 105.78, C |
| — | 166.11, C |
| — | 136.99, C |
| 7.732, d | 119.34, CH |
| 7.421, m | 125.26, CH |
| 7.421, m | 125.73, CH |
| 6.776, d | 129.86, CH |
| — | 137.16, C |
| 3.512, t | 49.73, CH₂ |
| 1.911, p | 27.20, CH₂ |
| 3.376, t | 46.27, CH₂ |
| 3.495, m | 47.89, CH₂ |
| 1.669, brs | 29.91, CH₂ |
| 1.669, brs | 28.68, CH₂ |
| 1.669, brs | 23.37, CH₂ |
| 2.847, t | 36.81, CH₂ |
| — | 175.67, CH |
| 2.624, t | 47.60, CH₂ |
| 3.950, brs | 57.02, CH₂ |
| 3.950, brs | 57.39, CH₂ |
| 2.130, m | 28.45, CH₂ |
| 2.538, t | 46.64, CH₂ |
| 2.413, s | 37.19, CH₃ |

Example 22: Synthesis of Compound 9 evaporated to remove DCM. The aqueous layer was lyophilized to get 48.6 g of Compound 9 (2-(4-methyl-4-oxidodiazepan-4-ium-1-yl)-N-((5-methylpyrazin-2-yl)methyl)-5-oxo-5H-benzo[4,5]thiazolo[3,2-a][1,8]naphthyridine-6-carboxamide) in approximately 100% yield with 98.2% purity. MS: m/z 530.187 [M+H]⁺. ¹H NMR and ¹³C NMR in CDCl₃ as shown below.

TABLE 38

¹H NMR and ¹³C NMR in CDCl₃ for Compound 9

| Chemical shift ($\delta_H$) | Chemical shift ($\delta_C$) |
|---|---|
| — | 172.59, C |
| — | 111.56, C |
| — | 148.80, C |
| — | 158.25, C |
| — | 159.11, C |
| 6.718, d | 122.40, CH |
| 8.133, d | 105.24, CH |
| — | 107.18, C |
| — | 166.79, C |
| — | 137.09, C |
| 8.760, s | 119.91, CH |
| 7.329, brs | 126.70, CH |
| 7.329, brs | 127.09, CH |
| 7.671, d | 129.87, CH |
| — | 136.90, C |
| 4.745, s | 49.79, CH, |
| — | 151.77, C |
| 8.600, s | 145.27, CH |
| — | 153.99, C |
| 8.600, s | 143.67, CH |
| 2.600, s | 21.20, CH₃ |
| 4.014, m | 43.41, CH₂ |
| 3.878, m | 69.47, CH₂ |
| 3.927, m | 71.08, CH₂ |
| 2.317, d | 21.73, CH₂ |
| 2.786, d | |
| 3.582, brs | 40.88, CH₂ |
| 3.659, s | 61.99, CH₃ |

Example 23: Synthesis of Compound 10

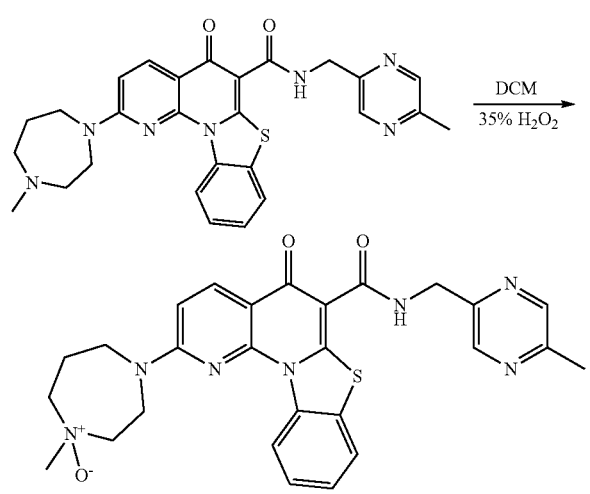

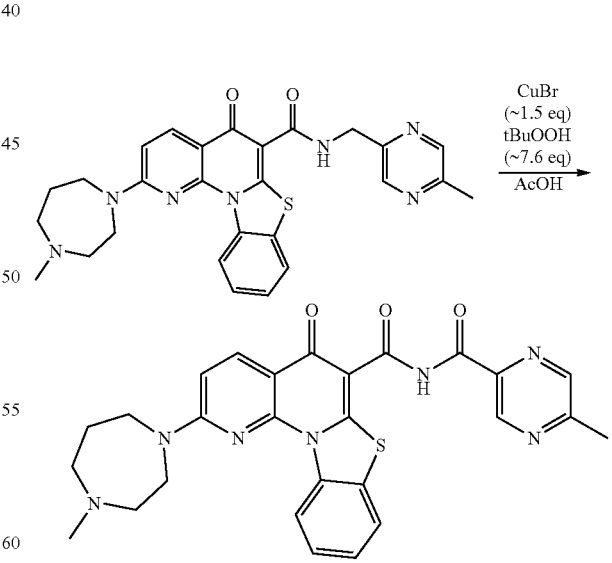

To a solution of Compound I (45 g; see WO 2009/046383 for synthesis) in DCM (1500 ml, ~33 parts (v/w)) was added 35% H₂O₂ (300 ml, ~35 equiv.) at 20-25° C. and the resulting mixture was stirred for ~18 hr. After phase separation, the organic layer was added 300 ml of purified process water (PPW) for extraction. After phase separation, the combined aqueous layers was added 300 ml of DCM for extraction. After phase separation, the aqueous layer was To a 1 L reactor was added Compound I (11.1 g) in acetic acid (220 ml) as a clear solution. To the mixture was added CuBr (4.61 g) to form slurry. To the mixture was added 70% t-BuOOH(aq) for ~1 hr of addition time while maintaining the temperature at no more than 30° C. The color of the solution turned from yellow slurry to green slurry. The mixture was stirred for 3-5 days. The mixture was added into 1500 ml of H$_2$O and 1600 ml of DCM. The mixture was added 28-33% NH$_3$(aq) to adjust pH to 11 while maintaining the temperature at no more than 30° C. The mixture was settled for phase separation and some solid was observed between organic and aqueous layer. The aqueous layer was extracted with 500 ml of DCM. The combine organic layer was extracted with 600 ml of 0.15% NH$_3$(aq). The organic layer was collected and the emulsion layer was discarded. The organic layer was evaporated to dryness. The residue was added 60 ml of DMSO and sonicated for 10 min to precipitate the product. The mixture was filtrated and the wet cake was washed with 10 ml MeOH. The wet cake was added 10 ml of DCM for slurry and then evaporated to dryness to remove the residual MeOH. Compound 10 (1.8 g; 2-(4-methyl-1,4-diazepan-1-yl)-N-((5-methylpyrazin-2-yl) carbonyl)-5-oxo-5H-benzo[4,5]thiazolo[3,2-a][1,8]naph-thyridine-6-carboxamide) was obtained in 15% yield with 93.6% purity. MS: m/z 528.183 [M+H]$^+$. $^1$H NMR and $^{13}$C NMR in CDCl$_3$ as shown below.

TABLE 39

$^1$H NMR and $^{13}$C NMR in CDCl$_3$ for Compound 10

| Chemical shift ($\delta_H$) | Chemical shift ($\delta_C$) |
|---|---|
| — | 173.36, C |
| — | 111.25, C |
| — | 149.62, C |
| — | 158.69, C |
| — | 157.62, C |
| 6.740, d | 121.94, CH |
| 8.563, d | 104.97, CH |
| — | 106.32, C |
| — | 164.61, C |
| — | 137.16, C |
| 7.748, d | 119.64, CH |
| 7.453, m | 125.78, CH |
| 7.435, m | 126.38, CH |
| 9.446, d | 129.53, CH |
| — | 137.47, C |
| — | 163.12, C |
| — | 160.14, C |
| 8.646, s | 143.13, CH |
| — | 144.57, C |
| 9.369, s | 142.23, CH |
| 2.676, s | 21.94, CH$_3$ |
| 2.830, brs | 47.80, CH$_2$ |
| 3.814, brs | 57.07, CH$_2$ |
| 3.814, brs | 57.38, CH$_2$ |
| 2.616, m | 27.19, CH$_2$ |
| 2.101, brs | 46.71, CH$_2$ |
| 2.395, s | 40.97, CH$_3$ |
| 14.942, s | |

Biological Examples

Example 24: Anti-Proliferation Assay

The sensitivity of DLD-1 Parental and BRCA2−/− isogenic cell lines Compound I and Compounds 1 and 7-10 were evaluated in 144 h proliferations assays. Cells were seeded into 384-well plates in McCoy's 5A medium supplemented with 10% FBS at the seeding densities indicated below and allowed to adhere overnight prior to addition of compound or vehicle control. Compounds were weighed out and stock solutions in DMSO were made immediately prior to treatment of cells. Serial dilutions of compounds were prepared in DMSO and diluted in media before being added to cells in quadruplicate to give the final concentrations indicated on graphs (10 µM top concentration, 9-point semi-log dilution series, 0.2% DMSO final concentration for all treatments). Cells were incubated with compounds for 144 h at 37° C., 5% C02 in a humidified atmosphere. At the assay endpoint, ATPlite (Perkin Elmer) reagent was added at a volume equal to the volume of cell culture medium already present in each well and the plates processed as per the manufacturer's instructions. Media only background values were subtract and ted and the data was analyzed using a 4-parameter logistic equation in GraphPad Prism. DLD-1 Parental (HD PAR-008) DLD-1 BRCA2−/− (HD 105-007) used.

The DLD-1 BRCA2−/− line was significantly more sensitive to Compound I relative to the parental line (over 200-fold), as seen previously (R2259). The sensitivity of the BRCA2 null line relative to the parental line varied with the other test agents. Compound 1 was extremely sensitive and Compounds 7-10 were highly/moderately sensitive. See Table 40. Dose Response Curves are shown in FIGS. 19A-19F.

It was noted that all agents tested showed signs of incomplete solubility when made up as 10 mM stock solutions in DMSO.

TABLE 40

Relative IC$_{50}$ (µM) of Compounds in proliferation assay

| Compound | IC$_{50}$ (µM) | | Fold Sensitivity of |
|---|---|---|---|
| | DLD-1 Parental | DLD-1 BRCA2$^{-/-}$ | BRCA2$^{-/-}$ line |
| I | 0.316 | 0.0015 | 210 |
| 1 | 1.88 | 0.0047 | 400 |
| 7 | 12.0* | 0.56 | 21 |
| 8 | 0.530 | 0.0072 | 74 |
| 9 | 8.78* | 1.59 | 5.5 |
| 10 | 1.58 | 0.62 | 2.5 |

*Where dose response curves are steep, or the top or bottom are poorly defined, the values should be considered as approximate.

The disclosures of all publications, patents, patent applications and published patent applications referred to herein by an identifying citation are hereby incorporated herein by reference in their entirety.

In the case of any conflict between a cited reference and this specification, the specification shall control. In describing embodiments of the present application, specific terminology is employed for the sake of clarity. However, the invention is not intended to be limited to the specific terminology so selected. Nothing in this specification should be considered as limiting the scope of the present invention. All examples presented are representative and non-limiting. The above-described embodiments may be modified or varied, without departing from the invention, as appreciated by those skilled in the art in light of the above teachings. It is therefore to be understood that, within the scope of the claims and their equivalents, the invention may be practiced otherwise than as specifically described.

The invention claimed is:

1. A pharmaceutical composition comprising a pharmaceutically acceptable excipient and a compound selected from:

155
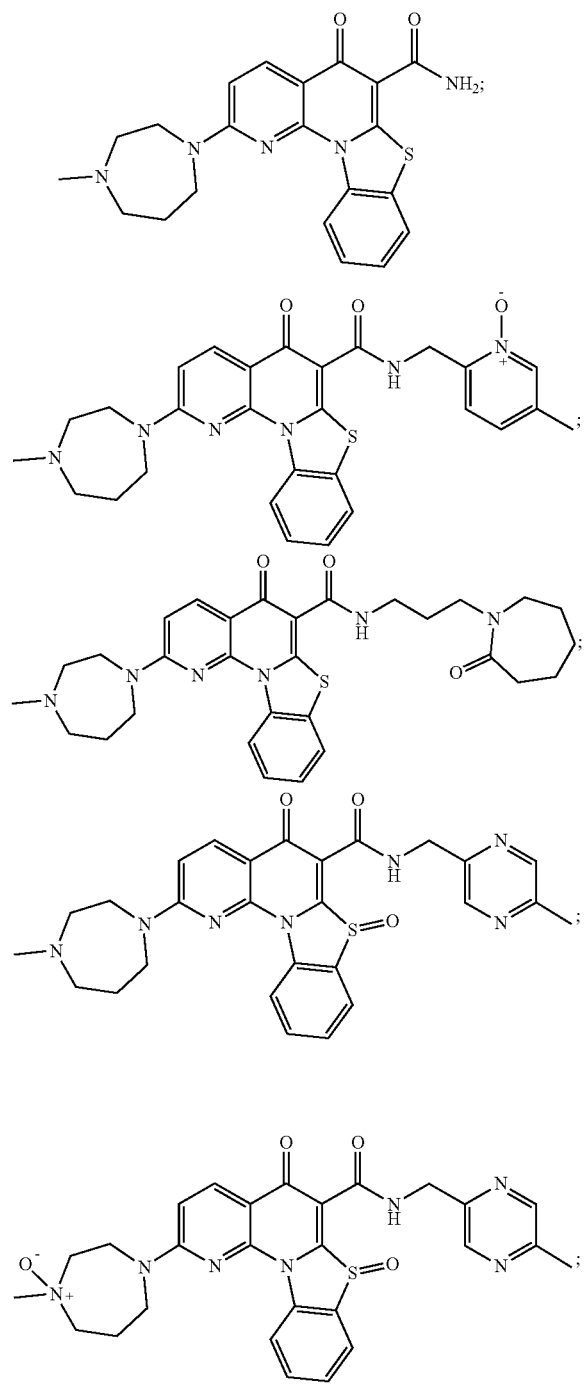
156
-continued
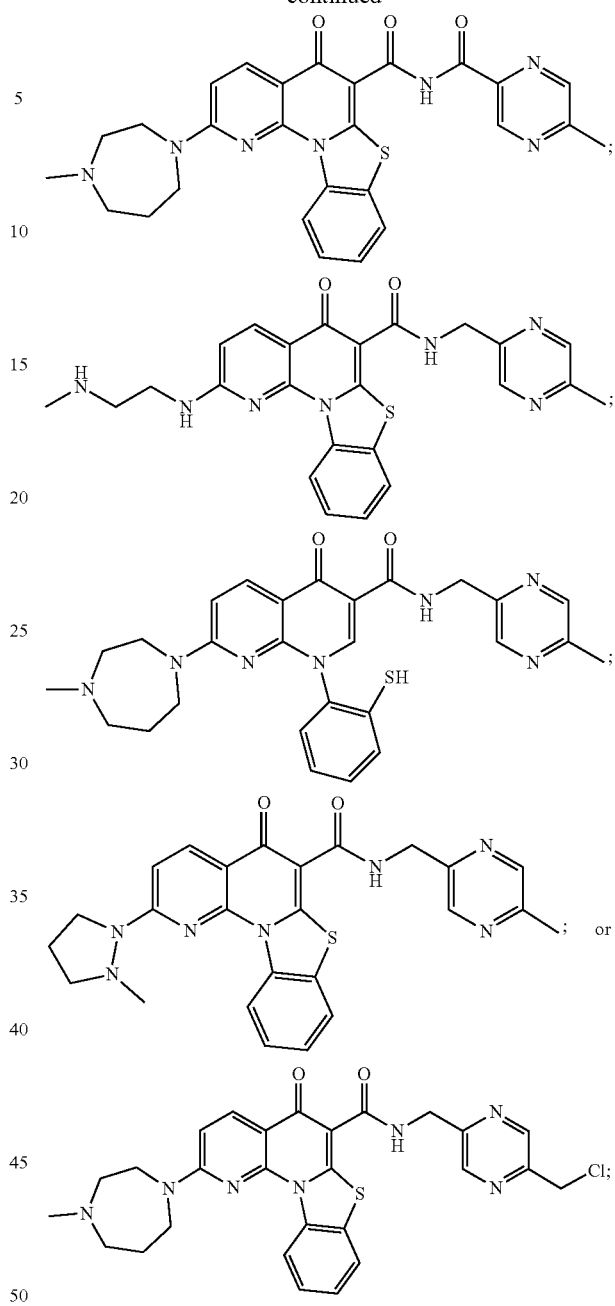
or a pharmaceutically acceptable salt thereof.
2. The pharmaceutical composition of claim 1, wherein the compound is
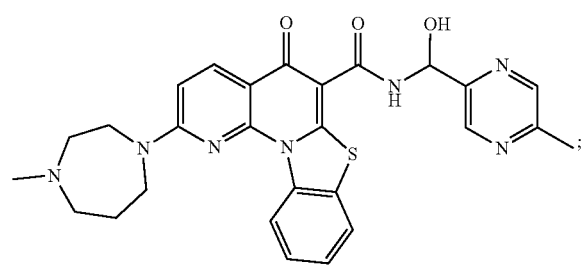
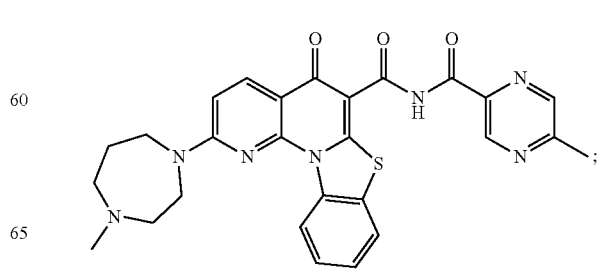

-continued

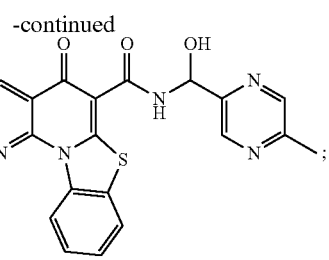

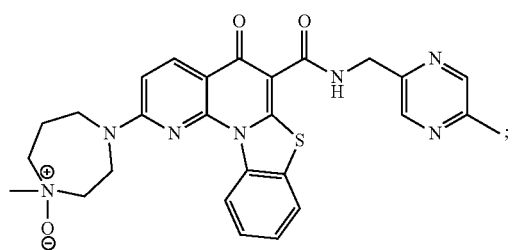

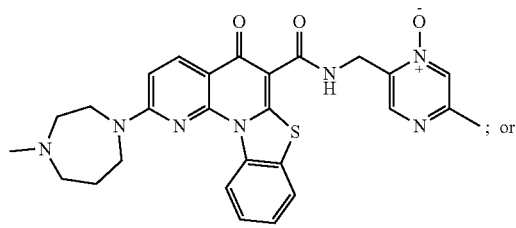

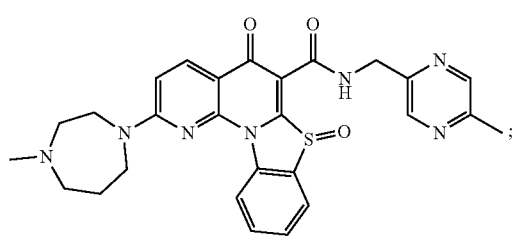

or a pharmaceutically acceptable salt thereof.

3. The pharmaceutical composition of claim 1, wherein the compound is

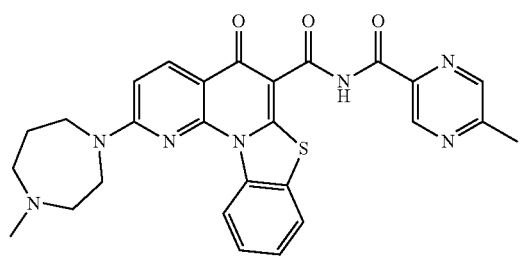

or a pharmaceutically acceptable salt thereof.

4. The pharmaceutical composition of claim 1, further comprising

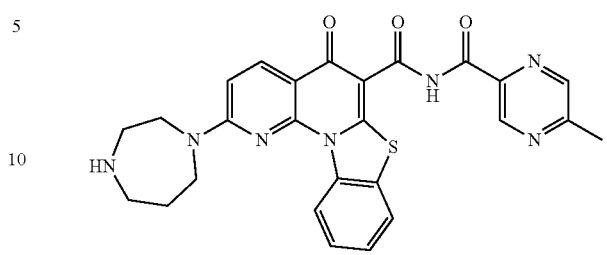

or a pharmaceutically acceptable salt thereof.

5. The pharmaceutical composition of claim 1, wherein the composition is a solid or liquid composition.

6. The pharmaceutical composition of claim 1, wherein the composition is a solid lyophilized composition.

7. The pharmaceutical composition of claim 5, wherein the liquid composition is an oral solution or injection solution.

8. The pharmaceutical composition of claim 1, wherein the pharmaceutically acceptable excipient is a bulking agent.

9. The pharmaceutical composition of claim 1, further comprising at least one pharmaceutically active agent.

10. The pharmaceutical composition of claim 9, wherein the at least one pharmaceutically active agent is an anticancer agent.

11. The pharmaceutical composition of claim 9, wherein the at least one pharmaceutically active agent is a PARP inhibitor or a CDK inhibitor.

12. The pharmaceutical composition of claim 1, further comprising Compound I:

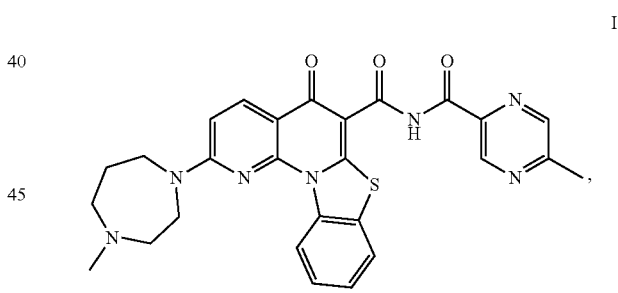

or a pharmaceutically acceptable salt or solvate thereof.

13. A method for treating or ameliorating cancer in a subject, said method comprising administering to a subject in need thereof a therapeutically effective amount of the pharmaceutical composition of claim 1.

14. The method of claim 13, wherein the cancer is selected from the group consisting of: heme cancer, colorectal cancer, breast cancer, lung cancer, liver cancer, ovarian cancer, cervical cancer, Ewing's sarcoma, pancreatic cancer, cancer of the lymph nodes, colon cancer, prostate cancer, brain cancer, cancer of the head and neck, bone cancer, skin cancer, kidney cancer, osteosarcoma, cancer of the heart, uterine cancer, gastrointestinal malignancies, and carcinomas of the larynx and oral cavity.

15. The method of claim 14, wherein the heme cancer is selected from the group consisting of: leukemia, lymphoma, myeloma, and multiple myeloma.

16. The method of claim 13, wherein the cancer is a BRCA mutant or BRCA-like mutant cancer.

17. The method of claim 16, wherein the BRCA mutant or BRCA-like mutant cancer is breast cancer, ovarian cancer, pancreatic cancer, or prostate cancer.

18. The method of claim 13, wherein the cancer is BRCA2 deficient or BRCA1 deficient cancer.

19. The method of claim 13, wherein the subject is human.

20. The method of claim 19, wherein the subject has a mutation in a DNA repair gene.

21. The method of claim 19, wherein the subject carries a BRCA mutation or BRCA-like mutation.

22. The method of claim 21, wherein the BRCA mutation or BRCA-like mutation is a BRCA2 mutation.

23. The method of claim 13, wherein the composition is injected directly into the subject.

24. The method of claim 13, wherein the composition is diluted in an I.V. solution/fluid bag or I.V. line that is administration to the subject.

25. The method of claim 13, wherein the composition is administered orally to the subject.

26. A compound selected from:

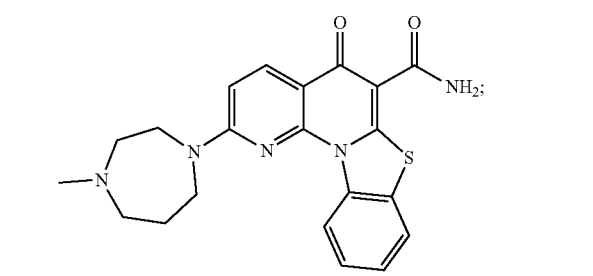

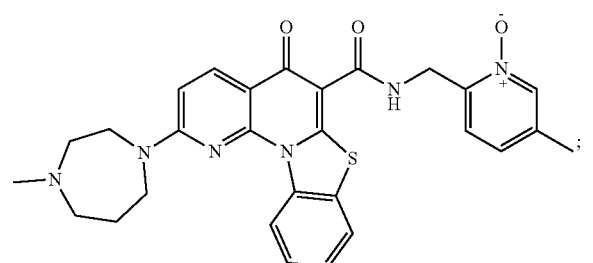

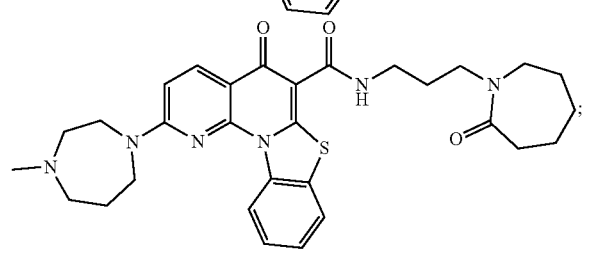

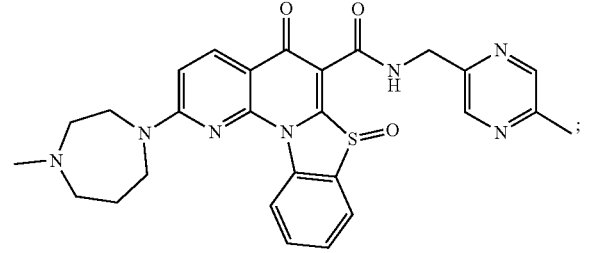

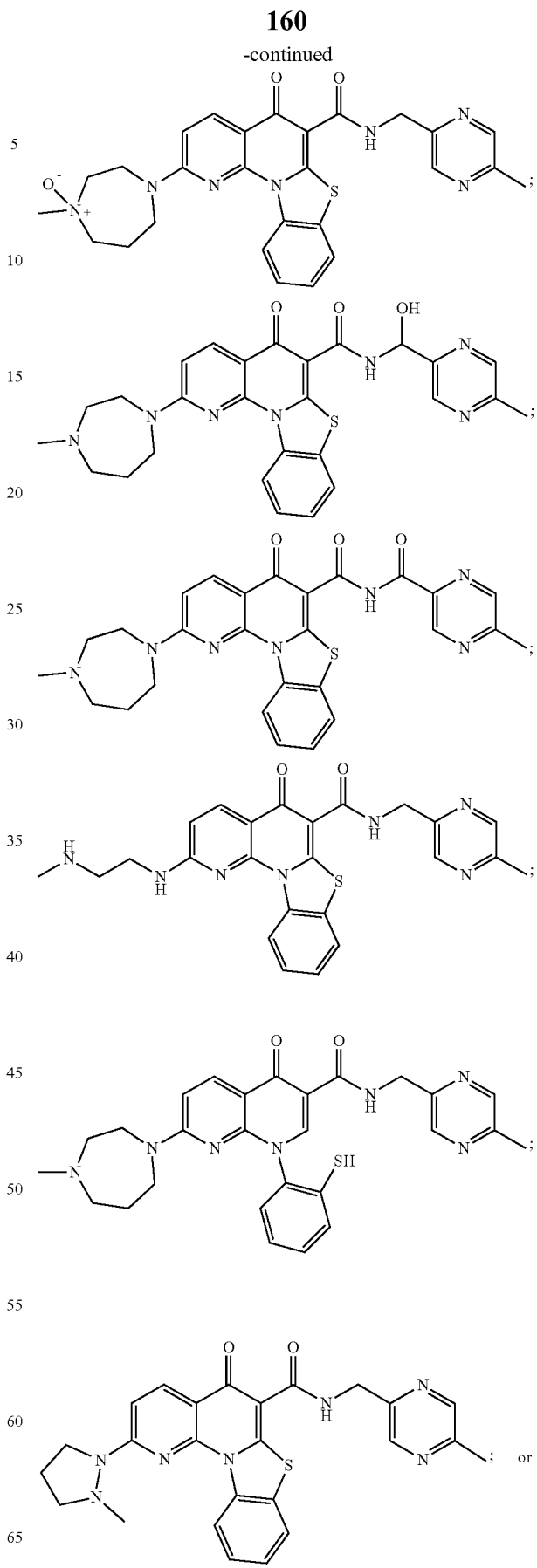

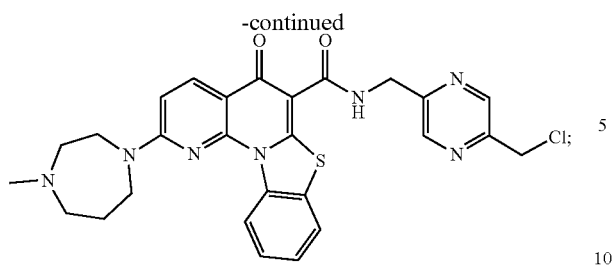
or a pharmaceutically acceptable salt thereof.
* * * * *

UNITED STATES PATENT AND TRADEMARK OFFICE
CERTIFICATE OF CORRECTION

PATENT NO. : 11,524,012 B1  Page 1 of 2
APPLICATION NO. : 17/394541
DATED : December 13, 2022
INVENTOR(S) : Hshiou-ting Liu et al.

It is certified that error appears in the above-identified patent and that said Letters Patent is hereby corrected as shown below:

In the Claims

Claim 1, Column 155, Lines 44-54: " 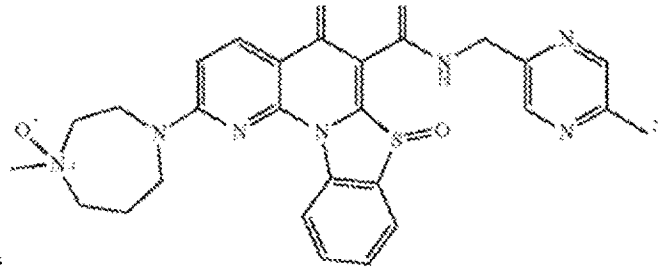 " should be -- 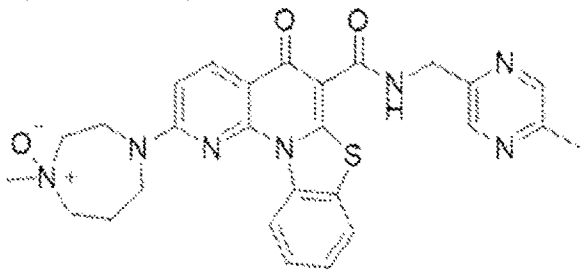 --

Claim 4, Column 158, Lines 5-15: " 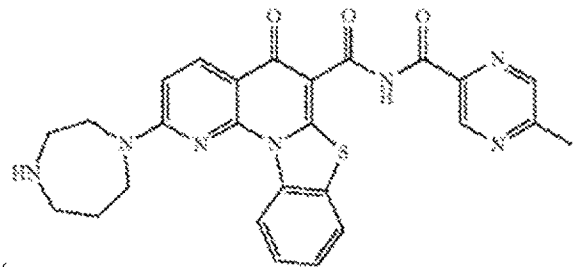 " should be

Signed and Sealed this
Thirty-first Day of January, 2023

Katherine Kelly Vidal
*Director of the United States Patent and Trademark Office*

CERTIFICATE OF CORRECTION (continued)
U.S. Pat. No. 11,524,012 B1

Page 2 of 2

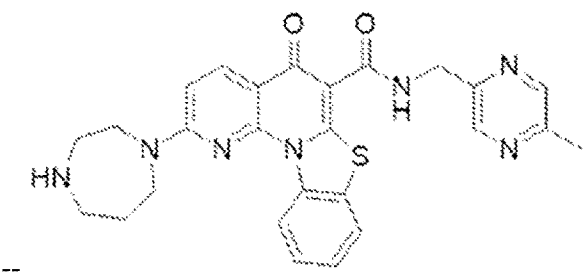

Claim 12, Column 158, Lines 40-50: " 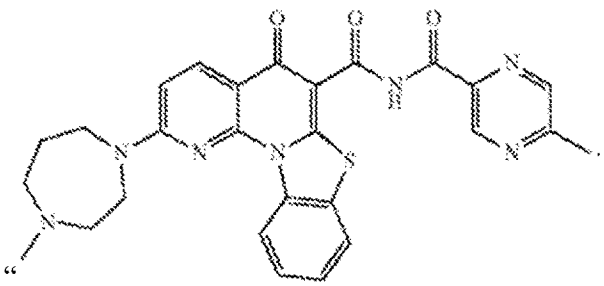 " should be

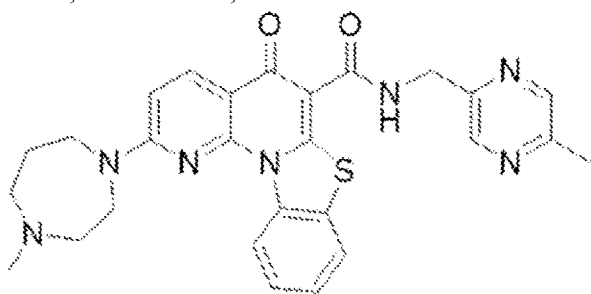

-- --